United States Patent
Kattamuri et al.

(10) Patent No.: US 11,767,291 B2
(45) Date of Patent: Sep. 26, 2023

(54) PREPARATION OF SECONDARY AMINES WITH ELECTROPHILIC N-LINCHPIN REAGENTS

(71) Applicant: WILLIAM MARSH RICE UNIVERSITY, Houston, TX (US)

(72) Inventors: Padmanabha Venkatesh Kattamuri, Houston, TX (US); Laszlo Kurti, Houston, TX (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 16/614,272

(22) PCT Filed: May 17, 2018

(86) PCT No.: PCT/US2018/033175
§ 371 (c)(1),
(2) Date: Nov. 15, 2019

(87) PCT Pub. No.: WO2018/213572
PCT Pub. Date: Nov. 22, 2018

(65) Prior Publication Data
US 2021/0261503 A1    Aug. 26, 2021

Related U.S. Application Data

(60) Provisional application No. 62/507,577, filed on May 17, 2017.

(51) Int. Cl.
C07C 311/19  (2006.01)
C07C 69/36   (2006.01)
C07C 69/675  (2006.01)
C07C 227/06  (2006.01)
C07C 381/00  (2006.01)
C07C 229/04  (2006.01)

(52) U.S. Cl.
CPC ............ *C07C 311/19* (2013.01); *C07C 69/36* (2013.01); *C07C 69/675* (2013.01); *C07C 227/06* (2013.01); *C07C 381/00* (2013.01); *C07C 229/04* (2013.01)

(58) Field of Classification Search
None
See application file for complete search history.

(56) References Cited

PUBLICATIONS

Mizota et al. (Tetrahedron 71, 2015, 5793). (Year: 2015).*
STN abstract of Mizota et al. (Tetrahedron 71, 2015, 5793). (Year: 2015).*
Aksenov et al., "Direct metal-free synthesis of diarylamines from 2-nitropropane via the twofold C—H functionalization of arenes," RSC Adv., 5:84849-84855, 2015.
Buchwald et al., "Industrial-scale palladium-catalyzed coupling of aryl halides and amines—a personal account," Adv. Synth. Catal., 348:23-39, 2006.

(Continued)

*Primary Examiner* — Sudhakar Katakam
*Assistant Examiner* — Jennifer C Sawyer
(74) *Attorney, Agent, or Firm* — Parker Highlander PLLC

(57) ABSTRACT

In one aspect, the present disclosure provides methods of preparing a secondary amine. In some embodiments, the secondary amine comprises two different groups or two identical groups. Also provided herein are compositions for use in the preparation of the secondary amine.

11 Claims, 10 Drawing Sheets

(56) References Cited

PUBLICATIONS

Cheung & Hu, "Amine synthesis via iron-catalysed reductive coupling of nitroarenes with alkyl halides," Nat. Commun., 7:12494, 2016.
Corcoran et al., "Aryl amination using ligand-free Ni(II) salts and photoredox catalysis," Science 353(6296):279-283, 2016.
Gao et al., "Rapid heteroatom transfer to arylmetals utilizing multifunctional reagent scaffolds," Nat. Chem., 9(7):681-688, 2017.
Gao et al., "Rapid synthesis of fused N-heterocycles by transition-metal-free electrophilic amination of arene C—H bonds," Angew. Chem., Int. Ed. 53:2701-2705, 2014.
Garrett, "The Art of Meeting Palladium Specifications in Active Pharmaceutical Ingredients Produced by Pd-Catalyzed Reactions," Adv. Synth. Catal. 346:889, 2004.
Gui et al., "Organic chemistry. Practical olefin hydroamination with nitroarenes," Science, 348(6237):886-891, 2015.
Kattamuri, et. al., "Practical Singly and Doubly Electrophilic Aminating Agents: A New, More Sustainable Platform for Carbon-Nitrogen Bond-Formation," *J Am Chem Soc.*, 139(32):11184-11196, 2017.
Kitamura et al., "Synthesis of primary amines by the electrophilic amination of Grignard reagents with 1,3-dioxolan-2-one O-sulfonyloxime," Org. Lett. 6:4619-4621, 2004.
Liegault et al., "Intramolecular Pd(II)-catalyzed oxidative biaryl synthesis under air: reaction development and scope," J. Org. Chem. 73(13):5022-5028, 2008.
Monnier & Taillefer, "Copper-catalyzed C(aryl)-N bond formation," Top. Organomet. Chem., 46:173-204, 2013.
Narasaka & Kitamura, "Amination with oximes," Eur. J. Org. Chem., 21:4505-4519, 2005.
Nohira, et al., "The reactions of nitrosobenzene and some methylene compounds," Bull. Chem. Soc. Jpn. 36:870-872, 1963.
Paudyal et al., "Dirhodium-catalyzed C—H arene amination using hydroxylamines," Science, 353:1144-1147, 2016.
PCT International Preliminary Report on Patentability issued in PCT/US2018/033175, dated Nov. 19, 2019.
PCT International Search Report and Written Opinion issued in PCT/US2018/033175, dated Oct. 1, 2018.
Peng et al., "New reactivity of oxaziridine: Pd(II)-catalyzed aromatic C—H ethoxycarbonylation via C—C bond cleavage," Org. Lett. 13:5244-5247, 2011.
PubChem CID No. 10132 dated Sep. 16, 2004.
PubChem CID No. 12224663 dated Feb. 7, 2007.
PubChem CID No. 55302507 dated Jan. 24, 2012.
PubChem CID No. 6399245 dated Aug. 8, 2005.
Qiao & Lam, "Copper-Promoted Carbon-Heteroatom Bond Cross-Coupling with Boronic Acids and Derivatives," Synthesis, 6:829-856, 2011.
Qiao & Lam, "Recent Advances in Chan-Lam Coupling Reaction: Copper-Promoted C-Heteroatom Bond Cross-Coupling Reactions with Boronic Acids and Derivatives" Boronic Acids (2nd Ed.), D. G. Hall, Ed., vol. 1, pp. 315-361, 2011.
Qiu & Norwood, "Identification of pharmaceutical impurities," J. Liq. Chromatogr. Relat. Technol., 30(5-7):877-935, 2007.
Rios & Cordova, "Aziridine Formation, in section C—N Bond Formation," Comprehensive Chirality, Carreira and Yamamoto, Eds. (Elsevier B.V.), 6:399-413, 2012.
Romero et al., "Site-selective arene C—H amination via photoredox catalysis," Science 349:1326-1330, 2015.
Sapountzis & Knochel, "A new general preparation of polyfunctional diarylamines by the addition of functionalized arylmagnesium compounds to nitroarenes," J. Am. Chem. Soc. 124:9390-9391, 2002.
Shin et al., "Transition-metal-catalyzed C—N bond forming reactions using organic azides as the nitrogen source: a journey for the mild and versatile C—H amination," Acc. Chem. Res., 48:1040-1052, 2015.
Sivan & Deepthi, "Facile synthesis of 1, 2, 3-tricarbonyls from 1,3-dicarbonyls mediated by cerium (IV) ammonium nitrate," Tetrahedron Lett, 55:1890-1893, 2014.
Surry & Buchwald, "Dialkylbiaryl Phosphines in Pd-Catalyzed Amination: A User's Guide," Chem. Sci., 2:27-50, 2011.
Sweeney, "Aziridine synthesis via nucleophilic attack of carbene equivalents on imines: the aza-Darzens reaction," Eur. J. Org. Chem., 29:4911-4919, 2009.
Thome & Bolm, "Transition-metal-free intramolecular N-arylations," Org. Lett., 14(7):1892-1895, 2012.
Welch et al., "Adsorbent Screening for Metal Impurity Removal in Pharmaceutical Process Research," Org. Process Res., Dev. 9:198-205, 2005.
Wolfe et al., "Rational development of practical catalysts for aromatic carbon-nitrogen bond formation," Acc. Chem. Res., 31:805-818, 1998.
Yan et al., "Recent progress in copper-catalyzed electrophilic amination," Catal. Sci. Technol. 4:4169, 2014.
Zhou et al., "Non-Deprotonative Primary and Secondary Amination of (Hetero)Arylmetals.," J. Am. Chem. Soc. 139:115-118, 2017.
Zhu et al., "Elusive metal-free primary amination of arylboronic acids: synthetic studies and mechanism by density functional theory," J. Am. Chem. Soc. 134:18253-18256, 2012.

\* cited by examiner

*Preparation and Use of Imines Acting as Electrophilic N-Sources:*

*Preparation and Use of Imines Acting as Electrophilic N-Sources:*

56a
Melting range = 51–55 °C

---

*Computationally determined possible transition state (TS) structures*

$S_N2$
Mg-C1=2.25
C1-N=2.40
N-O1=1.80
N-Mg=2.22

$S_N2$
Direct Displacement Pathway

*Computationally determined possible transition state (TS) structures*

TS1 (addition)
Mg-C1=2.30
C1-N=2.34
N-O1=1.37
N-Mg=2.10

N=C Direct Addition Pathway

TS2 (elimination)
C1-N=1.42
N-O1=1.67

PREPARATION OF SECONDARY AMINES WITH ELECTROPHILIC N-LINCHPIN REAGENTS

This application is a national phase application under 35 U.S.C. § 371 of International Application No. PCT/US2018/033175 filed on May 17, 2018 and claims the benefit of priority to U.S. Provisional Application Ser. No. 62/507,577, filed on May 17, 2017, the entire contents of which are hereby incorporated by reference.

This invention was made with government support under Grant No. GM114609 and CHE 1546097 awarded by the National Institute of Health and the National Science Foundation, respectively. The government has certain rights in the invention.

The development of this disclosure was funded in part by the Robert A. Welch Foundation under Grant No. C-1764.

BACKGROUND

1. Field

This disclosure relates to the methods of preparing secondary amines. In some aspects, the present disclosure provides methods of preparing a secondary amine without the use of a transition metal catalyst. In other aspects, compounds for use as reagents in the preparation of secondary amines are also provided.

2. Related Art

Amines and their derivatives are ubiquitous substances since they are present in the overwhelming majority of drug molecules, agrochemicals, functional materials as well as many compounds that are produced by plants and living organisms (e.g., natural products). (Hili & Yudin, 2006; Rappoport, 2007 and Ricci, 2008) Not surprisingly, organic chemists spend a considerable amount of time devising the synthesis and late-stage functionalization of amines that serve as key chemical building blocks for the preparation of biologically active compounds, especially in medicinal chemistry. (Kürti, 2015) Among these nitrogen-containing compounds, aromatic and heteroaromatic amines appear as core structures in more than one third of drug candidates and they also serve as important radical-trapping antioxidants utilized in a wide range of industries. The majority of currently utilized methods for the preparation of diaryl- and arylalkyl-amines fall into the following seven broad categories: (a) palladium- or copper-promoted/catalyzed cross-coupling of primary aliphatic or aromatic amines with aryl halides or pseudohalides [i.e., Ullmann-Goldberg reaction (Monnier & Taillefer, 2013) and Buchwald-Hartwig coupling (Wolfe et al, 1998; Buchwald et al, 2006 and Surry & Buchwald, 2011)]; (b) cross-coupling of aryl halides and amines utilizing merged Ni(II)- and photoredox catalysis (Corcoran et al, 2016); (c) copper-promoted N-arylation of primary anilines with boronic acid derivatives [i.e., Chan-Lam coupling](Qiao & Lam. 2011a and Qiao & Lam, 2011b); (d) transition metal- or photoredox-catalyzed, directed ortho-(Shin et al, 2015) as well as non-directed C—H amination (Romero et al, 2015 and Paudyal et al., 2016) of arenes with amines or their surrogates; (e) transition metal-catalyzed or promoted cross-coupling of organometallic species (e.g., B, Li, Mg, Zn) with activated amines (Yan et al, 2014 and Zhou et al, 2017); (f) direct addition of organometallic species (Sapountzis & Knochel, 2002; Gao et al, 2014 and Cheung & Hu, 2016) or radicals (Gui et al., 2015) to nitroarenes and more recently (g) transition metal-free, intra- and intermolecular carbon-nitrogen (C—N) bond-forming approaches. (Thome & Bolm, 2012 and Aksenov et al, 2015)

Most of the methods outlined above utilize transition metal catalysts, ligands and/or forcing conditions (elevated temperatures, high pressure, strong oxidants, etc.), which often require the extensive optimization of reaction parameters and ultimately lead to poor overall atom economy, reduced sustainability and limited substrate scope. Therefore, synthesis of (hetero)aromatic diaryl- and arylalkyl-amines under mild, operationally simple and environmentally friendly conditions (e.g., low temperature, absence of excess reagents or transition metal catalysts and additives) would be highly desirable. In fact, from both practical and environmental viewpoints, transition metal-free processes are much preferred, especially in the pharmaceutical industry, where frequent and extensive catalyst/ligand optimizations as well as the removal of undesired metal contamination can be expensive. (Garrett, 2004; Welch et al., 2005 and Qiu & Norwood, 2007).

Based on these facts, there is an urgent need for the development of fundamentally new and general C—N bond-forming methods that expand the toolbox of synthetic organic chemists and enable the environmentally friendly construction of complex molecular structures using the fewest number of chemical steps and generating the least amount of waste. Of particular advantage are methods of preparing carbon nitrogen bonds without the use of a catalyst.

SUMMARY

Thus, the present disclosure provides methods of preparing secondary amines as well as reagents for obtaining the same. In some aspects, the present disclosure provides compounds of the formula:

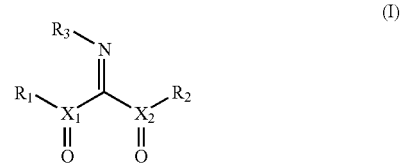

wherein:
  $X_1$ and $X_2$ are each independently C, S, or S(O);
  $R_1$ and $R_2$ are each independently amino, hydroxy, or alkoxy$_{(C\leq 12)}$, cycloalkoxy$_{(C\leq 12)}$, alkenyloxy$_{(C\leq 12)}$, alkynyloxy$_{(C\leq 12)}$, aryloxy$_{(C\leq 12)}$, aralkoxy$_{(C\leq 12)}$, heteroaryloxy$_{(C\leq 12)}$, heterocycloalkoxy$_{(C\leq 12)}$, alkylamino$_{(C\leq 12)}$, dialkylamino$_{(C\leq 12)}$, cycloalkylamino$_{(C\leq 12)}$, dicycloalkylamino$_{(C\leq 12)}$, alkenylamino$_{(C\leq 12)}$, dialkenylamino$_{(C\leq 12)}$, alkynylamino$_{(C\leq 12)}$, dialkynylamino$_{(C\leq 12)}$, arylamino$_{(C\leq 12)}$, diarylamino$_{(C\leq 12)}$, aralkylamino$_{(C\leq 12)}$, diaralkylamino$_{(C\leq 12)}$, heteroarylamino$_{(C\leq 12)}$, diheteroarylamino$_{(C\leq 12)}$, heterocycloalkylamino$_{(C\leq 12)}$, diheterocycloalkylamino$_{(C\leq 12)}$, or a substituted version of any of these groups; and
  $R_3$ is a leaving group or alkyl$_{(C\leq 18)}$, cycloalkyl$_{(C\leq 18)}$, alkenyl$_{(C\leq 18)}$, alkynyl$_{(C\leq 18)}$, aryl$_{(C\leq 18)}$, aralkyl$_{(C\leq 18)}$, heteroaryl$_{(C\leq 18)}$, heterocycloalkyl$_{(C\leq 18)}$, or a substituted version of any of these groups;
or a salt thereof. In some embodiments, the compounds are further defined as:

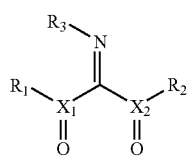

(I)

wherein:

$X_1$ and $X_2$ are each independently C, S, or S(O);

$R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups; and $R_3$ is a leaving group;

or a salt thereof. In some embodiments, the compounds are further defined as:

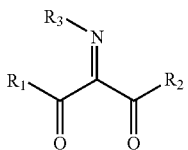

(II)

wherein:

$R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups; and $R_3$ is a leaving group;

or a salt thereof. In some embodiments, the compounds are further defined as:

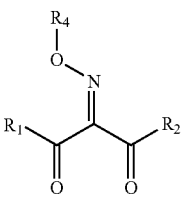

(III)

wherein:

$R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups; and $R_4$ is alkylsulfonyl$_{(C\leq12)}$, arylsulfonyl$_{(C\leq12)}$, or a substituted version of either of these groups;

or a salt thereof. In some embodiments, the compounds are further defined as:

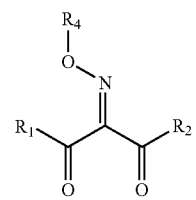

(III)

wherein:

$R_1$ and $R_2$ are each independently amino, hydroxy, or alkoxy$_{(C\leq12)}$, cycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, or a substituted version of any of these groups; and $R_4$ is alkylsulfonyl$_{(C\leq12)}$, arylsulfonyl$_{(C\leq12)}$, or a substituted version of either of these groups;

or a salt thereof.

In other embodiments, the compounds are further defined as:

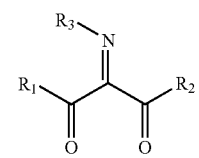

(II)

wherein:

$R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups; and $R_3$ is alkylsulfonyl$_{(C\leq12)}$, arylsulfonyl$_{(C\leq12)}$, or a substituted version of either of these groups;

or a salt thereof. In some embodiments, the compounds are further defined as:

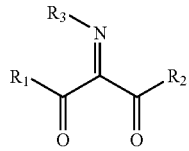

wherein:
R$_1$ and R$_2$ are each independently amino, hydroxy, or alkoxy$_{(C\leq12)}$, cycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, or a substituted version of any of these groups; and
R$_3$ is alkylsulfonyl$_{(C\leq12)}$, arylsulfonyl$_{(C\leq12)}$, or a substituted version of either of these groups;
or a salt thereof. In some embodiments, the compounds are further defined as:

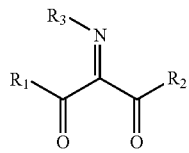

wherein:
R$_1$ and R$_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups; and
R$_3$ is alkyl$_{(C\leq18)}$, cycloalkyl$_{(C\leq18)}$, alkenyl$_{(C\leq18)}$, alkynyl$_{(C\leq18)}$, aryl$_{(C\leq18)}$, aralkyl$_{(C\leq18)}$, heteroaryl$_{(C\leq18)}$, heterocycloalkyl$_{(C\leq18)}$, or a substituted version of any of these groups;
or a salt thereof. In some embodiments, the compounds are further defined as:

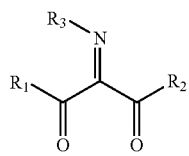

wherein:
R$_1$ and R$_2$ are each independently amino, hydroxy, or alkoxy$_{(C\leq12)}$, cycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, or a substituted version of any of these groups; and R$_3$ is alkyl$_{(C\leq18)}$, cycloalkyl$_{(C\leq18)}$, alkenyl$_{(C\leq18)}$, alkynyl$_{(C\leq18)}$, aryl$_{(C\leq18)}$, aralkyl$_{(C\leq18)}$, heteroaryl$_{(C\leq18)}$, heterocycloalkyl$_{(C\leq18)}$, or a substituted version of any of these groups;
or a salt thereof.

In some embodiments, R$_1$ is amino or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups. In some embodiments, R$_1$ is amino or alkoxy$_{(C\leq12)}$, cycloalkoxy$_{(C\leq12)}$, aryloxy$_{(C\leq12)}$, aralkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, or a substituted version of any of these groups. In some embodiments, R$_1$ is amino or alkoxy$_{(C\leq12)}$, cycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, or a substituted version of any of these groups. In some embodiments, R$_1$ is alkoxy$_{(C\leq12)}$ or substituted alkoxy$_{(C\leq12)}$ such as methoxy or ethoxy or alternatively isopropyloxy or t-butyloxy. In some embodiments, R$_2$ is amino or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups. In some embodiments, R$_2$ is amino or alkoxy$_{(C\leq12)}$, cycloalkoxy$_{(C\leq12)}$, aryloxy$_{(C\leq12)}$, aralkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, or a substituted version of any of these groups. In some embodiments, R$_2$ is amino or alkoxy$_{(C\leq12)}$, cycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, or a substituted version of any of these groups. In some embodiments, R$_2$ is alkoxy$_{(C\leq12)}$ or substituted alkoxy$_{(C\leq12)}$ such as methoxy or ethoxy or alternatively isopropyloxy or t-butyloxy.

In some embodiments, R$_3$ is a leaving group selected from halo, alkylsulfonyl$_{(C\leq12)}$, substituted alkylsulfonyl$_{(C\leq12)}$, arylsulfonyl$_{(C\leq12)}$, substituted arylsulfonyl$_{(C\leq12)}$, alkylsulfonyloxy$_{(C\leq12)}$, substituted alkylsulfonyloxy$_{(C\leq12)}$, arylsulfonyloxy$_{(C\leq12)}$, or substituted arylsulfonyloxy$_{(C\leq12)}$. In some embodiments, R$_4$ is alkylsulfonyl$_{(C\leq12)}$, substituted alkylsulfonyl$_{(C\leq12)}$, arylsulfonyl$_{(C\leq12)}$, or substituted arylsulfonyl$_{(C\leq12)}$. In other embodiments, R$_3$ is aryl$_{(C\leq18)}$, aralkyl$_{(C\leq18)}$, heteroaryl$_{(C\leq18)}$, heterocycloalkyl$_{(C\leq18)}$, or a substituted version of any of these groups. In some embodiments, R$_3$ is alkyl$_{(C\leq18)}$, cycloalkyl$_{(C\leq18)}$, alkenyl$_{(C\leq18)}$, alkynyl$_{(C\leq18)}$, or a substituted version of any of these groups.

In some embodiments, X$_1$ is C. In other embodiments, X$_1$ is S(O). In some embodiments, X$_2$ is C. In other embodiments, X$_2$ is S(O). In some embodiments, the compounds are further defined as:

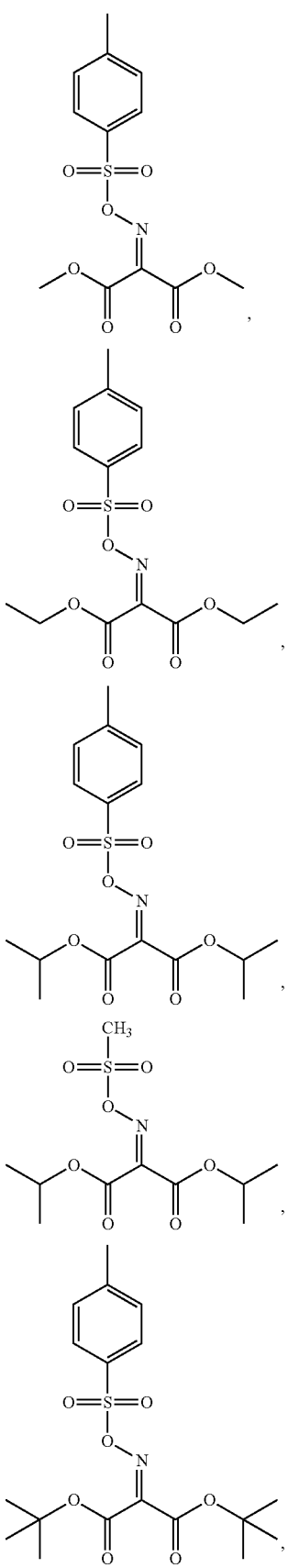

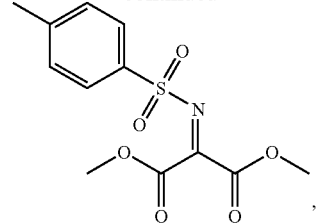

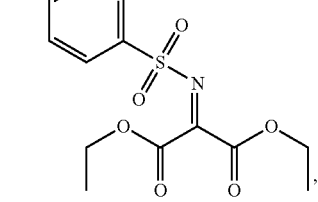

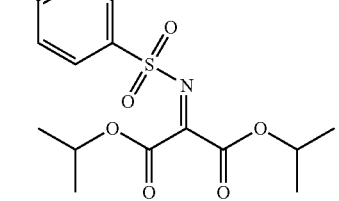

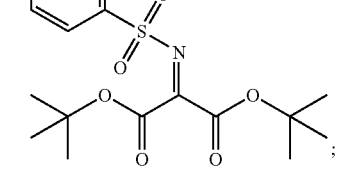

or a salt thereof. In some embodiments, the compound is:

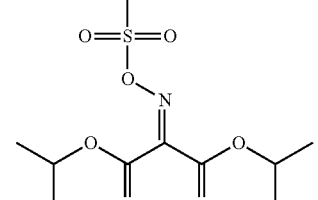

or a salt thereof.

In some embodiments, the compounds are present at least 90% of a single structure, is present at least 95% of a single structure, or is present at least 98% of a single structure. In some embodiments, the compounds are present in crystalline form. In some embodiments, the crystalline form comprises a unit cell with dimensions a=8.281±0.01 Å, b=11.437±0.01 Å, and c=10.852±0.01 Å. In some embodiments, the unit cell dimensions are a=8.281±0.002 Å, b=11.437±0.002 Å, and c=10.852+0.002 Å. In some embodiments, the unit cell dimensions include an α angle of 90°±1°, a β angle of 109.89°±1°, and a γ angle of 90°+1°. In some embodiments, the unit cell dimensions include an α angle of 90°±0.05°, a β angle of 109.89°±0.05°, and a γ angle of 90°±0.05°.

In another aspect, the present disclosure provides compounds of the formula:

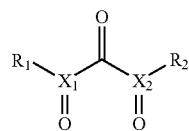
(III)

wherein:
$X_1$ and $X_2$ are each independently C, S, or S(O); and
$R_1$ and $R_2$ are each independently amino, hydroxy, or alkoxy$_{(C \leq 12)}$, cycloalkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heterocycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, alkenylamino$_{(C \leq 12)}$, dialkenylamino$_{(C \leq 12)}$, alkynylamino$_{(C \leq 12)}$, dialkynylamino$_{(C \leq 12)}$, arylamino$_{(C \leq 12)}$, diarylamino$_{(C \leq 12)}$, aralkylamino$_{(C \leq 12)}$, diaralkylamino$_{(C \leq 12)}$, heteroarylamino$_{(C \leq 12)}$, diheteroarylamino$_{(C \leq 12)}$, heterocycloalkylamino$_{(C \leq 12)}$, diheterocycloalkylamino$_{(C \leq 12)}$, or a substituted version of any of these groups;
or a salt thereof. In some embodiments, the compounds are further defined as:

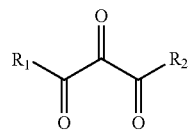
(IV)

wherein:
$R_1$ and $R_2$ are each independently amino, hydroxy, or alkoxy$_{(C \leq 12)}$, cycloalkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heterocycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, alkenylamino$_{(C \leq 12)}$, dialkenylamino$_{(C \leq 12)}$, alkynylamino$_{(C \leq 12)}$, dialkynylamino$_{(C \leq 12)}$, arylamino$_{(C \leq 12)}$, diarylamino$_{(C \leq 12)}$, aralkylamino$_{(C \leq 12)}$, diaralkylamino$_{(C \leq 12)}$, heteroarylamino$_{(C \leq 12)}$, diheteroarylamino$_{(C \leq 12)}$, heterocycloalkylamino$_{(C \leq 12)}$, diheterocycloalkylamino$_{(C \leq 12)}$, or a substituted version of any of these groups;
or a salt thereof. In some embodiments, the compounds are further defined as:

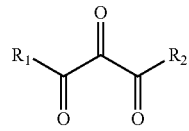
(IV)

wherein:
$R_1$ and $R_2$ are each independently amino, hydroxy, or alkoxy$_{(C \leq 12)}$, cycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, or a substituted version of any of these groups;
or a salt thereof. In some embodiments, the compounds are further defined as:

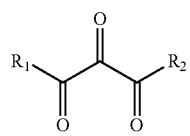
(IV)

wherein:
$R_1$ and $R_2$ are each independently alkoxy$_{(C \leq 12)}$ or substituted alkoxy$_{(C \leq 12)}$;
or a salt thereof.

In some embodiments, $R_1$ is alkoxy$_{(C \leq 12)}$ such as methoxy, ethoxy, isopropoxy, and t-butyloxy. In some embodiments, $R_2$ is alkoxy$_{(C \leq 12)}$ such as methoxy, ethoxy, isopropoxy, and t-butyloxy. In some embodiments, the compounds are further defined as:

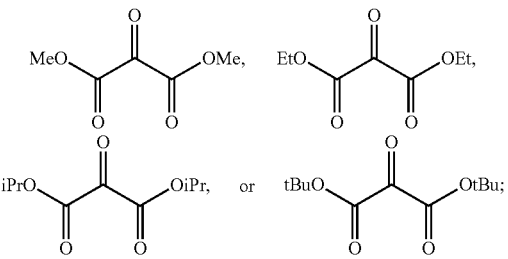

or a salt thereof. In some embodiments, the compounds are further defined as:

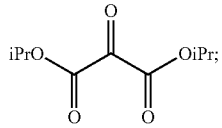

or a salt thereof.

In some embodiments, the compounds are at least 80% present as a single structure, is present at least 90% of a single structure, is present at least 95% of a single structure, or is present at least 98% of a single structure. In some embodiments, the compounds are present in crystalline form.

In still yet another aspect, the present disclosure provides compounds of the formula:

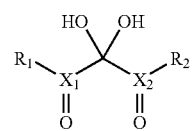
(V)

wherein:
  $X_1$ and $X_2$ are each independently C, S, or S(O); and
  $R_1$ and $R_2$ are each independently amino, hydroxy, or alkoxy$_{(C \leq 12)}$, cycloalkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heterocycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, alkenylamino$_{(C \leq 12)}$, dialkenylamino$_{(C \leq 12)}$, alkynylamino$_{(C \leq 12)}$, dialkynylamino$_{(C \leq 12)}$, arylamino$_{(C \leq 12)}$, diarylamino$_{(C \leq 12)}$, aralkylamino$_{(C \leq 12)}$, diaralkylamino$_{(C \leq 12)}$, heteroarylamino$_{(C \leq 12)}$, diheteroarylamino$_{(C \leq 12)}$, heterocycloalkylamino$_{(C \leq 12)}$, diheterocycloalkylamino$_{(C \leq 12)}$, or a substituted version of any of these groups;
or a salt thereof. In some embodiments, the compounds are further defined as:

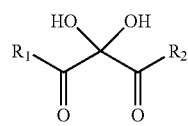

(VI)

wherein:
  $R_1$ and $R_2$ are each independently amino, hydroxy, or alkoxy$_{(C \leq 12)}$, cycloalkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heterocycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, alkenylamino$_{(C \leq 12)}$, dialkenylamino$_{(C \leq 12)}$, alkynylamino$_{(C \leq 12)}$, dialkynylamino$_{(C \leq 12)}$, arylamino$_{(C \leq 12)}$, diarylamino$_{(C \leq 12)}$, aralkylamino$_{(C \leq 12)}$, diaralkylamino$_{(C \leq 12)}$, heteroarylamino$_{(C \leq 12)}$, diheteroarylamino$_{(C \leq 12)}$, heterocycloalkylamino$_{(C \leq 12)}$, diheterocycloalkylamino$_{(C \leq 12)}$, or a substituted version of any of these groups;
or a salt thereof. In some embodiments, the compounds are further defined as:

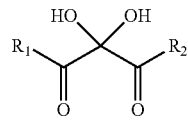

(VI)

wherein:
  $R_1$ and $R_2$ are each independently amino, hydroxy, or alkoxy$_{(C \leq 12)}$, cycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, or a substituted version of any of these groups;
or a salt thereof. In some embodiments, the compounds are further defined as:

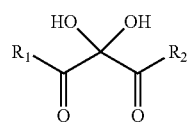

(VI)

wherein:
  $R_1$ and $R_2$ are each independently alkoxy$_{(C \leq 12)}$ or substituted alkoxy$_{(C \leq 12)}$;
or a salt thereof.
In some embodiments, $R_1$ is alkoxy$_{(C \leq 12)}$ such as methoxy, ethoxy, isopropoxy, and t-butyloxy. In some embodiments, $R_2$ is alkoxy$_{(C \leq 12)}$ such as methoxy, ethoxy, isopropoxy, and t-butyloxy. In some embodiments, the compounds are further defined as:

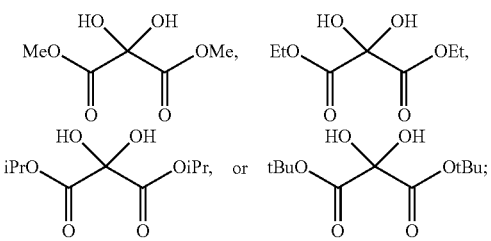

or a salt thereof. In some embodiments, the compounds are further defined as:

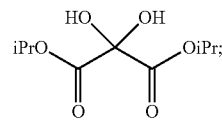 [SMILES: CC(C)OC(=O)C(O)(O)C(=O)OC(C)C]

or a salt thereof.
In some embodiments, the compounds are at least 80% present as a single structure, is present at least 90% of a single structure, is present at least 95% of a single structure, or is present at least 98% of a single structure. In some embodiments, the compounds are present in crystalline form. In some embodiments, the crystalline form comprises a unit cell with dimensions a=9.406±0.01 Å, b=13.924±0.01 Å, and c=10.168±0.01 Å. In some embodiments, the unit cell dimensions are a=9.406±0.003 Å, b=13.924±0.003 Å, and c=10.168±0.003 Å. In some embodiments, the unit cell dimensions include an α angle of 90°±1°, a β angle of 112.92°±1°, and a γ angle of 90°±1°. In some embodiments, the unit cell dimensions include an α angle of 90°+0.05°, a β angle of 112.92°+0.05°, and a γ angle of 90°+0.05°.

In yet another aspect, the present disclosure provides compounds of the formula:

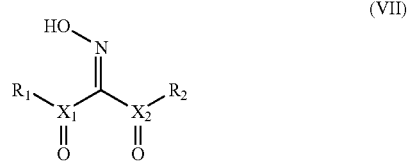

(VII)

wherein:
  $X_1$ and $X_2$ are each independently C, S, or S(O); and
  $R_1$ and $R_2$ are each independently amino, hydroxy, or alkoxy$_{(C \leq 12)}$, cycloalkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heterocycloalkoxy$_{(C \leq 12)}$, alkyl amino$_{(C \leq 12)}$, dialkylamino$_{(C \leq 12)}$, cycloalkylamino$_{(C \leq 12)}$, dicycloalkylamino$_{(C \leq 12)}$, alkenylamino$_{(C \leq 12)}$, dialkenylamino$_{(C \leq 12)}$, alkynylamino$_{(C≤12)}$, dialkynylamino$_{(C≤12)}$, arylamino$_{(C≤12)}$, diarylamino$_{(C≤12)}$, aralkylamino$_{(C≤12)}$, diaralkylamino$_{(C≤12)}$, heteroarylamino$_{(C≤12)}$, diheteroarylamino$_{(C≤12)}$, heterocycloalkylamino$_{(C≤12)}$, diheterocycloalkylamino$_{(C≤12)}$, or a substituted version of any of these groups;

or a salt thereof. In some embodiments, the compounds are further defined as:

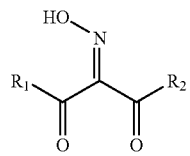

(VIII)

wherein:
R$_1$ and R$_2$ are each independently amino, hydroxy, or alkoxy$_{(C≤12)}$, cycloalkoxy$_{(C≤12)}$, alkenyloxy$_{(C≤12)}$, alkynyloxy$_{(C≤12)}$, aryloxy$_{(C≤12)}$, aralkoxy$_{(C≤12)}$, heteroaryloxy$_{(C≤12)}$, heterocycloalkoxy$_{(C≤12)}$, alkylamino$_{(C≤12)}$, dialkylamino$_{(C≤12)}$, cycloalkylamino$_{(C≤12)}$, dicycloalkylamino$_{(C≤12)}$, alkenylamino$_{(C≤12)}$, dialkenylamino$_{(C≤12)}$, alkynylamino$_{(C≤12)}$, dialkynylamino$_{(C≤12)}$, arylamino$_{(C≤12)}$, diarylamino$_{(C≤12)}$, aralkylamino$_{(C≤12)}$, diaralkylamino$_{(C≤12)}$, heteroarylamino$_{(C≤12)}$, diheteroarylamino$_{(C≤12)}$, heterocycloalkylamino$_{(C≤12)}$, diheterocycloalkylamino$_{(C≤12)}$, or a substituted version of any of these groups;

or a salt thereof. In some embodiments, the compounds are further defined as:

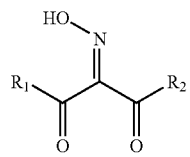

(VIII)

wherein:
R$_1$ and R$_2$ are each independently amino, hydroxy, or alkoxy$_{(C≤12)}$, cycloalkoxy$_{(C≤12)}$, alkylamino$_{(C≤12)}$, dialkylamino$_{(C≤12)}$, cycloalkylamino$_{(C≤12)}$, dicycloalkylamino$_{(C≤12)}$, or a substituted version of any of these groups;

or a salt thereof. In some embodiments, the compounds are further defined as:

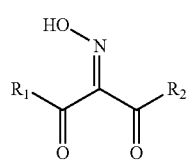

(VIII)

wherein:
R$_1$ and R$_2$ are each independently alkoxy$_{(C≤12)}$ or substituted alkoxy$_{(C≤12)}$;
or a salt thereof.

In some embodiments R$_1$ is alkoxy$_{(C≤12)}$ such as methoxy, ethoxy, isopropoxy, and t-butyloxy. In some embodiments, R$_2$ is alkoxy$_{(C≤12)}$ such as methoxy, ethoxy, isopropoxy, and t-butyloxy. In some embodiments, the compounds are further defined as:

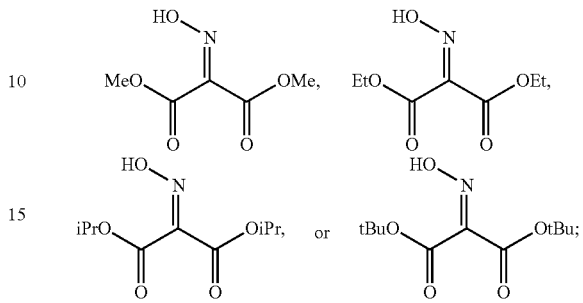

or a salt thereof. In some embodiments, the compounds are further defined as:

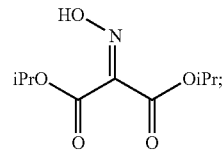 [SMILES: CC(C)OC(=O)C(=NO)C(=O)OC(C)C]

or a salt thereof.

In some embodiments, the compounds are at least 80% present as a single structure, is present at least 90% of a single structure, is present at least 95% of a single structure, or is present at least 98% of a single structure. In some embodiments, the compounds are present in crystalline form. In some embodiments, the compounds above have the same group for R$_1$ and R$_2$. In other embodiments, R$_1$ and R$_2$ are different groups.

In still another aspect, the present disclosure provides methods of preparing a tertiary amine comprising reacting a compound described herein with an hard carbanion or an enolate. In some embodiments, the hard carbanion is an organometallic reagent. In some embodiments, the hard carbanion is a Gringard reagent or an organolithium compound. In some embodiments, the Gringard reagent is further defined as:

MgX$_3$R$_4$ (IX)

wherein:
X$_3$ is halo; and
R$_4$ is alkyl$_{(C≤18)}$, cycloalkyl$_{(C≤18)}$, alkenyl$_{(C≤18)}$, cycloalkenyl$_{(C≤18)}$, alkynyl$_{(C≤18)}$, cycloalkynyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version any of these groups.

In other embodiments, the organolithium compound is further defined as:

LiR$_5$ (X)

wherein:
R$_5$ is alkyl$_{(C≤18)}$, cycloalkyl$_{(C≤18)}$, alkenyl$_{(C≤18)}$, cycloalkenyl$_{(C≤18)}$, alkynyl$_{(C≤18)}$, cycloalkynyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version any of these groups.

In other embodiments, the method comprises reacting an enolate.

In some embodiments, the tertiary amine comprises at least two identical groups. In other embodiments, the tertiary amine comprises three different groups. In some embodiments, the tertiary amine compound is further defined as:

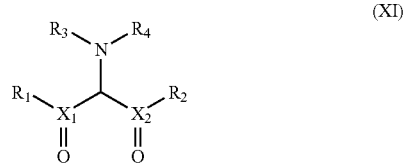

(XI)

wherein:

$X_1$ and $X_2$ are each independently C, S, or S(O);

$R_1$ and $R_2$ are each independently amino, hydroxy, or alkoxy$_{(C \leq 12)}$, cycloalkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heterocycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, alkenylamino$_{(C \leq 12)}$, dialkenylamino$_{(C \leq 12)}$, alkynylamino$_{(C \leq 12)}$, dialkynylamino$_{(C \leq 12)}$, arylamino$_{(C \leq 12)}$, diarylamino$_{(C \leq 12)}$, aralkylamino$_{(C \leq 12)}$, diaralkylamino$_{(C \leq 12)}$, heteroarylamino$_{(C \leq 12)}$, diheteroarylamino$_{(C \leq 12)}$, heterocycloalkylamino$_{(C \leq 12)}$, diheterocycloalkylamino$_{(C \leq 12)}$, or a substituted version of any of these groups; and $R_3$ and $R_4$ are each independently alkyl$_{(C \leq 18)}$, cycloalkyl$_{(C \leq 18)}$, alkenyl$_{(C \leq 18)}$, alkynyl$_{(C \leq 18)}$, aryl$_{(C \leq 18)}$, aralkyl$_{(C \leq 18)}$, heteroaryl$_{(C \leq 18)}$, heterocycloalkyl$_{(C \leq 18)}$, or a substituted version of any of these groups;

or a salt thereof.

In some embodiments, $R_3$ and $R_4$ are the same. In other embodiments, $R_3$ and $R_4$ are different. In some embodiments, $X_1$ and $X_2$ are C. In some embodiments, $R_1$ and $R_2$ are alkoxy$_{(C \leq 12)}$ or substituted alkoxy$_{(C \leq 12)}$. In some embodiments, the methods further comprise an organic solvent. In some embodiments, the organic solvent is a nonpolar organic solvent such as diethyl ether, tetrahydrofuran, or dichloromethane.

In some embodiments, the methods further comprise heating the reaction to a temperature from about 25° C. to about −100° C. In some embodiments, the temperature is from about −50° C. to about −100° C. In some embodiments, the methods comprise adding from about 0.5 equivalents to about 5 equivalents of the hard carbanion to the compound. In some embodiments, the methods comprise adding from about 1 equivalent to about 2.5 equivalents. In some embodiments, the methods comprise adding about 1.1 equivalents when $R_3$ and $R_4$ are different or when the tertiary amine contains no identical groups. In other embodiments, the methods comprise adding about 2.1 equivalents when $R_3$ and $R_4$ are the same or when the tertiary amine contains at least two identical groups.

In some embodiments, the methods comprise reacting the compound and the hard carbanion for a time period 10 minutes to about 8 hours. In some embodiments, the time period is from about 30 minutes to about 2 hours such as about 1 hour. In some embodiments, the methods comprise adding a mild acid such as NH$_4$Cl.

In some embodiments, the methods further comprise converting the tertiary amine into a secondary amine comprising:

(A) a mild base and air; or (B) a base and an oxidizing agent.

In some embodiments, the methods comprise a mild base and air. In some embodiments, the mild base is metal hydroxide such as potassium hydroxide. In some embodiments, the methods comprise sodium hydrogen sulfate. In some embodiments, the methods further comprise an organic solvent. In some embodiments, the organic solvent is a C1-C6 alcohol such as ethanol. In some embodiments, the methods further comprise adding a mild acid such as NH$_4$Cl.

In some embodiments, the methods comprise heating the reaction to a temperature from about 0° C. to about 50° C. such as about 25° C. or about room temperature.

In other embodiments, the base is a metal hydride such as sodium hydride. In some embodiments, the oxidizing agent is a halosuccinimde such as a chlorosuccinimide. In some embodiments, the methods further comprise an organic solvent. In some embodiments, the organic solvent is a C1-C6 ether such as tetrahydrofuran. In some embodiments, the methods further comprise adding about 0.5 equivalents to about 5 equivalents of the base to the tertiary amine such as about 1 equivalent of the base. In some embodiments, the methods further comprise adding about 0.5 equivalents to about 5 equivalents of the oxidizing agent to the tertiary amine such as about 1 equivalent of the oxidizing agent. In some embodiments, the methods further comprise heating the reaction to a temperature from about 25° C. to about −100° C. In some embodiments, the temperature is from about −50° C. to about −100° C. In some embodiments, the methods comprise reacting the compound and the hard carbanion for a time period 10 minutes to about 8 hours. In some embodiments, the time period is from about 30 minutes to about 2 hours such as about 1 hour.

In still yet another aspect, the present disclosure provides methods of preparing a compound of the formula:

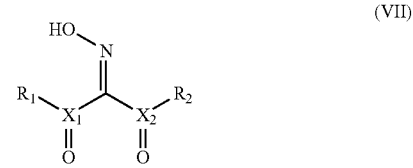

(VII)

wherein:

$X_1$ and $X_2$ are each independently C, S, or S(O); and $R_1$ and $R_2$ are each independently amino, hydroxy, or alkoxy$_{(C \leq 12)}$, cycloalkoxy$_{(C \leq 12)}$, alkenyloxy$_{(C \leq 12)}$, alkynyloxy$_{(C \leq 12)}$, aryloxy$_{(C \leq 12)}$, aralkoxy$_{(C \leq 12)}$, heteroaryloxy$_{(C \leq 12)}$, heterocycloalkoxy$_{(C \leq 12)}$, alkylamino$_{(C \leq 12)}$, dialkylamino$_{(C \leq 12)}$, cycloalkylamino$_{(C \leq 12)}$, dicycloalkylamino$_{(C \leq 12)}$, alkenylamino$_{(C \leq 12)}$, dialkenylamino$_{(C \leq 12)}$, alkynylamino$_{(C \leq 12)}$, dialkynylamino$_{(C \leq 12)}$, arylamino$_{(C \leq 12)}$, diarylamino$_{(C \leq 12)}$, aralkylamino$_{(C \leq 12)}$, diaralkylamino$_{(C \leq 12)}$, heteroarylamino$_{(C \leq 12)}$, diheteroarylamino$_{(C \leq 12)}$, heterocycloalkylamino$_{(C \leq 12)}$, diheterocycloalkylamino$_{(C \leq 12)}$, or a substituted version of any of these groups;

or a salt thereof, comprising reacting a compound of the formula:

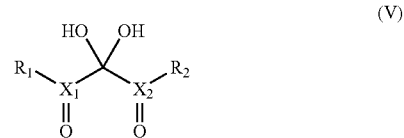

(V)

wherein $R_1$, $R_2$, $X_1$, and $X_2$ are as defined above; and hydroxylamine in a nonpolar solvent.

In some embodiments, the nonpolar solvent is an arene$_{(C\leq12)}$ such as toluene. In some embodiments, the methods comprise heating the nonpolar solvent to reflux. In some embodiments, the methods comprise reacting for a time period from about 2 hours to about 24 hours. In some embodiments, the time period is from about 4 hours to about 12 hours such as about 4 hours. In some embodiments, the method further comprises reacting the compound of formula VII with a leaving group agent. In some embodiments, the leaving group agent is tosyl halide such as tosyl chloride. In some embodiments, the methods further comprise adding a base. In some embodiments, the base is a nitrogenous base such as pyridine.

In some embodiments, the methods further comprise an organic solvent. In some embodiments, the organic solvent is a haloalkane$_{(C\leq8)}$ such as dichloromethane. In some embodiments, the methods comprise heating the reaction to a temperature from about 0° C. to about 50° C. such as about 25° C. or about room temperature. In some embodiments, the methods comprises reacting for a time period from about 1 hours to about 24 hours. In some embodiments, the time period is from about 2 hours to about 8 hours such as about 3 hours.

In still yet another aspect, the present disclosure provides methods of preparing a compound of the formula:

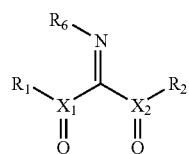

(XII)

wherein:
$X_1$ and $X_2$ are each independently C, S, or S(O); and
$R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups;
$R_6$ is alkyl$_{(C\leq18)}$, cycloalkyl$_{(C\leq18)}$, alkenyl$_{(C\leq18)}$, alkynyl$_{(C\leq18)}$, aryl$_{(C\leq18)}$, aralkyl$_{(C\leq18)}$, heteroaryl$_{(C\leq18)}$, heterocycloalkyl$_{(C\leq18)}$, or a substituted version of any of these groups;
or a salt thereof, comprising reacting a compound of the formula:

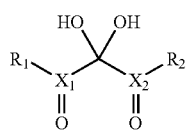

(V)

wherein $R_1$, $R_2$, $X_1$, and $X_2$ are as defined above; and a compound of the formula:

$$NH_2R_6 \quad (XIII)$$

in a nonpolar solvent.

In some embodiments, nonpolar solvent is an arene$_{(C\leq12)}$ such as toluene. In some embodiments, the methods comprise heating the nonpolar solvent to reflux. In some embodiments, the methods comprise reacting for a time period from about 2 hours to about 24 hours. In some embodiments, the time period is from about 4 hours to about 12 hours such as about 4 hours.

In still another aspect, the present disclosure provides methods of preparing a compound of the formula:

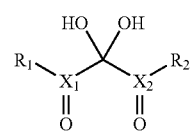

(V)

wherein:
$X_1$ and $X_2$ are each independently C, S, or S(O); and
$R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups;
or a salt thereof, comprising reacting a compound of the formula:

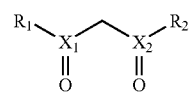

(XIV)

wherein $R_1$, $R_2$, $X_1$, and $X_2$ are as defined above; with an oxidizing agent in the presence of air.

In some embodiments, the methods further comprise an organic solvent. In some embodiments, the nonpolar solvent is an alkylnitrile$_{(C\leq12)}$ such as acetonitrile. In some embodiments, the methods comprise reacting for a time period from about 1 day to about 1 week. In some embodiments, the time period is from about 1 day to about 3 days such as about 2 days. In some embodiments, the methods comprise a temperature from about 0° C. to about 50° C. such as about 25° C. or about room temperature. In some embodiments, the oxidizing agent is an inorganic complex. In some embodiments, the oxidizing agent is a cerium compound such as cerium ammonium nitrate.

In yet another aspect, the present disclosure provides methods of preparing a compound of the formula:

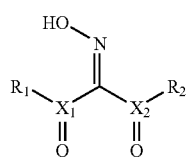

(VII)

wherein:

$X_1$ and $X_2$ are each independently C, S, or S(O); and $R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups;

or a salt thereof, comprising reacting a compound of the formula:

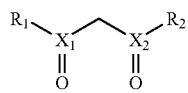

(XIV)

wherein $R_1$, $R_2$, $X_1$, and $X_2$ are as defined above; and metal nitrite in the presence of an acid in a solvent.

In some embodiments, the solvent is water In some embodiments, the methods are reacted at about room temperature. In some embodiments, the metal nitrite is sodium nitrite. In some embodiments, the methods comprise reacting for a time period from about 4 hours to about 72 hours. In some embodiments, the time period is from about 8 hours to about 24 hours such as about 14 hours.

In some embodiments, the methods further comprise reacting the compound of formula VII with a leaving group agent. In some embodiments, the leaving group agent is tosyl halide such as tosyl chloride. In some embodiments, the methods further comprise adding a base. In some embodiments, the base is a nitrogenous base such as pyridine. In some embodiments, the methods further comprise an organic solvent. In some embodiments, the organic solvent is a haloalkane$_{(C\leq8)}$ such as dichloromethane. In some embodiments, the method comprises heating the reaction to a temperature from about 0° C. to about 50° C. such as about 25° C. or about room temperature. In some embodiments, the methods comprise reacting for a time period from about 1 hours to about 24 hours. In some embodiments, the time period is from about 2 hours to about 8 hours such as about 3 hours.

In still yet another aspect, the present disclosure provides methods of preparing a compound of the formula:

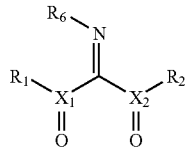

(XII)

wherein:

$X_1$ and $X_2$ are each independently C, S, or S(O); and $R_1$ and $R_2$ are each independently amino, hydroxy, or alkoxy$_{(C\leq12)}$, cycloalkoxy$_{(C\leq12)}$, alkenyloxy$_{(C\leq12)}$, alkynyloxy$_{(C\leq12)}$, aryloxy$_{(C\leq12)}$, aralkoxy$_{(C\leq12)}$, heteroaryloxy$_{(C\leq12)}$, heterocycloalkoxy$_{(C\leq12)}$, alkylamino$_{(C\leq12)}$, dialkylamino$_{(C\leq12)}$, cycloalkylamino$_{(C\leq12)}$, dicycloalkylamino$_{(C\leq12)}$, alkenylamino$_{(C\leq12)}$, dialkenylamino$_{(C\leq12)}$, alkynylamino$_{(C\leq12)}$, dialkynylamino$_{(C\leq12)}$, arylamino$_{(C\leq12)}$, diarylamino$_{(C\leq12)}$, aralkylamino$_{(C\leq12)}$, diaralkylamino$_{(C\leq12)}$, heteroarylamino$_{(C\leq12)}$, diheteroarylamino$_{(C\leq12)}$, heterocycloalkylamino$_{(C\leq12)}$, diheterocycloalkylamino$_{(C\leq12)}$, or a substituted version of any of these groups;

$R_6$ is alkyl$_{(C\leq18)}$, cycloalkyl$_{(C\leq18)}$, alkenyl$_{(C\leq18)}$, alkynyl$_{(C\leq18)}$, aryl$_{(C\leq18)}$, aralkyl$_{(C\leq18)}$, heteroaryl$_{(C\leq18)}$, heterocycloalkyl$_{(C\leq18)}$, or a substituted version of any of these groups;

or a salt thereof, comprising reacting a compound of the formula:

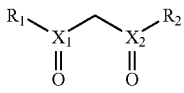

(XIV)

wherein $R_1$, $R_2$, $X_1$, and $X_2$ are as defined above; and a compound of the formula:

(O)NR$_6$ (XIII)

in an alcoholic solvent and a base.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Idealized conversion of a nucleophilic primary amine (1) to a well-defined electrophilic aminating agent (2) that reacts with a C-nucleophile (Nuc) in the absence of any catalyst to form a new C—N bond. The initially formed, and temporarily protected, secondary amine (3) yields the free secondary amine (4) upon removal of the reactivity-modifying umpolung reagent (UR). (FIG. 1B) Secondary aliphatic amines undergo facile oxidation with halonium ions to afford the corresponding electrophilic N-haloamines (6), which can either transfer the dialkylamino group or the halogen atom to a suitable C-nucleophile. (FIG. 1C) The N-halogenation of primary aliphatic (9) or aromatic amines (12) is not practical due to numerous side reactions. (FIG. 1D) A number of primary and secondary amines (15) can be oxidized to the corresponding O-benzoylhydroxylamines (16) that almost always require a transition metal to initiate C—N bond-formation with C-nucleophiles. (FIG. 1E) Usual vs unusual C=N bond-polarization. (FIG. 1F) Kagan's α-iminoester (22) that acts predominantly as an N-electrophile. (FIG. 1G) N-p-methoxyphenyl (PMP) substituted α-iminoesters (24) serve as precursors for the synthesis of α-amino acid derivatives. (FIG. 1H) The only known iminomalonate (27) that undergoes N-alkylation with alkylmetal reagents (i.e., no other examples have been reported since). (FIG. 1I) Design principles of practical singly (30) and doubly (31) N-electrophilic aminating agents that enable preferential N-versus C-attack by C-nucleophiles. The presence of two bulky electron-withdrawing groups significantly increases the electrophilicity of the nitrogen atom in these reagents compared to iminoesters, thus expands the scope of amination from a few simple alkylmetals to structurally diverse aryl-, heteroaryl- and alkylmetals.

FIG. 3 shows the single crystal X-ray structure of amine 56a.

DESCRIPTION OF ILLUSTRATIVE EMBODIMENTS

Figure 1A:
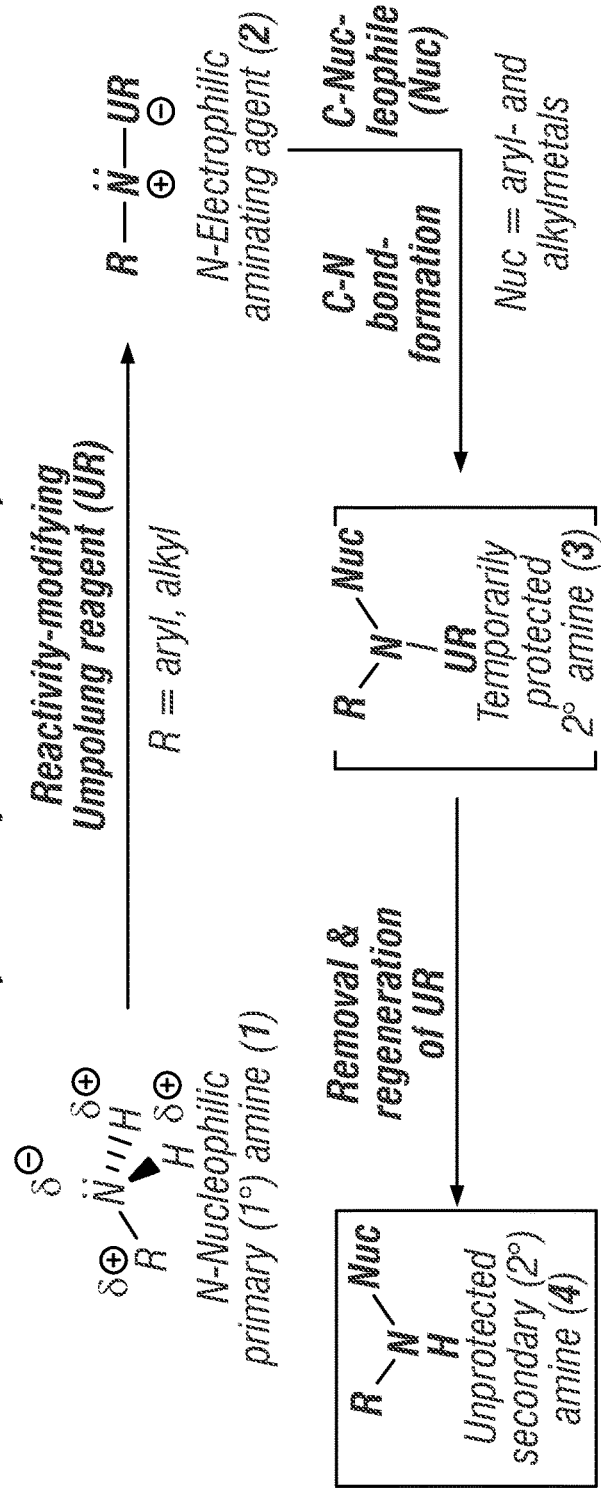
FIGS. 1A-1I shows current methods for the N-umpolung of alkyl and arylamines and design principles of sterically hindered ketomalonate imines and oxime O-sulfonates to be used as practical singly and doubly electrophilic aminating agents.
Figure 1B:
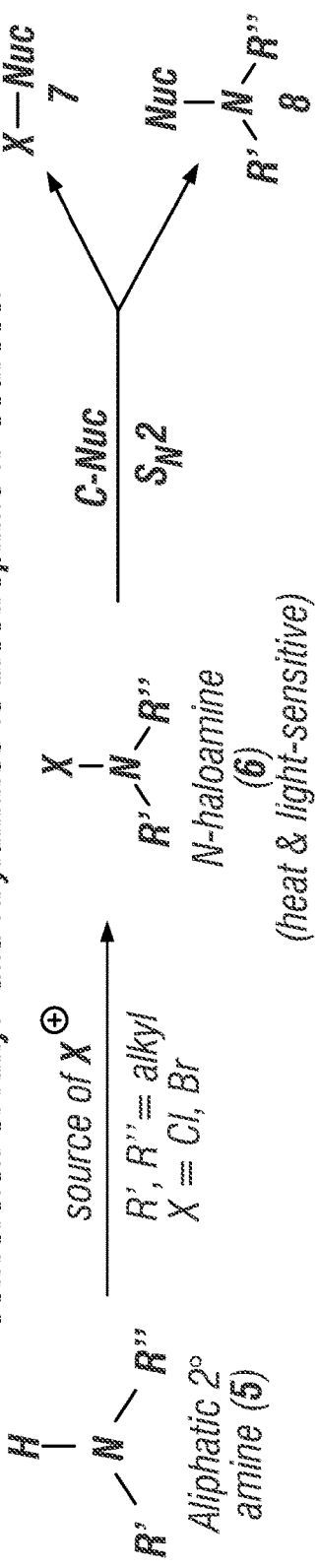
Figure 1C:
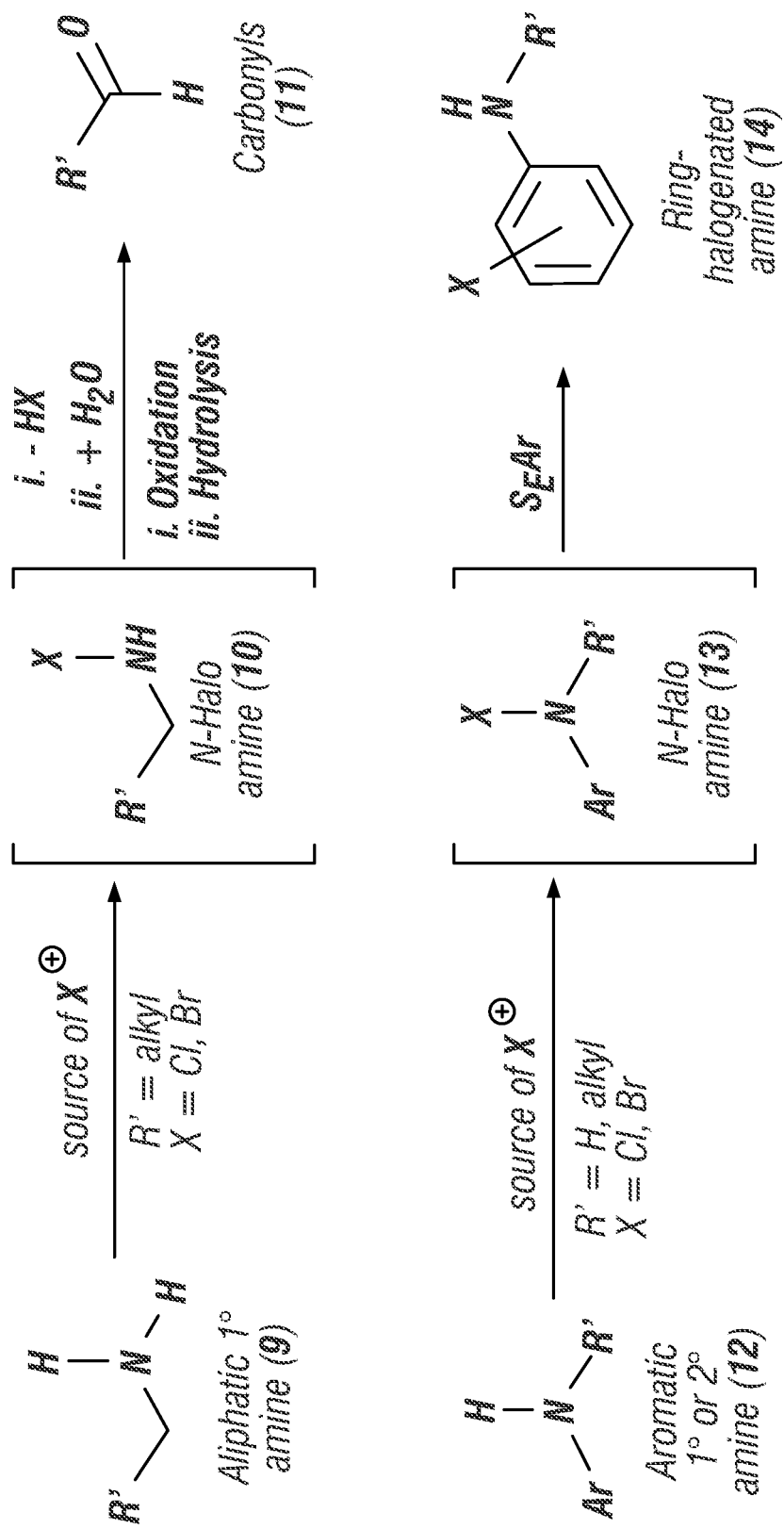
Figure 1D:
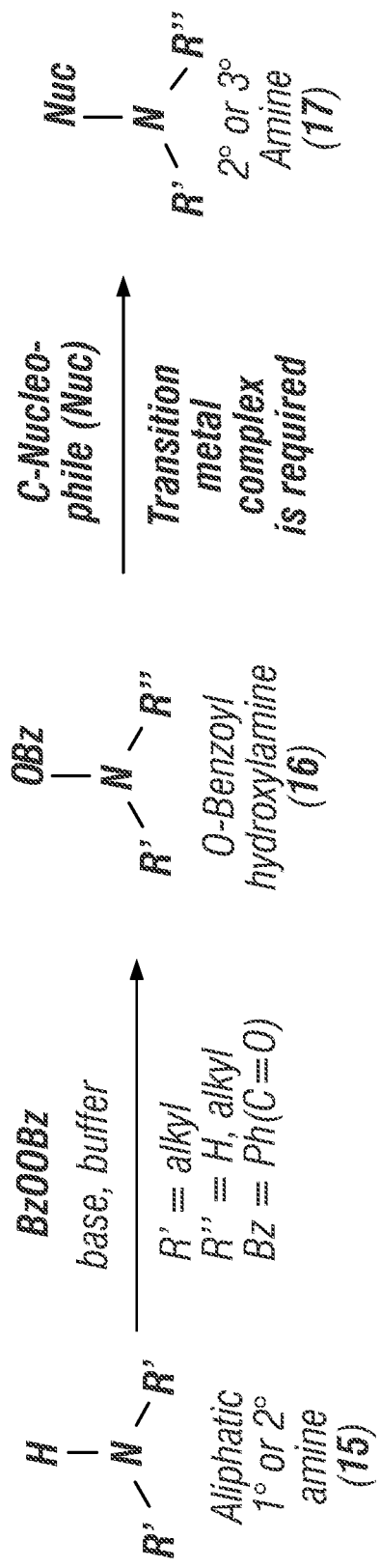
Figure 1E:
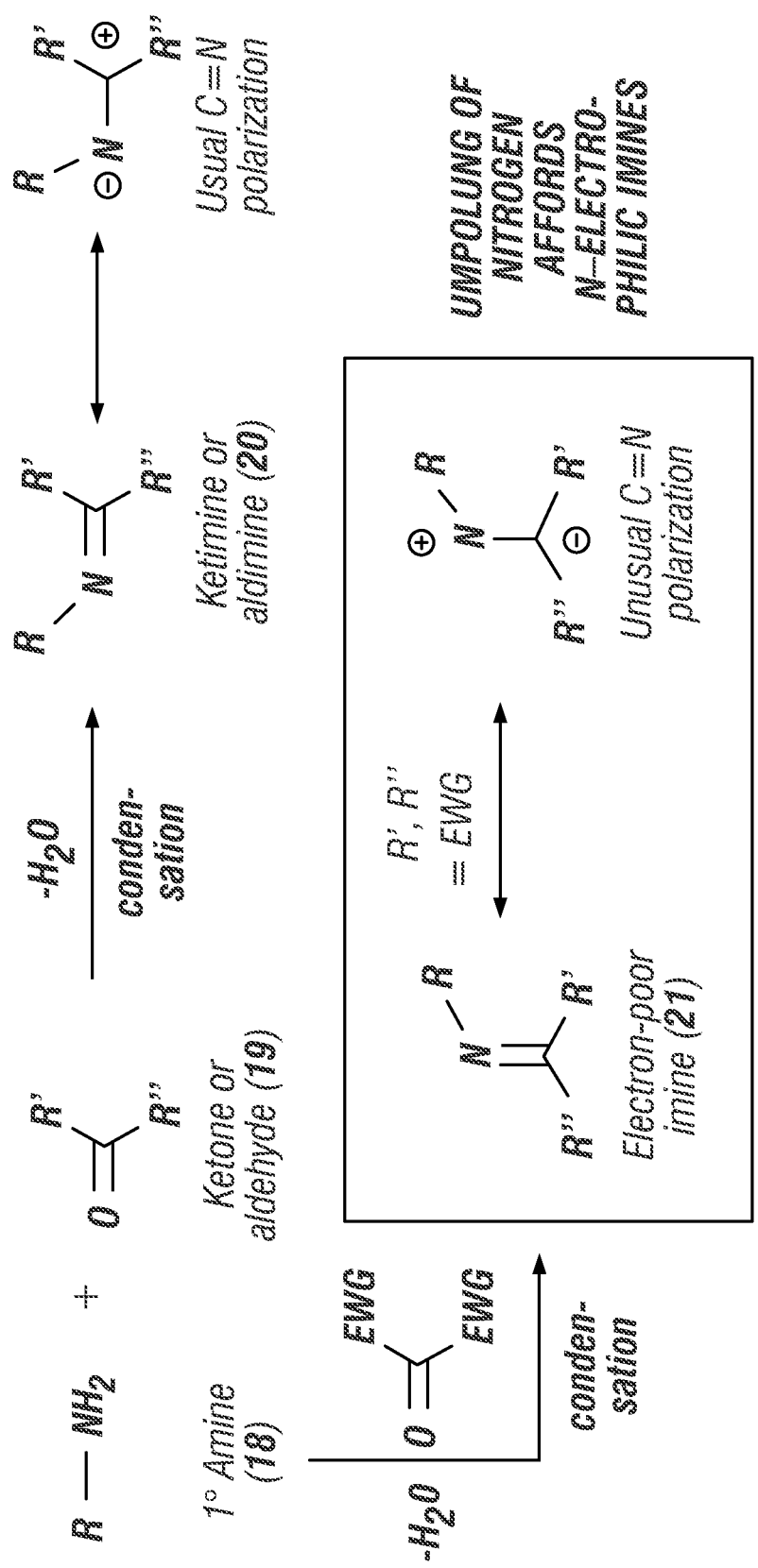
Figure 1F:
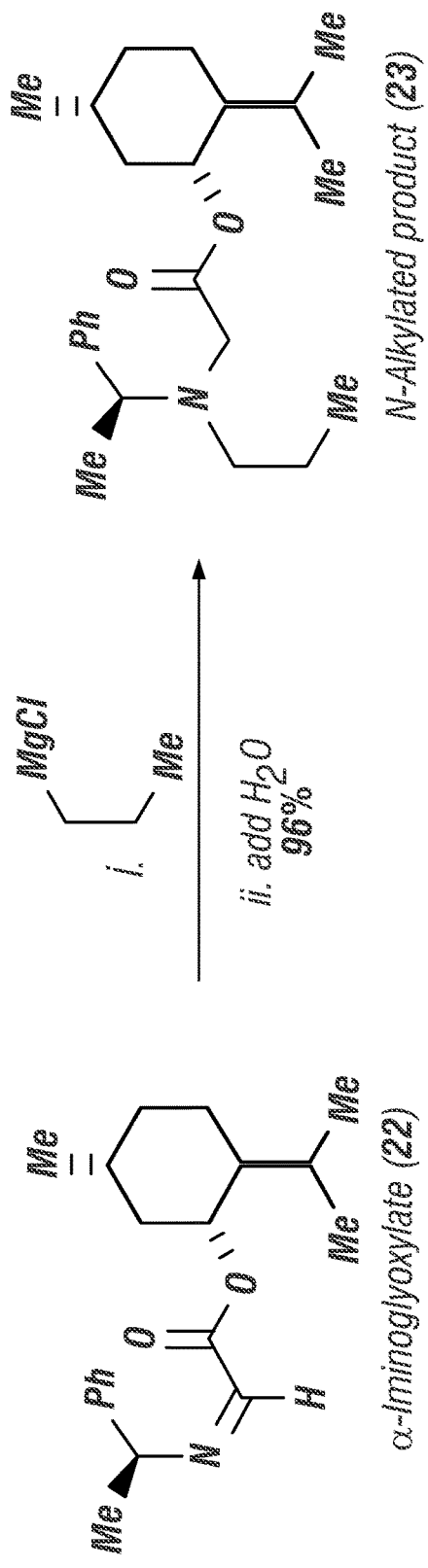
Figure 1G:
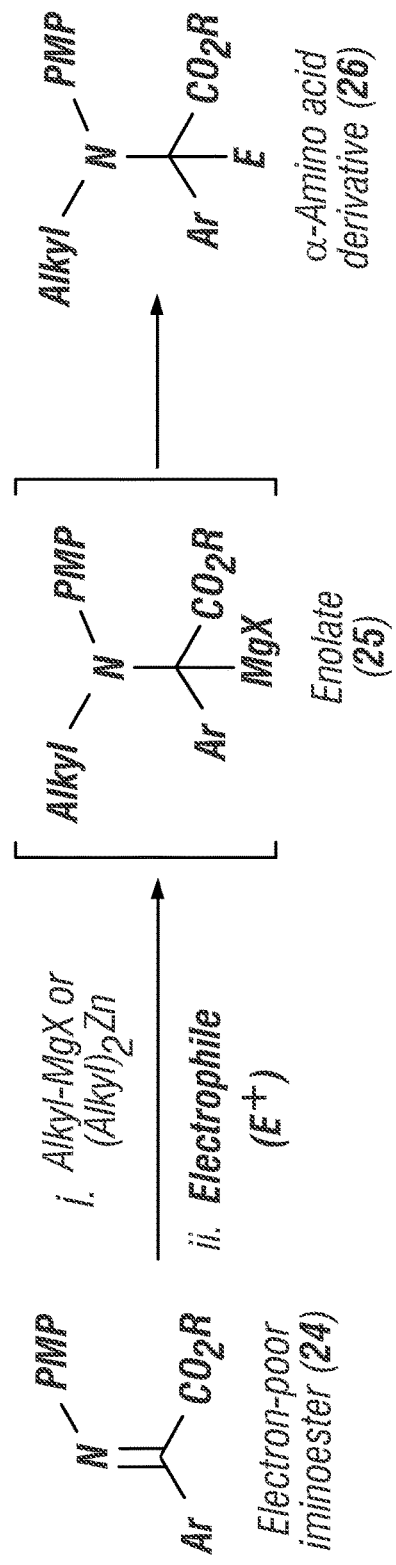
Figure 1H:
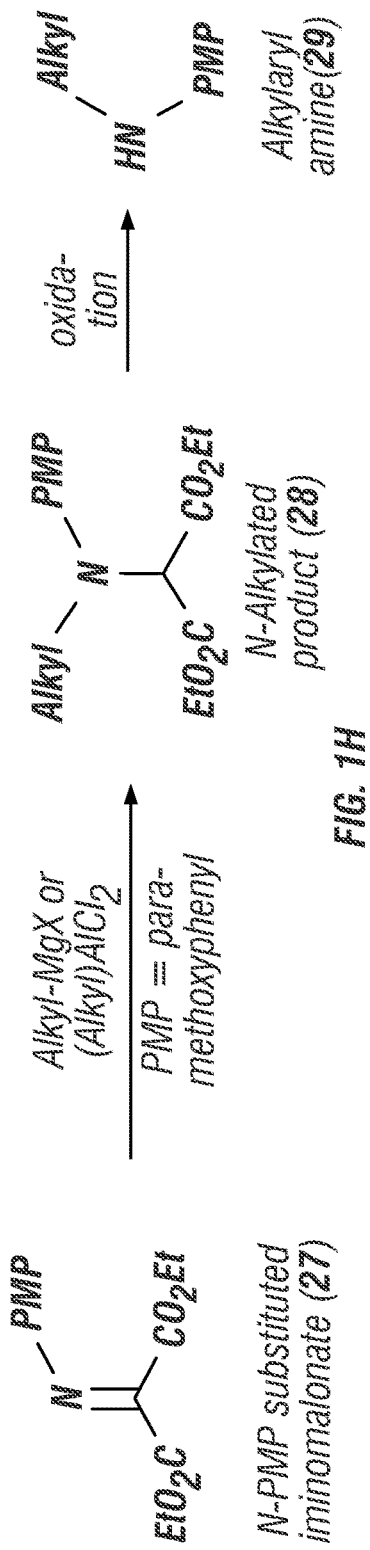
Figure 1I:
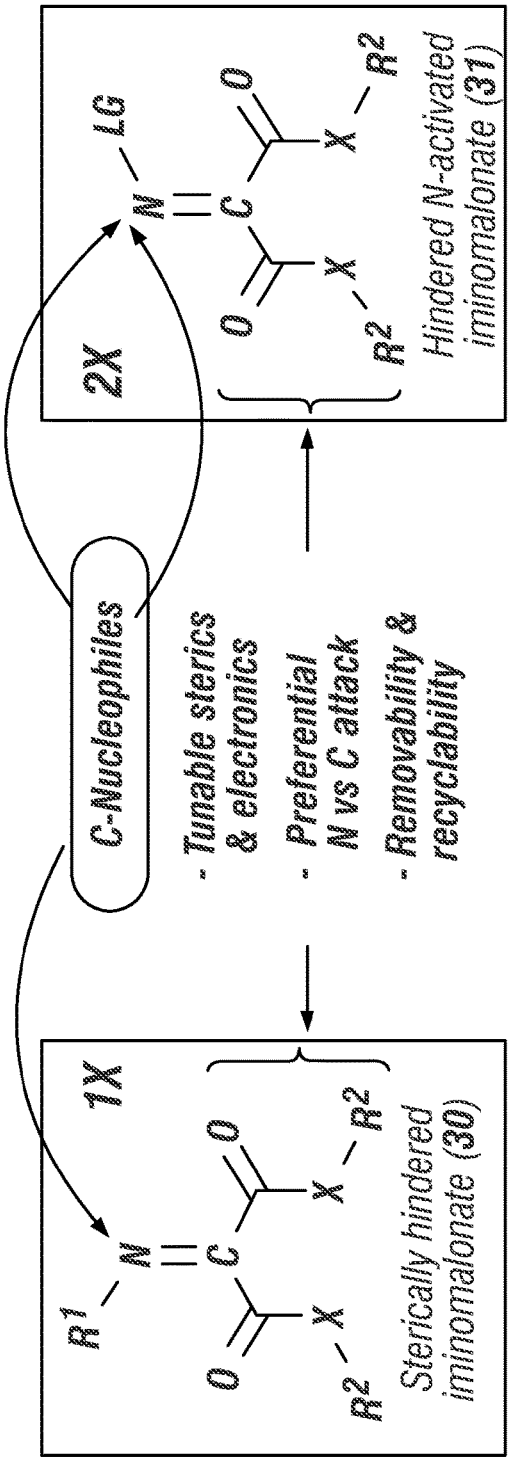

In some aspects, the present disclosure provides methods of preparing secondary amine compounds using one or more doubly reactive compounds. In one embodiments, the method comprises reacting one or more hard carbanions with the linchpin reagents to form a secondary amine. In some embodiments, the secondary amine may comprise two identical groups. In other embodiments, the secondary amine may comprise two unique groups.

Also provided herein are compounds which may be used as reagents to prepare the secondary amines. These reagents are prepared from iminomalonate derivatives and may result in a method which does not require the use of a transition metal or result in a more effective synthetic route.

I. HARD CARBANION

In one aspect, the present methods relating to reacting a hard carbanion with one or more linchpin reagents. In some embodiments, the hard carbanion is a Grignard reagent or an organolithium compound. The hard carbanion may be a Grignard reagent or an organolithium compound which comprises either an aliphatic or aromatic group. Additionally, the Grignard reagent or the organolithium compound is an aliphatic or aromatic group which is optionally substituted with one or more additional groups. These groups include alkyl group, a cycloalkyl group, an alkenyl group, an alkynyl group, aryl, heteroaryl, heterocycloalkyl, or a substituted version of any of these groups wherein the group consists of less than 12 carbon atoms. In some embodiments, the aromatic compound is substituted with another non carbon group such as amino, aminosulfonyl, carboxy, cyano, halo, hydroxy, hydroxyamino, hydroxysulfonyl, mercapto, nitro, oxo, or thio; or acyl$_{(C≤8)}$, alkoxy$_{(C≤8)}$, cycloalkoxy$_{(C≤8)}$, alkenyloxy$_{(C≤8)}$, aryloxy$_{(C≤8)}$, aralkoxy$_{(C≤8)}$, acyloxy$_{(C≤8)}$, cycloalkylalkoxy$_{(C≤8)}$, heterocycloalkylalkoxy$_{(C≤8)}$, heterocycloalkoxy$_{(C≤8)}$, alkylthio$_{(C≤8)}$, cycloalkylthio$_{(C≤8)}$, amido$_{(C≤8)}$, alkylamino$_{(C≤8)}$, dialkylamino$_{(C≤8)}$, alkylsulfonyl$_{(C≤8)}$, arylsulfonyl$_{(C≤8)}$, or a substituted version of these groups, or a protected amine group, a protected hydroxyl group, or a protected thiol group. The hard carbanion may be substituted 1, 2, 3, 4, 5, 6, 7, 8, 9, or 10 times with these groups. In some embodiments, the hard carbanion has from 6 carbon atoms to 100 carbon atoms, from 6 carbon atoms to 50 carbon atoms, from 6 carbon atoms to 30 carbon atoms, or from 6, 7, 8, 9, 10, 11, 12, 13, 14, 15, 16, 17, 18, 19, 20, 21, 22, 23, 24, 25, 26, 27, 28, 29, or 30 carbon atoms, or any range derivable therein. In some embodiments, the metal of the hard carbanion is a metal of Group 1 or Group 2 and may be further substituted with one or more monovalent anions such as a halide. The metal may be a magnesium halide or lithium.

In some aspects, the present methods result in a tertiary amine of the formula:

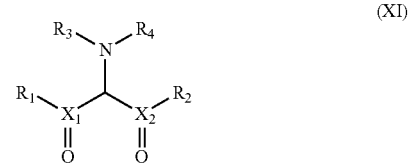

(XI)

wherein:
X$_1$ and X$_2$ are each independently C, S, or S(O);
R$_1$ and R$_2$ are each independently amino, hydroxy, or alkoxy$_{(C≤12)}$, cycloalkoxy$_{(C≤12)}$, alkenyloxy$_{(C≤12)}$, alkynyloxy$_{(C≤12)}$, aryloxy$_{(C≤12)}$, aralkoxy$_{(C≤12)}$, heteroaryloxy$_{(C≤12)}$, heterocycloalkoxy$_{(C≤12)}$, alkylamino$_{(C≤12)}$, dialkylamino$_{(C≤12)}$, cycloalkylamino$_{(C≤12)}$, dicycloalkylamino$_{(C≤12)}$, alkenylamino$_{(C≤12)}$, dialkenylamino$_{(C≤12)}$, alkynylamino$_{(C≤12)}$, dialkynylamino$_{(C≤12)}$, arylamino$_{(C≤12)}$, diarylamino$_{(C≤12)}$, aralkylamino$_{(C≤12)}$, diaralkylamino$_{(C≤12)}$, heteroarylamino$_{(C≤12)}$, diheteroarylamino$_{(C≤12)}$, heterocycloalkylamino$_{(C≤12)}$, diheterocycloalkylamino$_{(C≤12)}$, or a substituted version of any of these groups; and
R$_3$ and R$_4$ are each independently alkyl$_{(C≤18)}$, cycloalkyl$_{(C≤18)}$, alkenyl$_{(C≤18)}$, alkynyl$_{(C≤18)}$, aryl$_{(C≤18)}$, aralkyl$_{(C≤18)}$, heteroaryl$_{(C≤18)}$, heterocycloalkyl$_{(C≤18)}$, or a substituted version of any of these groups;
or a salt thereof.

In some embodiments, the methods further comprise reacting the tertiary compound to obtain a secondary compound in the present of either a mild base and air or a base and an oxidizing agent. In some embodiments, the mild base is a base with a pK$_a$ from about 7 to about 20. For example, some non-limiting examples of mild bases include metal hydroxides and nitrogenous bases. In other embodiments, the methods comprise a base with a pK$_a$ of greater than 20. Some non-limiting examples of such bases include metal hydrides and metal amides. In some embodiments, the base is a non-nucleophilic base. In other aspects, the methods may further comprise adding an oxidizing agent. An oxidizing agent is a compound which gains one or more electrons. Some non-limiting examples of oxidizing agents include halosuccinimides such a bromosuccinimide or chlorosuccinimide.

In some embodiments, the methods described herein include using from about 0.1 to about 10 equivalents of the hard carbanion to the linchpin reagent. The amount of the hard carbanion may be from about 0.5 to about 5 equivalents or from 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.75, 3, 4, to about 5 equivalents of the hard carbanion. In some embodiments, the methods use about 1.1 equivalents of the hard carbanion to the linchpin reagent when each compound is. In other embodiments, the methods use about 2.1 equivalents of the hard carbanion when the resultant amine compound contains two identical groups.

II. LINCHPIN REAGENT

In some aspects, the present methods describe the use of a linchpin reagent of the formula:

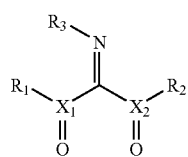

(I)

wherein:

X$_1$ and X$_2$ are each independently C, S, or S(O);

R$_1$ and R$_2$ are each independently amino, hydroxy, or alkoxy$_{(C≤12)}$, cycloalkoxy$_{(C≤12)}$, alkenyloxy$_{(C≤12)}$, alkynyloxy$_{(C≤12)}$, aryloxy$_{(C≤12)}$, aralkoxy$_{(C≤12)}$, heteroaryloxy$_{(C≤12)}$, heterocycloalkoxy$_{(C≤12)}$, alkylamino$_{(C≤12)}$, dialkylamino$_{(C≤12)}$, cycloalkylamino$_{(C≤12)}$, dicycloalkylamino$_{(C≤12)}$, alkenylamino$_{(C≤12)}$, dialkenylamino$_{(C≤12)}$, alkynylamino$_{(C≤12)}$, dialkynylamino$_{(C≤12)}$, arylamino$_{(C≤12)}$, diarylamino$_{(C≤12)}$, aralkylamino$_{(C≤12)}$, diaralkylamino$_{(C≤12)}$, heteroarylamino$_{(C≤12)}$, diheteroarylamino$_{(C≤12)}$, heterocycloalkylamino$_{(C≤12)}$, diheterocycloalkylamino$_{(C≤12)}$, or a substituted version of any of these groups; and R$_3$ is a leaving group or alkyl$_{(C≤18)}$, cycloalkyl$_{(C≤18)}$, alkenyl$_{(C≤18)}$, alkynyl$_{(C≤18)}$, aryl$_{(C≤18)}$, aralkyl$_{(C≤18)}$, heteroaryl$_{(C≤18)}$, heterocycloalkyl$_{(C≤18)}$, or a substituted version of any of these groups;

or a salt thereof.

Additional examples include:

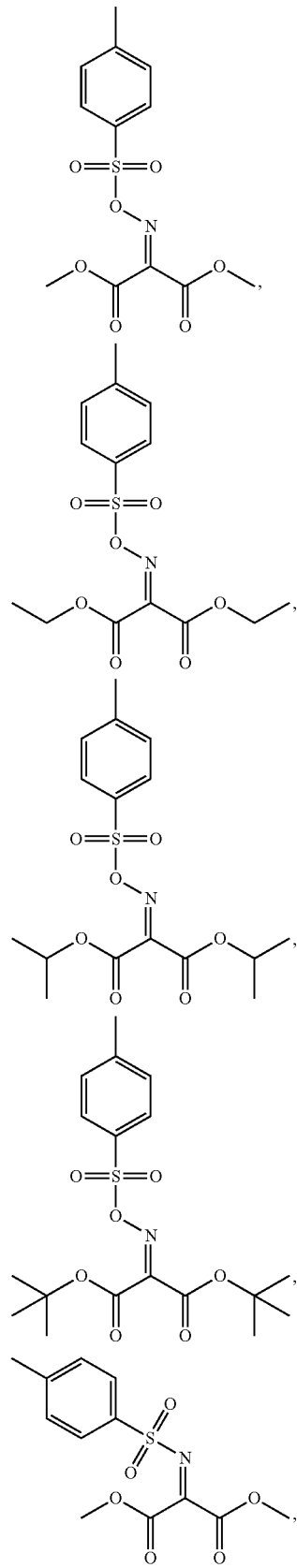

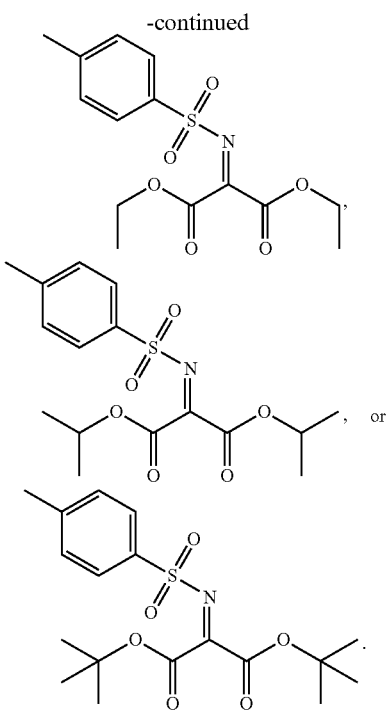

, or

In some embodiments, the linchpin reagent is present as a single compound. In other embodiments, the reagent is present as a crystalline form.

III. REACTION CONDITIONS

In some embodiments, the methods described herein may further comprise adjusting the conditions of a reaction mixture. Some non-limiting examples of such conditions include temperature, the amount of one or more components of the reaction mixture, the organic solvent, or the time period in which the reaction is run. In some embodiments, the temperature of the reaction mixture is a temperature from about −100° C. to about 25° C., from about −85° C. to about 0° C., or from about −80° C. to about −25° C. The temperature of the reaction mixture may be from about −100° C., −95° C., −90° C., −85° C., −80° C., −75° C., −70° C., −65° C., −60° C., −55° C., −50° C., −45° C., −40° C., −35° C., −30° C., −25° C., −20° C., −10° C., −0° C., −10° C., to about 25° C., or any range derivable therein. In some embodiments, the temperature is about −45° C. In other embodiments, the temperature is about −78° C.

In another aspect, the methods described herein may further comprise an organic solvent. Some non-limiting examples of organic solvents which may be used in the present methods include an ether such as diethyl ether or tetrahydrofuran. In other embodiments, the organic solvent is a haloalkane such as chloroform or dichloromethane. In other embodiments, the methods use a non-polar solvent such as diethyl ether, tetrahydrofuran, or dichloromethane. In some embodiments, the methods use a mixture of two or more solvents. In some embodiments, the organic solvent has a dipole moment of greater than 0.5 D.

In other aspect, the methods contemplate a reaction which is run for a time period from about 5 minutes to about 24 hours. In some embodiments, the time period is from 15 minutes to about 18 hours or 30 minutes to about 12 hours. In some embodiments, the time period is from about 10 minutes, 20 minutes, 30 minutes, 40 minutes, 50 minutes, 1 hour, 1.5 hours, 2 hours, 2.5 hours, 3 hours, 3.5 hours, 4 hours, 4.5 hours, 5 hours, 6 hours, 8 hours, 10 hours to about 12 hours, or any range derivable therein. In some embodiments, the time period is about 1 hour. In other embodiments, the time period is about 2 hours.

IV. SYNTHETIC METHODS

In some aspects, the compounds of this disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

A. Process Scale-Up

The synthetic methods described herein can be further modified and optimized for preparative, pilot- or large-scale production, either batch of continuous, using the principles and techniques of process chemistry as applied by a person skilled in the art. Such principles and techniques are taught, for example, in Practical Process Research & Development (2000), which is incorporated by reference herein. The synthetic method described herein may be used to produce preparative scale amounts of the secondary or tertiary amine compounds.

B. Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "hydroxysulfonyl" means —SO$_3$H, "aminosulfonyl" means —S(O)$_2$NH$_2$, "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⚌" represents a single bond or a double bond. Thus, the formula

covers, for example,

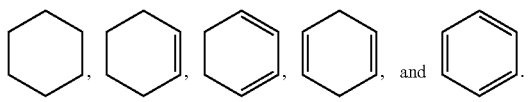

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol " " means a single bond where the group attached to the thick end of the wedge is "out of the page." The symbol " " means a single bond where the group attached to the thick end of the wedge is "into the page". The symbol " " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

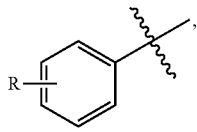

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

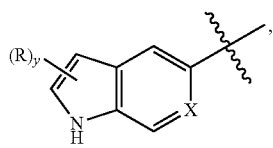

Then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefines" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH₃ (Me), —CH₂CH₃ (Et), —CH₂CH₂CH₃ (n-Pr or propyl), —CH(CH₃)₂ (i-Pr, $^i$Pr or isopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (tert-butyl, t-butyl, t-Bu or $^t$Bu), and —CH₂C(CH₃)₃ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH₂— (methylene), —CH₂CH₂—, —CH₂C(CH₃)₂CH₂—, and —CH₂CH₂CH₂— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH₂, =CH(CH₂CH₃), and =C(CH₃)₂. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The following groups are non-limiting examples of substituted alkyl groups: —CH₂OH, —CH₂Cl, —CF₃, —CH₂CN, —CH₂C(O)OH, —CH₂C(O)OCH₃, —CH₂C(O)NH₂, —CH₂C(O)CH₃, —CH₂OCH₃, —CH₂OC(O)CH₃, —CH₂NH₂, —CH₂N(CH₃)₂, and —CH₂CH₂Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH₂Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH₂F, —CF₃, and —CH₂CF₃ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH₂)₂ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

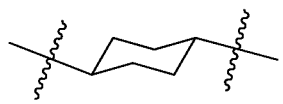 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH₃)CH₂—, —CH=CHCH₂—, and —CH₂CH=CHCH₂— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH₃, and —CH₂C≡CCH₃ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

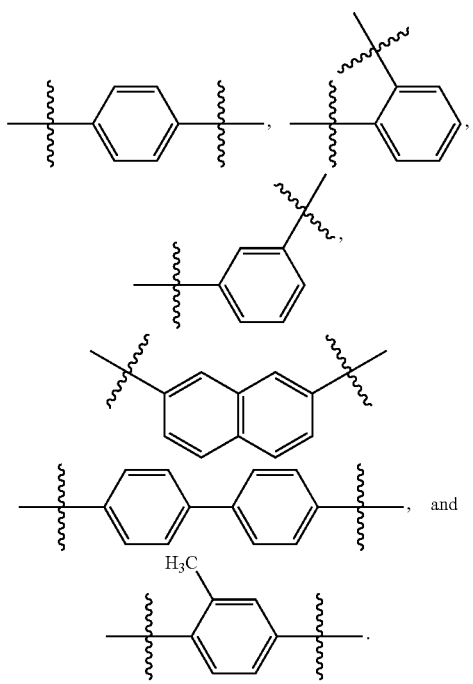

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group-alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C6H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane or cycloalkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —N$_3$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

A "base" in the context of this application is a compound which has a lone pair of electron that can accept a proton. Non-limiting examples of a base can include triethylamine, a metal hydroxide, a metal alkoxide, a metal hydride, or a metal alkane. An alkyllithium or organolithium is a compound of the formula alkyl$_{(C\leq12)}$-Li. A nitrogenous base is an alkylamine, dialkylamino, trialkylamine, nitrogen containing heterocycloalkane or heteroarene wherein the base can accept a proton to form a positively charged species. For example, but not limited to, a nitrogenous base could be 4,4-dimethylpyridine, pyridine, 1,8-diazabicyclo[5.4.0]undec-7-ene, diisopropylethylamine, or triethylamine. A metal alkoxide is an alkoxy group wherein rather than the oxygen atom which was the point of connectivity has an extra electron and thus a negative charge which is charged balanced by the metal ion. For example, a metal alkoxide could be a sodium tert-butoxide or potassium methoxide. A metal carbonate is a carbonate anion with two monovalent cations or a divalent cation. Some non-limiting examples include sodium carbonate, lithium carbonate, potassium carbonate, cesium carbonate, calcium carbonate, or magnesium carbonate.

A "leaving group" in the context of this application is a group which has the ability to be displaced from the molecule through nucleophilic attack. This group may also convert a hydroxyl group into a better leaving group by stabilizing the charge on the oxygen when the atom bears a negative charge thus making the hydroxyl group more susceptible to a nucleophilic attack and displacement. In some embodiments, the leaving group may be a halogen atom such as a tosylate or mesylate.

A "metal" in the context of this application is a transition metal or a metal of groups I or II. In some embodiments, a metal is lithium, sodium, or potassium. In other embodiments, a metal is calcium or magnesium.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth).

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxy carbonyl, 4-methoxybenzyloxycarbonyl, 2-nitro-4,5-dimethoxybenzyloxy carbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxy carbonyl (Boc), diisopropylmethoxycarbonyl, isopropyloxycarbonyl, ethoxy carbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

A "thiol protecting group" is well understood in the art. A thiol protecting group is a group which prevents the reactivity of the mercapto group during a reaction which modifies some other portion of the molecule and can be easily removed to generate the desired mercapto group. Thiol protecting groups can be found at least in Greene and Wuts, 1999, which is incorporated herein by reference. Some non-limiting examples of thiol protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

When the term "about" is used in the context of X-ray diffraction peaks, the term is used to express variation in the peak of ±0.2°2θ.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

An "isomer" of a first compound is a separate compound in which each molecule contains the same constituent atoms as the first compound, but where the configuration of those atoms in three dimensions differs.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

V. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods for the Preparation and Use of Aminating Reagents

A. Preparation of Singly Electrophilic Aminating Reagents

Calculation of the relative reduction potentials (0.3 V difference) and proton affinities indicate that 27 is significantly more electrophilic than the heavily studied α-iminoesters (see FIG. 1, F & G). Without wishing to be bound by any theory, it was reasoned that judicious structural modification of the iminomalonate system could impart higher stability as well as improved preference for N-versus C-attack in its reactions with a wide range of C-nucleophiles (see FIG. 1,1). Specifically, increasing the steric bulk of the ester $R^2$ moiety in ketomalonyl imine 30 from methyl (Me) or ethyl (Et) to iso-propyl (i-Pr) or tert-butyl (t-Bu) may not only result in reduced acid sensitivity but also lead to increased N-attack by C-nucleophiles due to a significantly more hindered imine (C=N) carbon atom. In addition, the presence of a leaving group on the nitrogen atom (e.g., O-2,4-dinitrophenyl, O-alkylsulfonyl, O-arylsulfonyl or part of an oxaziridine ring) renders it more electrophilic. (Zhu et al, 2012; Gao et al, 2016; Paudyal et al, 2016 and Zhou et al, 2017) Thus, combining two different types of N-umpolung approaches (conjugation of the C=N bond with two strongly electron-withdrawing groups paired with a good leaving group on the N atom) in a single reagent may potentially render the nitrogen doubly electrophilic. Given these considerations, O-sulfonylated and sterically hindered ketomalonate oximes (31) were expected to be bench-stable doubly N-electrophilic (i.e., N-linchpin) reagents. Once the single or double C—N bond-formation is complete, removal of the malonyl group under mild oxidative conditions and the concomitant regeneration of the reactivity-modifying umpolung reagent (UR) could be used to furnish both symmetrical and unsymmetrical diaryl-, arylalkyl and dialkylamines; therefore this approach thus provide a more sustainable alternative to current transition metal-catalyzed C—N cross-coupling methods.

In order to fully understand the factors that render diethyl ketomalonate (32) to be an unsuitable reagent for the preparation of iminomalonates, it was condensed with an equimolar amount of aniline (33) under classical Dean-Stark conditions (Scheme 1, A). The crude reaction mixture indicated the presence of both the anticipated imine (34) as well as the corresponding aminal (35). Upon silica gel purification of the crude mixture, aminal 35 was obtained exclusively and with high efficiency (i.e., 50% isolated yield). This result indicated that the imine (34) was prone to undergo both acid-catalyzed hydrolysis as well as aminal formation, presumably because the highly electrophilic imine carbon atom was fully exposed to nucleophilic attack. (Nohira et al, 1963) Since the sterically more hindered di-iso-propyl and di-tert-butyl ketomalonates were not available commercially, the corresponding N-phenyl iminomalonates (39 & 40) were prepared in good yields by condensing malonate esters 37 and 38 with nitrosobenzene (36) under basic conditions (i.e., Ehrlich-Sachs reaction; Scheme 1, B). (Nohira et al, 1963) Iminomalonates 39 and 40 were found to be stable compounds that could be purified by column chromatography without the accompanied formation of aminal derivatives, indicating that the larger alkyl groups (i.e., i-Pr and r-Bu) on the ester moiety provide effective shielding to the imine carbon against nucleophilic attack (i.e., hydrolysis).

Exposing iminomalonate 39 to phenylmagnesium bromide in 2-Me-THF or THF yielded the N-arylated product

(41) in 51% and 65% yield, respectively (Scheme 1, C). An extensive solvent screen revealed that when the iminomalonate was dissolved in non-polar dichloromethane (CH₂Cl₂ or DCM) and the ethereal solution of the aryl-Grignard reagent was added at −78° C., the yield of the N-arylated product 41 was substantially (51% or 65%→78%) increased. It is worth noting that the undesired C-arylated product was formed in 13% yield, however it was readily separated from the N-arylated product. Consistent with these results, transition-state calculations using (PhMgBr)₂ with the methyl ester of 39 indicate competitive N-attack and C-attack where subtle changes in solvent likely have a significant impact on selectivity. Both the selectivity and the efficiency of the N-attack were lower in the case of di-tert-butyl-N-phenyl iminomalonate (40), so the N-arylated product (42) was only obtained in 53% yield (Scheme 1, D). These results prompted a new focus on utilizing the di-isopropylmalonyl group as the key reagent substructure in the studies.

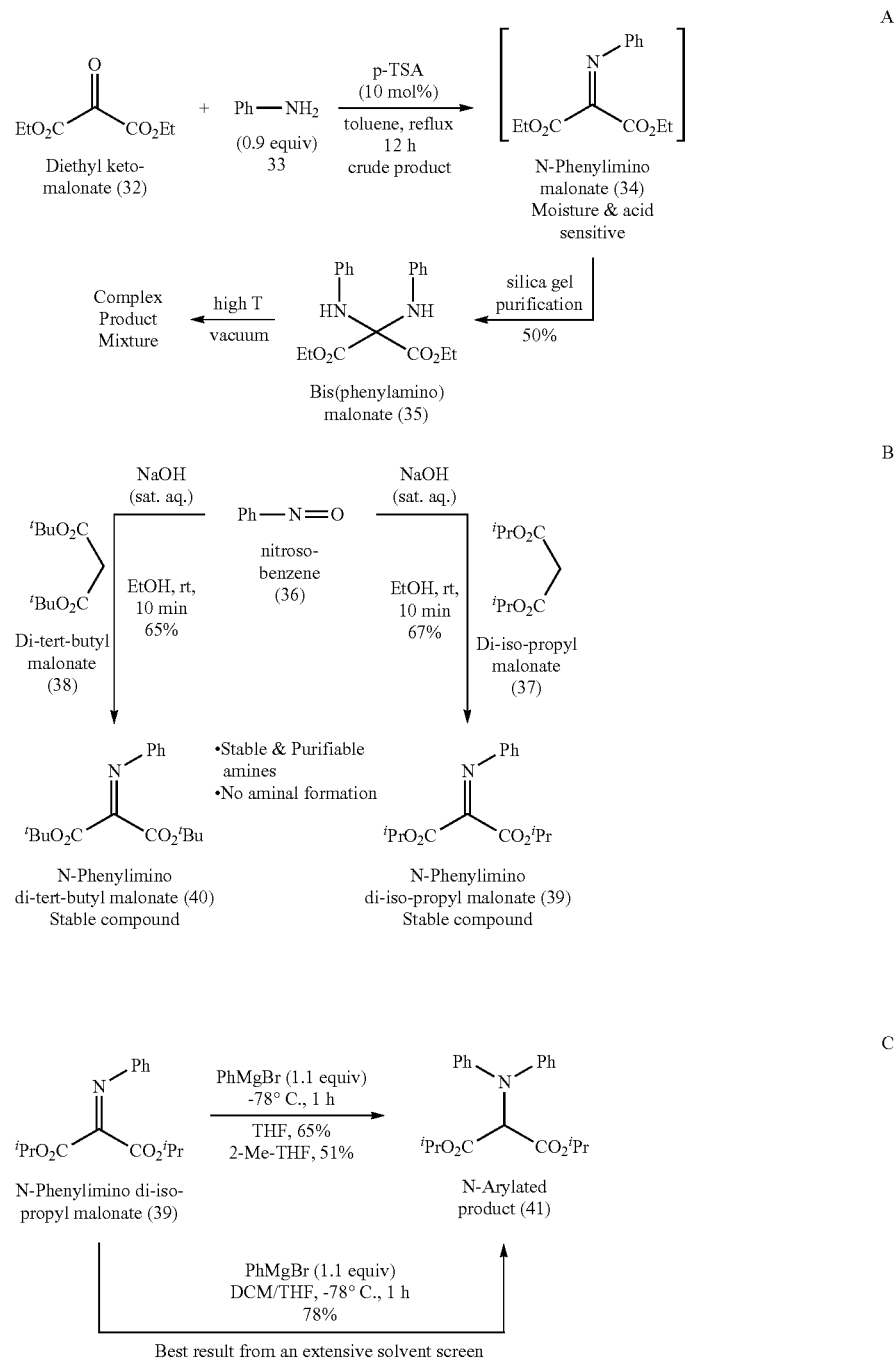

Scheme 1. Synthesis of singly and doubly electrophilic N-substituted iminomalonates and their reactions with C-nucleophiles.

-continued

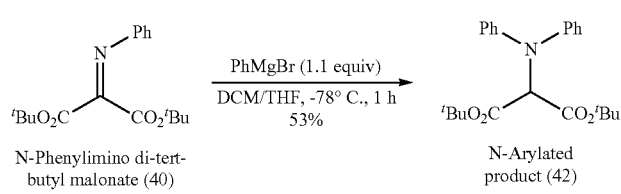

D

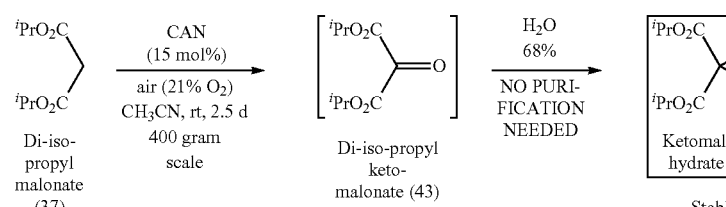

E

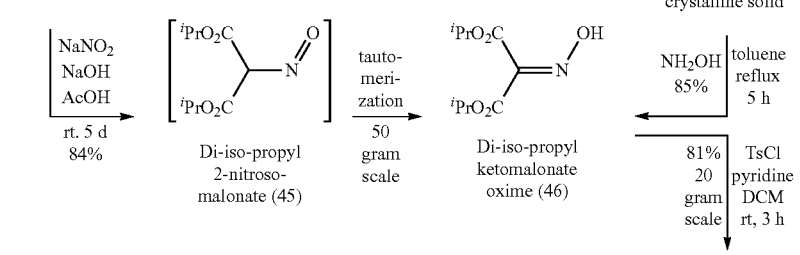

F

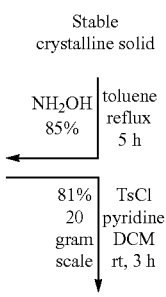

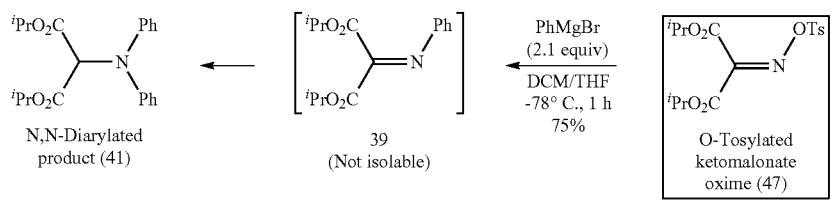

G

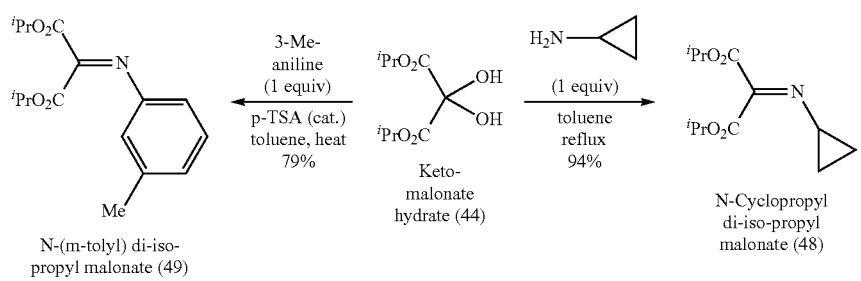

H

A) When reacted with primary amines, non-sterically hindered ketomalonates, such as 32, preferentially afford aminals (35) rather than imines (34) under even slightly acidic conditions. (B) Nitrosobenzene (36) reacts rapidly with sterically hindered dialkyl malonates (37 & 38) under basic conditions to afford stable and purifiable N-phenyl iminomalonates (39 & 40). (C & D) N-Phenyl iminomalonates 39 & 40 both undergo preferential N-attack by phenylmagnesium bromide. After an extensive solvent screen, DCM/THF (3:1 to 5:1) was found to be the best solvent mixture for N-arylation, presumably because the relatively non-polar DCM keeps the Grignard reagents mostly in their dimeric forms (vide infra). The less hindered di-iso-propyl iminomalonate (39) gave better results than the di-tert-butyl derivative (40). (E) Di-i-Pr malonate (37) can be readily oxidized on multi-hundred gram scale to the corresponding ketomalonate hydrate (44) that is a stable crystalline solid. (F) When di-iso-propyl malonate (37) is treated under nitrosylation conditions, the corresponding oxime (46) is obtained. This oxime can also be prepared in good yields by heating hydrate 44 with hydroxylamine. (G)O-Tosylated ketomalonate oxime (47), a stable crystalline solid, serves as a doubly electrophilic A-linchpin reagent when reacted with two equivalents of aryl-Grignard reagent to afford the expected N,N-diarylated product (41). (H) Ketomalonate hydrate 44 undergoes facile condensation with both aliphatic and aromatic amines.

Figure 2B:
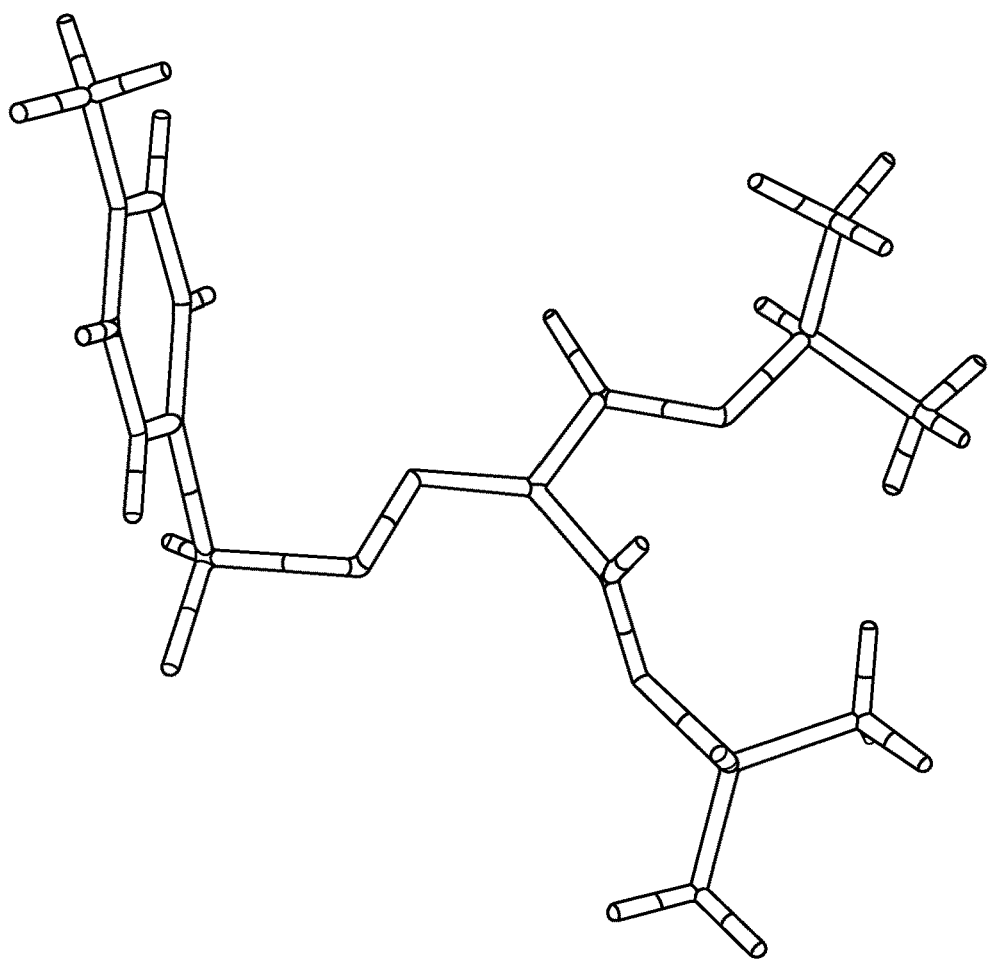
FIG. 2B shows single crystal X-ray structures of 47 (melting range=84-86° C., DSC onset: 181° C.).
Figure 2A:
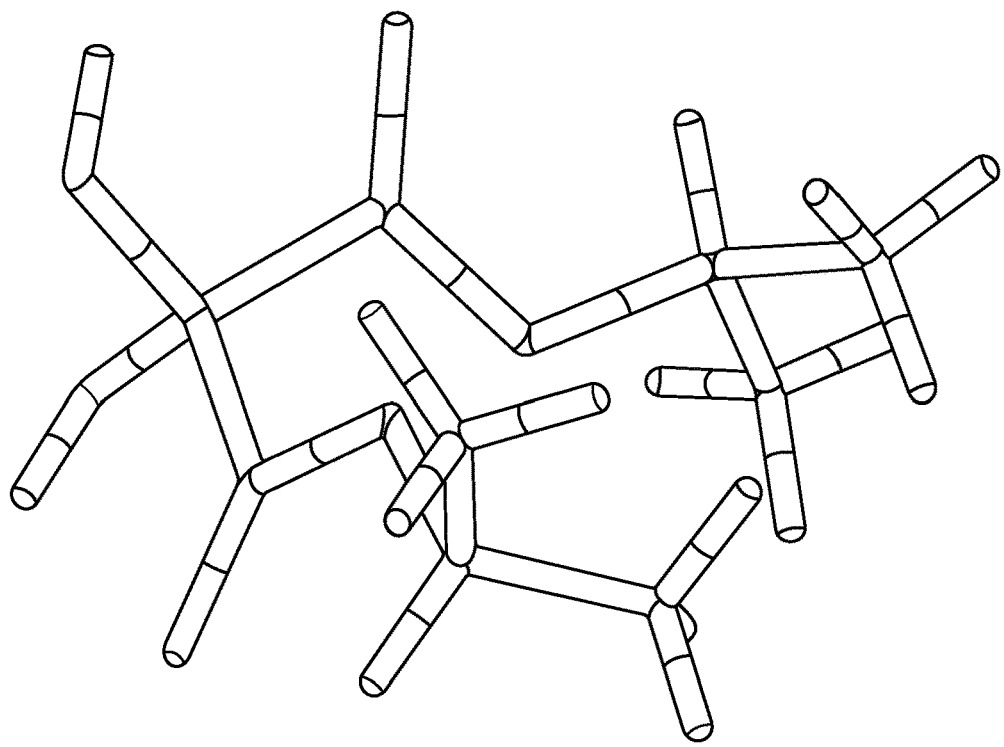
FIG. 2A shows single crystal X-ray structures of 44 (melting range=56-61° C.).

Accordingly, a multi-hundred gram scale synthesis of diisopropyl keto malonate (43) was developed from commercially available di-isopropyl malonate (37). (Sivan & Deepthi, 2014) This route is not only operationally simple but also environmentally friendly and inexpensive, given the use of air as the terminal oxidant (Scheme 1, E). It was quickly established that due to the hygroscopic nature of ketomalonate 43, the corresponding hydrate (44) was much easier to handle as it is a stable crystalline solid and obtained directly in pure form after simple filtration (i.e., no column chromatography is needed). The efficient preparation of di-isopropyl ketomalonate oxime (46) was achieved by either subjecting di-isopropyl malonate (37) to nitrosylation conditions (Peng et al., 2011) or condensing di-isopropyl ketomalonate hydrate (44) with hydroxylamine (Scheme 1, F). Upon treatment with p-toluenesulfonyl chloride (TsCl), oxime 46 was smoothly converted to the O-tosylated derivative (47), which is a bench-stable white crystalline solid. As anticipated, 47 acted as a very efficient doubly electrophilic N-linchpin reagent when exposed to two equivalents of phenylmagnesium bromide (Scheme 1, G). The N,N-diarylated product (41) was formed in 75% yield while the CN-diarylated product was obtained in 13% yield. The presumptive N-phenyl iminomalonate (39) intermediate could not be isolated possibly due to its high reactivity towards the Grignard reagent—when 47 was treated with one equivalent of phenylmagnesium bromide, only product 41 and unreacted 47 were isolated. Structural confirmation for both the ketomalonate hydrate (44) and oxime O-tosylate (47) reagents were obtained using single crystal X-ray crystallography (see FIG. 2a and FIG. 2b). It was found that di-isopropyl ketomalonate hydrate (44) smoothly underwent condensation with both aliphatic and aromatic primary amines and the corresponding N-substituted iminomalonates (48 & 49) were isolated in good to excellent yields (Scheme 1, H).

Figure 3:
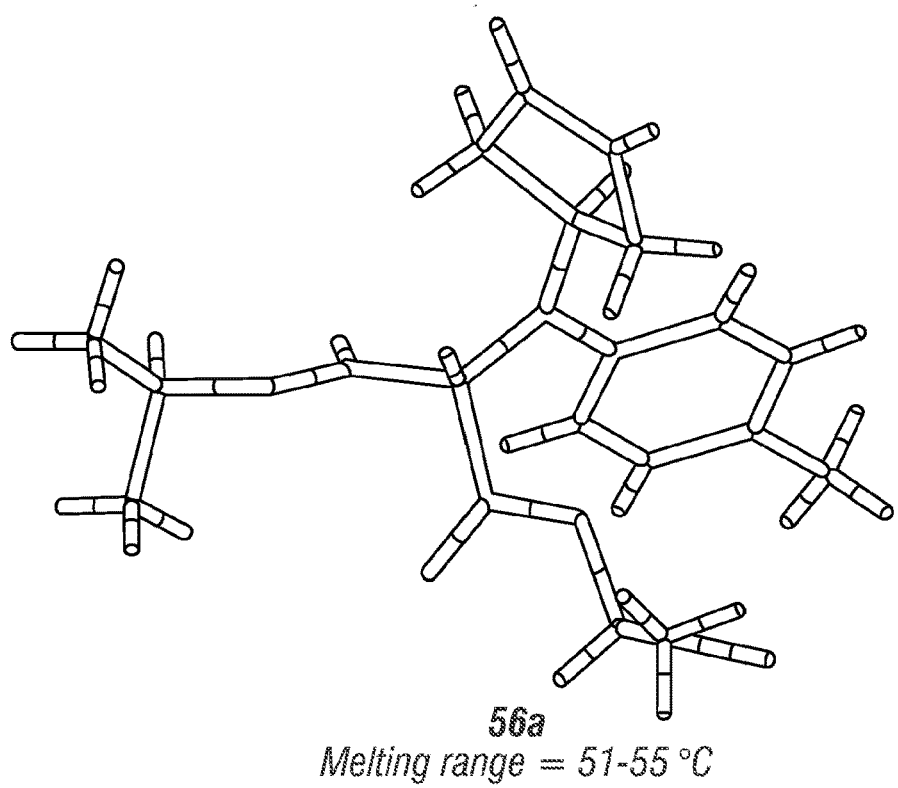

The highly encouraging results presented in Scheme 1 initiated experimentation to investigate the full scope and limitations of the general single and double N-umpolung method (Schemes 2-4). First, ten different acyclic and cyclic primary aliphatic amines (50a-j) were condensed with nitrogen-umpolung reagent 44 (Scheme 2) and the corresponding bench-stable singly A-electrophilic iminomalonates (51) were treated with twenty-one (21) different aromatic and aliphatic Grignard as well as lithium reagents. In each case, electrophilic amination took place rapidly at low temperature to afford aminated products 55a-z & 56a-h. The examples in Scheme 2 & 3 are particularly noteworthy: (a) N-cyclopropyl iminomalonate (51d) allowed the rapid preparation of not only N,N-dicyclopropyl- and N-cyclobutyl-N-cyclopropyl amines (55f & 55g) but also N-arylated derivatives (55h & 55i); (b) A-butyl iminomalonate (51e, entries 11-21) underwent smooth A-arylation by a set of eleven structurally and electronically diverse aryl Grignard reagents to give uniformly high yields of the corresponding arylalkyl amine derivatives (55k-u); (c) N-cyclopentyl (51g) and N-cyclohexyl (51h) as well as N-(4-piperidinyl) (51i) iminomalonates furnished six N-(hetero)arylated products (55z & 56a-e, Scheme 2 & Scheme 3 and FIG. 3) in moderate to good isolated yields; (d) di-iminomalonate 51j (entries 32-34) derived from an aliphatic α,ω-diamine (50j) was efficiently di-N-arylated with two equivalents of an aryl Grignard reagent to afford the corresponding symmetrical diamines (56f & 56g, Scheme 3), however, only a modest yield of the unsymmetrical diamine (56h, entry 34) was obtained when two different aryl Grignard reagents were added sequentially.

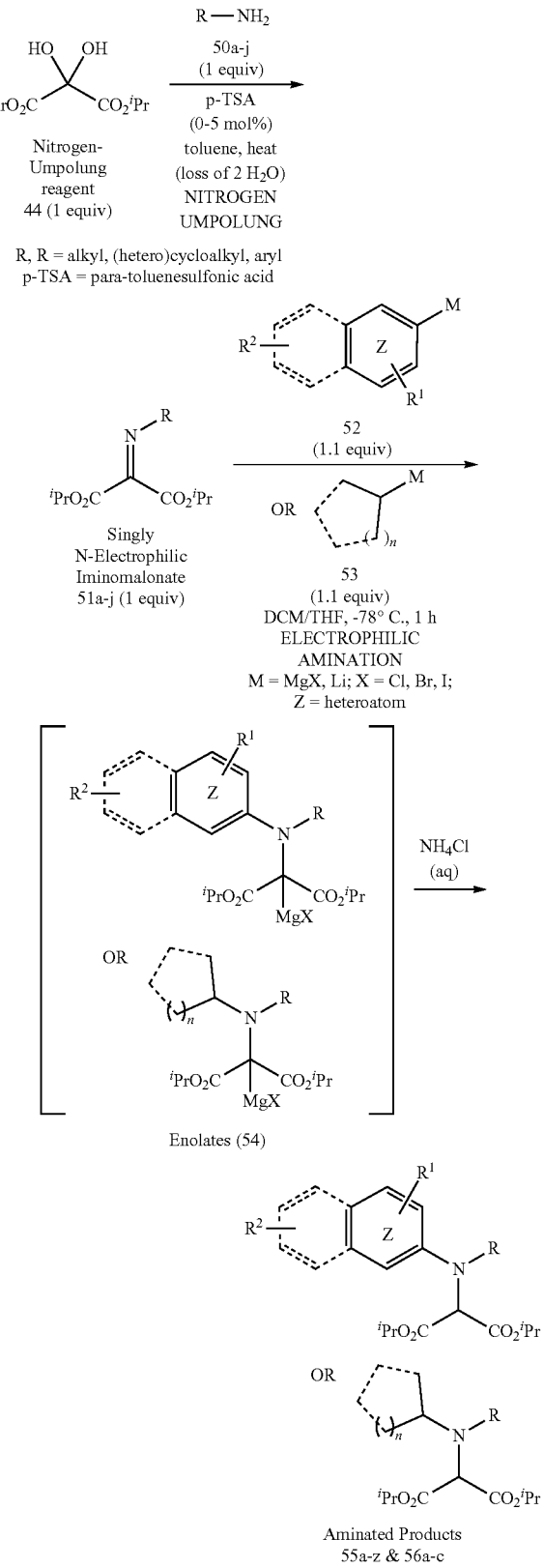

Scheme 2. Scope of substrates using singly N-electrophilic iminomalonates as aminating agents.

Structure of Symmetrical/Unsymmetrical Dialkyl- and Arylalkylamine Products
(Entry): Compound #; M (Metal), Isolated Yield (%), Scale (Mmol)
Intermolecular Amination of (Cyclo)Alkyl- and (Hetero)Arylmetals with Singly N-Electrophilic Iminomalonates
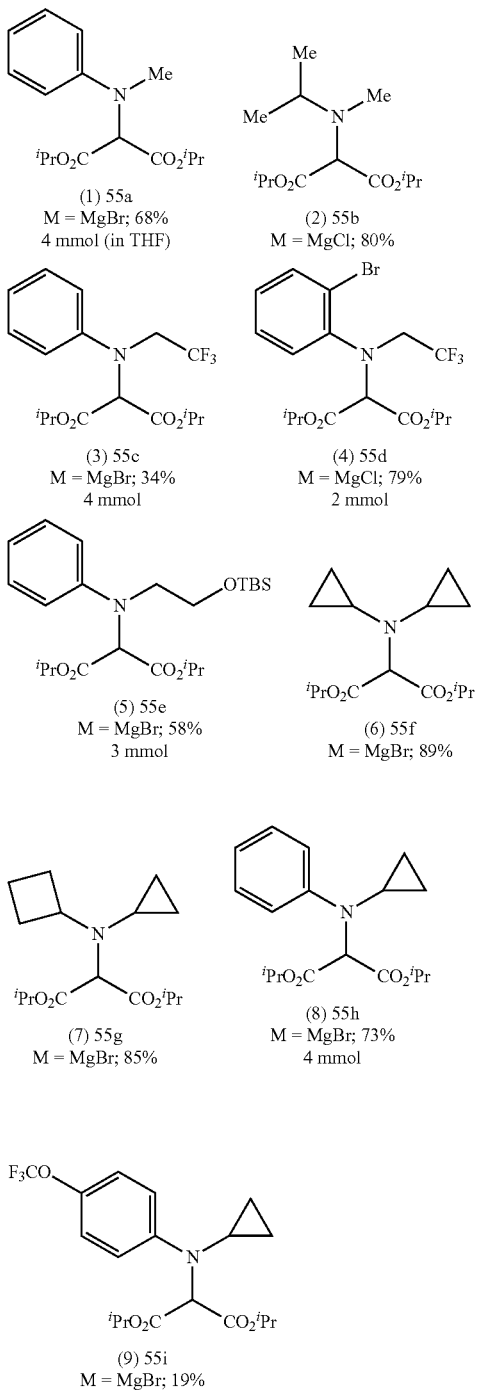
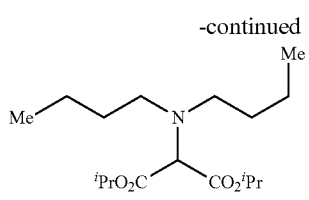
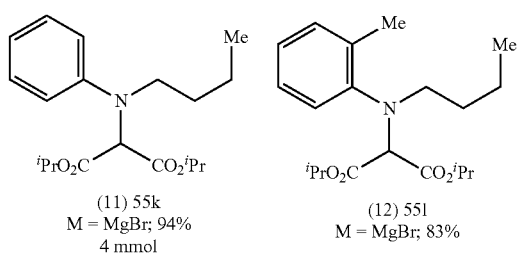
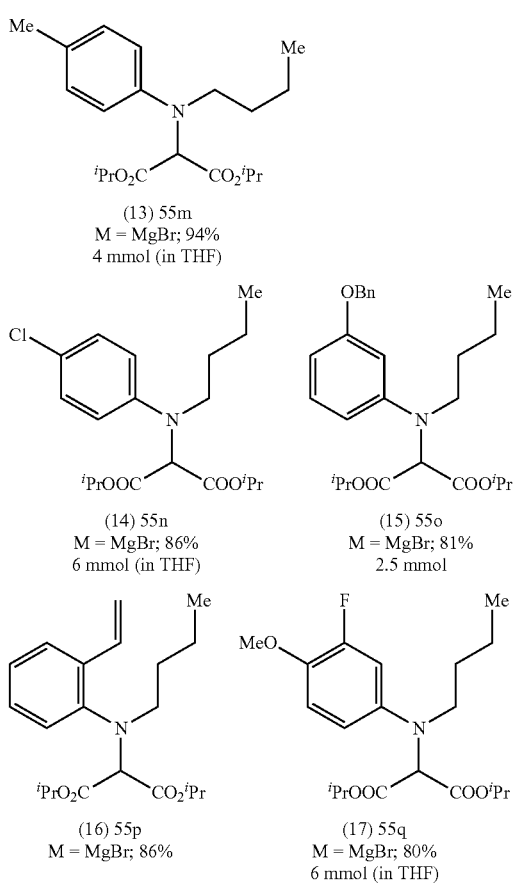
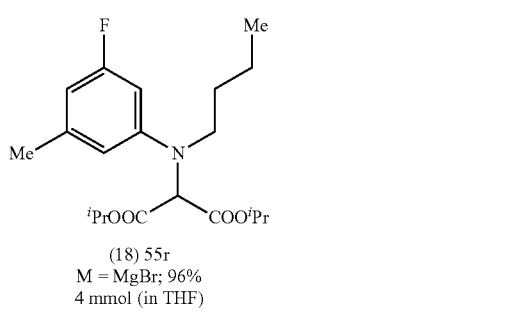

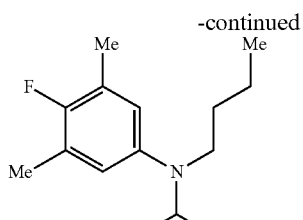

(19) 55s
M = MgBr; 91%
4 mmol (in THF)

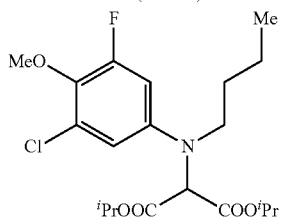

(20) 55t
M = MgBr; 54%
2 mmol (in THF)

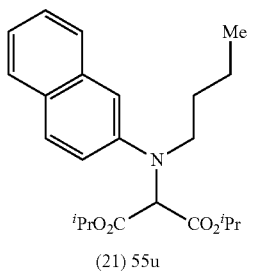

(21) 55u
M = MgBr; 95%
4 mmol (in THF)

(22) 55v
M = Li, THF only
39%

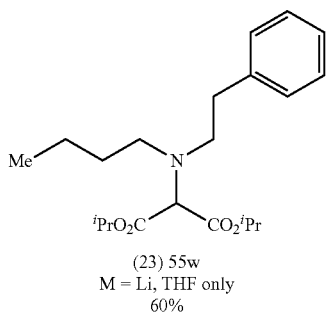

(23) 55w
M = Li, THF only
60%

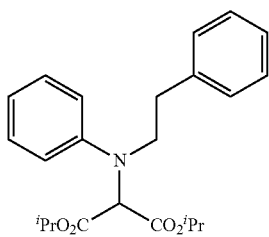

(24) 55x
M = Li, THF only; 25%
M = MgBr; 54%

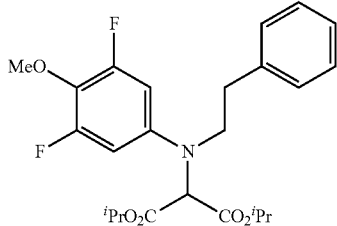

(25) 55y
M = MgBr; 43%

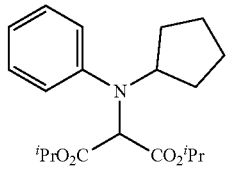

(26) 55z
M = MgBr; 82%
2 mmol

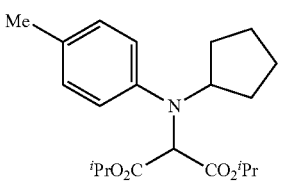

(27) 56a
M = MgBr; 66%

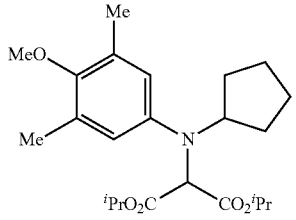

(28) 56b
M = MgBr; 70%
2 mmol

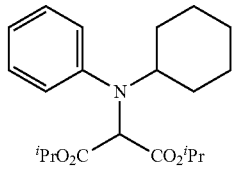

(29) 56c
M = MgBr; 83%
2 mmol

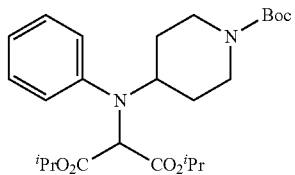

(30) 56d
M = MgBr; 48%
2 mmol

All aromatic (52) and aliphatic (53) Grignard reagents have been prepared from the corresponding aryl halides using turnings of freshly activated Mg metal and THF as solvent. All lithium reagents (MeLi, n-BuLi and PhLi) were purchased. The concentration of the arylmetal solution was targeted to be around 0.8-1.0 M but was carefully determined by titration immediately before use. The amination reactions were conducted on a 1 mmol scale in DCM/THF (unless indicated otherwise) at the indicated temperature and considered complete upon the full consumption of the individual animating agents (51) by TLC analysis.

Scheme 3. Scope of substrates using singly N-electrophilic iminomalonates (51) as aminating agents.
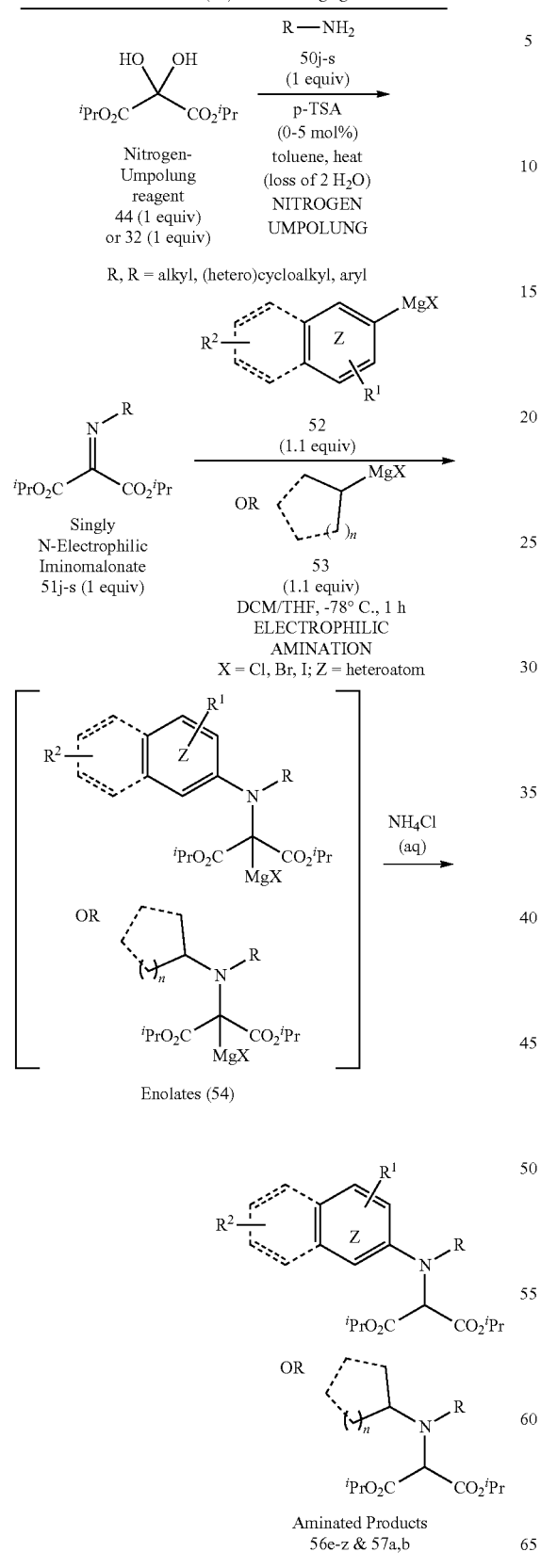
Structure of Unsymmetrical Arylalkyl- and Diarylamine Products
(Entry): Compound #; Isolated Yield (%)
Intermolecular Amination of (Cyclo)Alkyl- and (Hetero)Arylmetals with Iminomalonates (Continued from FIG. 3)
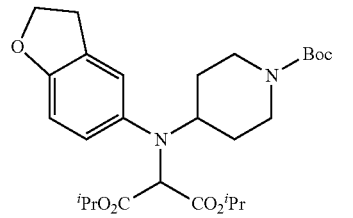
(31) 56e
M = MgBr; 32%
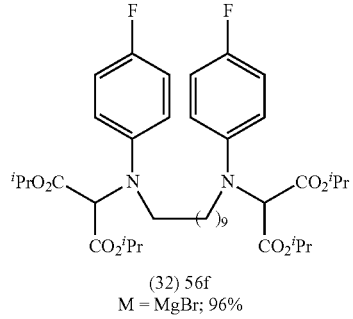
(32) 56f
M = MgBr; 96%
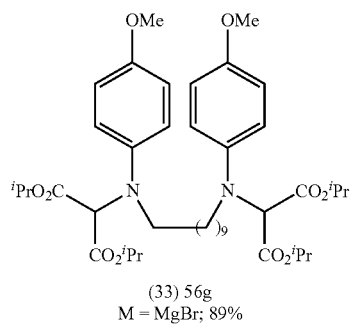
(33) 56g
M = MgBr; 89%
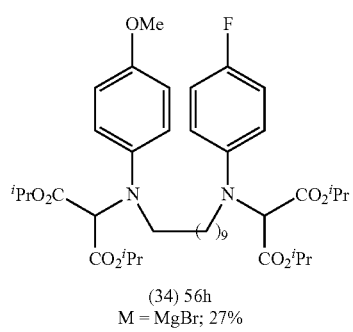
(34) 56h
M = MgBr; 27%

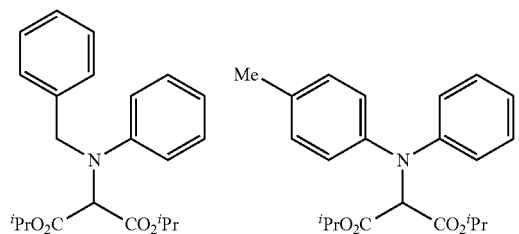
(35) 56i
M = MgBr; 49%
(36) 56j
M = MgBr; 59%
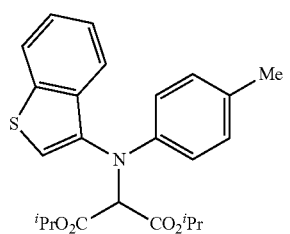
(42) 56p
M = MgCl; 46%
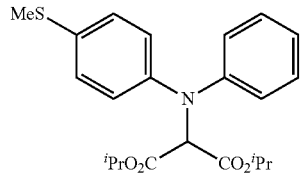
(37) 56k
M = MgBr; 52%
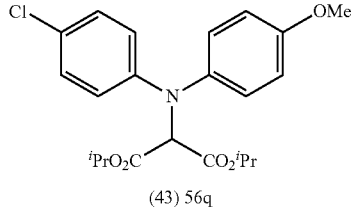
(43) 56q
M = MgBr; 36%
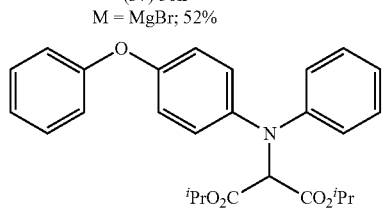
(38) 56l
M = MgBr; 43%
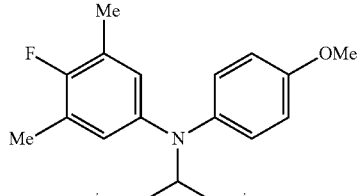
(44) 56r
M = MgBr; 49%
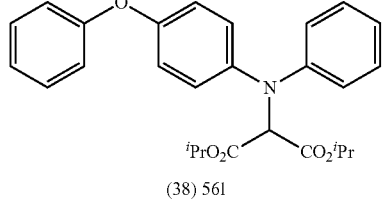
(39) 56m
M = MgBr; 60%
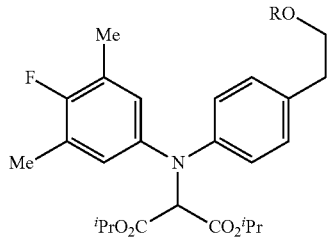
(45) 56s, R = Si(Me)₂t-Bu
M = MgBr; 57%
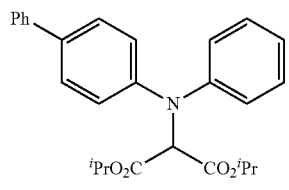
(40) 56n
M = MgBr; 55%
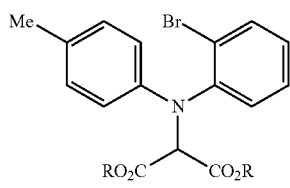
(46) 56t
M = MgBr; R = ⁱPr; 18%
M = MgBr; R = Et; 56%
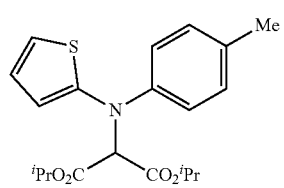
(41) 56o
M = MgBr; 61%
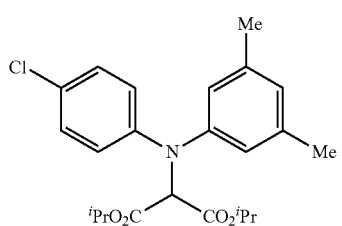
(47) 56u
M = MgBr; 33%

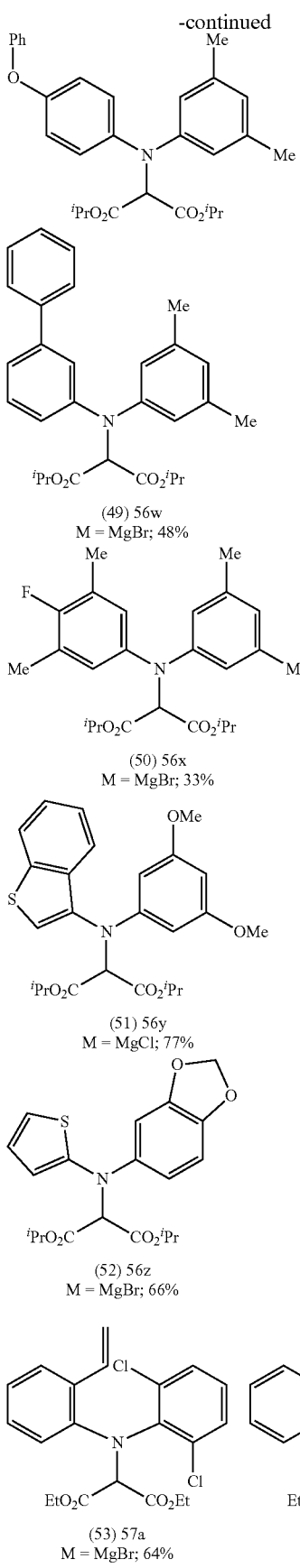

All aromatic (52) and aliphatic (53) Grignard reagents have been prepared from the corresponding aryl halides using turnings of freshly activated Mg metal and THF as the solvent. The concentration of the arylmetal solution was targeted to be around 0.8-1.0 M but was carefully determined by titration immediately before use. The amination reactions were conducted on a 1 mmol scale at the indicated temperature and considered complete upon the full consumption of the individual animating agents (51) by TLC analysis.

Additional optimization may be carried out to increase the yield for some aryl metals; (e) nine (9) different N-aryl-iminomalonates (51k-s, Scheme 3), derived from aromatic amines (50k-s), were exposed to thirteen (13) different aryl Grignard reagents to produce nineteen (19) unsymmetrical N,N-diarylamine products (56j-z & 57a & 57b) in moderate to good isolated yields; (f) sterically hindered (i.e., mostly or/ho-substituted) arylamines not only gave significantly higher yields of the corresponding iminomalonates when condensed with a sterically less hindered ketomalonate (32), but were also more efficiently N-arylated with sterically hindered aryl Grignard reagents (56t, 57a & 57b). The last three examples showcase the fact that the structure of the reactivity-modifying umpolung reagent can be adjusted to match the structural variations in both the primary amine substrates and aryl Grignard reagents, in order to obtain synthetically useful yields of the desired diarylamine products.

B. Preparation of Doubly Electrophilic Aminating Reagents

Next, the scope and limitations of doubly N-electrophilic iminomalonates (47a-c, Scheme 4) as nitrogen linchpin agents were explored. Fifteen (15) different arylmetals (52), representing diverse steric and electronic properties, were coupled to furnish symmetrical diarylamines (59a-o) in moderate to good yields. Sterically hindered arylmetals (entries 62-65 & 69; Scheme 4) were coupled with much greater efficiency when the ester groups on the nitrogen linchpin reagents were sterically less encumbered (47b & c, R=Me or Et). For all other arylmetal substrates, the more sterically hindered di-isopropyl linchpin reagent (47a) proved to be ideal. A thorough study of the literature revealed that the preparation of symmetrical diarylamines is far from being a trivial task as it often requires two different functionalities (e.g., arylboronic acid and arylamine or aryl halide and arylamine) to be cross-coupled in the presence of transition metal catalysts. Therefore, utilization of a doubly electrophilic nitrogen linchpin reagent in combination of two equivalents of a particular arylmetal reagent at low temperature qualifies this approach, as both a fast and mild method for the preparation of this class of aromatic compounds.

Figure 4:
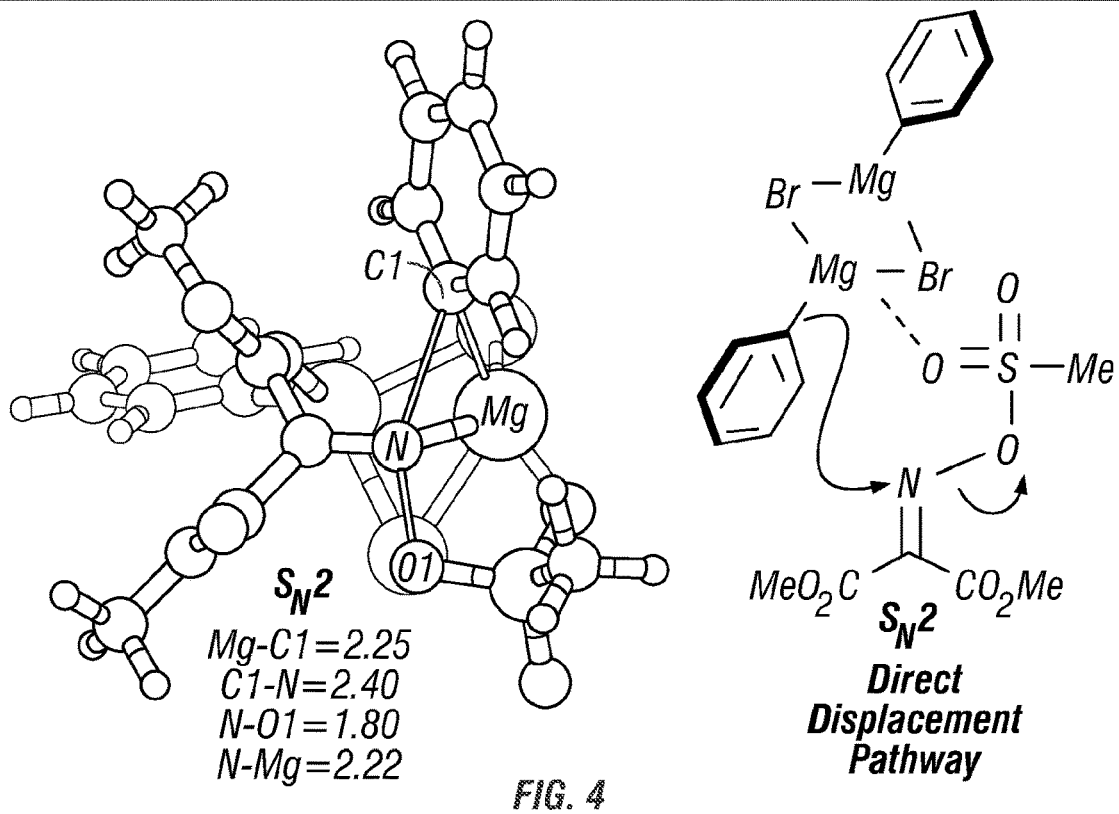
FIG. 4 shows structures of three possible transition states.
Figure 4:
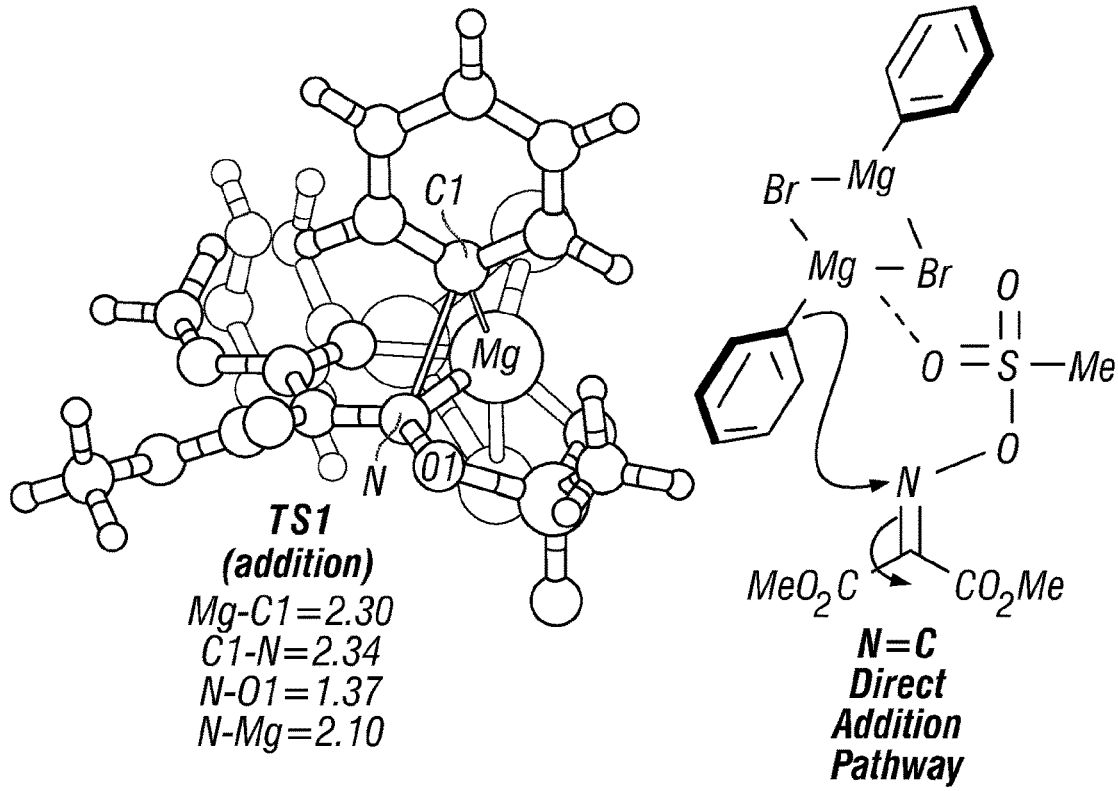
Figure 4:
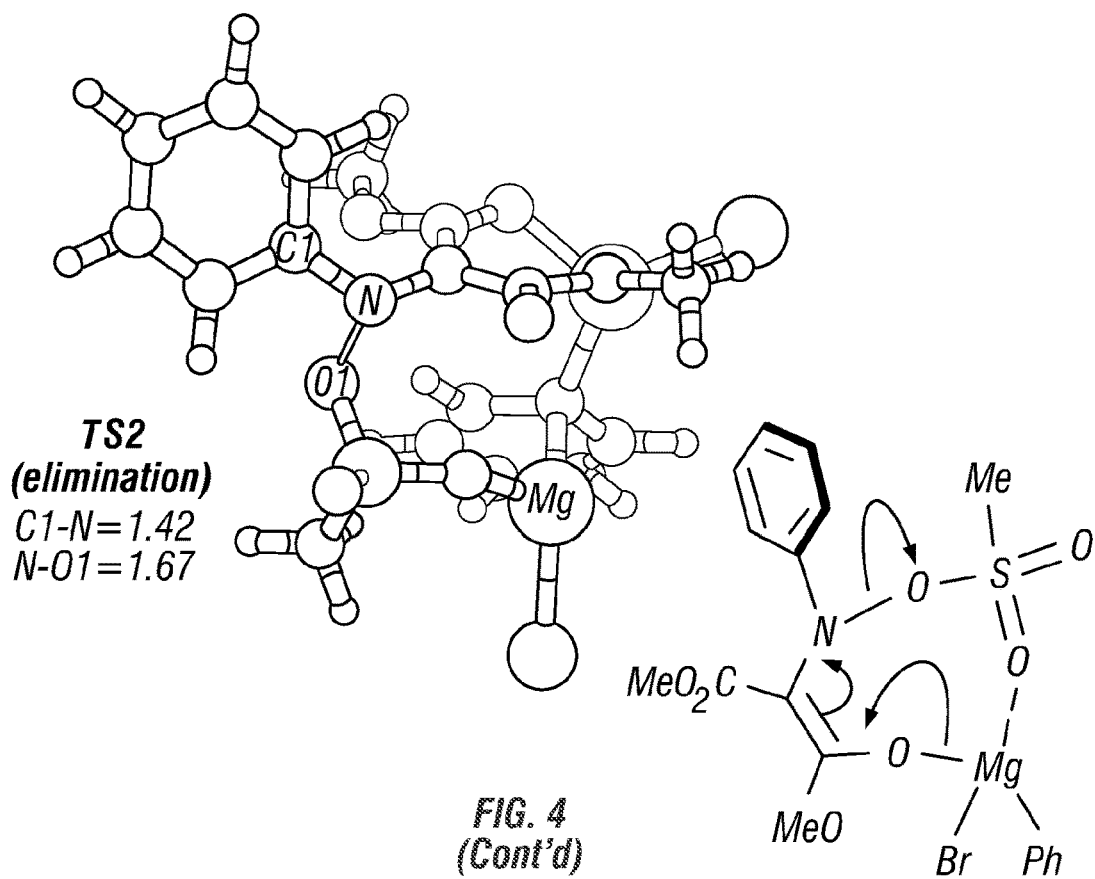

Density-functional calculations (M06-2X/def2-TZVP) provide mechanistic and reactivity insights into the success of the diarylation of 47 with PhMgBr. Previous computational studies suggest that a single-step concerted N-substitution can occur at $sp^2$-hybridized nitrogen atoms with leaving groups (0-methanesulfonyl and G-p-toluenesulfonyl). (Kitamura et al, 2004 and Narasaka & Kitamura, 2005) However, the one-step $S_N2$-type transition state between $(PhMgBr)_2$ and the methyl ester linchpin reagent 47b has a $\Delta G^\ddagger > 30$ kcal/mol. This is a much larger barrier than the alternative stepwise mechanism that involves an addition-elimination sequence via TS1 and TS2 as shown in FIG. 4. TS1 that has coordination between the $(PhMgBr)_2$ and the OMs group requires $\Delta G^\ddagger = 10.4$ kcal/mol and generates a highly stabilized intermediate ($\Delta G = -52.4$ kcal/mol) due to the presence of the two ester functional groups. Ejection of the mesylate anion (MsO⁻) from this intermediate via TS2 requires ΔG‡=15.0 kcal/mol (relative to the intermediate) and results in the formation of N-phenyl iminomalonate. Calculations indicate that the transition state for aryl Grignard addition to the ester is disfavored with a ΔG‡>20 kcal/mol barrier. This computational model also shows that the transition state for N-attack is slightly lower in energy than for C-attack. The ΔG‡ for phenyl addition to the N-phenyl iminomalonate requires ΔG‡=19.4 kcal/mol and is slightly larger than the barrier for Grignard addition to 47 with the more electron-deficient nitrogen. While the second aryl Grignard addition is slower, the N,N-diarylated product is observed because the Grignard reagent likely reacts as a multinuclear species, such as (PhMgBr)$_2$, and does not separate from the N-phenyl iminomalonate intermediate (Scheme 4).

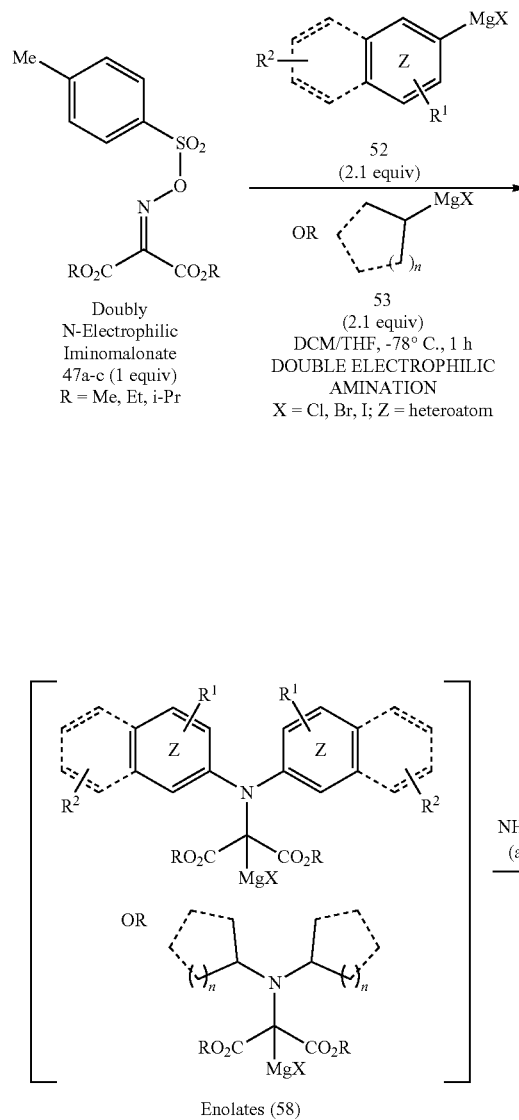

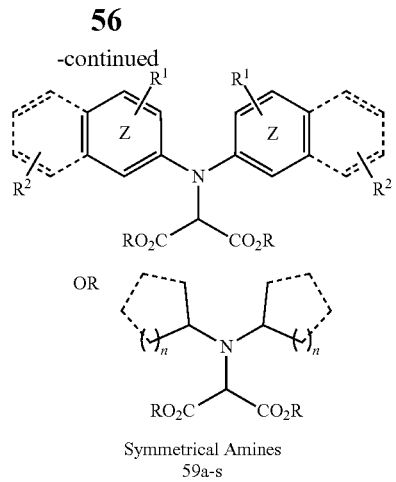

Symmetrical Amines
59a-s

Structure of Symmetrical Diaryl- and Dialkylamine Products (Entry): Compound #; Isolated Yield (%)

Intermolecular Double (Linchpin) Amination of Aryl- and (Cyclo)alkylmetals with O-Sulfonyl Oximes

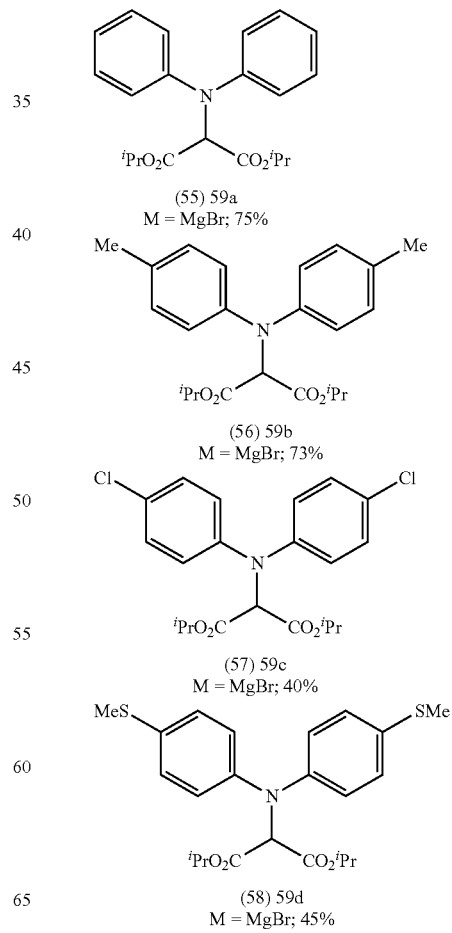

-continued
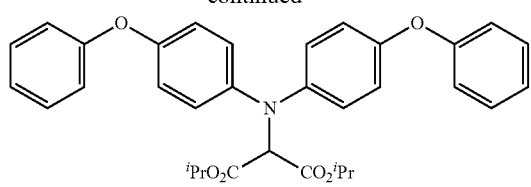
(59) 59e
M = MgBr; 41%
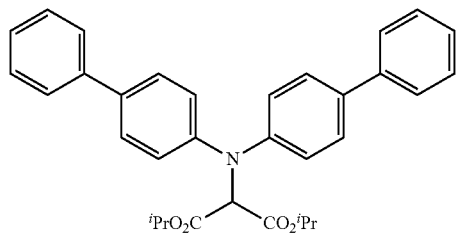
(60) 59f
M = MgBr; 60%
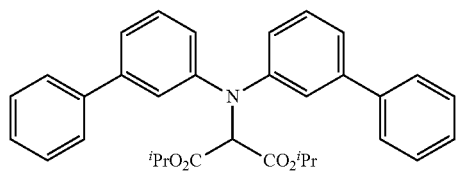
(61) 59g
M = MgBr; 65%
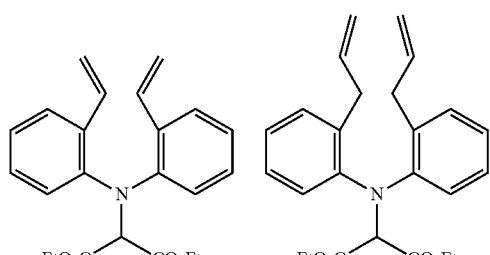
(62) 59h           (63) 59i
M = MgBr; 47%     M = MgBr; 26%
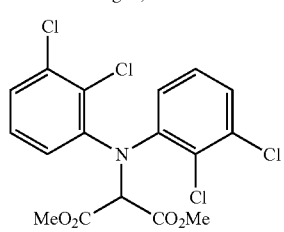
(64) 59j
M = MgBr; 54%
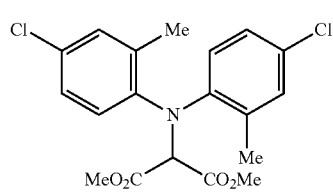
(65) 59k
M = MgBr; 72%
-continued
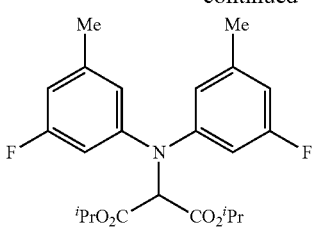
(66) 59l
M = MgBr; 29%
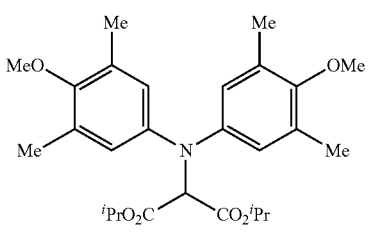
(67) 59m
M = MgBr; 67%
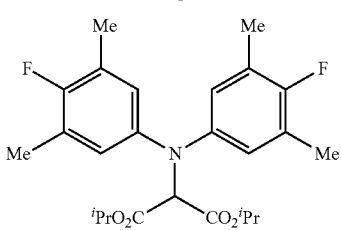
(68) 59n
M = MgBr; 45%
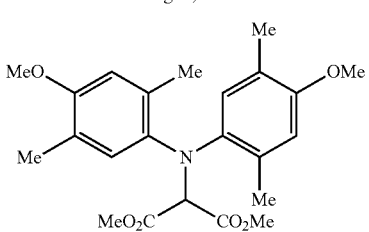
(69) 59o
M = MgBr; 55%
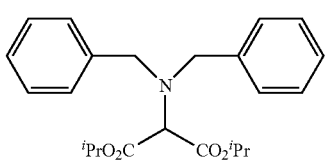
(70) 59q
M = MgBr; 53%
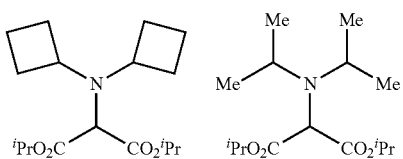
(71) 59r           (72) 59s
M = MgBr; 39%     M = MgBr; 32%
The amination reactions were conducted on a 1 mmol scale at the indicated temperature and considered complete upon the full consumption of the individual aminating agents (47a-c) by TLC analysis.

Scheme 5. Removal of the dialkylmalonyl group under oxidative conditions.
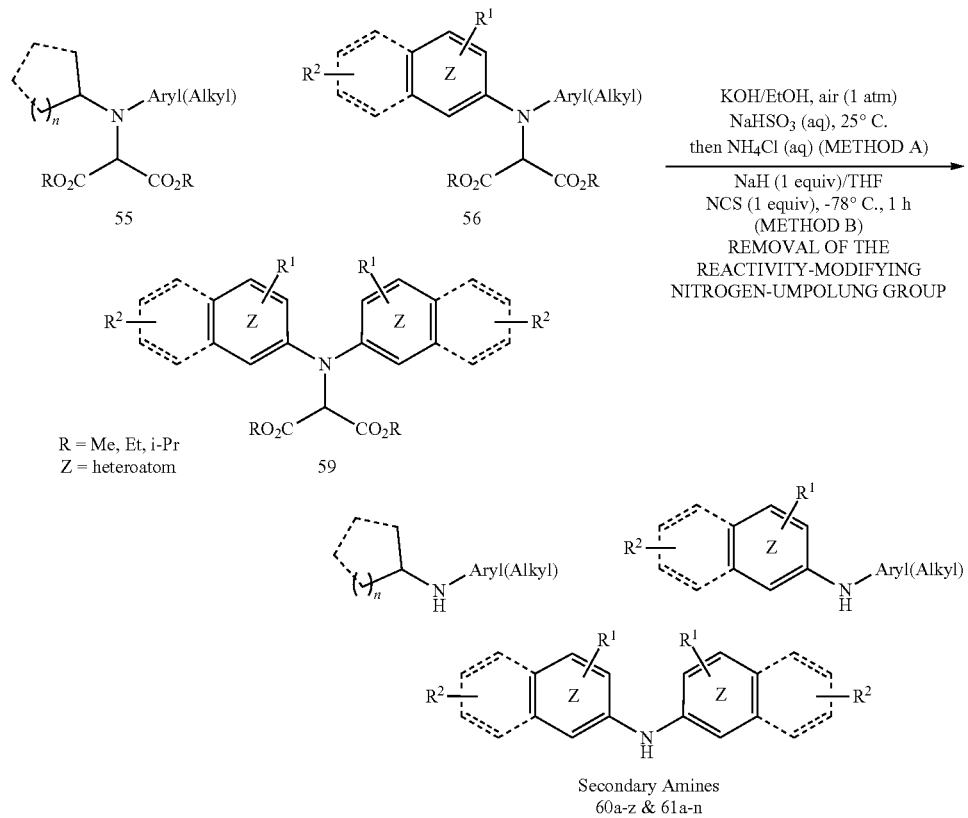
R = Me, Et, i-Pr
Z = heteroatom
Secondary Amines
60a-z & 61a-n
Structure of Symmetrical and Unsymmetrical Secondary Amine Products
(Entry): Compound #; Isolated Yield (%)
Oxidative Removal of the Reactivity-Modifying Nitrogen Umpolung Group to Furnish Secondary Amines
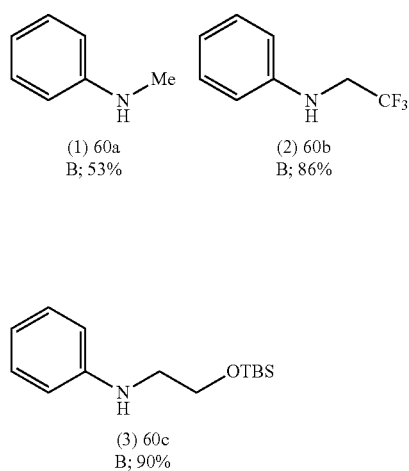
(1) 60a
B; 53%
(2) 60b
B; 86%
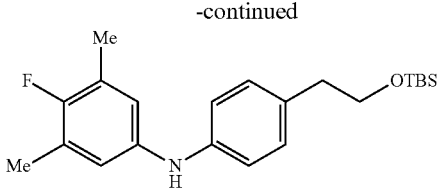
(3) 60c
B; 90%
(4) 60d
B; 82%
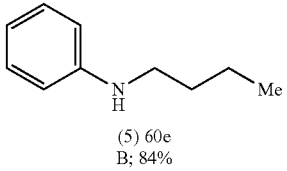
(5) 60e
B; 84%
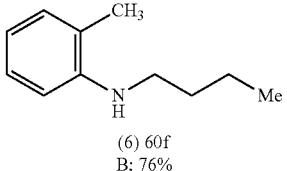
(6) 60f
B; 76%
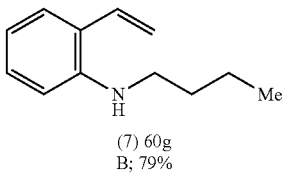
(7) 60g
B; 79%

-continued
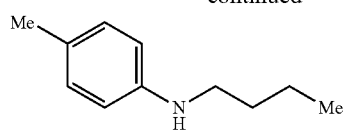
(8) 60h
B; 59%
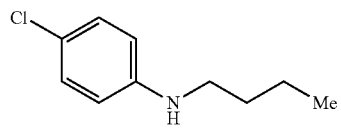
(9) 60i
B; 49%
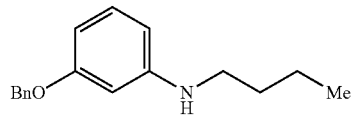
(10) 60j
B; 41%
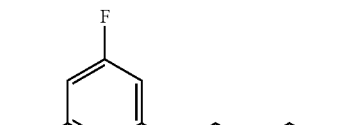
(11) 60k
B; 92%
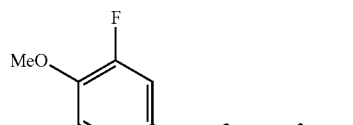
(12) 60l
B; 85%
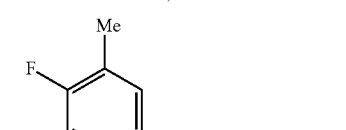
(13) 60m
B; 60%
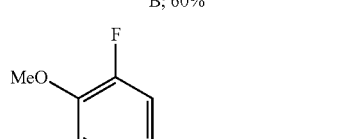
(14) 60n
B; 85%
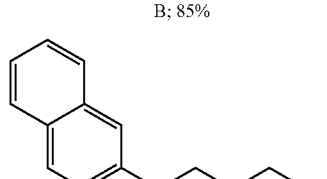
(15) 60o
B; 59%
-continued
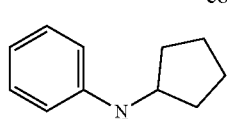
(16) 60p
B; 90%
(17) 60q
B; 53%
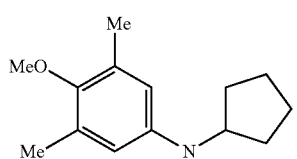
(18) 60r
B; 74%
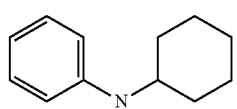
(19) 60s
B; 61%
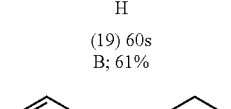
(20) 60t
B; 88%
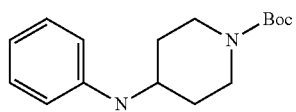
(21) 60u
B; 80%
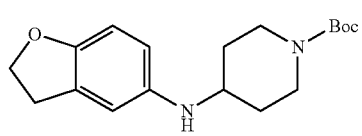
(22) 60v
B; 34%
(23) 60w
B; 88%
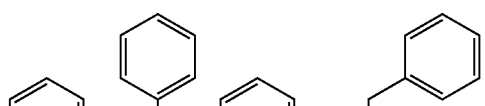
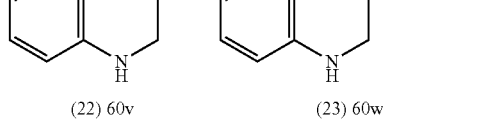
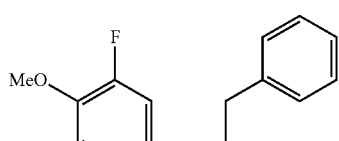
(24) 60x
B; 53%
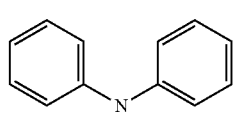
(25) 60y
A; 90%

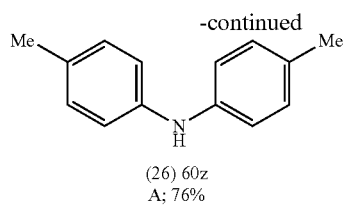
(26) 60z
A; 76%
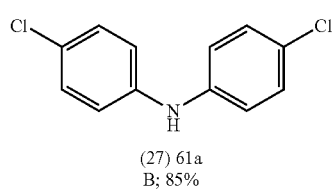
(27) 61a
B; 85%
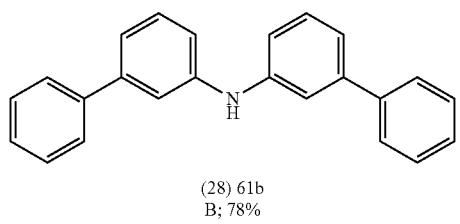
(28) 61b
B; 78%
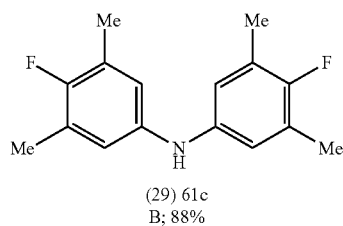
(29) 61c
B; 88%
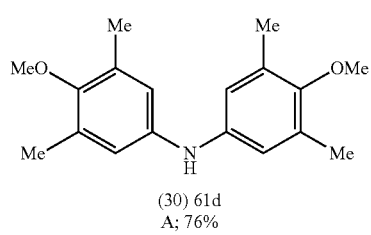
(30) 61d
A; 76%
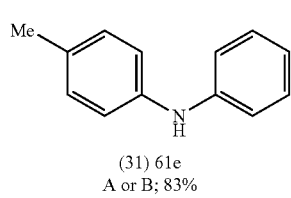
(31) 61e
A or B; 83%
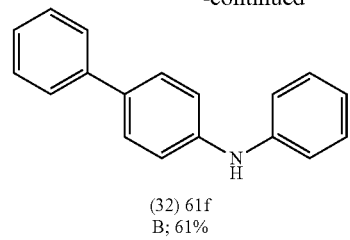
(32) 61f
B; 61%
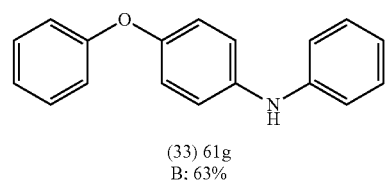
(33) 61g
B; 63%
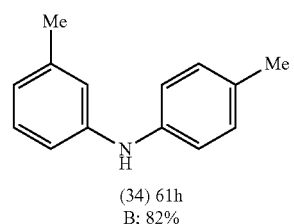
(34) 61h
B; 82%
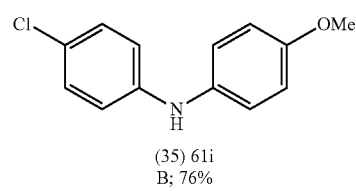
(35) 61i
B; 76%
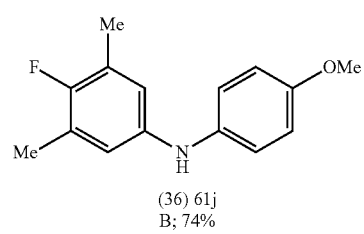
(36) 61j
B; 74%
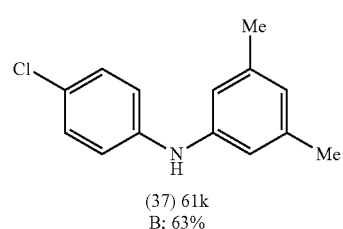
(37) 61k
B; 63%

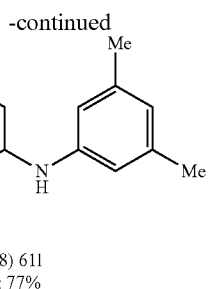

(38) 61l
B; 77%

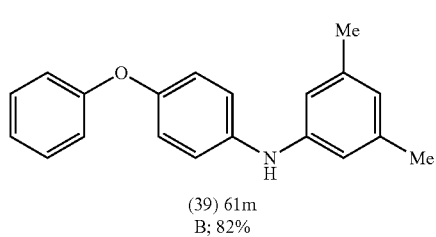

(39) 61m
B; 82%

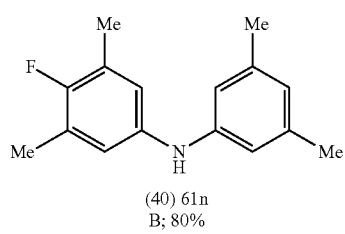

(40) 61n
B; 80%

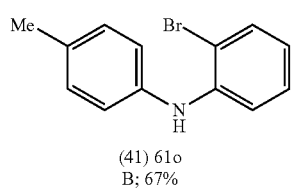

(41) 61o
B; 67%

The symmetrical and unsymmetrical amine products, obtained after the C—N bond formation, were subjected to either one of the two conditions (A or B).

The considerable synthetic power of these two novel C—N bond-forming methods (54 examples in Scheme 2 & Scheme 3 and 19 examples in Scheme 4) becomes even more apparent when one considers the very high number (>3,000) of commercially available and structurally diverse arylamine, aryl halide or arylmetal substrates that could be cross-coupled. There are several advantages of this N-umpolung approach over existing metal-catalyzed/mediated methods, including the operational simplicity and mild reaction conditions.

The presence of the dialkylmalonyl substituent on the nitrogen atom of the singly and doubly aminated compounds (55, 56, 57 & 59) appears problematic as the N-malonyl C—N linkage has to be cleaved in order to reveal the free dialkyl-, arylalkyl- and diarylamine products (60 & 61, Scheme 5). In fact, the N-malonyl group effectively protects the electron-rich amine products from the common oxidative decomposition pathways that usually occur in the presence of light and oxygen. Fortunately, this temporary protecting group can be effectively removed on demand either by using (1) mildly basic conditions and air at room temperature (Method A) or (2) a base and a mild oxidant, such as N-chloro succinimide (NCS), at low temperature (Method B, Scheme 5). Forty (40) structurally diverse N-malonyl substrates were subjected to one or both of these conditions and found that Method B was far more general than Method A and afforded the N-deprotected secondary amine products (60 & 61) in good to excellent isolated yields. It is noteworthy that the oxidative cleavage of the N-malonyl C—N bond effectively regenerates the ketomalonate (43) and/or ketomalonate hydrate (44) umpolung reagents that can be recovered and reused if desired.

Besides the dozens of successful electrophilic aminations using hard C-nucleophiles (Scheme 2-4), the ability of the N-electrophilic iminomalonates to undergo C—N bond-formation with softer C-nucleophiles such as enolates is also demonstrated (Scheme 6). Indeed, the lithium enolate derived from α-bromoester 62 reacted with three different N-aryl iminomalonates (52t-v) to afford the corresponding N-aryl aziridines (64a-c) in one-pot via presumptive intermediate 63 (Scheme 6, A). These are remarkable examples of the aza-Darzens reaction that usually requires the presence of a strongly electron-withdrawing moiety on the nitrogen atom. (Sweeney, 2009 and Rios & Cordova, 2012) The lithium enolate derived from acetophenone 65 reacted with imine 51w to furnish α-aminoaryl ketone 66 that was converted further to a brand new and highly-substituted morpholine (68) in two steps via a Lewis acid-mediated cyclization of amino alcohol 67.

Unsymmetrical diarylamine 61k yielded carbazole 69 under Fagnou's dehydrogenative cross-coupling conditions, however this process requires considerable optimization in order to be reliable on large-scale (Scheme 6, B). (Liegault et al, 2008)

The present disclosure also demonstrates that the sterically hindered diarylamine skeleton of the non-steroidal anti-inflammatory drug (NSAID) diclofenac 70 could be readily prepared in just two steps from the N-arylated compound 57b without using transition metal catalysts or harsh reaction conditions (Scheme 6, C).

Finally, medium-sized nitrogen-containing ring-systems could be prepared from N-linchpin products 59h & 59i. Under ring-closing metathesis conditions these compounds smoothly cyclized to the corresponding 7- and 9-membered N-heterocycles (Scheme 6, D). The 7-membered compound contains the skeleton of the anti-seizure medicine Carbamazepine™. Based on this efficient synthetic route, the rapid and straightforward synthesis of a library of structurally diverse carbamazepine analogs in which no catalyst/ligand optimizations would be required for the C—N bond-forming step is envisioned.

The transformations displayed in Scheme 6 are representative examples of synthetic possibilities that the single and double umpolung of nitrogen will enable organic chemists to exploit for the synthesis of nitrogen-containing compounds.

Scheme 6. Demonstrating additional synthetic possibilities for N-electrophilic iminomalonates and N,N-diarylamines.
A Addition of Soft C-Nucleophiles and Subsequent Formation 3- and 6-Membered Heterocycles:
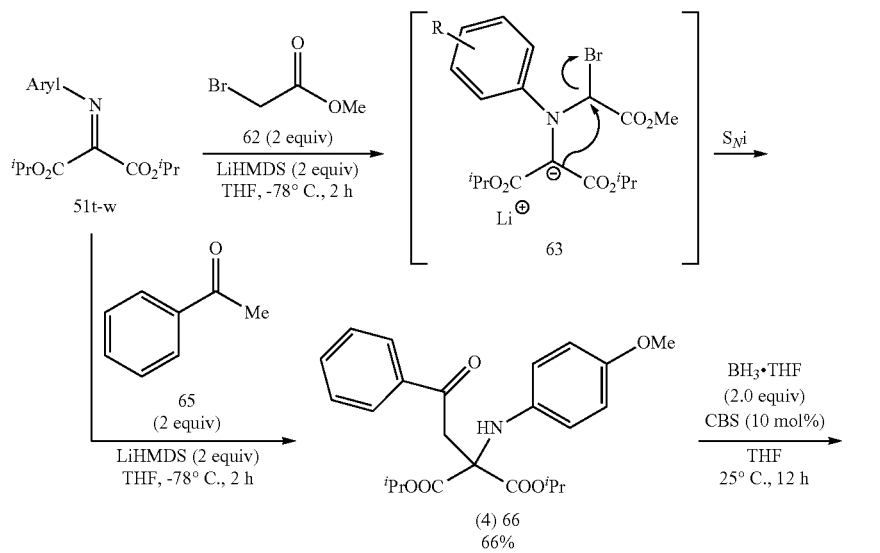
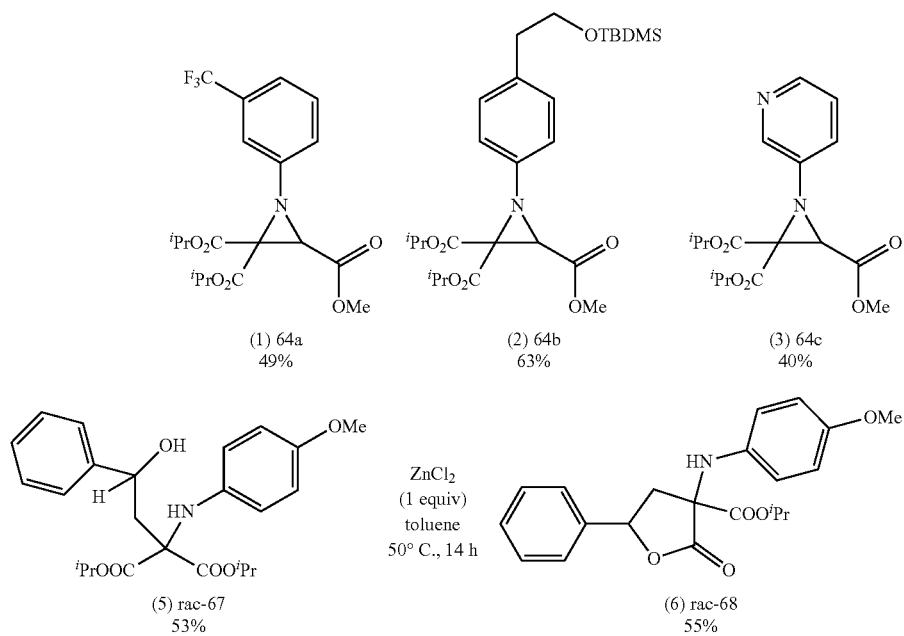
B Preparation of a Diversely Substituted Carbazole
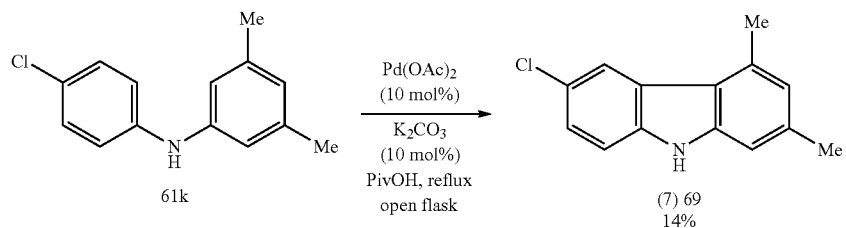
C Preparation of an Aromatic Amino Acid Derivative -continued

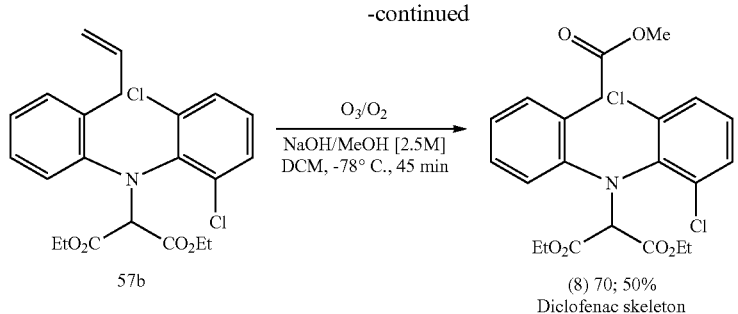

(8) 70; 50%
Diclofenac skeleton

D Preparation of Medium-Sized N-Heterocycles

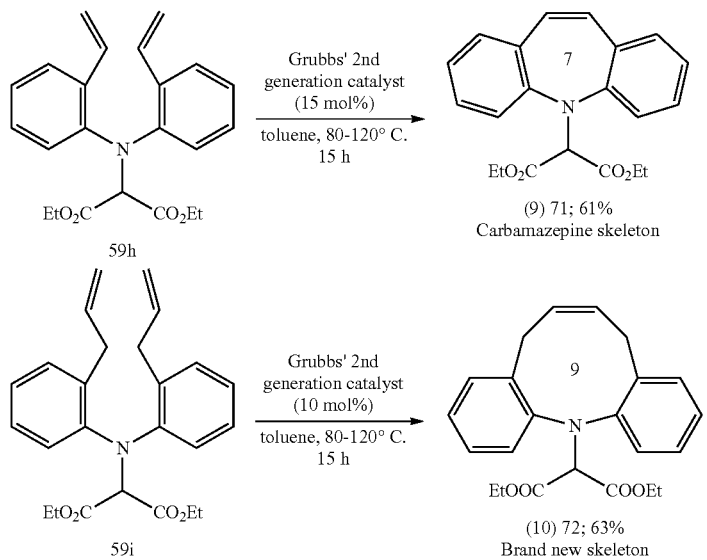

(9) 71; 61%
Carbamazepine skeleton

(10) 72; 63%
Brand new skeleton (A) Besides hard C-nucleophiles such as aryl Grignard reagents and alkyl/aryllithiums, softer C-nucleophiles derived from esters and ketones also readily add to the nitrogen of iminomalonates. The Li-enolate of 62 underwent spontaneous aziridine ring-formation with three different N-aryl iminomalonates. Aminoketone 66 could be reduced to the corresponding aminoalcohol 67 which underwent Lewis acid-mediated ring closure to afford highly substituted morpholine derivative 68. (B) Substituted N-unprotected unsymmetrical N,N-diarylamine 61k underwent dehydrogenative cross-coupling to afford the corresponding carabazole 69. (C) The skeleton of the non-steroidal anti-inflammatory drug (NSAID) Diclofenac (70) was synthesized from diarylamine 57b in one step—importantly, the key aryl-nitrogen linkage in compound 70 was prepared from readily available building blocks in the absence of transition metal catalysts. (C) Ring-closing metathesis of di-ortho vinyl-substituted as well as di-ortho allyl-substituted diarylamines 59h & 59i afford 7- and 9-membered N-heterocycles 71 & 72, respectively. Compound 71 contains the skeleton of the anti-seizure medicine carbamazepine while the ring system in compound 72 has not been previously constructed.

Example 2—General Methods and Materials

Reagents were purchased at the highest quality from the commercially available sources and used without further purification. Dichloromethane (DCM) and tetrahydrofuran (THF) for the reactions were obtained from pure process technology solvent system by passing the previously degassed solvents through an activated alumina column under argon. All reactions were carried out in flame-dried glass ware under an atmosphere of argon with magnetic stirring. All reactions were monitored by either H NMR or thin layer chromatography (TLC) carried out on 0.25 mm pre-coated E. Merck silica plates (60F-254), using short-wave UV light as visualizing agent and $KMnO_4$ or phosphomolybdic acid (PMA) and heat as developing agents. Flash column chromatography was performed using Biotage Isolera One automated chromatograph with pre-packed KP-Sil cartridges. $^1H$ and $^{13}C$ NMR spectra were recorded on a Bruker DRX-600 spectrometer operating at 600 MHz for proton and 151 MHz for carbon nuclei and were calibrated using residual undeuterated solvent as an internal reference ($CDCl_3$: 7.26 ppm $^1H$ NMR and 77.00 ppm $^{13}C$ NMR; DMSO-$d_6$: 2.50 ppm H NMR and 39.52 ppm $^{13}C$ NMR). For reporting NMR peak multiplicities, the following abbreviations were used: s=singlet, d=doublet, t=triplet, q=quartet, p=pentet, hept=heptet, m=multiplet. High-resolution mass spectra (HRMS) were recorded on an Agilent UHPLC TOF mass spectrometer using electrospray ionization time-of-flight (ESI-TOF) or chemical ionization time-of-flight (CI-TOF) reflectron experiments. Melting points and ranges were recorded on Mettler Toledo MP50 melting point system.

Example 3—Compound Characterization

Gram-Scale Preparation of diisopropyl 2,2-dihydroxymalonate (44)

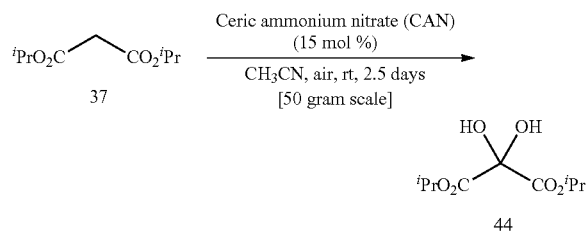

In a 3 L three-necked round bottom flask, diisopropyl malonate (50 g, 265.64 mmol, 1 equiv) was first dissolved in acetonitrile (1.32 L, 0.2M) and to the resulting solution ceric ammonium nitrate (CAN; 21.84 g, 15 mol %) was added in one portion under constant stirring. The reaction vessel was fitted with gas dispenser and a slow stream of air was bubbled through the reaction mixture under constant stirring. Progress of the reaction was monitored by checking the crude H-NMR of the reaction mixture. After 2.5 days, the starting material was totally consumed. Important: During the course of the reaction, there is a decrease in the amount of solvent due to purging and based on the amount of solvent lost, the same amount of solvent is added to the reaction mixture as needed. After confirming the consumption of the starting material, water (1.5 L) was added to the reaction mixture and stirred until the reaction mixture became colorless (e.g., usually an overnight period was allowed to hydrate all the ketomalonate in the reaction mixture). Next, the reaction mixture was extracted with ethyl acetate thrice (3×1 L). The combined organic layers were washed with brine (1 L), dried over anhydrous $Na_2SO_4$ and concentrated in vacuo. The crude product was obtained as a thick slurry which was then triturated with hexanes (100 mL) and filtered (i.e., a white crystalline solid). During the filtration, some additional product crystallized from the mother liquor which was then recovered by filtration. The combined filtrates were washed with hexanes (3×50 mL) three times to afford 44 as white crystalline solid (43 g, 73%) that requires no further purification.

Synthesis of 44 on 400 g Scale

Diisopropyl 2,2-dihydroxymalonate 44 was synthesized on 400 g scale (by largely adapting the above procedure) in a 10 L ChemGlass jacketed reactor that is outfitted with a large gas disperser as well as overhead mechanical stirring (see pictures). First, diisopropyl malonate (400 g, 2.12 mol, 1 equiv) was dissolved in acetonitrile (9 L) under constant stirring and to this solution ceric ammonium nitrate (CAN; 174.77 g, 15 mol %) was added in one portion. Next, a slow stream of air was introduced via the gas disperser and over the next 2 h period the temperature of the reaction mixture increased by 2° C. (22.5° C. to 24.6° C.). After continued vigorous stirring (at 200 rpm) overnight, the temperature remained at 24.7° C. Progress of the reaction was monitored by $^1$H-NMR and after 2.5 d of stirring the reaction was totally complete. At this point the bubbling of air was stopped and 4 L of deionized water was added to the reaction mixture under constant stirring (i.e., the 10 L reactor has >3 L of overhead space to allow extra volume during workup). During the workup the temperature initially dropped from 24° C. to 16° C. and stirring continued overnight (~15 h). At this point the reaction mixture was colorless and temperature of the reaction mixture was 24° C. After draining through the bottom reactor valve, acetonitrile was removed under reduced pressure. The aqueous layer was extracted with ethyl acetate thrice (3×3 L). The combined organic layers were dried over anhydrous $Na_2SO_4$ (150 g) and concentrated. The slurry that was formed after concentration was triturated with 300 mL of hexanes and filtered. The solid was washed repeatedly with another 500 mL of hexanes to afford a pure white crystalline solid (320 g, 68%). Repeated washing of the above product with hexanes is important for obtaining the pure product.

Diisopropyl 2,2-dihydroxymalonate (44)

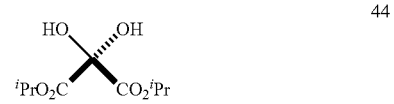

Yield: 73% Physical State: white crystalline solid (m.p.=56-61° C.); $R_f$=0.23 (20% EtOAc/hexanes); $^1$H NMR (600 MHz, $CDCl_3$): δ 5.15 (hept, J=6.3 Hz, 2H), 4.80 (s, 2H), 1.30 (d, J=6.3 Hz, 12H); $^{13}$C NMR (151 MHz, $CDCl_3$): δ 168.02, 89.86, 71.68, 21.39; HRMS (ESI-TOF): calc'd for $C_9H_{16}O_6$ [M+Na]$^+$ 243.0839; found 243.0840.

Preparation of di-tert-butyl 2,2-dihydroxymalonate (38a)

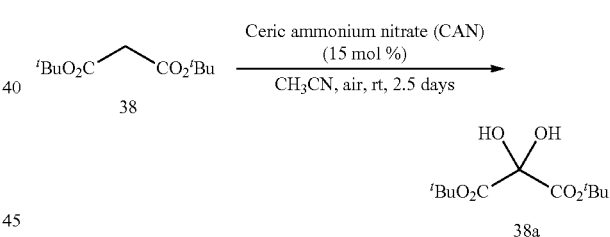

Compound 38a was prepared according to the procedure described for the preparation of 44. YA-tert-butyl malonate (38; 10 g, 46.23 mmol, 1 equiv) was first dissolved in acetonitrile (232 mL, 0.2M) and to this solution ceric ammonium nitrate (CAN; 3.8 g, 15 mol %) was added in one portion under constant stirring. The three-necked round bottom flask was fitted with gas dispenser and a slow stream of air was bubbled through the reaction mixture under constant stirring. Progress of the reaction was monitored by checking the crude $^1$H-NMR of the reaction mixture. After 2.5 days the NMR analysis indicated total consumption of the starting material (38). Any solvent lost during the course of the reaction due to the constant bubbling of air was replaced as needed. After confirming the completion of reaction, deionized water (250 mL) was added and stirring continued until the brownish yellow color of the reaction mixture turned colorless. Next, the reaction mixture was extracted with ethyl acetate thrice (3×250 mL). The combined organic layers were washed with brine (300 mL), dried over anhydrous $Na_2SO_4$ and concentrated in vacuo.

The crude product was obtained as thick slurry. This slurry was then triturated with hexanes (25 mL) and filtered. During the filtration process some of the product crystallized in the filtrate—these crystals were then recovered. The combined crops were washed with hexanes (3×20 mL) three times to afford 38a as white crystalline solid (5.9 g, 52%) that requires no further purification.

Di-tert-butyl 2,2-dihydroxymalonate (38a)

Yield: 52%; Physical State: white solid (m.p. 140-147° C.); $R_f$=0.20 (20% EtOAc/hexanes); $^1$H NMR (600 MHz, CDCl$_3$): δ 4.60 (s, 1H), 1.51 (s, 18H); $^{13}$C NMR (151 MHz, CDCl$_3$): δ 167.76, 89.91, 84.42, 27.67; HRMS (ESI-TOF): calc'd for $C_{11}H_{20}O_6$ [M+Na]$^+$ 271.1152; found 271.1152.

Preparation of diisopropyl 2-(hydroxyimino)malonate (46) (Methods A & B)

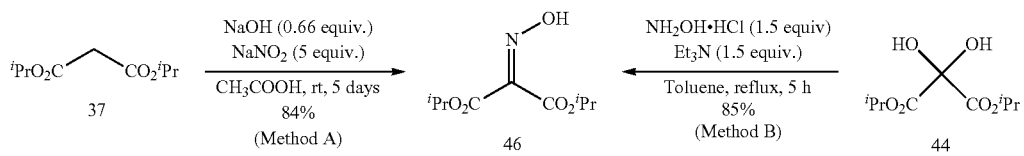

Method A: This procedure was adapted from literature reports (1-3). Sodium hydroxide (0.997 g, 24.93 mmol, 0.66 equiv) was dissolved in glacial acetic acid (7.55 mL) under constant stirring. A thick, white slurry was formed. Then, a solution of diisopropyl malonate (7.1 g, 37.77 mmol, 1 equiv) in glacial acetic acid (2.11 mL) was added dropwise to the ice bath-cooled slurry (0° C.) over a period of 5 minutes. After this addition was complete, a 0° C. solution of sodium nitrite (13.03 g, 188.87 mmol, 5 equiv) in water (23.61 mL) was added dropwise over a period of one hour (!) to the reaction mixture by means of an addition funnel, maintaining the temperature of the reaction mixture at 0° C. After the addition of sodium nitrite was complete, the addition funnel was replaced with a septum fitted with an empty balloon and the reaction mixture was allowed to warm to room temperature and stirred for 5 days. After 5 days, the reaction mixture was saturated with solid sodium chloride and extracted with ethyl acetate thrice (3×75 mL). The combined organic extracts were washed with a 1:1 mixture of saturated aqueous solution of NaHCO$_3$ and brine until the pH of the aqueous layer becomes basic (pH 8-9). Then the organic layer was dried over anhydrous Na$_2$SO$_4$ and concentrated in vacuo. The crude product was purified by column chromatography to afford the 46 as a colorless viscous oily liquid (6.85 g, 84%). Note: In this method, the reaction goes to 85% completion only and 15% of the starting material was recovered during the chromatographic purification.

Method B: Diisopropyl 2,2-dihydroxymalonate 44 (20 g, 90.81 mmol, 1 equiv) was dissolved in toluene (227 mL) and to this solution hydroxylamine hydrochloride (9.46 g, 136.22 mmol. 1.5 equiv) was added followed by triethylamine (18.98 mL, 136.22 mmol, 1.5 equiv) at room temperature under constant stirring. Then the reaction mixture was heated to reflux under Dean-Stark conditions for 5 h. Progress of the reaction was monitored by H-NMR. After confirming the completion of the reaction by crude NMR, heating was stopped and the reaction mixture was allowed to cool to room temperature. Next, the precipitated triethylamine hydrochloride salt was filtered and washed with ethyl acetate thrice (3×25 mL). The combined organic layers were washed once with saturated aqueous NaHCO$_3$ solution (150 mL) followed by brine, dried over anhydrous sodium sulfate and concentrated. The crude product was purified by column chromatography to afford the product 46 as colorless viscous oily liquid (16.8 g, 85%).

Diisopropyl 2-(hydroxyimino)malonate (46)

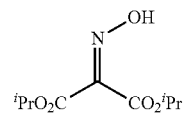

Yield: 85% (Method B) Physical State: colorless viscous oily liquid; $R_f$=0.45 (20% EtOAc/hexanes); $^1$H NMR (600 MHz, CDCl$_3$): δ 10.41 (s, 1H), 5.22 (hept, J=6.3 Hz, 1H), 5.15 (hept, J=6.2 Hz, 1H), 1.29 (dd, J=17.2, 6.3 Hz, 12H); $^{13}$C NMR (151 MHz, CDCl$_3$): δ 160.09, 159.38, 144.33, 70.54, 70.38, 21.20, 21.18; HRMS (ESI-TOF): calc'd for $C_9H_{15}NO_5$ [M+Na]$^+$ 240.0842; found 240.0843.

Preparation of di-tert-butyl 2-(hydroxyimino)malonate

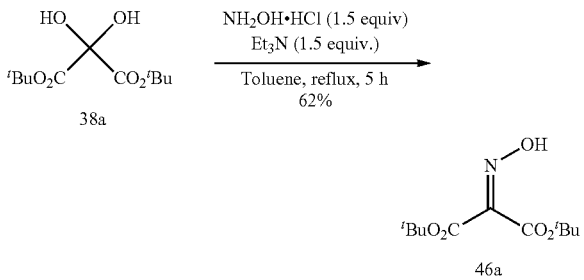

Di-tert-butyl 2-(hydroxyimino)malonate was prepared on 1 gram scale according to the procedure described in Method B for the preparation of 46. The product was obtained as colorless viscous oily liquid (614 mg, 62% yield).

Di-tert-butyl 2-(hydroxyimino)malonate (46a)

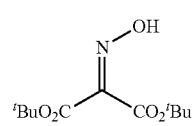

Yield: 62%; Physical State: colorless oily liquid; $R_f$=0.24 (20% EtOAc/hexanes); $^1$H NMR (600 MHz, CDCl$_3$): δ 10.58 (s, 1H), 1.49 (d, J=17.0 Hz, 18H); $^{13}$C NMR (151 MHz, CDCl$_3$): δ 159.89, 158.97, 145.39, 84.31, 84.06, 27.88, 27.76; HRMS (ESI-TOF): calc'd for C$_{11}$H$_{19}$NO$_5$ [M+Na]$^+$ 268.1155; found 168.1155.

Preparation of Dimethyl and Diethyl Oximinomalonates (46b, 46c)

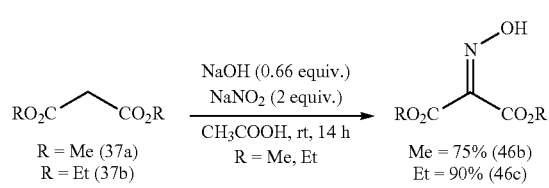

Both the dimethyl and diethyl oximinomalonates were prepared according to literature reported procedures (Shaw & Nolan, 1957; May & Lash, 1992 and Peng, et al., 2011) First, sodium hydroxide (3.99 g, 99.91 mmol, 0.66 equiv) was dissolved in glacial acetic acid (30 mL) under constant stirring. A, thick white slurry was formed. Then, a solution of dimethyl malonate (20 g, 151.38 mmol, 1 equiv) in glacial acetic acid (8.4 mL) was added dropwise over a period of 5 minutes to the ice bath-cooled slurry. After this addition was complete, a 0° C. solution of sodium nitrite (20.89 g, 302.77 mmol, 2 equiv) in water (160 mL) was added dropwise over a period of 1 h to the reaction mixture by means of an addition funnel, while carefully maintaining the temperature of the reaction mixture at 0° C. After the addition of NaNO$_2$ was completed, the addition funnel was replaced with a septum fitted with an empty balloon and the reaction mixture was allowed to warm to room temperature and stirred overnight (14 h). After overnight stirring, the reaction mixture was saturated with sodium chloride and extracted with ethyl acetate thrice (3×100 mL). The combined organic extracts were washed with a 1:1 mixture of saturated aqueous solution of NaHCO$_3$ and brine until the pH of the aqueous layer was basic (pH 8-9). Next, the organic layer was dried over anhydrous Na$_2$SO$_4$ and concentrated in vacuo. The crude product was purified by column chromatography to afford the pure dimethyl oximinomalonate as a colorless viscous oily liquid which became a white solid (18.2 g, 75%) upon standing in the refrigerator. The diethyl oximinomalonate was also prepared by this same procedure: pale yellow colored viscous oily liquid (90% yield). The characterization data for these oximinomalonates is consistent with the literature reported data.

Dimethyl 2-(hydroxyimino)malonate (46b)

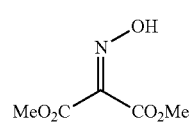

Yield: 75%; Physical State: White solid; $R_f$=0.12 (20% EtOAc/hexanes); $^1$H NMR (600 MHz, CDCl$_3$): δ 10.73 (s, 1H), 3.86 (d, J=17.8 Hz, 6H); $^{13}$C NMR (151 MHz, CDCl$_3$): δ 160.99, 160.48, 143.58, 53.27, 52.98; Spectral data is in accordance with the literature report (May & Lash, 1992).

Diethyl 2-(hydroxyimino)malonate (46c)

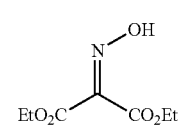

Yield: 90%; Physical State: Pale yellow colored viscous oily liquid; $R_f$=0.2 (20% EtOAc/hexanes); $^1$H NMR (600 MHz, CDCl$_3$): δ 10.47 (s, 1H), 4.33 (dq, J=25.4, 7.1 Hz, 4H), 1.30 (dt, J=14.1, 7.1 Hz, 6H); $^{13}$C NMR (151 MHz, CDCl$_3$): δ 160.51, 159.98, 144.05, 62.66, 62.46, 13.79, 13.75; Spectral data is in accordance with the literature report (May & Lash, 1992);

TABLE 2

Activation of oximinomalonates with different sulfonyl chlorides

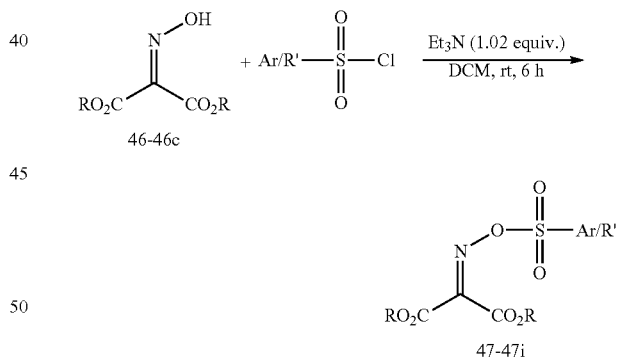

| Entry | R | Ar/R' | Yield (%) |
|---|---|---|---|
| 1 | Me | Me | 93 |
| 2 | Me | 4-MeC$_6$H$_4$ | 83 |
| 3 | Et | Me | 82 |
| 4 | Et | 4-MeC$_6$H$_4$ | 72 |
| 5 | $^i$Pr | Me | 70 |

TABLE 2-continued

Activation of oximinomalonates with different sulfonyl chlorides

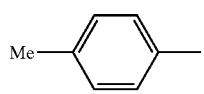

| Entry | R | Ar/R' | Yield (%) |
|---|---|---|---|
| 6 | $^i$Pr | Me—⟨C6H4⟩— | 72 |
| 7 | $^i$Pr | F$_3$C—⟨C6H4⟩— | 76 |
| 8 | $^i$Pr | 2,4,6-trimethylphenyl (Me, Me, Me) | 74 |
| 9 | $^i$Pr | 2,4,6-triisopropylphenyl | 85 |
| 10 | $^t$Bu | Me—⟨C6H4⟩— | 79 |

Standard Procedure for Oximinomalonate Activation with Sulfonyl Chlorides

This procedure was adapted from the literature (Peng, et al., 2011) with small changes. To a solution of hydroxyimino malonate (1 equiv) and sulfonyl chloride (1 equiv) in DCM (0.56 M) under argon, was added neat Et$_3$N (1.02 equiv) in one portion at room temperature under constant stirring. The reaction mixture was stirred at room temperature for 6 hours. After confirming the complete consumption of starting material by thin layer chromatography (TLC), the reaction mixture was diluted with DCM (two volumes of the reaction mixture) and washed with water thrice. The organic layer was then dried over anhydrous Na$_2$SO$_4$ and concentrated. The crude product was purified by column chromatography.

General Procedure for the Synthesis of Diisopropyl 2-((Tosyloxy)Imino)Malonate (47)

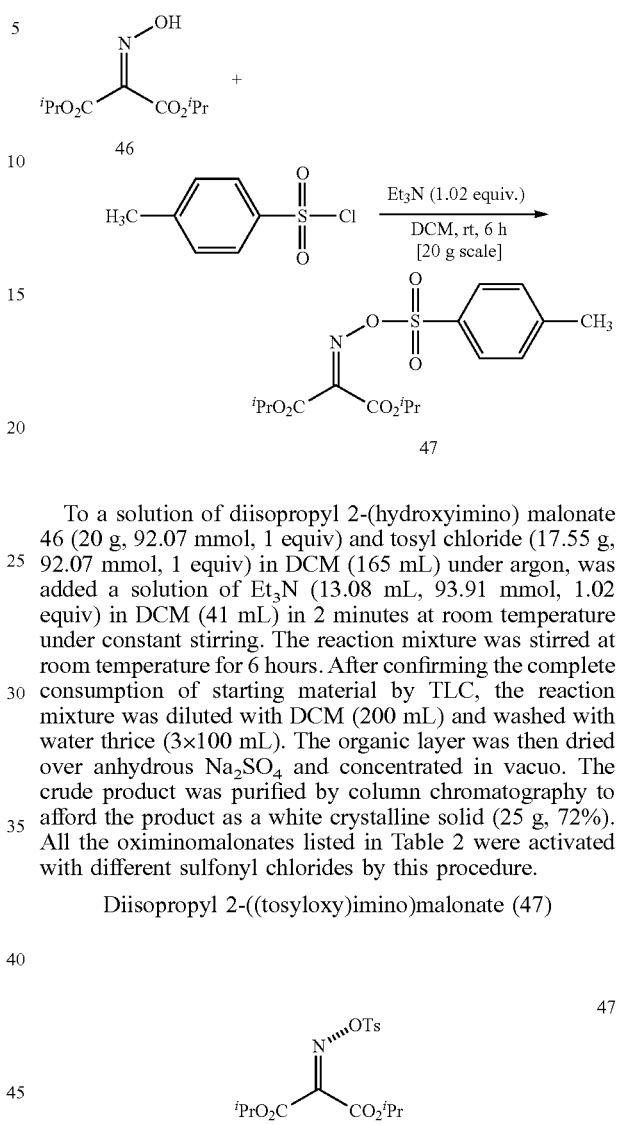

To a solution of diisopropyl 2-(hydroxyimino) malonate 46 (20 g, 92.07 mmol, 1 equiv) and tosyl chloride (17.55 g, 92.07 mmol, 1 equiv) in DCM (165 mL) under argon, was added a solution of Et$_3$N (13.08 mL, 93.91 mmol, 1.02 equiv) in DCM (41 mL) in 2 minutes at room temperature under constant stirring. The reaction mixture was stirred at room temperature for 6 hours. After confirming the complete consumption of starting material by TLC, the reaction mixture was diluted with DCM (200 mL) and washed with water thrice (3×100 mL). The organic layer was then dried over anhydrous Na$_2$SO$_4$ and concentrated in vacuo. The crude product was purified by column chromatography to afford the product as a white crystalline solid (25 g, 72%). All the oximinomalonates listed in Table 2 were activated with different sulfonyl chlorides by this procedure.

Diisopropyl 2-((tosyloxy)imino)malonate (47)

Yield: 81%; Physical State: white crystalline solid (m.p. 82-87° C.); $R_f$=0.20 (10% EtOAc/hexanes); $^1$H NMR (600 MHz, CDCl$_3$): δ 7.87 (d, J=7.9 Hz, 2H), 7.35 (d, J=8.3 Hz, 2H), 5.24 (hept, J=6.1 Hz, 1H), 5.12 (hept, J=6.0 Hz, 1H), 2.45 (s, 3H), 1.31 (dd, J=24.3, 6.3 Hz, 12H); $^{13}$C NMR (151 MHz, CDCl$_3$): δ 157.57, 157.33, 150.26, 146.11, 131.16, 129.81, 129.16, 71.83, 71.74, 21.70, 21.44, 21.41; HRMS (ESI-TOF): calc'd for C$_{16}$H$_{21}$NO$_7$S [M+H]$^+$ 372.1111; found 372.1119.

Diisopropyl 2-(((methylsulfonyl)oxy)imino)malonate (47a)

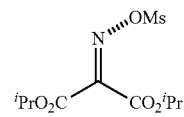

Yield: 70%; Physical State: off-white solid (m.p.=50-55° C.); $R_f$=0.26 (20% EtOAc/hexanes); $^1$H NMR (600 MHz, CDCl$_3$): δ 5.28 (hept, J=6.3 Hz, 1H), 5.21 (hept, J=6.4 Hz, 1H), 3.24 (s, 3H), 1.35 (t, J=6.0 Hz, 12H); $^{13}$C NMR (151 MHz, CDCl$_3$): δ 157.32, 157.17, 150.94, 72.20, 72.04, 36.92, 21.37; HRMS (ESI-TOF): calc'd for C$_{10}$H$_{17}$NO$_7$S [M+K]$^+$ 334.0357; found 334.0368.

Diisopropyl 2-((((4-(trifluoromethyl)phenyl)sulfonyl)oxy)imino)malonate (47b)

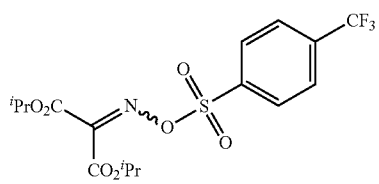

Yield: 76%; Physical State: white solid (m.p.=73-78° C.); $R_f$=0.29 (10% EtOAc/hexanes); $^1$H NMR (600 MHz, CDCl$_3$): δ 8.15 (d, J=8.3 Hz, 2H), 7.86 (d, J=8.3 Hz, 2H), 5.26 (hept, J=6.2 Hz, 1H), 5.13 (hept, J=6.2 Hz, 1H), 1.34 (d, J=6.3 Hz, 6H), 1.29 (d, J=6.3 Hz, 6H); $^{13}$C NMR (151 MHz, CDCl$_3$): δ 157.20, 156.97, 151.06, 137.78, 136.57, 136.35, 136.13, 135.91, 129.75, 126.37, 126.35, 125.61, 123.80, 121.99, 120.18, 72.17, 72.08, 21.40, 21.35; HRMS (ESI-TOF): calc'd for C$_{16}$H$_{18}$F$_3$NO$_7$S [M+Na]$^+$ 448.0648; found 448.0663.

Diisopropyl 2-(((mesitylsulfonyl)oxy)imino)malonate (47c)

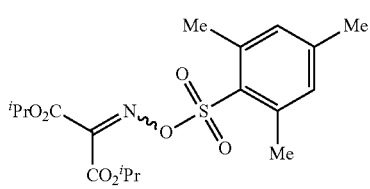

Yield: 74%; Physical State: white solid (m.p. 73-78° C.); $R_f$=0.48 (20% EtOAc/hexanes); $^1$H NMR (600 MHz, CDCl$_3$): δ 6.99 (s, 2H), 5.27 (hept, J=6.3 Hz, 1H), 5.10 (hept, J=6.2 Hz, 1H), 2.64 (s, 6H), 2.32 (s, 3H), 1.35 (d, J=6.3 Hz, 6H), 1.27 (d, J=6.3 Hz, 6H); $^{13}$C NMR (151 MHz, CDCl$_3$): δ 157.77, 157.51, 149.54, 144.55, 141.40, 131.81, 129.35, 71.74, 71.67, 22.72, 21.51, 21.43, 21.12; HRMS (ESI-TOF): calc'd for C$_{18}$H$_{25}$NO$_7$S [M+H]$^+$ 400.1424; found 400.1315.

Diisopropyl 2-((((2,4,6-triisopropylphenyl)sulfonyl)oxy)imino)malonate (47d)

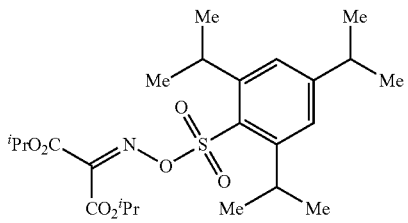

Yield: 85%; Physical State: white solid (m.p. 74-78° C.); $R_f$=0.37 (10% EtOAc/hexanes); $^1$H NMR (600 MHz, CDCl$_3$): δ 7.21 (s, 2H), 5.28 (p, J=6.2 Hz, 1H), 5.11 (p, J=6.3 Hz, 1H), 4.12 (hept, J=6.8 Hz, 2H), 2.92 (p, J=6.9 Hz, 1H), 1.36 (d, J=6.4 Hz, 6H), 1.27 (t, J=5.2 Hz, 24H); $^{13}$C NMR (151 MHz, CDCl$_3$): δ 157.80, 157.77, 154.84, 152.26, 149.33, 128.02, 124.05, 71.69, 71.68, 34.29, 29.92, 24.67, 23.44, 21.50, 21.48; HRMS (ESI-TOF): calc'd for C$_{24}$H$_{37}$NO$_7$S [M+H]$^+$ 484.2363; found 484.2349.

Diethyl 2-((tosyloxy)imino)malonate (47e)

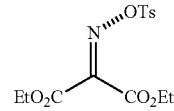

Yield: 72%; Physical State: white solid (m.p. 63-68° C.); $R_f$=0.44 (20% EtOAc/hexanes); $^1$H NMR (600 MHz, CDCl$_3$): δ 7.88 (d, J=8.0 Hz, 2H), 7.36 (d, J=8.0 Hz, 2H), 4.40 (q, J=7.2 Hz, 2H), 4.32 (q, J=7.1 Hz, 2H), 2.46 (s, 3H), 1.33 (dt, J=20.1, 7.1 Hz, 6H); $^{13}$C NMR (151 MHz, CDCl$_3$): δ 157.99, 157.95, 149.70, 146.21, 131.10, 129.89, 129.18, 63.41, 63.27, 21.75, 13.90, 13.84; HRMS (ESI-TOF): calc'd for C$_{14}$H$_{17}$NO$_7$S [M+H]$^+$ 344.0798 [M+Na]$^+$ 366.0618; found 344.0799, 366.0623.

Dimethyl 2-((tosyloxy)imino)malonate (47f)

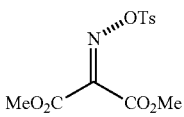

Yield: 83%; Physical State: off-white solid (m.p. 91-96° C.); $R_f$=0.21 (20% EtOAc/hexanes); $^1$H NMR (600 MHz, CDCl$_3$): δ 7.87 (d, J=8.0 Hz, 2H), 7.37 (d, J=8.0 Hz, 2H), 3.93 (s, 3H), 3.87 (s, 3H), 2.46 (s, 3H); $^{13}$C NMR (151 MHz, CDCl$_3$): δ 158.47, 158.30, 149.10, 146.32, 130.99, 129.96, 129.18, 53.81, 53.60, 21.76; HRMS (ESI-TOF): calc'd for C$_{12}$H$_{13}$NO$_7$S [M+H]$^+$ 316.0485 [M+Na]$^+$ 338.0305; found 316.0482, 338.0317.

Diethyl 2-(((methylsulfonyl)oxy)imino)malonate (47g)

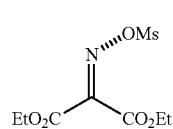

47g

Yield: 82%; Physical State: white solid (m.p.=52-56° C.); $R_f$=0.21 (20% EtOAc/hexanes); $^1$H NMR (600 MHz, CDCl$_3$): δ 4.38 (dq, J=14.5, 7.1 Hz, 4H), 3.22 (s, 3H), 1.34 (t, J=7.1 Hz, 6H); $^{13}$C NMR (151 MHz, CDCl$_3$): δ 157.74, 157.64, 150.28, 63.68, 63.44, 36.94, 13.77, 13.75; HRMS (CI-TOF): calc'd for C$_8$H$_{13}$NO$_7$S [M+H]$^+$ 268.0491; found 268.0486.

Dimethyl 2-(((methylsulfonyl)oxy)imino)malonate (47h)

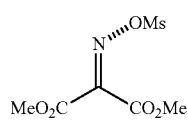

47h

Yield: 93%; Physical State: off-white solid (m.p.=68-73° C.); $R_f$=0.20 (30% EtOAc/hexanes); $^1$H NMR (600 MHz, CDCl$_3$): δ 3.91 (d, J=7.8 Hz, 6H), 3.22 (s, 3H); $^{13}$C NMR (151 MHz, CDCl$_3$): δ 158.15, 157.95, 149.61, 53.93, 53.65, 36.94; HRMS (CI-TOF): calc'd for C$_6$H$_9$NO$_7$S [M+H]$^+$ 240.0178; found 240.0176.

Di-tert-butyl 2-((tosyloxy)imino)malonate (47i)

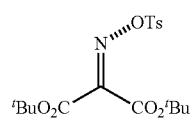

47i

Yield: 79%; Physical State: white solid (m.p. 72-77° C.); $R_f$=0.43 (20% EtOAc/hexanes); $^1$H NMR (600 MHz, CDCl$_3$): δ 7.83 (d, J=8.0 Hz, 2H), 7.32 (d, J=8.1 Hz, 2H), 2.41 (s, 3H), 1.48 (d, J=30.9 Hz, 18H); $^{13}$C NMR (151 MHz, CDCl$_3$): δ 157.09, 156.46, 151.18, 145.94, 131.16, 129.67, 128.99, 85.88, 85.28, 27.76, 27.55, 21.53; HRMS (ESI-TOF): calc'd for C$_{18}$H$_{25}$NO$_7$S [M+Na]$^+$ 422.1244; found 422.1240.

Scheme 7. List of diisopropyl and diethyl iminomalonates

Preparation of diisopropyl and diethyl iminomalonates (51a-v)

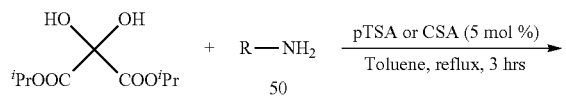

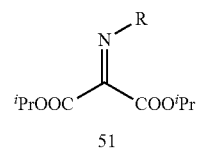

51

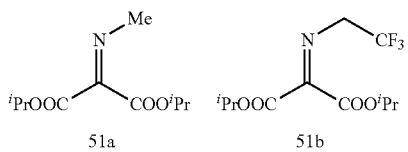

51a     51b

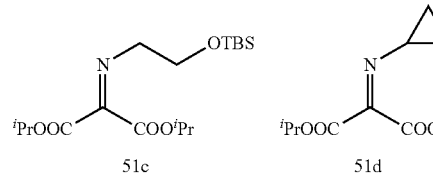

51c     51d

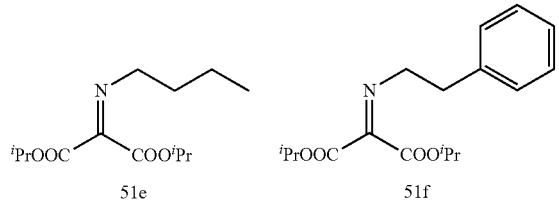

51e     51f

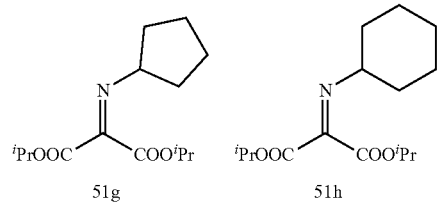

51g     51h

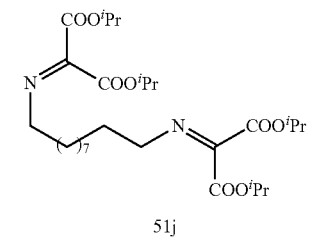

51i     51j

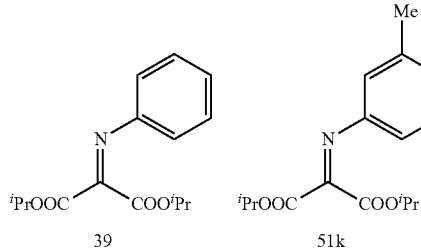

39     51k

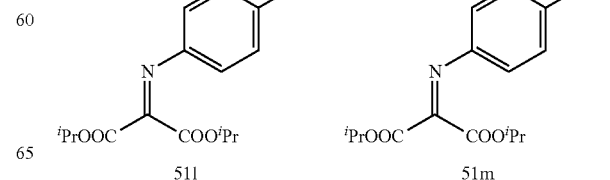

51l     51m

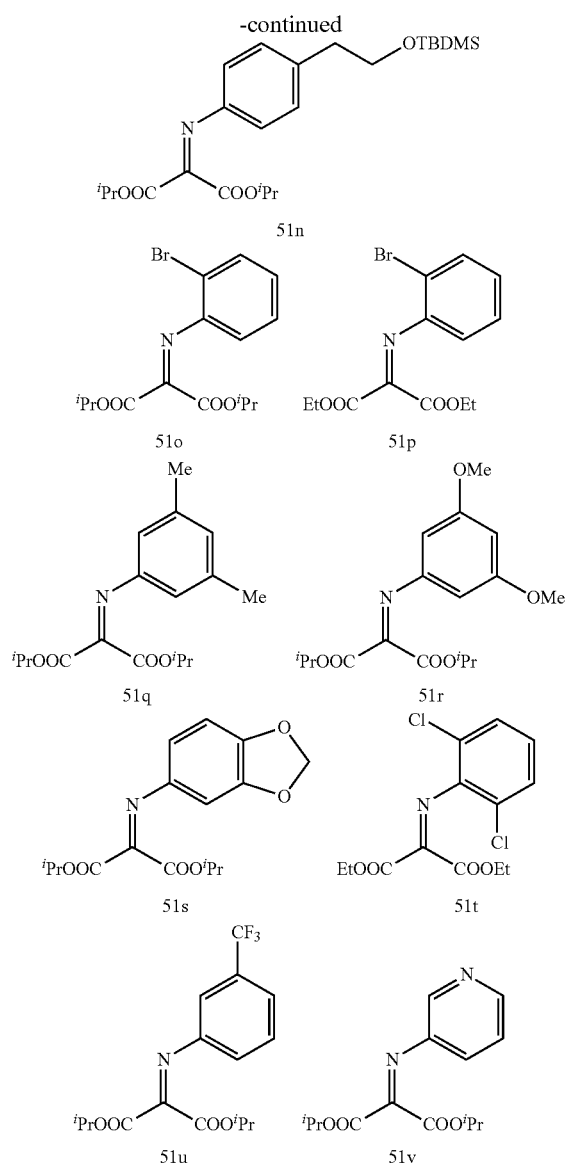

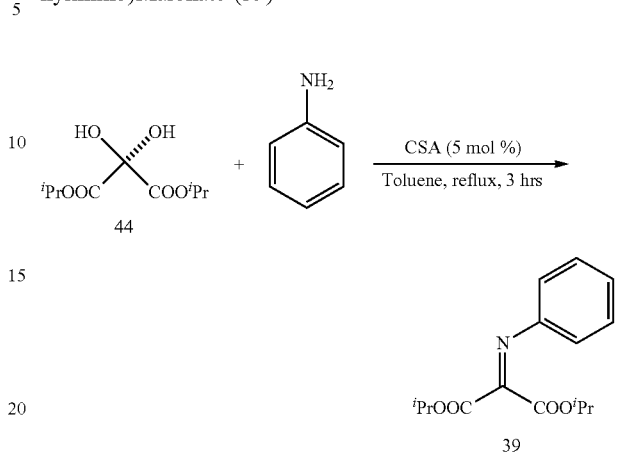

Standard Procedure for the Preparation of Iminomalonates Presented Above

Diisopropyl 2,2-dihydroxymalonate 44 (1 equiv) was taken in a flame dried flask and to this aliphatic or aromatic amine (1 equiv) was added followed by pTSA or CSA (5 mol %). To this mixture 5 Å molecular sieves were added followed by dry toluene (0.2 M) and heated to reflux using a Dean-Stark adapter for 3 h. Progress of the reaction was monitored by TLC. After confirming the completion of the reaction, heating was stopped and the reaction mixture was allowed to cool to room temperature. Toluene was removed under reduced pressure and the crude product was purified by column chromatography.

Note: One can use either pTSA or CSA and both are equally efficient in catalyzing the imine-formation reaction. The reaction also proceeds in the absence of catalyst but it takes twice as long. It is always better to purify the crude imine immediately after the reaction in order to obtain better yields. The imines are stable for 3 to 4 days in the freezer (−20° C.). Aliphatic imines are generally more stable and can be stored for longer periods of time compared to aromatic imines. All the above mentioned imines (39 to 51v) were prepared according to this standard procedure.

General Procedure for the Synthesis of Diisopropyl 2-(Phenylimino)Malonate (39)

Diisopropyl 2,2-dihydroxymalonate 44 (500 mg, 2.27 mmol, 1 equiv) was taken in a flame dried flask and to this aniline (0.20 mL, 2.27 mmol, 1 equiv) was added followed by camphor sulfonic acid (CSA) (26.4 mg, 5 mol %). To this mixture 5 Å molecular sieves were added followed by dry toluene (0.2 M, 11.4 mL) and heated to reflux using a Dean-Stark adapter for 3 h. Progress of the reaction was monitored TLC. After confirming the completion of the reaction, heating was stopped and the reaction mixture was allowed to cool to room temperature. Toluene was removed under reduced pressure and the crude product was purified by column chromatography to afford 39 as yellow viscous oil (420 mg, 67%).

Characterization Data of the Iminomalonate Substrates (as Displayed in Scheme 7)

1. Diisopropyl 2-(phenylimino)malonate (39)

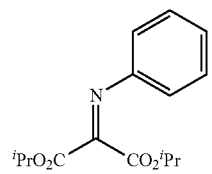

Standard procedure described above was followed for converting 4.54 mmol of 44 and aniline to 39 Yield: 67%; Physical State: yellow colored viscous oily liquid; $R_f$=0.37 (10% EtOAc/hexanes); $^1$H NMR (600 MHz, CDCl$_3$): δ 7.23 (t, J=7.8 Hz, 2H), 7.09 (t, J=7.5 Hz, 1H), 6.89 (d, J=7.6 Hz, 2H), 5.18 (hept, J=6.2 Hz, 1H), 4.94 (hept, J=6.2 Hz, 1H), 1.29 (d, J=6.4 Hz, 6H), 0.99 (d, J=6.5 Hz, 6H); $^{13}$C NMR (151 MHz, CDCl$_3$): δ 161.60, 160.11, 153.05, 147.57, 128.48, 126.17, 119.13, 70.66, 69.89, 21.26, 20.93; HRMS (CI-TOF): calc'd for $C_{15}H_{19}NO_4$ [M]$^+$ 277.1314; found 277.1314.

2. Diisopropyl 2-(methylimino)malonate (51a)

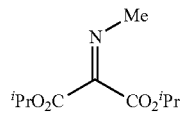

Standard procedure described above was followed for converting 9.08 mmol of 44 and methyl amine to 51a.

Yield: 33%; Physical State: pale yellow colored oily liquid; $R_f$=0.26 (10% EtOAc/hexanes); $^1$H NMR (600 MHz, CDCl$_3$): δ 5.02 (hept, J=6.4 Hz, 1H), 4.96 (hept, J=6.4 Hz, 1H), 3.25 (s, 3H), 1.11 (dd, J=8.1, 6.4 Hz, 12H); $^{13}$C NMR (151 MHz, CDCl$_3$): δ 161.06, 159.87, 155.04, 69.75, 69.47, 41.50, 21.02, 20.93; HRMS (ESI-TOF): calc'd for C$_{10}$H$_{17}$NO$_4$ [M+H]$^+$ 216.1230; found 216.1233.

3. Diisopropyl 2-((2,2,2-trifluoroethyl)imino)malonate (51b)

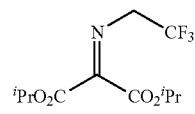

Standard procedure described above was followed for converting 2.27 mmol of 44 and trifluoroethyl amine to 51b.

Yield: 42%; Physical State: pale beige colored oily liquid; $R_f$=0.19 (10% EtOAc/hexanes); $^1$H NMR (600 MHz, CDCl$_3$): δ 5.21 (dhept, J=18.7, 6.1 Hz, 2H), 4.20 (q, J=9.1 Hz, 2H), 1.33 (dd, J=6.2, 2.0 Hz, 12H); $^{13}$C NMR (151 MHz, CDCl$_3$): δ 160.51, 159.42, 157.22, 126.60, 124.77, 122.93, 121.10, 71.16, 71.00, 55.23, 55.01, 54.79, 54.57, 21.52, 21.47; HRMS (ESI-TOF): calc'd for C$_{11}$H$_{16}$F$_3$NO$_4$ [M+Na]$^+$ 306.0924; found 306.0939.

4. Diisopropyl 2-((2-((tert-butyldimethylsilyl)oxy)ethyl)imino)malonate (51c)

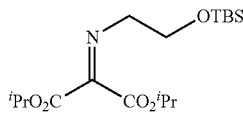

Standard procedure described above was followed for converting 3.80 mmol of 44 and TBDMS protected ethanolamine to 51c.

Yield: 26%; Physical State: pale yellow colored oily liquid; $R_f$=0.34 (10% EtOAc/hexanes); $^1$H NMR (600 MHz, CDCl$_3$): δ 5.19 (dp, J=29.1, 6.3 Hz, 2H), 3.92 (t, J=6.1 Hz, 2H), 3.70 (t, J=6.1 Hz, 2H), 1.32-1.28 (m, 12H), 0.84 (s, 9H), 0.02 (s, 6H); $^{13}$C NMR (151 MHz, CDCl$_3$): δ 161.67, 160.52, 154.95, 70.33, 70.07, 62.13, 57.47, 25.79, 21.59, 21.50, 18.24, −5.36; HRMS (CI-TOF): calc'd for C$_{17}$H$_{33}$NO$_5$Si [M+H]$^+$ 360.2206; found 360.2208.

5. Diisopropyl 2-(cyclopropylimino)malonate (51d)

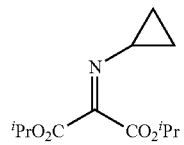

Standard procedure described above was followed for converting 2.27 mmol of 44 and cyclopropyl amine to 51d.

Yield: 94%; Physical State: colorless viscous oily liquid; $R_f$=0.41 (10% EtOAc/hexanes); $^1$H NMR (600 MHz, CDCl$_3$): δ 5.22 (hept, J=6.3 Hz, 1H), 5.13 (hept, J=6.3 Hz, 1H), 3.13 (tt, J=6.5, 3.1 Hz, 1H), 1.30 (d, J=6.3 Hz, 6H), 1.26 (d, J=6.3 Hz, 6H), 1.18 (p, J=4.2, 3.5 Hz, 2H), 1.10 (dt, J=6.6, 3.6 Hz, 2H); $^{13}$C NMR (151 MHz, CDCl$_3$): δ 162.21, 160.57, 151.72, 69.98, 69.78, 37.32, 21.56, 21.48, 11.80; HRMS (ESI-TOF): calc'd for C$_{12}$H$_{19}$NO$_4$ [M+H]$^+$ 242.1387; found 242.1343.

6. Diisopropyl 2-(butylimino)malonate (51e)

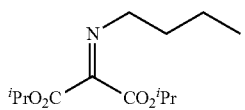

Standard procedure described above was followed for converting 4.54 mmol of 44 and n-butyl amine to 51e.

Yield: 53%; Physical State: colorless oily liquid; $R_f$=0.45 (10% EtOAc/hexanes); $^1$H NMR (600 MHz, CDCl$_3$): δ 5.22 (dq, J=12.6, 6.1 Hz, 1H), 5.16 (dq, J=12.4, 6.2 Hz, 1H), 3.55 (t, J=7.1 Hz, 2H), 1.68 (p, J=7.2 Hz, 2H), 1.38-1.25 (m, 14H), 0.89 (t, J=7.4 Hz, 3H); $^{13}$C NMR (151 MHz, CDCl$_3$): δ 162.17, 160.45, 153.93, 70.35, 69.90, 55.24, 31.87, 21.57, 21.49, 20.42, 13.64; HRMS (ESI-TOF): calc'd for C$_{13}$H$_{23}$NO$_4$ [M+H]$^+$ 258.1700; found 258.1702.

7. Diisopropyl 2-(phenethylimino)malonate (51f)

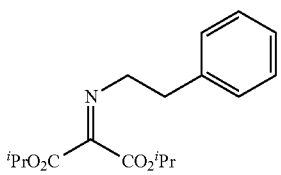

Standard procedure described above was followed for converting 4.54 mmol of 44 and phenethyl amine to 51f.

Yield: 77%; Physical State: pale yellow colored oily liquid; $R_f$=0.32 (10% EtOAc/hexanes); $^1$H NMR (600 MHz, CDCl$_3$): δ 7.25 (dd, J=9.5, 5.6 Hz, 2H), 7.19-7.14 (m, 3H), 5.18 (pd, J=6.3, 2.5 Hz, 2H), 4.01-3.69 (m, 2H), 3.15-2.88 (m, 2H), 1.28 (dd, J=22.7, 6.3 Hz, 12H); $^{13}$C NMR (151 MHz, CDCl$_3$): δ 161.54, 160.29, 154.19, 138.66, 128.48, 128.23, 126.17, 70.24, 69.87, 56.84, 36.16, 21.38, 21.32; HRMS (CI-TOF): calc'd for $C_{17}H_{23}NO_4$ [M+H]$^+$ 306.1705; found 306.1711.

8. Diisopropyl 2-(cyclopentylimino)malonate (51g)

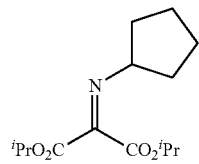

Standard procedure described above was followed for converting 4.54 mmol of 44 and cyclopentyl amine to 51g.

Yield: 84%; Physical State: pale yellow colored oily liquid; $R_f$=0.43 (10% EtOAc/hexanes); $^1$H NMR (600 MHz, CDCl$_3$): δ 5.04 (ddt, J=39.8, 12.1, 6.0 Hz, 2H), 3.98-3.44 (m, 1H), 1.76-1.64 (m, 4H), 1.58 (dq, J=14.2, 8.1, 7.4 Hz, 2H), 1.47 (t, J=5.8 Hz, 2H), 1.16 (dd, J=10.8, 6.5 Hz, 12H); $^{13}$C NMR (151 MHz, CDCl$_3$): δ 162.09, 160.09, 151.85, 69.78, 69.34, 65.09, 33.89, 24.55, 21.23, 21.13; HRMS (ESI-TOF): calc'd for $C_{14}H_{23}NO_4$ [M+H]$^+$ 270.1700; found 270.1712.

9. Diisopropyl 2-(cyclohexylimino)malonate (51h)

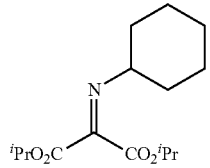

Standard procedure described above was followed for converting 2.27 mmol of 44 and cyclohexyl amine to 51h.

Yield: 66%; Physical State: pale yellow colored oily liquid; $R_f$=0.36 (10% EtOAc/hexanes); $^1$H NMR (600 MHz, CDCl$_3$): δ 5.24 (hept, J=6.1 Hz, 1H), 5.18 (hept, J=6.2 Hz, 1H), 3.33 (tt, J=10.1, 4.0 Hz, 1H), 1.79 (d, J=12.5 Hz, 2H), 1.68 (d, J=10.7 Hz, 2H), 1.65-1.55 (m, 3H), 1.31 (t, J=6.5 Hz, 12H), 1.23 (dq, J=24.4, 12.3, 11.8 Hz, 3H); $^{13}$C NMR (151 MHz, CDCl$_3$): δ 162.60, 160.54, 152.17, 70.37, 69.73, 64.66, 32.82, 25.19, 24.14, 21.62, 21.55; HRMS (ESI-TOF): calc'd for $C_{15}H_{25}NO_4$ [M+H]$^+$ 284.1856; found 284.1869.

10. Diisopropyl 2-((1-(tert-butoxycarbonyl)piperidin-4-yl)imino)malonate (51i)

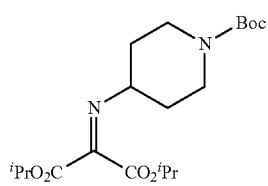

Standard procedure described above was followed for converting 4.54 mmol of 44 and boc protected 4-piperidinyl amine to 51i.

Yield: 82%; Physical State: colorless oily liquid; $R_f$=0.57 (30% EtOAc/hexanes); $^1$H NMR (600 MHz, CDCl$_3$): δ 5.02 (hept, J=6.0 Hz, 1H), 4.94 (hept, J=6.1 Hz, 1H), 3.82 (s, 2H), 3.34 (dt, J=9.4, 5.0 Hz, 1H), 2.67 (s, 2H), 1.57-1.49 (m, 2H), 1.45 (d, J=10.2 Hz, 2H), 1.22 (s, 9H), 1.09 (dd, J=9.0, 6.4 Hz, 12H); $^{13}$C NMR (151 MHz, CDCl$_3$): δ 161.38, 159.76, 154.06, 152.58, 78.81, 69.88, 69.50, 61.33, 31.33, 27.82, 21.08, 20.98; HRMS (ESI-TOF): calc'd for $C_{19}H_{32}N_2O_6$ [M+Na]$^+$ 407.2153; found 407.2168.

11. Tetraisopropyl 2,2'-(decane-1,10-diylbis(azanylylidene))dimalonate (51j)

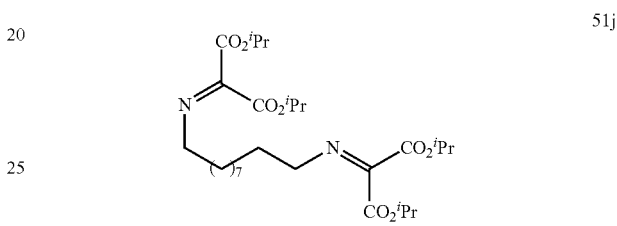

Standard procedure described above was followed for converting 8.0 mmol of 44 and 1,10-diaminodecane to 51j.

Yield: 79%; Physical State: colorless oily liquid; $R_f$=0.27 (20% EtOAc/hexanes); $^1$H NMR (600 MHz, CDCl$_3$): δ 5.29-5.09 (m, 4H), 3.54 (t, J=7.2 Hz, 4H), 1.68 (p, J=7.0 Hz, 4H), 1.29 (dd, J=6.3, 2.8 Hz, 26H), 1.24 (d, J=6.6 Hz, 10H); $^{13}$C NMR (151 MHz, CDCl$_3$): δ 162.14, 160.43, 153.88, 70.35, 69.89, 55.55, 29.82, 29.30, 29.18, 27.26, 21.58, 21.50; HRMS (ESI-TOF): calc'd for $C_{28}H_{48}N_2O_8$ [M+Na]$^+$ 563.3303; found 563.3317.

12. Diisopropyl 2-(m-tolylimino)malonate (51k)

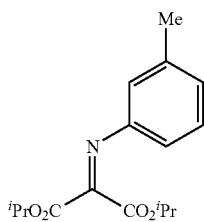

Standard procedure described above was followed for converting 4.54 mmol of 44 and m-toulidine to 51k.

Yield: 72%; Physical State: yellow colored oily liquid; $R_f$=0.41 (10% EtOAc/hexanes); $^1$H NMR (600 MHz, CDCl$_3$): δ 7.18 (t, J=7.6 Hz, 1H), 6.98 (d, J=7.6 Hz, 1H), 6.77 (d, J=8.6 Hz, 2H), 5.25 (hept, J=6.3 Hz, 1H), 5.04 (hept, J=6.3 Hz, 1H), 2.30 (s, 3H), 1.36 (d, J=6.3 Hz, 6H), 1.09 (d, J=6.3 Hz, 6H); $^{13}$C NMR (151 MHz, CDCl$_3$): δ 162.00, 160.42, 152.98, 147.74, 138.55, 128.56, 127.20, 119.98, 116.57, 70.88, 70.08, 21.53, 21.21, 21.19; HRMS (ESI-TOF): calc'd for $C_{16}H_2INO_4$ [M+H]$^+$292.1543; found 292.1556.

13. Diisopropyl 2-(p-tolylimino)malonate (51l)

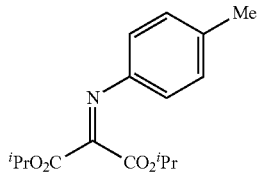

Standard procedure described above was followed for converting 2.27 mmol of 44 and p-toulidine to 51l.

Yield: 78%; Physical State: yellow colored oily liquid; $R_f$=0.40 (10% EtOAc/hexanes); $^1$H NMR (600 MHz, CDCl$_3$): δ 7.02 (d, J=7.9 Hz, 2H), 6.82 (d, J=7.9 Hz, 2H), 5.15 (dt, J=12.3, 6.1 Hz, 1H), 4.97 (dt, J=12.4, 6.1 Hz, 1H), 2.21 (s, 3H), 1.27 (d, J=6.3 Hz, 6H), 1.02 (d, J=6.3 Hz, 6H); $^{13}$C NMR (151 MHz, CDCl$_3$): δ 161.97, 160.18, 152.28, 144.91, 136.32, 129.05, 119.57, 70.47, 69.77, 21.22, 20.95, 20.60; HRMS (CI-TOF): calc'd for C$_{16}$H$_{21}$NO$_4$ [M]$^+$ 291.1471; found 291.1468.

14. Diisopropyl 2-((4-methoxyphenyl)imino)malonate (51m)

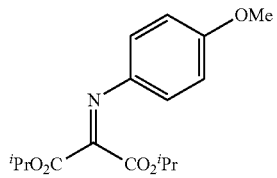

Standard procedure described above was followed for converting 2.27 mmol of 44 and p-anisidine to 51m.

Yield: 87%; Physical State: dark yellow colored viscous oily liquid; $R_f$=0.35 (20% EtOAc/hexanes); $^1$H NMR (600 MHz, CDCl$_3$): δ 7.03 (d, J=8.9 Hz, 2H), 6.83 (d, J=8.9 Hz, 2H), 5.23 (hept, J=6.3 Hz, 1H), 5.10 (hept, J=6.3 Hz, 1H), 3.76 (s, 3H), 1.34 (d, J=6.3 Hz, 6H), 1.14 (d, J=6.3 Hz, 6H); $^{13}$C NMR (151 MHz, CDCl$_3$): δ 162.86, 160.59, 158.92, 151.15, 140.40, 122.34, 113.99, 70.68, 70.07, 55.31, 21.52, 21.29. HRMS (ESI-TOF): calc'd for C$_{14}$H$_{18}$N$_2$O$_4$ [M+H]$^+$ 308.1492; found 308.1443.

15. Diisopropyl 2-((4-(2-((tert-butyldimethylsilyl)oxy)ethyl)phenyl)imino)malonate (51n)

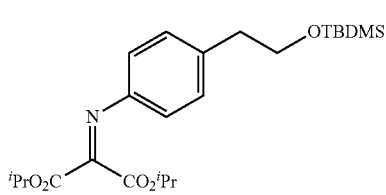

Standard procedure described above was followed for converting 3.80 mmol of 44 and 4-(2-((tert-butyldimethylsilyl)oxy)ethyl)aniline to 51n.

Yield: 54%; Physical State: dark yellow colored oily liquid; $R_f$=0.39 (10% EtOAc/hexanes); $^1$H NMR (600 MHz, CDCl$_3$): δ 7.13 (d, J=8.3 Hz, 2H), 6.90 (d, J=8.3 Hz, 2H), 5.23 (hept, J=6.2 Hz, 1H), 5.03 (hept, J=6.3 Hz, 1H), 3.74 (t, J=6.7 Hz, 2H), 2.75 (t, J=6.7 Hz, 2H), 1.34 (d, J=6.4 Hz, 6H), 1.08 (d, J=6.3 Hz, 6H), 0.82 (s, 9H), −0.08 (s, 6H); $^{13}$C NMR (151 MHz, CDCl$_3$): δ 162.13, 160.38, 152.64, 145.74, 138.07, 129.43, 119.64, 70.76, 69.99, 64.05, 38.92, 25.77, 21.49, 21.20, 18.14, −5.57; HRMS (ESI-TOF): calc'd for C$_{23}$H$_{37}$NO$_5$Si [M+H]$^+$ 436.2514; found 436.2541.

16. Diisopropyl 2-((2-bromophenyl)imino)malonate (51o)

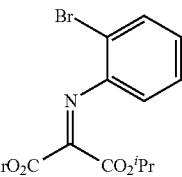

Standard procedure described above was followed for converting 4.54 mmol of 44 and 2-bromo aniline to 51o.

Yield: 52%; Physical State: pale yellow colored oily liquid; $R_f$=0.35 (10% EtOAc/hexanes); $^1$H NMR (600 MHz, CDCl$_3$): δ 7.53 (dd, J=8.0, 1.1 Hz, 1H), 7.19 (td, J=7.7, 1.2 Hz, 1H), 6.99 (td, J=7.8, 1.5 Hz, 1H), 6.74 (dd, J=7.9, 1.5 Hz, 1H), 5.24 (hept, J=6.3 Hz, 1H), 4.94 (hept, J=6.3 Hz, 1H), 1.35 (d, J=6.3 Hz, 6H), 1.01 (d, J=6.3 Hz, 6H); $^{13}$C NMR (151 MHz, CDCl$_3$): δ 160.44, 160.00, 154.34, 146.80, 132.65, 127.44, 126.87, 118.68, 113.70, 71.09, 70.32, 21.43, 21.04; HRMS (CI-TOF): calc'd for C$_{15}$H$_{18}$BrNO$_4$ [M+H]$^+$ 357.0399; found 357.0390.

17. Diethyl 2-((2-bromophenyl)imino)malonate (51p)

Standard procedure described above was followed for converting 4.35 mmol of diethylketomalonate and 2-bromo aniline to 51p.

Yield: 79%; Physical State: yellow colored oily liquid; $R_f$=0.50 (20% EtOAc/hexanes); $^1$H NMR (600 MHz, CDCl$_3$): δ 7.52 (dd, J=8.0, 1.0 Hz, 1H), 7.19 (td, J=7.7, 1.1 Hz, 1H), 6.99 (td, J=7.9, 1.4 Hz, 1H), 6.76-6.69 (m, 1H), 4.39 (q, J=7.1 Hz, 2H), 4.07 (q, J=7.1 Hz, 2H), 1.34 (t, J=7.2 Hz, 3H), 0.96 (t, J=7.1 Hz, 3H); $^{13}$C NMR (151 MHz, CDCl$_3$): δ 160.71, 160.46, 153.51, 146.53, 132.66, 127.50, 127.04, 118.43, 113.77, 62.88, 61.96, 13.79, 13.41; HRMS (ESI-TOF): calc'd for C$_{13}$H$_{14}$BrNO$_4$ [M+H]$^+$ 328.0179; found 328.0179.

18. Diisopropyl 2-((3,5-dimethylphenyl)imino)malonate (51q)

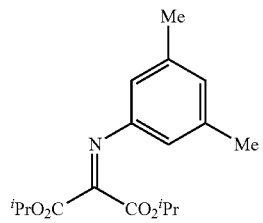

Standard procedure described above was followed for converting 4.54 mmol of 44 and 3,5-dimethyl aniline to 51q Yield: 66%; Physical State: yellow colored oily liquid; $R_f$=0.40 (10% EtOAc/hexanes); $^1$H NMR (600 MHz, CDCl$_3$): δ 6.80 (s, 1H), 6.59 (s, 2H), 5.24 (hept, J=6.3 Hz, 1H), 5.05 (hept, J=6.3 Hz, 1H), 2.25 (s, 6H), 1.35 (d, J=6.3 Hz, 6H), 1.11 (d, J=6.3 Hz, 6H); $^{13}$C NMR (151 MHz, CDCl$_3$): δ 162.07, 160.42, 152.65, 147.67, 138.31, 128.10, 117.18, 70.73, 69.96, 21.47, 21.19, 21.03; HRMS (ESI-TOF): calc'd for C$_{17}$H$_{23}$NO$_4$ [M+H]$^+$ 306.1700; found 306.1789.

19. Diisopropyl 2-((3,5-dimethoxyphenyl)imino)malonate (51r)

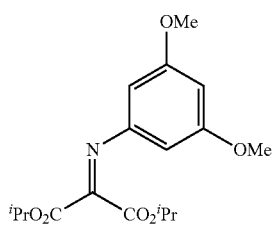

Standard procedure described above was followed for converting 2.27 mmol of 44 and 3,5-dimethoxy aniline to 51r Yield: 23%; Physical State: dark yellow colored viscous oily liquid; $R_f$=0.38 (20% tOAc/hexanes); $^1$H NMR (600 MHz, CDCl$_3$): δ 6.21 (s, 1H), 6.06 (d, J=2.0 Hz, 2H), 5.17 (hept, J=6.2 Hz, 1H), 4.99 (hept, J=6.2 Hz, 1H), 3.65 (s, 6H); 1.29 (d, J=6.3 Hz, 6H), 1.05 (d, J=6.3 Hz, 6H); $^{13}$C NMR (151 MHz, CDCl$_3$): δ 161.60, 160.71, 160.07, 153.14, 149.33, 98.34, 97.51, 70.76, 70.01, 55.07, 21.32, 21.29, 21.02; HRMS (ESI-TOF): calc'd for C$_{17}$H$_{23}$NO$_6$ [M+Na]$^+$ 360.1418; found 360.1418.

20. Diisopropyl 2-(benzo[d][1,3]dioxol-5-ylimino) malonate (51s)

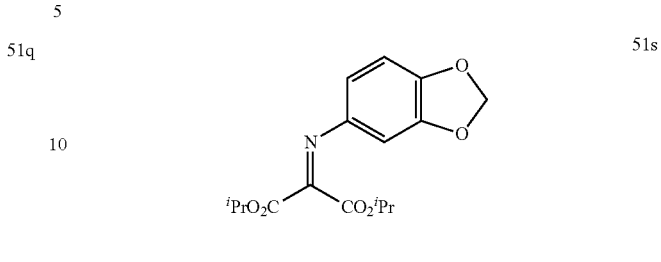

Standard procedure described above was followed for converting 4.54 mmol of 44 and 3,4-methylenedioxy) aniline to 51s Yield: 73%; Physical State: dark yellow colored oily liquid; $R_f$=0.24 (10% EtOAc/hexanes); $^1$H NMR (600 MHz, CDCl$_3$): δ 6.72 (d, J=8.2 Hz, 1H), 6.60 (d, J=2.1 Hz, 1H), 6.53 (dd, J=8.2, 2.1 Hz, 1H), 5.93 (s, 2H), 5.22 (hept, J=6.3 Hz, 1H), 5.11 (hept, J=6.3 Hz, 1H), 1.33 (d, J=6.3 Hz, 6H), 1.16 (d, J=6.3 Hz, 6H); $^{13}$C NMR (151 MHz, CDCl$_3$): δ 162.57, 160.44, 151.69, 147.97, 146.82, 141.74, 114.21, 107.98, 102.23, 101.50, 70.77, 70.16, 21.49, 21.28; HRMS (CI-TOF): calc'd for C$_{16}$H$_{19}$NO$_6$ [M]$^+$ 321.1212; found 321.1208.

21. Diethyl 2-((2,6-dichlorophenyl)imino)malonate (51t)

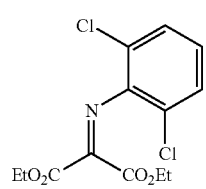

Standard procedure described above was followed for converting 5.74 mmol of diethylketomalonate and 2,6-dichloro aniline to 51t.

Yield: 83%; Physical State: yellow colored oily liquid; $R_f$=0.45 (10% EtOAc/hexanes); $^1$H NMR (600 MHz, CDCl$_3$): δ 7.28 (d, J=8.1 Hz, 2H), 7.00 (t, J=8.1 Hz, 1H), 4.46 (q, J=7.1 Hz, 2H), 4.15 (q, J=7.1 Hz, 2H), 1.41 (t, J=7.2 Hz, 3H), 1.05 (t, J=7.1 Hz, 3H); $^{13}$C NMR (151 MHz, CDCl$_3$): δ 160.84, 159.02, 155.71, 143.23, 127.88, 125.79, 123.03, 63.12, 62.40, 13.91, 13.48; HRMS (ESI-TOF): calc'd for C$_{13}$H$_{13}$Cl$_2$NO$_4$ [M+H]$^+$ 318.0294; found 318.0294.

22. Diisopropyl 2-((3-(trifluoromethyl)phenyl)imino)malonate (51u)

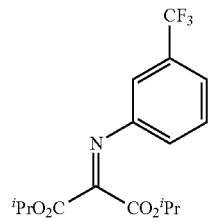

51u

Standard procedure described above was followed for converting 2.27 mmol of 44 and m-trifluoromethyl aniline to 51u Yield: 81%; Physical State: yellow colored oily liquid; $R_f$=0.36 (10% EtOAc/hexanes); $^1$H NMR (600 MHz, CDCl$_3$): δ 7.37-7.30 (m, 2H), 7.09 (s, 1H), 7.05-7.01 (m, 1H), 5.14 (hept, J=6.3 Hz, 1H), 4.90 (hept, J=6.2 Hz, 1H), 1.24 (d, J=6.4 Hz, 6H), 0.95 (d, J=6.4 Hz, 6H); $^{13}$C NMR (151 MHz, CDCl$_3$): δ 160.84, 159.72, 154.48, 148.07, 131.33, 131.11, 130.90, 130.68, 129.28, 126.09, 124.29, 122.50, 120.68, 115.73, 115.70, 115.68, 115.65, 70.94, 70.36, 21.08, 20.72; HRMS (ESI-TOF): calc'd for C$_{16}$H$_{18}$F$_3$NO$_4$ [M+H]$^+$ 346.1261; found 346.1261.

23. Diisopropyl 2-(pyridin-3-ylimino)malonate (51v)

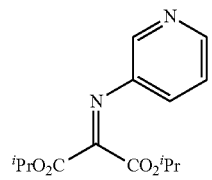

51v

Standard procedure described above was followed for converting 4.54 mmol of 44 and 3-aminopyridine to 51v Yield: 86%; Physical State: yellow colored oily liquid; $R_f$=0.28 (30% EtOAc/hexanes); $^1$H NMR (600 MHz, CDCl$_3$): δ 8.39 (dd, J=4.6, 1.5 Hz, 1H), 8.20 (d, J=2.4 Hz, 1H), 7.29-7.21 (m, 2H), 5.21 (hept, J=6.3 Hz, 1H), 4.99 (hept, J=6.3 Hz, 1H), 1.32 (d, J=6.4 Hz, 6H), 1.04 (d, J=6.4 Hz, 6H); $^{13}$C NMR (151 MHz, CDCl$_3$): δ 160.93, 159.78, 154.76, 147.40, 143.77, 139.84, 126.77, 123.12, 71.23, 70.68, 21.38, 21.12; HRMS (ESI-TOF): calc'd for C$_{14}$H$_{18}$N$_2$O$_4$ [M+H]$^+$ 279.1339; found 279.1336.

Procedure for the Synthesis of 39 Using Nitroso Benzene (this Procedure was Adapted from Literature Reported Procedure)(4)

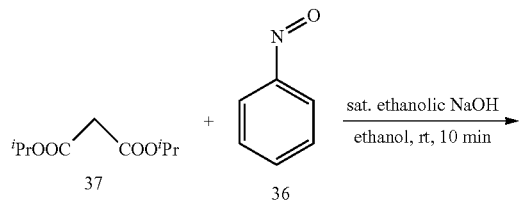

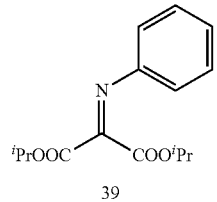

39

To a solution of diisopropyl malonate (500 mg, 2.65 mmol, 1 equiv) and nitroso benzene (313 mg, 2.92 mmol, 1 equiv) in absolute ethanol (1.25 mL, 2.2M), a saturated ethanolic solution of NaOH was added dropwise until the blue color of the solution turns pale brown. The reaction mixture was allowed to stir for 10 minutes and the solvent was removed under reduced pressure and the crude product was purified by column chromatography to afford 39 as viscous yellow colored oily liquid (449 mg, 61%). Note: The crude imine prepared by this method is very unstable and should be used immediately.

Optimization of the Reaction Conditions for Amination

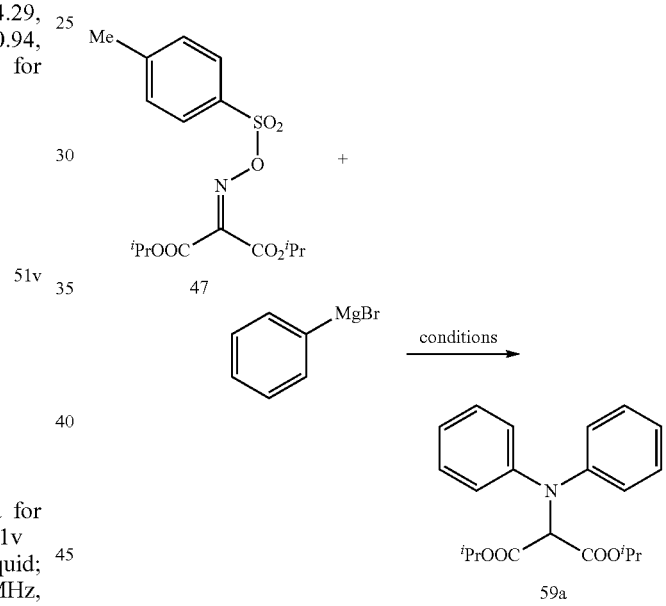

TABLE 4

Optimization of conditions for amination

| Entry | Solvent (M) | PhMgBr (M) | Temperature (° C.) | Time | Yield (%) |
|---|---|---|---|---|---|
| 1 | THF (0.2M) | 0.7M in THF | −78° C. | 10 min | 22 |
| 2 | DCM (0.2M) | 0.7M in THF | −78° C. (3 h) to RT | Overnight | 61 |
| 3 | DME (0.2M) | 0.76M in THF | −78° C. | 3 h | 24 |
| 4 | Et$_2$O (0.2M) | 0.88M in THF | −78° C. | 3 h | (Starting material was not totally consumed) |
| 5 | DCE (0.2M) | 0.26M in THF | −78° C. (3 h) to RT | Overnight | 22 |
| 6 | Toluene (0.2M) | 0.26M in THF | −78° C. (3 h) to RT | Overnight | 31 |

TABLE 4-continued

Optimization of conditions for amination

| Entry | Solvent (M) | PhMgBr (M) | Temperature (°C.) | Time | Yield (%) |
|---|---|---|---|---|---|
| 7 | DCM (0.2M) | 0.6M in THF | −78° C. | 1 h | 30 |
| 8 | DCE (0.2M) | 0.6M in THF | −78° C. | 1 h | 13 |
| 9 | Toluene (0.2M) | 0.6M in THF | −78° C. | 1 h | 42 |
| 10 | Toluene (0.2M) | 0.74M in THF | −42° C. | 1 h 15 min | 45 |
| 11 | DCM (0.2M) | 0.74M in THF | −42° C. | 1 h 15 min | 56 |
| 12 | DCM (0.2M) | 0.76M in THF | −78° C. | 1 h | 63 |
| 13 | DCM (0.1M) | 0.76M in THF | −78° C. | 1 h | 75 |
| 14 | DCM (0.1M) | 0.76M in THF | −42° C. | 1 h | 63 |
| 15 | DCM (0.1M) | 1.6M in Et$_2$O | −78° C. | 1 h | (Reaction was messy with lot of spots on TLC) |
| 16 | DCM (0.05M) | 1.6M in Et$_2$O | −78° C. | 1 h | (Reaction was messy with lot of spots on TLC) |
| 17 | DCM (0.1M) | 0.66M in THF | −78° C. | 1 h | 66 |
| 18 | DCM (0.05M) | 0.66M in THF | −78° C. | 1 h | 66 |

Screening of Different Activating Groups

TABLE 5

Evaluation of different activating groups

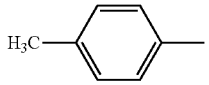

| Entry | R | Yield (%) |
|---|---|---|
| 1 | —CH$_3$ | 68% |
| 2 | 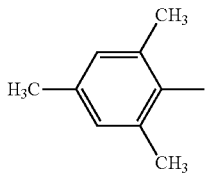 | 75% |
| 3 | 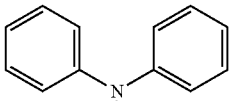 | 67% |

TABLE 5-continued

Evaluation of different activating groups

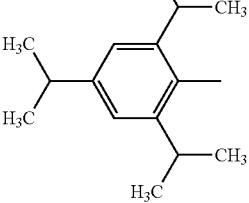

| Entry | R | Yield (%) |
|---|---|---|
| 4 | 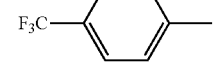 | 60% |
| 5 | 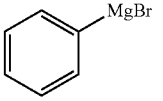 | 62% |

Screening of Different Animating Agents

TABLE 6

Evaluation of different aminating agents

| Entry | R | Yield (%) |
|---|---|---|
| 1 | Me | 63 |
| 2 | Et | 62 |
| 3 | $^i$Pr | 75 |
| 4 | $^t$Bu | 55 |

General Experimental Procedures (Methods C Through H) Amination of Aryl and Alkyl Metals Using Doubly Electrophilic Aminating Agent 47

Method C: To a flame dried 25 mL round bottom flask, activated magnesium turnings (7.5 mmol, 1.5 equiv) were added under argon followed by 2.5 mL of anhydrous THF. To this mixture 2 drops of 1,2-dibromoethane were added under constant stirring. After 5 min, a solution of aryl or alkyl bromide (5.0 mmol, 1.0 equiv) in 2.5 mL of anhydrous THF was added dropwise over 10-15 minutes to the suspension. This reaction is slightly exothermic but no external cooling is required. After the flask cools to room temperature by itself, the Grignard reagent is titrated using the standard procedure (Love & Jones, 1999) and the concentration is determined. Next, to a thick-walled flame dried reaction vial, aminating agent 47 (1.0 mmol, 1.0 equiv) followed by anhydrous DCM (10 mL, 0.1M) were added under argon. The resulting solution of 47 was cooled to −78° C. by means of dry ice/acetone bath and the freshly prepared Grignard reagent (2.1 mmol, 2.1 equiv) was added via syringe over a period of 1 min under constant stirring. After stirring for 1 hour at −78° C., the reaction mixture was quenched using saturated $NH_4Cl$ solution (3 mL) and allowed to warm to room temperature.

Workup and purification: After quenching, the reaction mixture was diluted with water (20 mL) and the organic layer was separated. The aqueous layer was then extracted with DCM twice (2×20 mL) and the combined organic layers were dried over anhydrous $Na_2SO_4$ and concentrated. The crude product was purified by column chromatography.

Method D: This procedure was adapted from the literature (Krasovskiy & Knochel, 2004). To a flame dried 25 mL round bottom flask, commercially available iPrMgCl.LiCl solution in THF (1.3M; 1.1 mmol, 1.1 eq) was added under argon. This mixture was cooled to −15° C. in case of aryl bromides and to −45° C. in case of aryl iodides and the corresponding solution of aryl bromide or iodide (1.0 mmol, 1.0 equiv) in THF was added in 1 min and stirred for 30 min. This turbo Grignard reagent was then titrated and the concentration was determined. To a thick-walled flame dried reaction vial, aminating agent (1.0 mmol, 1.0 equiv) followed by anhydrous DCM (10 mL, 0.1M) was added under argon. This reaction mixture was cooled to −78° C. by means of dry ice/acetone bath and the freshly prepared Grignard reagent (2.1 mmol, 2.1 equiv) was added in 1 min under constant stirring. After stirring for 1 hour at −78° C. the reaction mixture was quenched using saturated $NH_4Cl$ solution (3 mL) and allowed to warm to room temperature.

Workup and purification: After quenching, the reaction mixture was diluted with water (20 mL) and the organic layer was separated. The aqueous layer was then extracted with DCM twice (2×20 mL) and the combined organic layers were dried over anhydrous $Na_2SO_4$ and concentrated. The crude product was purified by column chromatography.

Method E (Amination Using N-Substituted Diisopropyl Iminomalonates):

To a flame dried 25 mL round bottom flask, activated magnesium turnings (7.5 mmol, 1.5 equiv) were added under argon followed by 2.5 mL of anhydrous THF. To this mixture 2 drops of 1,2-dibromoethane were added under constant stirring. After 5 min, a solution of aryl or alkyl bromide (5.0 mmol, 1.0 equiv) in 2.5 mL of anhydrous THF was added dropwise over 10-15 minutes to the suspension. This reaction is slightly exothermic but no external cooling is required. After the flask cools to room temperature by itself, the Grignard reagent is titrated using the standard procedure (Love & Jones, 1999) and the concentration is determined. For making the turbo Grignard reagent, follow Method D. To a thick-walled flame dried reaction vial, iminomalonate (1.0 mmol, 1.0 equiv) dissolved in anhydrous DCM (10 mL, 0.1M) was added under argon. This reaction mixture was cooled to −78° C. by means of dry ice/acetone bath and the freshly prepared Grignard reagent (1.1 mmol, 1.1 equiv) was added over 1 min while maintaining constant stirring. After stirring for 1 hour at −78° C. the reaction was quenched using saturated $NH_4Cl$ solution (3 mL) and allowed to warm to room temperature.

Workup and purification: After quenching, the reaction mixture was diluted with water (20 mL) and the organic layer was separated. The aqueous layer was then extracted with DCM twice (2×20 mL) and the combined organic layers were dried over anhydrous $Na_2SO_4$ and concentrated. The crude product was purified by column chromatography.

Method F: To a thick-walled flame dried reaction vial, iminomalonate (1.0 mmol, 1.0 equiv) dissolved in anhydrous THF (10 mL, 0.1M) was added under argon. This solution was cooled to −78° C. by means of dry ice/acetone bath and the commercially available aryl or alkyl lithium solution in THF (1.1 mmol, 1.1 equiv) was added dropwise under constant stirring. After stirring for 1 hour at −78° C. the reaction was quenched using saturated $NH_4Cl$ solution (3 mL).

Method G: This procedure was adapted from the literature with slight modifications (Kattamuri et al, 2013). In a thick-walled flame dried reaction vial, methyl-2-bromo acetate (2.0 mmol, 2.0 equiv) was taken in anhydrous THF (10 mL, 0.2M) under argon and cooled to −78° C. using dry ice/acetone bath. To this cooled reaction mixture, commercially available LiHMDS (1M solution in THF) (2.1 mmol, 2.1 equiv) was added dropwise and stirred for 45 min. Then iminomalonate (1.0 mmol, 1.0 equiv) dissolved in anhydrous THF (10 mL, 0.1M) was added slowly dropwise to the enolate solution and continued stirring for 2 h. Then the reaction was quenched using saturated $NH_4Cl$ solution (3 mL).

Workup and purification: After quenching, the reaction mixture was diluted with water (20 mL) and the organic layer was separated. The aqueous layer was then extracted with EtOAc twice (2×20 mL) and the combined organic layers were washed with brine (30 mL) once, dried over anhydrous $Na_2SO_4$ and concentrated. The crude product was purified by column chromatography.

Method H: In a thick-walled flame dried reaction vial, acetophenone (2.0 mmol, 2.0 equiv) was dissolved in anhydrous THF (5 mL, 0.4M) under argon and cooled to −78° C. using dry ice/acetone bath. To this cooled reaction mixture, commercially available LiHMDS (1M solution in THF) (2.1 mmol, 2.1 equiv) was added dropwise and stirred for 45 min. Then iminomalonate (1.0 mmol, 1.0 equiv) dissolved in anhydrous THF (5 mL, 0.2M) was added slowly dropwise to the enolate solution and continued stirring for 2 h at −78° C. Then the reaction was quenched using saturated $NH_4Cl$ solution (3 mL).

Workup and purification: After quenching, the reaction mixture was diluted with water (20 mL) and the organic layer was separated. The aqueous layer was then extracted with EtOAc twice (2×20 mL) and the combined organic layers were washed with brine (30 mL) once, dried over anhydrous $Na_2SO_4$ and concentrated. The crude product was purified by column chromatography.

Characterization Data of the Products Made Using the Singly- and Doubly-Electrophilic Aminating Agents (as Displayed in Schemes 2-4)

1. Diisopropyl 2-(methyl(phenyl)amino)malonate (55a)

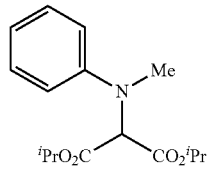

Yield: 68% (Method E); Physical State: dark purple colored waxy solid; $R_f$=0.52 (8:1 EtOAc:hexanes); $^1$H NMR (600 MHz, CDCl$_3$): δ 7.31-7.24 (m, 2H), 6.86-6.80 (m, 3H), 5.16 (hept, J=6.3 Hz, 2H), 5.08 (s, 1H), 3.11 (s, 3H), 1.31 (d, J=6.3 Hz, 12H); $^{13}$C NMR (151 MHz, CDCl$_3$): δ 167.18, 149.04, 129.11, 118.32, 113.31, 69.52, 66.14, 35.75, 21.62, 21.58; HRMS (ESI-TOF): calc'd for $C_{16}H_{23}NO_4$ [M+H]$^+$ 294.1700; found 294.1703.

2. Diisopropyl 2-(isopropyl(methyl)amino)malonate (55b)

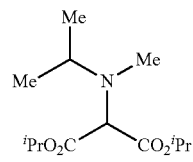

Yield: 80% (Method E); Physical State: colorless oily liquid; $R_f$=0.62 (20% EtOAc/hexanes); $^1$H NMR (600 MHz, CDCl$_3$): δ 4.97 (hept, J=6.3 Hz, 2H), 4.06 (s, 1H), 2.90 (hept, J=6.5 Hz, 1H), 2.37 (s, 3H), 1.15 (d, J=6.4 Hz, 12H), 0.97 (d, J=6.6 Hz, 6H); $^{13}$C NMR (151 MHz, CDCl$_3$): δ 167.78, 68.29, 66.87, 52.83, 33.92, 21.29, 21.27, 19.53; HRMS (ESI-TOF): calc'd for $C_{13}H_{25}NO_4$ [M+H]$^+$ 260.1856; found 260.1846.

Note: For this reaction to form 55b, directly iPrMgCl.LiCl solution in THF was added on to the imine.

3. Diisopropyl 2-(phenyl(2,2,2-trifluoroethyl)amino)malonate (55c)

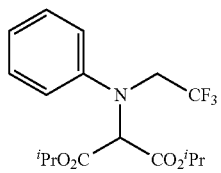

Yield: 34% (Method E); Physical State: orange colored waxy solid; $R_f$=0.59 (8:1 EtOAc:hexanes); $^1$H NMR (600 MHz, CDCl$_3$): δ 7.28 (t, J=7.9 Hz, 2H), 7.04 (d, J=8.1 Hz, 2H), 6.98 (t, J=7.3 Hz, 1H), 5.10 (hept, J=6.2 Hz, 2H), 4.88 (s, 1H), 4.24-4.14 (m, 2H), 1.26 (dd, J=16.6, 6.3 Hz, 12H); $^{13}$C NMR (151 MHz, CDCl$_3$): δ 166.81, 148.25, 129.22, 127.82, 125.96, 124.10, 122.23, 121.98, 118.19, 70.10, 68.20, 51.28, 51.06, 50.84, 50.62, 21.50; HRMS (ESI-TOF): calc'd for $C_{17}H_{22}F_3NO_4$ [M+H]$^+$ 362.1574; found 362.1581.

4. Diisopropyl 2-((2-bromophenyl)(2,2,2-trifluoroethyl)amino)malonate (55d)

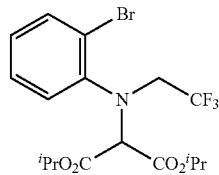

Yield: 79% (Method E); Physical State: colorless oily liquid; $R_f$=0.72 (20% EtOAc/hexanes); $^1$H NMR (600 MHz, CDCl$_3$): δ 7.63 (d, J=7.8 Hz, 1H), 7.32 (t, J=7.4 Hz, 1H), 7.25-7.17 (m, 2H), 5.99 (d, J=52.9 Hz, 1H), 5.14 (dt, J=12.3, 6.0 Hz, 1H), 5.03 (s, 1H), 4.07-3.51 (m, 2H), 1.79-0.76 (m, 12H); $^{13}$C NMR (151 MHz, CDCl$_3$): δ 169.21, 155.69, 155.46, 133.60, 133.39, 133.19, 130.72, 130.54, 130.42, 127.52, 126.69, 126.45, 124.82, 124.63, 122.96, 122.77, 121.08, 120.92, 70.57, 69.67, 63.59, 46.52, 46.30, 46.07, 45.83, 22.01, 21.88, 21.78, 21.64, 21.47; HRMS (ESI-TOF): calc'd for $C_{17}H_{21}BrF_3NO_4$ [M+H]$^+$ 440.0679; found 440.0674.

5. Diisopropyl 2-((2-((tert-butyldimethylsilyl)oxy)ethyl)(phenyl)amino)malonate (55e)

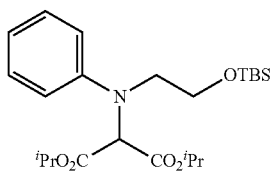

Yield: 58% (Method E); Physical State: dark yellow colored oily liquid; $R_f$=0.53 (8:1 EtOAc:hexanes); $^1$H NMR (600 MHz, CDCl$_3$): δ 7.23 (t, J=8.0 Hz, 2H), 6.86 (d, J=8.2 Hz, 2H), 6.81 (t, J=7.3 Hz, 1H), 5.11 (hept, J=6.2 Hz, 2H), 5.00 (s, 1H), 3.80 (t, J=7.3 Hz, 2H), 3.59 (t, J=7.3 Hz, 2H), 1.27 (dd, J=8.8, 6.3 Hz, 12H), 0.91 (s, 9H), 0.06 (s, 6H); $^{13}$C NMR (151 MHz, CDCl$_3$): δ 167.31, 147.98, 129.07, 118.83, 114.46, 69.59, 67.10, 60.88, 51.64, 25.88, 21.59, 18.23; HRMS (ESI-TOF): calc'd for $C_{23}H_{39}NO_5Si$ [M+H]$^+$ 438.2670; found 438.3076.

6. Diisopropyl 2-(dicyclopropylamino)malonate (55f)

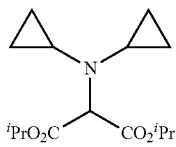
55f

Yield: 89% (Method E); Physical State: colorless oily liquid; $R_f$=0.21 (5% EtOAc/hexanes); $^1$H NMR (600 MHz, CDCl$_3$): δ 5.00 (hept, J=6.2 Hz, 2H), 4.15 (s, 1H), 2.52 (tt, J=6.8, 3.9 Hz, 2H), 1.18 (dd, J=6.4, 3.2 Hz, 12H), 0.39 (p, J=4.6, 3.8 Hz, 4H), 0.37-0.31 (m, 4H); $^{13}$C NMR (151 MHz, CDCl$_3$): δ 167.43, 70.39, 68.46, 34.51, 21.51, 21.44, 6.31; HRMS (ESI-TOF): calc'd for C$_{15}$H$_{25}$NO$_4$ [M+H]$^+$ 284.1856; found 284.1861.

7. Diisopropyl 2-(cyclobutyl(cyclopropyl)amino)malonate (55g)

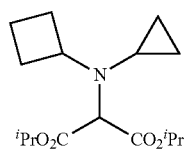
55g

Yield: 85% (Method E); Physical State: colorless oily liquid; $R_f$=0.39 (10% EtOAc/hexanes); $^1$H NMR (600 MHz, CDCl$_3$): δ 5.00 (hept, J=6.3 Hz, 2H), 4.10 (s, 1H), 3.58 (ddd, J=16.8, 9.4, 7.4 Hz, 1H), 2.29 (tt, J=6.7, 3.9 Hz, 1H), 2.06-1.97 (m, 2H), 1.96-1.89 (m, 2H), 1.56-1.38 (m, 2H), 1.20 (dd, J=6.5, 3.2 Hz, 12H), 0.49-0.43 (m, 2H), 0.42-0.35 (m, 2H); $^{13}$C NMR (151 MHz, CDCl$_3$): δ 167.78, 68.45, 67.55, 57.47, 30.98, 28.79, 21.47, 21.40, 14.57, 6.57; HRMS (ESI-TOF): calc'd for C$_{16}$H$_{27}$NO$_4$ [M+H]$^+$ 298.2013; found 298.2024.

8. Diisopropyl 2-(cyclopropyl(phenyl)amino)malonate (55h)

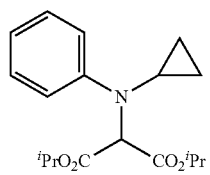
55h

Yield: 73% (Method E); Physical State: dark brown colored oily liquid; $R_f$=0.63 (8:1 EtOAc:hexanes); $^1$H NMR (600 MHz, CDCl$_3$): δ 7.22 (t, J=7.9 Hz, 2H), 6.92 (d, J=8.2 Hz, 2H), 6.82 (t, J=7.3 Hz, 1H), 5.11 (hept, J=6.1 Hz, 2H), 4.91 (s, 1H), 2.87-2.76 (m, 1H), 1.27 (d, J=6.2 Hz, 6H), 1.23 (d, J=6.2 Hz, 6H), 0.87-0.81 (m, 2H), 0.78 (d, J=6.6 Hz, 2H); $^{13}$C NMR (151 MHz, CDCl$_3$): δ 167.35, 148.71, 128.66, 118.80, 114.85, 69.52, 69.00, 31.63, 21.60, 21.57, 9.39; HRMS (ESI-TOF): calc'd for C$_{18}$H$_{25}$NO$_4$ [M+H]$^+$ 320.1856; found 320.1865.

9. Diisopropyl 2-(cyclopropyl(4-(trifluoromethoxy)phenyl)amino)malonate (55i)

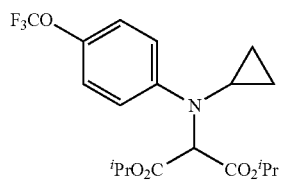
55i

Yield: 19% (Method E); Physical State: beige colored viscous oily liquid; $R_f$=0.42 (10% EtOAc/hexanes); $^1$H NMR (600 MHz, CDCl$_3$): δ 7.07 (d, J=8.7 Hz, 2H), 6.91 (d, J=9.2 Hz, 2H), 5.09 (hept, J=6.3 Hz, 2H), 4.87 (s, 1H), 2.85-2.79 (m, 1H), 1.26 (d, J=6.3 Hz, 6H), 1.19 (d, J=6.3 Hz, 6H), 0.83-0.76 (m, 4H); $^{13}$C NMR (151 MHz, CDCl$_3$): δ 167.10, 147.33, 141.73, 121.59, 115.61, 69.76, 69.23, 32.53, 21.58, 21.50, 9.53; HRMS (ESI-TOF): calc'd for C$_{19}$H$_{24}$F$_3$NO$_5$ [M+H]$^+$ 404.1679; found 404.1680.

10. Diisopropyl 2-(dibutylamino)malonate (55j)

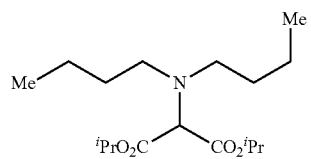
55j

Yield: 56% (Method F); Physical State: colorless oily liquid; $R_f$=0.53 (10% EtOAc/hexanes); $^1$H NMR (600 MHz, CDCl$_3$): δ 5.06 (hept, J=6.0 Hz, 2H), 4.13 (s, 1H), 2.66-2.61 (m, 4H), 1.42 (p, J=7.5 Hz, 4H), 1.28 (dt, J=15.0, 7.4 Hz, 4H), 1.23 (d, J=6.3 Hz, 12H), 0.87 (t, J=7.3 Hz, 6H); $^{13}$C NMR (151 MHz, CDCl$_3$): δ 167.99, 68.60, 67.63, 52.05, 30.76, 21.68, 21.65, 20.27, 13.97; HRMS (ESI-TOF): calc'd for C$_{17}$H$_{33}$NO$_4$ [M+H]$^+$ 316.2482; found 316.2489.

11. Diisopropyl 2-(butyl(phenyl)amino)malonate (55k)

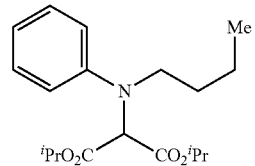
55k

Yield: 94% (Method E); Physical State: dark brown oily liquid; $R_f$=0.66 (8:1 EtOAc:hexanes); $^1$H NMR (600 MHz, CDCl$_3$): δ 7.23 (dd, J=8.8, 7.2 Hz, 2H), 6.85-6.78 (m, 3H), 5.12 (hept, J=6.3 Hz, 2H), 4.98 (s, 1H), 3.50-3.35 (m, 2H), 1.63 (p, J=7.8 Hz, 2H), 1.35 (h, J=7.4 Hz, 2H), 1.27 (dd, J=11.1, 6.3 Hz, 12H); $^{13}$C NMR (151 MHz, CDCl$_3$): δ 167.42, 147.91, 128.96, 118.56, 114.81, 69.41, 67.38, 49.26, 30.08, 21.54, 20.11, 13.82; HRMS (ESI-TOF): calc'd for C$_{19}$H$_{29}$NO$_4$[M+H]$^+$ 336.2169; found 336.2180.

12. Diisopropyl 2-(butyl(o-tolyl)amino)malonate (55l)

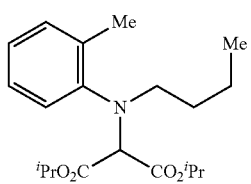

55l

Yield: 83% (Method E); Physical State: colorless oily liquid; R$_f$=0.51 (10% EtOAc/hexanes); $^1$H NMR (600 MHz, CDCl$_3$): δ 7.33 (d, J=7.9 Hz, 1H), 7.16 (d, J=7.4 Hz, 1H), 7.10 (t, J=7.5 Hz, 1H), 6.98 (t, J=7.4 Hz, 1H), 5.10 (hept, J=6.2 Hz, 2H), 4.27 (s, 1H), 3.40 (t, J=6.8 Hz, 2H), 3.40 (t, J=6.8 Hz, 3H), 1.30 (dd, J=14.7, 5.2 Hz, 4H), 1.25 (dd, J=8.1, 6.4 Hz, 12H), 0.82 (t, J=7.0 Hz, 3H); $^{13}$C NMR (151 MHz, CDCl$_3$): δ 167.46, 147.38, 134.81, 130.84, 125.84, 124.11, 124.00, 69.84, 68.57, 48.35, 30.41, 21.43, 21.37, 19.95, 17.67, 13.70; HRMS (ESI-TOF): calc'd for C$_{20}$H$_{31}$NO$_4$ [M+H]$^+$ 350.2326; found 350.2388.

13. Diisopropyl 2-(butyl(p-tolyl)amino)malonate (55m)

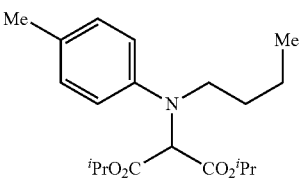

55m

Yield: 94% (Method E); Physical State: brown colored viscous oily liquid; R$_f$=0.60 (8:1 EtOAc:hexanes); $^1$H NMR (600 MHz, CDCl$_3$): δ 7.05 (d, J=7.7 Hz, 2H), 6.76 (d, J=8.0 Hz, 2H), 5.16-5.07 (m, 2H), 4.93 (s, 1H), 3.46-3.33 (m, 2H), 2.26 (s, 3H), 1.59 (s, 2H), 1.33 (dd, J=14.6, 7.3 Hz, 2H), 1.32-1.23 (m, 12H), 0.93 (t, J=7.1 Hz, 3H); $^{13}$C NMR (151 MHz, CDCl$_3$): δ 167.56, 145.74, 129.51, 128.09, 115.56, 69.31, 67.93, 49.17, 30.21, 21.57, 20.24, 20.14, 13.85; HRMS (ESI-TOF): calc'd for C$_{20}$H$_{31}$NO$_4$ [M+H]$^+$ 350.2326; found 350.2336.

14. Diisopropyl 2-(butyl(4-chlorophenyl)amino)malonate (55n)

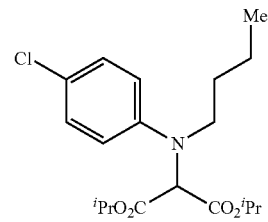

55n

Yield: 86% (Method E); Physical State: brown colored viscous oily liquid; R$_f$=0.58 (8:1 EtOAc:hexanes); $^1$H NMR (600 MHz, CDCl$_3$): δ 7.15 (d, J=9.0 Hz, 2H), 6.73 (d, J=9.0 Hz, 2H), 5.09 (hept, J=6.3 Hz, 2H), 4.87 (s, 1H), 3.43-3.31 (m, 2H), 1.57 (p, J=7.7 Hz, 2H), 1.31 (h, J=1.4 Hz, 2H), 1.25 (dd, J=13.6, 6.3 Hz, 12H), 0.91 (t, J=7.4 Hz, 3H); $^{13}$C NMR (151 MHz, CDCl$_3$): δ 167.12, 146.51, 128.79, 123.48, 116.16, 69.64, 67.57, 49.66, 29.91, 21.55, 20.07, 13.80; HRMS (ESI-TOF): calc'd for C$_{19}$H$_{28}$ClNO$_4$ [M+H]$^+$ 370.1780; found 370.1785.

15. Diisopropyl 2-((3-(benzyloxy)phenyl)(butyl)amino)malonate (55o)

55o

Yield: 81% (Method E); Physical State: pale yellow colored oily liquid; R$_f$=0.50 (8:1 EtOAc:hexanes); $^1$H NMR (600 MHz, CDCl$_3$): δ 7.48 (d, J=7.3 Hz, 2H), 7.42 (t, J=7.5 Hz, 2H), 7.36 (t, J=7.3 Hz, 1H), 7.18 (t, J=8.2 Hz, 1H), 6.54-6.44 (m, 3H), 5.16 (hept, J=6.2 Hz, 2H), 5.09 (s, 2H), 5.02 (s, 1H), 3.47-3.42 (m, 2H), 1.65 (ddd, J=15.6, 8.8, 6.8 Hz, 2H), 1.37 (dt, J=15.1, 7.5 Hz, 2H), 1.32 (dd, J=9.7, 6.3 Hz, 12H), 0.97 (t, J=7.4 Hz, 3H); $^{13}$C NMR (151 MHz, CDCl$_3$): δ 167.33, 159.77, 149.36, 137.18, 129.66, 128.44, 127.75, 127.37, 107.72, 104.39, 102.17, 69.81, 69.46, 67.23, 49.34, 30.09, 21.55, 20.11, 13.82; HRMS (ESI-TOF): calc'd for C$_{26}$H$_{35}$NO$_5$ [M+H]$^+$ 442.2588; found 442.2624.

16. Diisopropyl 2-(butyl(2-vinylphenyl)amino)malonate (55p)

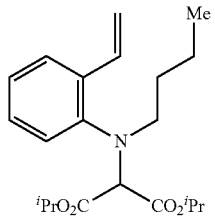

Yield: 86% (Method E); Physical State: pale yellow colored oily liquid; $R_f$=0.49 (10% EtOAc/hexanes); $^1$H NMR (600 MHz, CDCl$_3$): δ 7.49 (dd, J=7.7, 1.4 Hz, 1H), 7.29 (d, J=7.5 Hz, 1H), 7.20 (td, J=7.9, 1.5 Hz, 1H), 7.15 (dd, J=17.8, 11.0 Hz, 1H), 7.05 (t, J=7.4 Hz, 1H), 5.66 (dd, J=17.8, 1.5 Hz, 1H), 5.23 (dd, J=11.0, 1.4 Hz, 1H), 5.10 (hept, J=63 Hz, 2H), 4.36 (s, 1H), 3.40 (t, J=7.1 Hz, 2H), 1.36 (p, J=7.7, 6.9 Hz, 2H), 1.30 (dt, J=15.4, 7.2 Hz, 2H), 1.27-1.21 (m, 12H), 0.83 (t, J=7.3 Hz, 3H); $^{13}$C NMR (151 MHz, CDCl$_3$): δ 167.52, 146.41, 134.32, 133.89, 127.75, 126.61, 123.97, 123.22, 114.23, 70.64, 68.81, 47.86, 30.37, 21.58, 21.51, 20.08, 13.83; HRMS (ESI-TOF): calc'd for C$_{21}$H$_{31}$NO$_4$ [M+H]$^+$ 362.2326; found 362.2382.

17. Diisopropyl 2-(butyl(3-fluoro-4-methoxyphenyl)amino)malonate (55q)

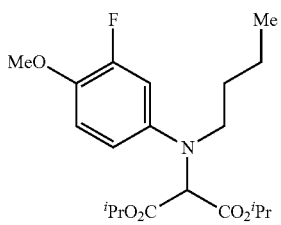

Yield: 80% (Method E); Physical State: dark brown colored viscous oily liquid; $R_f$=0.40 (8:1 EtOAc:hexanes); $^1$H NMR (600 MHz, CDCl$_3$): δ 6.85 (t, J=9.3 Hz, 1H), 6.68 (dd, J=14.1, 2.9 Hz, 1H), 6.59-6.53 (m, 1H), 5.09 (hept, J=6.3 Hz, 2H), 4.79 (s, 1H), 3.82 (s, 3H), 3.38-3.24 (m, 2H), 1.54 (p, J=7.7 Hz, 2H), 1.32 (dt, J=15.0, 7.5 Hz, 2H), 1.26 (dd, J=10.0, 6.3 Hz, 12H), 0.91 (t, J=7.4 Hz, 3H); $^{13}$C NMR (151 MHz, CDCl$_3$): δ 167.23, 153.73, 152.12, 142.71, 142.65, 140.91, 140.83, 114.91, 114.89, 111.69, 111.68, 105.52, 105.37, 69.63, 68.41, 57.10, 49.94, 30.13, 21.63, 21.62, 20.13, 13.88; HRMS (ESI-TOF): calc'd for C$_{20}$H$_{30}$FNO$_5$ [M+H]$^+$ 384.2181; found 384.2192.

18. Diisopropyl 2-(butyl(3-fluoro-5-methylphenyl)amino)malonate (55r)

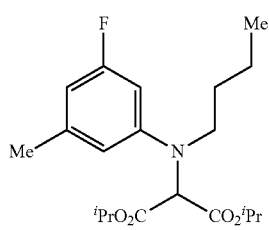

Yield: 96% (Method E); Physical State: brown colored viscous oily liquid; $R_f$=0.60 (8:1 EtOAc:hexanes); $^1$H NMR (600 MHz, CDCl$_3$): δ 6.35 (s, 1H), 6.31 (d, J=10.7 Hz, 2H), 5.11 (hept, J=6.2 Hz, 2H), 4.91 (s, 1H), 3.42-3.34 (m, 2H), 2.27 (s, 3H), 1.61 (p, J=7.8 Hz, 2H), 1.33 (dq, J=14.9, 7.5 Hz, 2H), 1.27 (dd, J=9.5, 6.3 Hz, 12H), 0.93 (t, J=7.4 Hz, 3H); $^{13}$C NMR (151 MHz, CDCl$_3$): δ 167.09, 164.54, 162.94, 149.44, 149.36, 140.39, 140.32, 110.66, 105.92, 105.77, 98.95, 98.78, 69.64, 67.17, 49.60, 29.96, 21.80, 21.78, 21.52, 20.08, 13.78; HRMS (ESI-TOF): calc'd for C$_{20}$H$_{30}$FNO$_4$ [M+H]$^+$ 368.2232; found 368.2240.

19. Diisopropyl 2-(butyl(4-fluoro-3,5-dimethylphenyl)amino)malonate (55s)

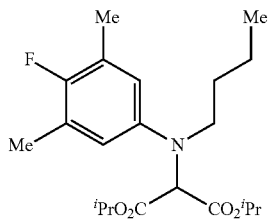

Yield: 91% (Method E); Physical State: dark brown colored oily liquid; $R_f$=0.67 (8:1 EtOAc:hexanes); $^1$H NMR (600 MHz, CDCl$_3$): δ 6.51 (d, J=6.0 Hz, 2H), 5.10 (hept, J=6.2 Hz, 2H), 4.82 (s, 1H), 3.42-3.25 (m, 2H), 2.20 (s, 6H), 1.53 (p, J=7.7 Hz, 2H), 1.32 (dq, J=15.0, 7.5 Hz, 2H), 1.26 (dd, J=9.4, 6.3 Hz, 12H), 0.91 (t, J=7.4 Hz, 3H); $^{13}$C NMR (151 MHz, CDCl$_3$): δ 167.45, 154.90, 153.33, 143.56, 143.55, 124.36, 124.23, 116.86, 116.84, 69.23, 68.65, 49.30, 30.24, 21.49, 20.06, 14.88, 14.85, 13.78; HRMS (ESI-TOF): calc'd for C$_{21}$H$_{32}$FNO$_4$ [M+H]$^+$ 382.2388; found 382.2387.

20. Diisopropyl 2-(butyl(3-chloro-5-fluoro-4-methoxyphenyl)amino)malonate (55t)

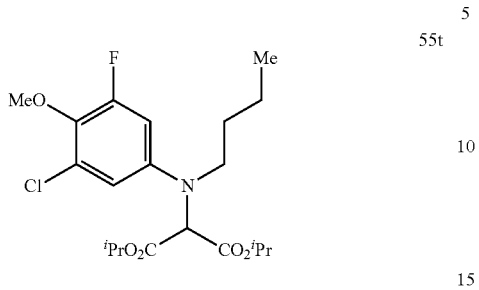

Yield: 54% (Method E); Physical State: dark brown colored oily liquid; $R_f$=0.60 (8:1 EtOAc:hexanes); $^1$H NMR (600 MHz, CDCl$_3$): δ 6.57-6.52 (m, 1H), 6.46 (dd, J=13.6, 3.0 Hz, 1H), 5.10 (hept, J=6.2 Hz, 2H), 4.77 (s, 1H), 3.83 (s, 3H), 3.36-3.27 (m, 2H), 1.56 (p, J=7.8 Hz, 2H), 1.35-1.28 (m, 2H), 1.26 (dd, J=11.4, 6.3 Hz, 12H), 0.92 (t, J=7.4 Hz, 3H); $^{13}$C NMR (151 MHz, CDCl$_3$): δ 166.77, 157.36, 155.72, 144.54, 144.47, 136.46, 136.36, 128.84, 128.80, 111.34, 102.45, 102.29, 69.91, 67.42, 61.56, 61.54, 50.01, 29.84, 21.55, 21.54, 20.03, 13.77; HRMS (ESI-TOF): calc'd for C$_{20}$H$_{29}$ClFNO$_5$ [M+H]$^+$ 418.1791; found 418.1791.

21. Diisopropyl 2-(butyl(naphthalen-2-yl)amino)malonate (55u)

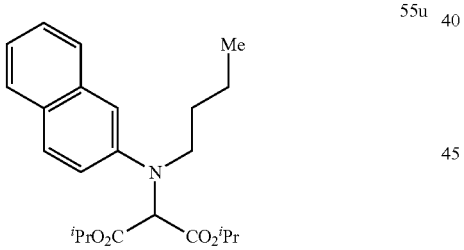

Yield: 95% (Method E); Physical State: dark reddish brown colored oily liquid; $R_f$=0.56 (8:1 EtOAc:hexanes); $^1$H NMR (600 MHz, CDCl$_3$): δ 7.75 (t, J=9.1 Hz, 2H), 7.69 (d, J=8.2 Hz, 1H), 7.42 (t, J=7.5 Hz, 1H), 7.29 (t, J=1.4 Hz, 1H), 7.22 (dd, J=9.0, 2.5 Hz, 1H), 7.13 (d, J=2.2 Hz, 1H), 5.18 (dq, J=12.6, 6.3 Hz, 2H), 5.15 (s, 1H), 3.64-3.53 (m, 2H), 1.72 (p, J=7.8 Hz, 2H), 1.43 (h, J=7.4 Hz, 2H), 1.32 (dd, J=12.2, 6.3 Hz, 12H), 0.99 (t, J=7.4 Hz, 3H); $^{13}$C NMR (151 MHz, CDCl$_3$): δ 167.43, 145.70, 134.52, 128.75, 127.87, 127.30, 126.47, 126.16, 122.87, 117.83, 109.88, 69.55, 67.83, 49.35, 30.20, 21.60, 20.20, 13.89; HRMS (ESI-TOF): calc'd for C$_{23}$H$_{31}$NO$_4$ [M+H]$^+$ 386.2326; found 386.2331.

22. Diisopropyl 2-(methyl(phenethyl)amino)malonate (55v)

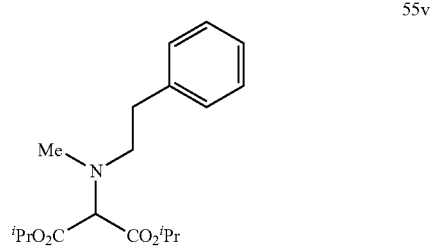

Yield: 39% (Method F); Physical State: Pale yellow colored viscous oily liquid; $R_f$=0.29 (10% EtOAc/hexanes); $^1$H NMR (600 MHz, CDCl$_3$): δ 7.36 (t, J=7.5 Hz, 2H), 7.31-7.26 (m, 3H), 5.20 (hept, J=6.3 Hz, 2H), 4.21 (s, 1H), 3.02-2.97 (m, 2H), 2.92 (dd, J=10.3, 5.4 Hz, 2H), 2.66 (s, 3H), 1.36 (d, J=6.3 Hz, 12H); $^{13}$C NMR (151 MHz, CDCl$_3$): δ 167.19, 139.92, 139.29, 128.72, 128.29, 125.98, 70.28, 68.96, 56.89, 39.45, 34.89, 21.76, 21.69. HRMS (ESI-TOF): calc'd for C$_{10}$H$_{17}$NO$_4$ [M+H]$^+$ 322.2013; found 322.2014.

23. Diisopropyl 2-(butyl(phenethyl)amino)malonate (55w)

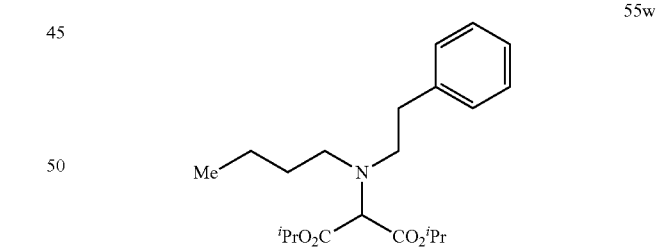

Yield: 60% (Method F; Physical State: colorless oily liquid; $R_f$=0.53 (10% EtOAc/hexanes); $^1$H NMR (600 MHz, CDCl$_3$): δ 7.28 (t, J=7.5 Hz, 2H), 7.24-7.17 (m, 3H), 5.11 (hept, J=6.2 Hz, 2H), 4.22 (s, 1H), 3.00-2.94 (m, 2H), 2.83-2.78 (m, 2H), 2.78-2.73 (m, 2H), 1.47 (p, J=7.5 Hz, 2H), 1.32 (dt, J=15.0, 7.4 Hz, 2H), 1.28 (dd, J=6.3, 1.6 Hz, 12H), 0.92 (t, J=7.4 Hz, 3H); $^{13}$C NMR (151 MHz, CDCl$_3$): δ 167.77, 140.08, 128.66, 128.08, 125.75, 68.62, 67.75, 54.35, 52.20, 35.59, 30.68, 21.61, 21.56, 20.16, 13.90; HRMS (ESI-TOF): calc'd for C$_{21}$H$_{33}$NO$_4$ [M+H]$^+$ 364.2482; found 364.2493.

24. Diisopropyl 2-(phenethyl(phenyl)amino)malonate (55x)

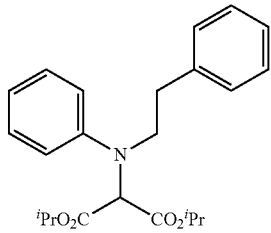

Yield: 25% (M=Li), 54% (M=MgBr) (Method F for M=Li and Method E for M=MgBr); Physical State: dark orange colored non-viscous liquid; $R_f$=0.42 (10% EtOAc/hexanes); $^1$H NMR (600 MHz, CDCl$_3$): δ 7.33-7.25 (m, 4H), 7.25-7.19 (m, 3H), 6.90 (d, J=8.0 Hz, 2H), 6.84 (t, J=7.3 Hz, 1H), 5.10 (hept, J=6.3 Hz, 2H), 5.02 (s, 1H), 3.73-3.61 (m, 2H), 3.00-2.86 (m, 2H), 1.26 (dd, J=9.0, 6.3 Hz, 12H); $^{13}$C NMR (151 MHz, CDCl$_3$): δ 167.36, 147.59, 139.51, 129.22, 128.67, 128.45, 126.17, 118.94, 69.66, 67.35, 50.93, 34.37, 21.66; HRMS (ESI-TOF): calc'd for C$_{23}$H$_{29}$NO$_4$ [M+H]$^+$ 384.2169; found 384.2191.

25. Diisopropyl 2-((3,5-difluoro-4-methoxyphenyl)(phenethyl)amino)malonate (55y)

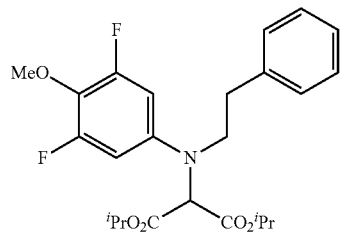

Yield: 43% (Method E); Physical State: colorless viscous oily liquid; $R_f$=0.35 (10% EtOAc/hexanes); $^1$H NMR (600 MHz, CDCl$_3$): δ 7.30-7.25 (m, 2H), 7.19 (d, J=7.1 Hz, 3H), 6.38 (d, J=10.8 Hz, 2H), 5.08 (hept, J=6.2 Hz, 2H), 4.82 (s, 1H), 3.85 (s, 3H), 3.61-3.52 (m, 2H), 2.92-2.84 (m, 2H), 1.25 (dd, J=11.2, 6.3 Hz, 12H); $^{13}$C NMR (151 MHz, CDCl$_3$): δ 166.60, 157.33, 157.27, 155.71, 155.65, 143.58, 138.78, 128.56, 128.48, 126.32, 98.85, 98.67, 69.96, 67.20, 61.99, 51.62, 34.12, 21.51, 21.48; HRMS (ESI-TOF): calc'd for C$_{24}$H$_{29}$F$_2$NO$_5$ [M+H]$^+$ 450.2087; found 450.2110.

26. Diisopropyl 2-(cyclopentyl(phenyl)amino)malonate (55z)

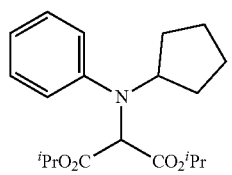

Yield: 82% (Method E); Physical State: dark brown colored oily liquid; $R_f$=0.73 (8:1 EtOAc:hexanes); $^1$H NMR (600 MHz, CDCl$_3$): δ 7.20-7.14 (m, 2H), 7.01 (d, J=8.2 Hz, 2H), 6.81 (t, J=7.3 Hz, 1H), 5.02 (hept, J=6.3 Hz, 2H), 4.74 (s, 1H), 4.12 (p, J=8.3 Hz, 1H), 2.03-1.94 (m, 2H), 1.77-1.68 (m, 2H), 1.58 (dh, J=15.7, 7.6, 6.8 Hz, 4H), 1.22 (d, J=6.3 Hz, 6H), 1.08 (d, J=6.3 Hz, 6H); $^{13}$C NMR (151 MHz, CDCl$_3$): δ 168.21, 148.06, 128.58, 119.89, 118.09, 69.43, 65.27, 62.15, 29.80, 23.79, 21.59, 21.35; HRMS (ESI-TOF): calc'd for C$_{20}$H$_{29}$NO$_4$ [M+H]$^+$ 348.2169; found 348.2180.

27. Diisopropyl 2-(cyclopentyl(p-tolyl)amino)malonate (56a)

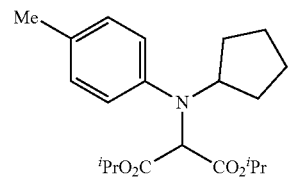

Figure 5:
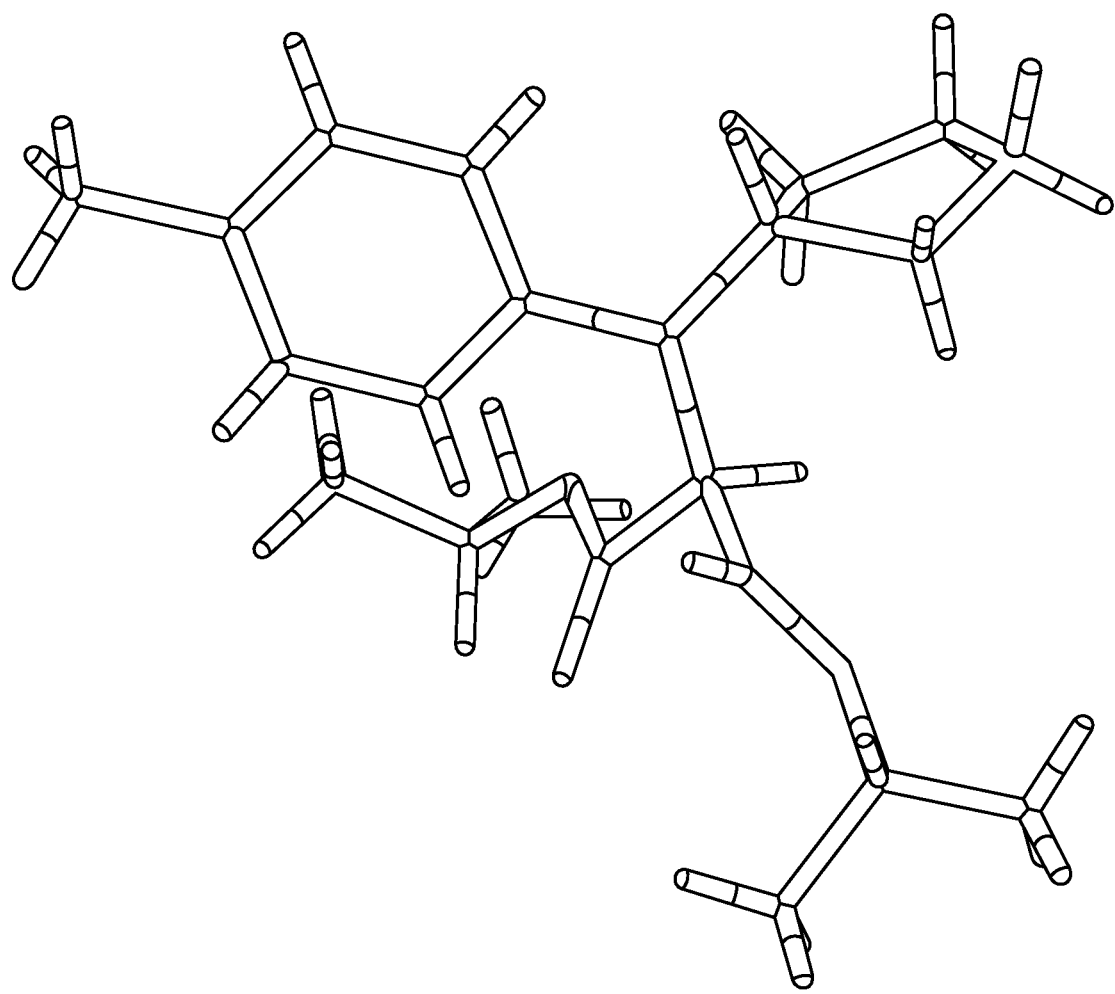
FIG. 5 shows the X-ray crystal structure of diisopropyl 2-(cyclopentyl(p-tolyl)amino)malonate (56a).

Yield: 66% (Method E); Physical State: orange colored crystalline solid (m.p.=51-55.2° C.); $R_f$=0.45 (10% EtOAc/hexanes); $^1$H NMR (600 MHz, CDCl$_3$): δ 6.97 (d, J=8.4 Hz, 2H), 6.92 (d, J=8.6 Hz, 2H), 5.02 (hept, J=6.2 Hz, 2H), 4.70 (s, 1H), 4.05 (p, J=8.0 Hz, 1H), 2.23 (s, 3H), 1.95 (dd, J=14.0, 5.5 Hz, 2H), 1.70 (s, 2H), 1.61-1.50 (m, 4H), 1.21 (d, J=6.4 Hz, 6H), 1.11 (d, J=6.4 Hz, 6H); $^{13}$C NMR (151 MHz, CDCl$_3$): δ 168.29, 145.73, 129.29, 128.88, 119.11, 69.05, 65.81, 61.99, 30.01, 23.65, 21.46, 21.29, 20.31; HRMS (ESI-TOF): calc'd for C$_{21}$H$_{31}$NO$_4$ [M+H]$^+$ 362.2326; found 362.2359. For X-ray crystal structure, see FIG. 5.

28. Diisopropyl 2-(cyclopentyl(4-methoxy-3,5-dimethylphenyl)amino)malonate (56b)

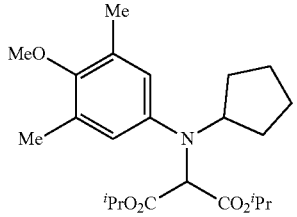

Yield: 70% (Method E); Physical State: off white waxy solid; $R_f$=0.47 (10% EtOAc/hexanes); $^1$H NMR (600 MHz, CDCl$_3$): δ 6.66 (s, 2H), 5.06-4.93 (m, 2H), 4.63 (s, 1H), 4.05-3.92 (m, 1H), 3.60 (s, 3H), 2.18 (s, 6H), 1.91 (s, 2H), 1.66 (s, 2H), 1.60-1.41 (m, 4H), 1.18 (d, J=6.5 Hz, 6H), 1.09 (d, J=6.5 Hz, 6H); $^{13}$C NMR (151 MHz, CDCl$_3$): δ 168.23, 150.81, 143.87, 130.07, 119.59, 68.89, 65.81, 62.07, 59.54, 30.03, 23.58, 21.39, 21.19, 16.13; HRMS (ESI-TOF): calc'd for C$_{23}$H$_{35}$NO$_5$ [M+H]$^+$ 406.2588; found 406.2644.

29. Diisopropyl 2-(cyclohexyl(phenyl)amino)malonate (56c)

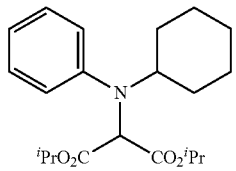

Yield: 83% (Method E); Physical State: dark brown colored oily liquid; $R_f$=0.60 (8:1 EtOAc:hexanes); $^1$H NMR (600 MHz, CDCl$_3$): δ 7.14 (dd, J=8.8, 7.1 Hz, 2H), 6.92 (d, J=8.2 Hz, 2H), 6.75 (t, J=7.3 Hz, 1H), 5.02 (hept, J=6.2 Hz, 2H), 4.78 (s, 1H), 3.60 (td, J=11.2, 3.2 Hz, 1H), 1.97 (d, J=11.5 Hz, 2H), 1.84 (d, J=12.7 Hz, 2H), 1.68 (d, J=13.4 Hz, 1H), 1.36 (dp, J=23.6, 12.6 Hz, 4H), 1.23 (d, J=63 Hz, 6H), 1.18-1.10 (m, 1H), 1.05 (d, J=6.3 Hz, 6H); $^{13}$C NMR (151 MHz, CDCl$_3$): δ 168.37, 147.59, 128.45, 118.74, 116.24, 63.83, 59.08, 31.07, 25.94, 25.67, 21.48, 21.17; HRMS (ESI-TOF): calc'd for C$_{21}$H$_{31}$NO$_4$ [M+H]$^+$ 362.2326; found 362.2335.

30. Diisopropyl 2-((1-(tert-butoxycarbonyl)piperidin-4-yl)(phenyl)amino)malonate (56d)

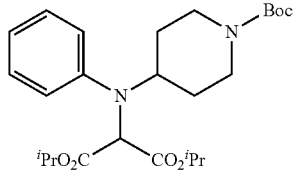

Yield: 48% (Method E); Physical State: dark brownish yellow waxy solid; $R_f$=0.47 (4:1 EtOAc:hexanes); $^1$H NMR (600 MHz, CDCl$_3$): δ 7.16 (t, J=8.0 Hz, 2H), 6.94 (d, J=8.0 Hz, 2H), 6.81 (t, J=7.3 Hz, 1H), 5.01 (hept, J=6.1 Hz, 2H), 4.70 (s, 1H), 4.20 (s, 2H), 3.70 (t, J=10.0 Hz, 1H), 2.77 (s, 2H), 1.90 (d, J=12.2 Hz, 2H), 1.59-1.49 (m, 2H), 1.45 (s, 9H), 1.22 (d, J=6.3 Hz, 6H), 1.07 (d, J=6.1 Hz, 6H); $^{13}$C NMR (151 MHz, CDCl$_3$): δ 168.10, 154.60, 147.25, 128.69, 120.07, 117.80, 79.59, 69.47, 64.53, 57.82, 43.52, 30.45, 28.37, 21.56, 21.31; HRMS (ESI-TOF): calc'd for C$_{25}$H$_{38}$N$_2$O$_6$ [M+H]$^+$ 463.2803; found 463.2812.

31. Diisopropyl 2-((1-(tert-butoxycarbonyl)piperidin-4-yl)(2,3-dihydrobenzofuran-5-yl)amino)malonate (56e)

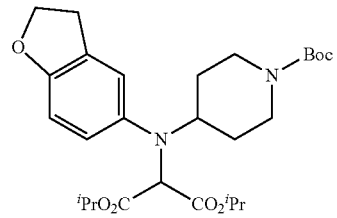

Yield: 32% (Method E); Physical State: pale yellow colored gummy substance; $R_f$=0.30 (20% EtOAc/hexanes); $^1$H NMR (600 MHz, CDCl$_3$): δ 7.00 (d, J=2.4 Hz, 1H), 6.85 (dd, J=8.6, 2.4 Hz, 1H), 6.57 (d, J=8.5 Hz, 1H), 4.99 (hept, J=6.2 Hz, 2H), 4.57 (s, 1H), 4.47 (t, J=8.6 Hz, 2H), 4.24-3.87 (m, 2H), 3.37 (tt, J=11.4, 3.4 Hz, 1H), 3.09 (t, J=8.6 Hz, 2H), 2.69 (s, 2H), 1.84 (d, J=11.8 Hz, 2H), 1.39 (s, 11H), 1.15 (dd, J=14.0, 6.3 Hz, 12H); $^{13}$C NMR (151 MHz, CDCl$_3$): δ 168.28, 156.25, 154.52, 139.80, 126.88, 124.63, 122.14, 108.48, 79.30, 71.13, 69.04, 67.61, 58.33, 31.32, 29.87, 28.26, 21.41, 21.40; HRMS (ESI-TOF): calc'd for C$_{27}$H$_{40}$N$_2$O$_7$ [M+H]$^+$ 505.2908; found 505.2928.

32. Tetraisopropyl 2,2'-(decane-1,10-diylbis((4-fluorophenyl)azanediyl))dimalonate (56f)

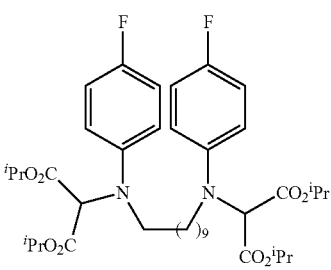

Yield: 96% (Method E); Physical State: colorless oily liquid; $R_f$=0.55 (20% EtOAc/hexanes); $^1$H NMR (600 MHz, CDCl$_3$): δ 6.92 (t, J=8.6 Hz, 4H), 6.79 (dd, J=9.0, 4.4 Hz, 4H), 5.09 (hept, J=6.2 Hz, 4H), 4.81 (s, 2H), 3.40-3.27 (m, 4H), 1.54 (s, 4H), 1.24 (dd, J=8.6, 6.4 Hz, 36H); $^{13}$C NMR (151 MHz, CDCl$_3$): δ 167.39, 157.90, 155.54, 144.43, 144.41, 117.51, 117.44, 115.50, 115.28, 69.49, 68.53, 50.03, 29.52, 29.40, 28.03, 26.93, 21.60, 21.59; HRMS (ESI-TOF): calc'd for C$_{40}$H$_{58}$F$_2$N$_2$O$_8$ [M+H]$^+$ 733.4234; found 733.4249.

33. Tetraisopropyl 2,2'-(decane-1,10-diylbis((4-methoxyphenyl)azanediyl)) dimalonate (56g)

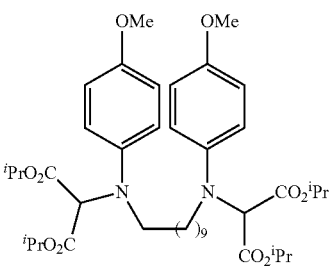

Yield: 89% (Method E); Physical State: dark brown oily liquid; $R_f$=0.30 (20% EtOAc/hexanes); $^1$H NMR (600 MHz, CDCl$_3$): δ 6.93-6.72 (m, 8H), 5.08 (hept, J=6.2 Hz, 4H), 4.79 (s, 2H), 3.75 (s, 6H), 3.37-3.28 (m, 4H), 1.51 (s, 4H), 1.24 (t, J=6.3 Hz, 36H); $^{13}$C NMR (151 MHz, CDCl$_3$): δ 167.65, 153.46, 142.14, 118.68, 114.34, 69.24, 69.10, 55.52, 49.84, 29.56, 29.45, 28.26, 27.00, 21.63, 21.61; HRMS (ESI-TOF): calc'd for C$_{42}$H$_{64}$N$_2$O$_{10}$ [M+H]$^+$ 757.4634; found 757.4641.

34. Diisopropyl 2-((10-((1,3-diisopropoxy-1,3-dioxopropan-2-yl)(4-fluorophenyl)amino)decyl)(4-methoxyphenyl)amino)malonate (56h)

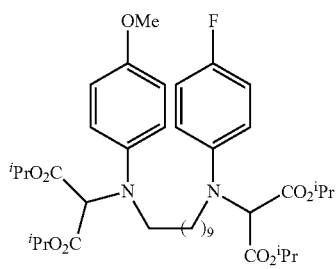

Yield: 27% (Method E); Physical State: dark brown colored oily liquid; $R_f$=0.50 (20% EtOAc/hexanes); $^1$H NMR (600 MHz, CDCl$_3$): δ 6.91 (t, J=8.7 Hz, 2H), 6.86 (d, J=9.1 Hz, 2H), 6.79 (dd, J=9.2, 3.4 Hz, 4H), 5.08 (dtt, J=12.5, 6.2, 3.1 Hz, 4H), 4.80 (d, J=11.3 Hz, 2H), 3.74 (s, 3H), 3.33 (q, J=6.9 Hz, 4H), 1.56-1.48 (m, 4H), 1.30-1.18 (m, 36H); $^{13}$C NMR (151 MHz, CDCl$_3$): δ 167.64, 167.37, 157.88, 155.51, 153.47, 144.41, 144.39, 142.12, 118.71, 117.47, 117.40, 115.49, 115.26, 114.33, 69.48, 69.24, 69.11, 68.51, 55.50, 50.04, 49.81, 29.52, 29.42, 29.39, 28.24, 28.02, 26.98, 26.92, 21.61, 21.59; HRMS (ESI-TOF): calc'd for $C_{41}H_{61}FN_2O_9$ [M+H]$^+$ 745.4434; found 745.4441.

35. Diisopropyl 2-(benzyl(phenyl)amino)malonate (56i)

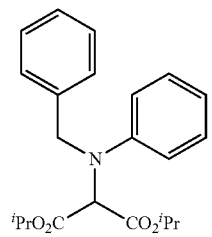

Yield: 49% (Method E); Physical State: yellow colored solid (m.p.=76-81° C.); $R_f$=0.43 (10% EtOAc/hexanes); $^1$H NMR (600 MHz, CDCl$_3$): δ 7.41 (d, J=7.6 Hz, 2H), 7.34 (t, J=7.6 Hz, 2H), 7.25 (dt, J=26.0, 7.3 Hz, 3H), 6.83 (dd, J=12.8, 8.0 Hz, 3H), 5.24 (s, 1H), 5.09 (hept, J=6.2 Hz, 2H), 4.80 (s, 2H), 1.26 (d, J=6.4 Hz, 6H), 1.20 (d, J=6.4 Hz, 6H); $^{13}$C NMR (151 MHz, CDCl$_3$): δ 167.19, 148.34, 139.01, 128.96, 128.18, 126.55, 126.51, 118.92, 114.29, 69.72, 66.46, 54.01, 21.44, 21.37; HRMS (ESI-TOF): calc'd for $C_{22}H_{27}NO_4$ [M+H]$^+$ 370.2013; found 370.2052.

36. Diisopropyl 2-(phenyl(p-tolyl)amino)malonate (56j)

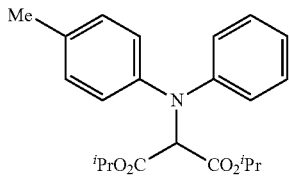

Yield: 56% (Method E); Physical State: colorless viscous oily liquid; $R_f$=0.23 (10% EtOAc/hexanes); $^1$H NMR (600 MHz, CDCl$_3$): δ 7.22 (t, J=8.0 Hz, 2H), 7.13 (s, 4H), 6.92 (dd, J=12.2, 7.6 Hz, 3H), 5.35 (s, 1H), 5.04 (hept, J=6.2 Hz, 2H), 2.34 (s, 3H), 1.19 (d, J=6.4 Hz, 6H), 1.15 (d, J=6.4 Hz, 6H); $^{13}$C NMR (151 MHz, CDCl$_3$): δ 166.70, 146.89, 143.02, 133.58, 129.73, 128.81, 124.79, 120.94, 119.20, 69.53, 67.94, 21.37, 21.32, 20.68; HRMS (ESI-TOF): calc'd for $C_{22}H_{27}NO_4$ [M+H]$^+$ 370.2013; found 370.2033.

37. Diisopropyl 2-((4-(methylthio)phenyl)(phenyl)amino)malonate (56k)

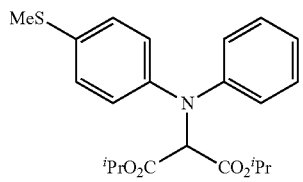

Yield: 52% (Method E); Physical State: pale yellow colored oily liquid; $R_f$=0.46 (10% EtOAc/hexanes); $^1$H NMR (600 MHz, CDCl$_3$): δ 7.16 (td, J=12, 1.9 Hz, 2H), 7.12 (d, J=8.7 Hz, 2H), 6.92 (d, J=8.6 Hz, 5H), 5.22 (s, 1H), 4.93 (hept, J=6.3 Hz, 2H), 2.35 (s, 3H), 1.08 (d, J=6.3 Hz, 6H), 1.04 (d, J=6.3 Hz, 6H); $^{13}$C NMR (151 MHz, CDCl$_3$): δ 166.59, 146.21, 143.84, 131.80, 129.12, 123.18, 122.54, 121.60, 69.77, 67.92, 21.43, 21.39, 17.06; HRMS (ESI-TOF): calc'd for $C_{22}H_{27}NO_4S$ [M+H]$^+$ 402.1734; found 402.1739.

38. Diisopropyl 2-((4-phenoxyphenyl)(phenyl)amino)malonate (56l)

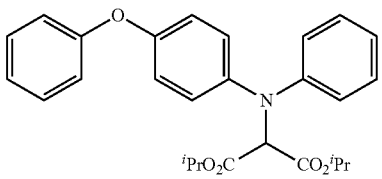

Yield: 43% (Method E); Physical State: pale yellow colored viscous oily liquid; $R_f$=0.37 (10% EtOAc/hexanes); $^1$H NMR (600 MHz, CDCl$_3$): δ 7.38 (t, J=7.8 Hz, 2H), 7.32-7.24 (m, 4H), 7.14 (t, J=7.3 Hz, 1H), 7.07 (d, J=8.0 Hz, 2H), 7.03 (d, J=8.7 Hz, 2H), 6.97 (t, J=7.3 Hz, 1H), 6.93 (d, J=8.1 Hz, 2H), 5.39 (s, 1H), 5.10 (hept, J=6.0 Hz, 2H), 1.25 (d, J=6.4 Hz, 6H), 1.21 (d, J=6.4 Hz, 6H); $^{13}$C NMR (151 MHz, CDCl$_3$): δ 166.59, 157.25, 153.82, 147.03, 140.53, 129.58, 128.92, 127.03, 123.02, 120.84, 119.51, 118.48, 118.45, 69.63, 67.91, 21.37, 21.34; HRMS (ESI-TOF): calc'd for C$_{27}$H$_{29}$NO$_5$ [M+H]$^+$ 448.2118; found 448.2185.

39. Diisopropyl 2-([1,1'-biphenyl]-4-yl(phenyl)amino)malonate (56m)

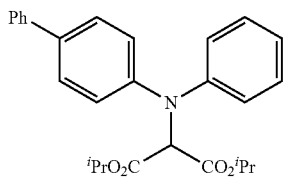

56m

Yield: 60% (Method E); Physical State: dark brown colored oily liquid; R$_f$=0.40 (10% EtOAc/hexanes); $^1$H NMR (600 MHz, CDCl$_3$): δ 7.60 (d, J=8.4 Hz, 2H), 7.53 (d, J=8.7 Hz, 2H), 7.44 (t, J=7.8 Hz, 2H), 7.34 (q, J=7.6, 7.0 Hz, 3H), 7.21 (d, J=7.6 Hz, 2H), 7.14-7.04 (m, 3H), 5.43 (s, 1H), 5.08 (hept, J=6.3 Hz, 2H), 1.22 (d, J=6.3 Hz, 6H), 1.17 (d, J=6.3 Hz, 6H); $^{13}$C NMR (151 MHz, CDCl$_3$): δ 166.63, 145.84, 145.71, 140.64, 134.82, 129.19, 128.62, 127.62, 126.64, 126.55, 123.38, 123.30, 121.20, 69.75, 67.97, 21.43, 21.36; HRMS (ESI-TOF): calc'd for C$_{27}$H$_{29}$NO$_4$ [M+H]$^+$ 432.2169; found 432.2218.

40. Diisopropyl 2-(m-tolyl(p-tolyl)amino)malonate (56n)

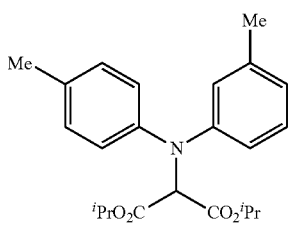

56n

Yield: 55% (Method E); Physical State: white solid (m.p.=75-78° C.); R$_f$=0.45 (10% EtOAc/hexanes); $^1$H NMR (600 MHz, CDCl$_3$): δ 7.20-7.01 (m, 5H), 6.83-6.64 (m, 3H), 5.32 (s, 1H), 5.11-4.96 (m, 2H), 2.33 (s, 3H), 2.27 (s, 3H), 1.17 (dd, J=24.5, 6.4 Hz, 12H); $^{13}$C NMR (151 MHz, CDCl$_3$): δ 166.81, 146.90, 143.09, 138.60, 133.34, 129.69, 128.73, 124.55, 122.04, 120.17, 116.70, 116.68, 69.53, 67.99, 21.52, 21.42, 21.37, 20.72; HRMS (ESI-TOF): calc'd for C$_{23}$H$_{29}$NO$_4$ [M+H]$^+$ 384.2169; found 384.2195.

41. Diisopropyl 2-(thiophen-2-yl(p-tolyl)amino)malonate (56o)

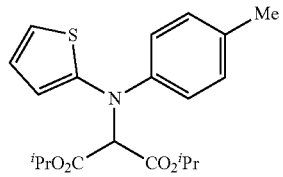

56o

Yield: 61% (Method E); Physical State: yellow-colored oily liquid; R$_f$=0.46 (10% EtOAc/hexanes); $^1$H NMR (600 MHz, CDCl$_3$): δ 7.44 (dd, J=3.7, 1.1 Hz, 1H), 7.31 (dd, J=5.1, 1.1 Hz, 1H), 7.00 (dd, J=5.0, 3.7 Hz, 1H), 6.89 (d, J=8.2 Hz, 2H), 6.50 (d, J=8.4 Hz, 2H), 5.62 (s, 1H), 5.04 (hept, J=6.2 Hz, 2H), 2.19 (s, 3H), 1.19 (d, J=6.4 Hz, 6H), 1.08 (d, J=6.4 Hz, 6H); $^{13}$C NMR (151 MHz, CDCl$_3$): δ 167.39, 141.71, 139.49, 129.20, 127.98, 127.80, 126.72, 126.54, 114.81, 70.44, 69.35, 21.13, 21.11, 20.27; HRMS (ESI-TOF): calc'd for C$_{20}$H$_{25}$NO$_4$S [M+H]$^+$ 376.1577; found 376.1573.

42. Diisopropyl 2-(benzo[b]thiophen-3-yl(p-tolyl)amino)malonate (56p)

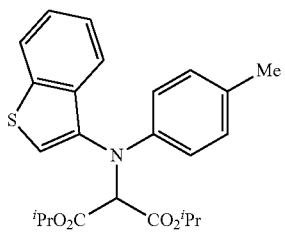

56p

Yield: 46% (Method E); Physical State: orange colored waxy solid; R$_f$=0.42 (10% EtOAc/hexanes); $^1$H NMR (600 MHz, CDCl$_3$): δ 8.19 (dd, J=6.3, 2.9 Hz, 1H), 8.15 (s, 1H), 7.81 (dd, J=5.9, 2.9 Hz, 1H), 7.30 (td, J=6.5, 5.6, 3.7 Hz, 2H), 6.84 (d, J=8.3 Hz, 2H), 6.56 (d, J=8.4 Hz, 2H), 5.48 (s, 1H), 5.05 (hept, J=6.2 Hz, 2H), 2.16 (s, 3H), 1.11 (dd, J=15.7, 6.3 Hz, 12H); $^{13}$C NMR (151 MHz, CDCl$_3$): δ 167.42, 141.75, 140.53, 137.12, 129.95, 129.21, 128.62, 128.06, 125.23, 123.94, 123.57, 122.34, 115.61, 70.36, 69.87, 21.34, 21.33, 20.35; HRMS (ESI-TOF): calc'd for C$_{24}$H$_{27}$NO$_4$S [M+H]$^+$ 426.1734; found 426.1788.

43. Diisopropyl 2-((4-chlorophenyl)(4-methoxyphenyl)amino)malonate (56q)

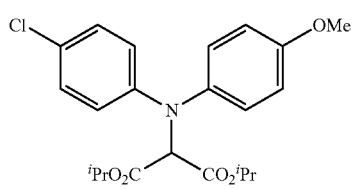

56q

Yield: 36% (Method E); Physical State: dark yellow colored oily liquid; $R_f$=0.43 (10% EtOAc/hexanes); $^1$H NMR (600 MHz, CDCl$_3$): δ 7.29 (d, J=8.9 Hz, 2H), 7.08 (d, J=9.0 Hz, 2H), 6.89 (d, J=8.9 Hz, 2H), 6.56 (d, J=9.0 Hz, 2H), 5.21 (s, 1H), 5.01 (hept, J=6.2 Hz, 2H), 3.79 (s, 3H), 1.15 (dd, J=11.2, 6.3 Hz, 12H); $^{13}$C NMR (151 MHz, CDCl$_3$): δ 166.42, 157.91, 146.49, 137.23, 129.71, 128.53, 123.94, 116.60, 114.64, 69.78, 68.08, 55.32, 21.39, 21.38; HRMS (ESI-TOF): calc'd for $C_{22}H_{26}ClNO_5$ [M+H]$^+$ 420.1572; found 420.1576.

44. Diisopropyl 2-((4-fluoro-3,5-dimethylphenyl)(4-methoxyphenyl)amino)malonate (56r)

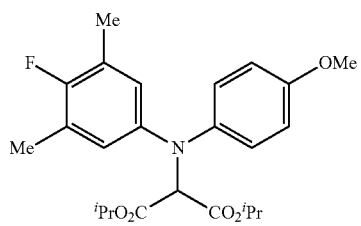

Yield: 49% (Method E); Physical State: brown colored solid (m.p.=72-78° C.); $R_f$=0.31 (10% EtOAc/hexanes); $^1$H NMR (600 MHz, CDCl$_3$): δ 7.13 (d, J=8.9 Hz, 2H), 6.84 (d, J=9.0 Hz, 2H), 6.49 (d, J=6.1 Hz, 2H), 5.23 (s, 1H), 5.03 (hept, J=6.2 Hz, 2H), 3.78 (s, 3H), 2.16 (d, J=1.6 Hz, 6H), 1.16 (dd, J=15.7, 6.3 Hz, 12H); $^{13}$C NMR (151 MHz, CDCl$_3$): δ 166.81, 156.34, 155.79, 154.22, 142.61, 138.88, 126.39, 124.49, 124.37, 119.27, 114.35, 69.50, 68.33, 55.33, 21.40, 21.38, 14.78, 14.76; HRMS (ESI-TOF): calc'd for $C_{24}H_{30}FNO_5$ [M+H]$^+$ 432.2181; found 432.2178.

45. Diisopropyl 2-((4-(2-((tert-butyldimethylsilyl)oxy)ethyl)phenyl)(4-fluoro-3,5-dimethylphenyl)amino)malonate (56s)

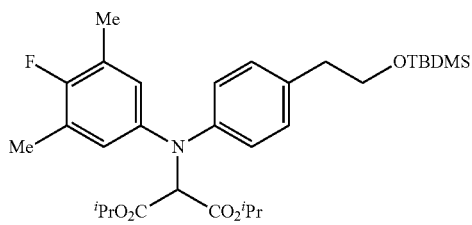

Yield: 57% (Method E); Physical State: yellow colored oily liquid; $R_f$=0.48 (10% EtOAc/hexanes); $^1$H NMR (600 MHz, CDCl$_3$): δ 7.06 (d, J=8.4 Hz, 2H), 6.84 (d, J=6.3 Hz, 2H), 6.80 (d, J=8.5 Hz, 2H), 5.26 (s, 1H), 5.03 (hept, J=6.2 Hz, 2H), 3.77 (t, J=7.1 Hz, 2H), 2.75 (t, J=7.1 Hz, 2H), 2.20 (s, 6H), 1.17 (dd, J=21.4, 6.3 Hz, 12H), 0.89 (s, 9H), 0.01 (s, 6H); $^{13}$C NMR (151 MHz, CDCl$_3$): δ 166.72, 157.51, 155.91, 145.26, 140.76, 140.74, 131.88, 129.60, 125.08, 125.05, 124.83, 124.70, 119.31, 69.50, 68.08, 64.58, 38.71, 25.85, 21.41, 21.37, 18.24, 14.65, 14.62, −5.46; HRMS (ESI-TOF): calc'd for $C_{31}H_{46}FNO_5Si$ [M+H]$^+$ 560.3202; found 560.3256.

46. Diisopropyl 2-((2-bromophenyl)(p-tolyl)amino)malonate (56t)

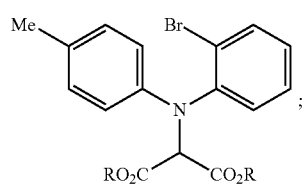

Yield: 18% (Method E); Physical State: yellow colored oily liquid; $R_f$=0.40 (10% EtOAc/hexanes); $^1$H NMR (600 MHz, CDCl$_3$): δ 7.76 (dd, J=7.9, 1.5 Hz, 1H), 7.64 (dd, J=8.0, 1.4 Hz, 1H), 7.34 (td, J=1.1, 1.4 Hz, 1H), 7.14 (td, J=7.8, 1.6 Hz, 1H), 6.97 (d, J=8.4 Hz, 2H), 6.50 (d, J=8.6 Hz, 2H), 5.33 (s, 1H), 5.02 (hept, J=6.3 Hz, 2H), 2.23 (s, 3H), 1.21 (d, J=6.3 Hz, 6H), 1.10 (d, J=6.3 Hz, 6H); $^{13}$C NMR (151 MHz, CDCl$_3$): δ 166.58, 143.82, 143.69, 133.70, 131.65, 129.33, 128.77, 128.67, 128.11, 125.67, 115.39, 69.78, 67.73, 21.47, 21.31, 20.36; HRMS (ESI-TOF): calc'd for $C_{22}H_{26}BrNO_4$ [M+H]$^+$ 448.1118 [M+Na]$^+$ 470.0937; found 448.1045, 470.0877.

47. Diisopropyl 2-((4-chlorophenyl)(3,5-dimethylphenyl)amino)malonate (56u)

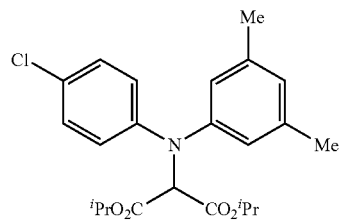

Yield: 33% (Method E); Physical State: dark yellow colored solid (m.p.=55-62° C.); $R_f$=0.48 (10% EtOAc/hexanes); $^1$H NMR (600 MHz, CDCl$_3$): δ 7.17 (d, J=8.9 Hz, 2H), 6.89 (d, J=8.9 Hz, 2H), 6.72 (d, J=8.0 Hz, 3H), 5.26 (s, 1H), 5.03 (hept, J=6.3 Hz, 2H), 2.25 (s, 6H), 1.19 (d, J=6.3 Hz, 6H), 1.14 (d, J=6.3 Hz, 6H); $^{13}$C NMR (151 MHz, CDCl$_3$): δ 166.59, 145.87, 145.04, 138.98, 128.80, 126.72, 125.64, 121.99, 121.26, 69.79, 68.11, 21.48, 21.42; HRMS (ESI-TOF): calc'd for $C_{23}H_{28}ClNO_4$ [M+H]$^+$ 418.1780; found 418.1785.

48. Diisopropyl 2-((3,5-dimethylphenyl)(4-phenoxyphenyl)amino)malonate (56v)

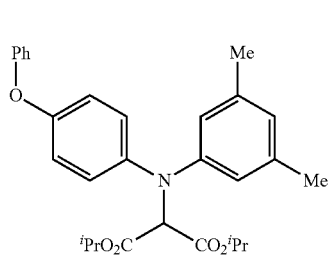

Yield: 35% (Method E); Physical State: dark brown colored oily liquid; $R_f$=0.42 (10% EtOAc/hexanes); $^1$H NMR (600 MHz, CDCl$_3$): δ 7.34 (t, J=7.9 Hz, 2H), 7.20 (d, J=8.8 Hz, 2H), 7.10 (t, J=7.3 Hz, 1H), 7.03 (d, J=7.9 Hz, 2H), 6.97 (d, J=8.9 Hz, 2H), 6.61 (s, 1H), 6.53 (s, 2H), 5.33 (s, 1H), 5.06 (hept, J=6.2 Hz, 2H), 2.25 (s, 6H), 1.21 (d, J=6.3 Hz, 6H), 1.18 (d, J=6.3 Hz, 6H); $^{13}$C NMR (151 MHz, CDCl$_3$): δ 166.77, 157.43, 153.38, 147.06, 140.79, 138.59, 129.60, 126.45, 123.16, 122.96, 119.49, 118.46, 116.99, 69.59, 68.02, 21.45, 21.42; HRMS (ESI-TOF): calc'd for C$_{29}$H$_{33}$NO$_5$ [M+H]$^+$ 476.2431; found 476.2465.

49. Diisopropyl 2-([1,1'-biphenyl]-3-yl(3,5-dimethylphenyl)amino)malonate (56w)

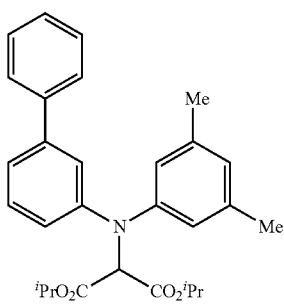

Yield: 48% (Method E); Physical State: yellow colored viscous oily liquid; $R_f$=0.40 (10% EtOAc/hexanes); $^1$H NMR (600 MHz, CDCl$_3$): δ 7.60 (d, J=7.4 Hz, 2H), 7.45 (t, J=7.6 Hz, 2H), 7.39-7.33 (m, 3H), 7.28 (d, J=7.7 Hz, 1H), 7.06 (d, J=8.2 Hz, 1H), 6.83 (s, 2H), 6.76 (s, 1H), 5.45 (s, 1H), 5.10 (hept, J=6.2 Hz, 2H), 2.32 (s, 6H), 1.23 (d, J=6.3 Hz, 6H), 1.17 (d, J=6.3 Hz, 6H); $^{13}$C NMR (151 MHz, CDCl$_3$): δ 166.74, 146.67, 146.02, 141.91, 141.07, 138.68, 129.23, 128.55, 127.12, 126.95, 124.97, 120.87, 120.55, 120.46, 120.09, 69.55, 68.15, 21.41, 21.33; HRMS (ESI-TOF): calc'd for C$_{29}$H$_{33}$NO$_4$ [M+H]$^+$ 460.2482; found 460.2451.

50. Diisopropyl 2-((3,5-dimethylphenyl)(4-fluoro-3,5-dimethylphenyl)amino) malonate (56x)

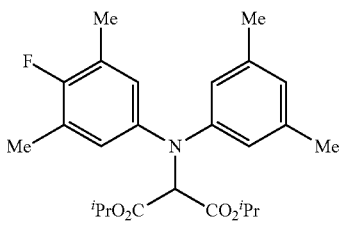

Yield: 33% (Method E); Physical State: pale brown colored solid (m.p.=65-71° C.); $R_f$=0.48 (10% EtOAc/hexanes); $^1$H NMR (600 MHz, CDCl$_3$): δ 6.94 (d, J=6.3 Hz, 2H), 6.56 (s, 1H), 6.43 (s, 2H), 5.28 (s, 1H), 5.06 (hept, J=6.2 Hz, 2H), 2.24 (s, 12H), 1.21 (d, J=6.3 Hz, 6H), 1.18 (d, J=6.3 Hz, 6H); $^{13}$C NMR (151 MHz, CDCl$_3$): δ 166.74, 157.98, 156.38, 147.30, 140.10, 140.08, 138.38, 126.70, 126.66, 124.85, 124.73, 122.40, 115.80, 69.45, 68.00, 21.42, 21.40, 21.36, 14.63, 14.61; HRMS (ESI-TOF): calc'd for C$_{25}$H$_{32}$FNO$_4$ [M+H]$^+$ 430.2388; found 430.2401.

51. Diisopropyl 2-(benzo[6]thiophen-3-yl(3,5-dimethoxyphenyl)amino)malonate (56y)

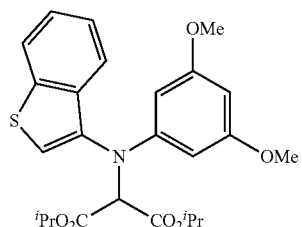

Yield: 77% (Method E); Physical State: yellow colored waxy solid; $R_f$=0.25 (30% EtOAc/hexanes); $^1$H NMR (600 MHz, CDCl$_3$): δ 8.28 (s, 1H), 8.17 (dd, J=6.7, 2.4 Hz, 1H), 7.82 (dd, J=6.5, 2.4 Hz, 1H), 7.35-7.26 (m, 2H), 5.91 (d, J=2.1 Hz, 2H), 5.87 (t, J=2.1 Hz, 1H), 5.71 (s, 1H), 5.09 (hept, J=6.2 Hz, 2H), 3.62 (s, 6H), 1.17 (d, J=6.3 Hz, 6H), 1.12 (d, J=6.3 Hz, 6H); $^{13}$C NMR (151 MHz, CDCl$_3$): δ 167.24, 161.01, 145.98, 140.25, 137.01, 129.64, 128.33, 124.81, 123.93, 123.59, 122.29, 93.81, 91.51, 70.45, 69.28, 54.88, 21.26, 21.22; HRMS (ESI-TOF): calc'd for C$_{25}$H$_{29}$NO$_6$S [M+H]$^+$ 472.1788; found 472.1809.

52. Diisopropyl 2-(benzo[d][1,3]dioxol-5-yl(thiophen-2-yl)amino)malonate (56z)

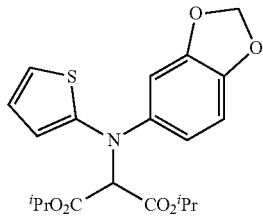

Yield: 66% (Method E); Physical State: yellow colored oily liquid; $R_f$=0.29 (10% EtOAc/hexanes); $^1$H NMR (600 MHz, CDCl$_3$): δ 7.41 (dd, J=3.6, 1.0 Hz, 1H), 7.30 (dd, J=5.1, 1.0 Hz, 1H), 6.99 (dd, J=5.0, 3.8 Hz, 1H), 6.52 (d, J=8.4 Hz, 1H), 6.21 (d, J=2.3 Hz, 1H), 5.99 (dd, J=8.4, 2.3 Hz, 1H), 5.78 (s, 2H), 5.51 (s, 1H), 5.01 (hept, J=6.2 Hz, 2H), 1.16 (d, J=6.3 Hz, 6H), 1.08 (d, J=6.3 Hz, 6H); $^{13}$C NMR (151 MHz, CDCl$_3$): δ 167.29, 147.76, 140.43, 139.48, 139.46, 128.09, 126.81, 126.64, 108.10, 106.85, 100.49, 97.86, 70.53, 69.67, 21.21, 21.13; HRMS (ESI-TOF): calc'd for $C_{20}H_{23}NO_6S$ [M+H]$^+$ 406.1319; found 406.1320.

53. Diethyl 2-((2,6-dichlorophenyl)(2-vinylphenyl)amino)malonate (57a)

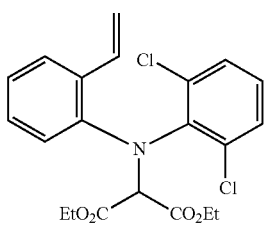

Yield: 64% (Method E); Physical State: beige colored viscous oily liquid; $R_f$=0.48 (20% EtOAc/hexanes); $^1$H NMR (600 MHz, CDCl$_3$): δ 7.44 (d, J=7.9 Hz, 1H), 7.34 (d, J=7.7 Hz, 1H), 7.31-7.20 (m, 2H), 7.12 (t, J=7.5 Hz, 1H), 7.06-6.99 (m, 2H), 6.97 (t, J=7.6 Hz, 1H), 6.08 (s, 1H), 5.61 (d, J=17.3 Hz, 1H), 5.38 (d, J=11.0 Hz, 1H), 4.51-3.95 (m, 4H), 1.24 (t, J=7.1 Hz, 3H), 1.16 (t, J=7.1 Hz, 3H); $^{13}$C NMR (151 MHz, CDCl$_3$): δ 170.00, 155.20, 138.74, 137.72, 135.84, 135.22, 134.46, 129.68, 129.38, 128.94, 128.54, 128.28, 127.76, 126.86, 126.66, 117.91, 62.47, 61.29, 61.07, 14.41, 13.96; HRMS (ESI-TOF): calc'd for $C_{21}H_{21}Cl_2NO_4$ [M+H]$^+$ 422.0920; found 422.0858.

54. Diethyl 2-((2-allylphenyl)(2,6-dichlorophenyl)amino)malonate (57b)

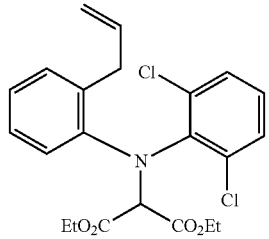

Yield: 72% (Method E); Physical State: beige colored viscous oily liquid; $R_f$=0.19 (10% EtOAc/hexanes); $^1$H NMR (600 MHz, CDCl$_3$): δ 7.43 (d, J=7.9 Hz, 1H), 7.26 (d, J=5.1 Hz, 1H) 7.07 (d, J=4.1 Hz, 2H), 7.04-7.01 (m, 1H), 6.99 (t, J=8.0 Hz, 1H), 6.93-6.86 (m, 1H), 6.04-5.87 (m, 2H), 5.03 (d, J=13.7 Hz, 2H), 4.27-4.07 (m, 4H), 3.71 (dd, J=15.8, 6.2 Hz, 1H), 3.46 (dd, J=15.8, 6.8 Hz, 1H), 1.21 (t, J=7.1 Hz, 3H), 1.14 (t, J=7.1 Hz, 1H); $^{13}$C NMR (151 MHz, CDCl$_3$): δ 169.89, 155.15, 139.57, 137.69, 136.79, 135.71, 135.29, 130.35, 129.97, 129.56, 128.94, 128.52, 128.39, 127.79, 125.65, 116.11, 62.44, 61.22, 60.87, 37.39, 14.39, 13.92; HRMS (ESI-TOF): calc'd for $C_{22}H_{23}Cl_2NO_4$ [M+H]$^+$ 436.1077; found 436.1076.

55. Diisopropyl 2-(diphenylamino)malonate (59a)

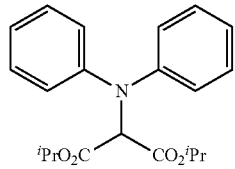

Yield: 75% (Method C); Physical State: pale brown colored waxy solid; $R_f$=0.42 (10% EtOAc/hexanes); $^1$H NMR (600 MHz, CDCl$_3$): δ 7.17 (t, J=7.8 Hz, 4H), 6.96 (d, J=8.0 Hz, 4H), 6.92 (t, J=7.3 Hz, 2H), 5.25 (s, 1H), 4.93 (hept, J=6.2 Hz, 2H), 1.08 (d, J=6.3 Hz, 6H), 1.02 (d, J=6.3 Hz, 6H); $^{13}$C NMR (151 MHz, CDCl$_3$): δ 166.63, 146.10, 129.01, 122.59, 122.08, 69.60, 67.90, 21.36, 21.29; HRMS (ESI-TOF): calc'd for $C_{21}H_{25}NO_4$ [M+H]$^+$ 356.1856; found 356.1856.

56. Diisopropyl 2-(di-p-tolylamino)malonate (59b)

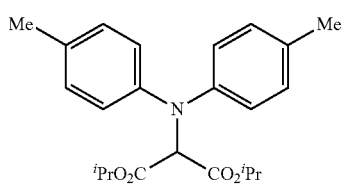

Yield: 73% (Method C); Physical State: off white waxy solid; $R_f$=0.46 (10% EtOAc/hexanes); $^1$H NMR (600 MHz, CDCl$_3$): δ 7.10 (d, J=8.2 Hz, 4H), 6.99 (d, J=8.4 Hz, 4H), 5.35 (s, 1H), 5.06 (hept, J=6.1 Hz, 2H), 2.33 (s, 6H), 1.22 (d, J=6.4 Hz, 6H), 1.17 (d, J=6.5 Hz, 6H); $^{13}$C NMR (151 MHz, CDCl$_3$): δ 166.74, 143.91, 131.73, 129.47, 121.94, 69.38, 67.95, 21.32, 21.29, 20.48; HRMS (ESI-TOF): calc'd for C$_{23}$H$_{29}$NO$_4$ [M+H]$^+$ 384.2169; found 384.2218.

57. Diisopropyl 2-(bis(4-chlorophenyl)amino)malonate (59c)

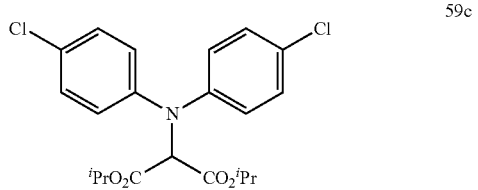

59c

Yield: 40% (Method C); Physical State: yellow colored waxy solid; $R_f$=0.50 (10% EtOAc/hexanes); $^1$H NMR (600 MHz, CDCl$_3$): δ 7.21 (d, J=8.9 Hz, 4H), 6.97 (d, J=8.9 Hz, 4H), 5.24 (s, 1H), 5.02 (hept, J=6.2 Hz, 2H), 1.18 (d, J=6.4 Hz, 6H), 1.13 (d, J=6.4 Hz, 6H); $^{13}$C NMR (151 MHz, CDCl$_3$): δ 166.19, 144.53, 129.20, 128.27, 123.47, 70.06, 67.93, 21.41, 21.38; HRMS (ESI-TOF): calc'd for C$_{21}$H$_{23}$Cl$_2$NO$_4$ [M+H]$^+$ 424.1077; found 424.1038.

58. Diisopropyl 2-(bis(4-(methylthio)phenyl)amino)malonate (59d)

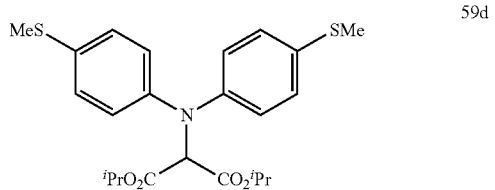

59d

Yield: 45% (Method C); Physical State: brown colored oily liquid; $R_f$=0.37 (10% EtOAc/hexanes); $^1$H NMR (600 MHz, CDCl$_3$): δ 7.20 (d, J=8.3 Hz, 4H), 6.98 (d, J=8.4 Hz, 4H), 5.28 (s, 1H), 5.02 (hept, J=6.3 Hz, 2H), 2.43 (s, 6H), 1.16 (dd, J=25.9, 6.4 Hz, 12H); $^{13}$C NMR (151 MHz, CDCl$_3$): δ 166.33, 143.78, 131.61, 128.61, 122.52, 69.70, 67.79, 21.32, 21.29, 16.93; HRMS (ESI-TOF): calc'd for C$_{23}$H$_{29}$NO$_4$S$_2$ [M+H]$^+$ 448.1611; found 448.1616.

59. Diisopropyl 2-(bis(4-phenoxyphenyl)amino)malonate (59e)

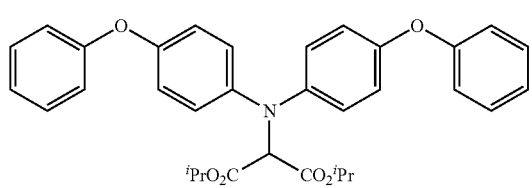

59e

Yield: 41% (Method C); Physical State: dark purple colored viscous oily liquid; $R_f$=0.35 (10% EtOAc/hexanes); $^1$H NMR (600 MHz, CDCl$_3$): δ 7.33 (t, J=7.9 Hz, 4H), 7.08 (dd, J=16.6, 8.2 Hz, 6H), 7.01 (d, J=8.0 Hz, 4H), 6.96 (d, J=8.9 Hz, 4H), 5.32 (s, 1H), 5.08 (hept, J=6.1 Hz, 2H), 1.21 (dd, J=21.7, 6.3 Hz, 12H); $^{13}$C NMR (151 MHz, CDCl$_3$): δ 166.69, 157.66, 152.30, 142.04, 129.58, 123.42, 122.80, 119.84, 118.20, 69.77, 68.28, 21.46, 21.44; HRMS (ESI-TOF): calc'd for C$_{33}$H$_{33}$NO$_6$ [M+H]$^+$ 540.2381; found 540.2389.

60. Diisopropyl 2-(di([1,1'-biphenyl]-4-yl)amino)malonate (59f)

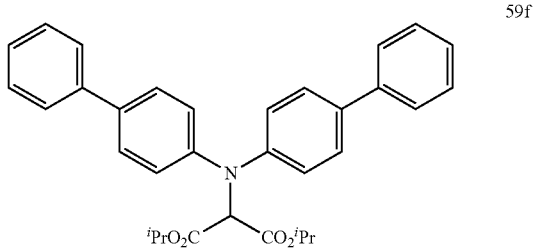

59f

Yield: 60% (Method C); Physical State: pale yellow colored waxy solid; $R_f$=0.38 (10% EtOAc/hexanes); $^1$H NMR (600 MHz, CDCl$_3$): δ 7.65 (dd, J=23.1, 8.0 Hz, 8H), 7.51 (t, J=7.6 Hz, 4H), 7.39 (t, J=7.3 Hz, 2H), 7.28 (d, J=8.5 Hz, 2H), 5.53 (s, 1H), 5.16 (hept, J=6.1 Hz, 2H), 1.29 (d, J=6.3 Hz, 6H), 1.24 (d, J=6.3 Hz, 6H); $^{13}$C NMR (151 MHz, CDCl$_3$): δ 166.58, 145.39, 140.55, 135.54, 128.64, 127.73, 126.76, 126.60, 122.39, 69.82, 67.98, 21.43, 21.36; RMS (ESI-TOF): calc'd for C$_{33}$H$_{33}$NO$_4$ [M+H]$^+$ 508.2482 [M+Na]$^+$ 530.2302; found 508.2522, 530.2346.

61. Diisopropyl 2-(di([1,1'-biphenyl]-3-yl)amino)malonate (59g)

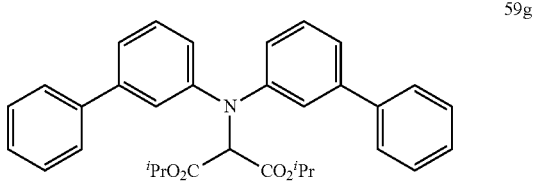

59g

Yield: 65% (Method C); Physical State: pale yellow colored oily liquid; $R_f$=0.45 (10% EtOAc/hexanes); $^1$H NMR (600 MHz, CDCl$_3$): δ 7.66 (d, J=7.7 Hz, 4H), 7.50 (dd, J=14.6, 7.1 Hz, 6H), 7.45 (t, J=7.8 Hz, 2H), 7.43-7.36 (m, 4H), 7.22 (d, J=7.8 Hz, 2H), 5.60 (s, 1H), 5.15 (hept, J=5.9 Hz, 2H), 1.26 (d, J=6.4 Hz, 6H), 1.20 (d, J=6.4 Hz, 6H); $^{13}$C NMR (151 MHz, CDCl$_3$): δ 166.62, 146.50, 142.18, 140.85, 129.48, 128.59, 127.22, 126.92, 121.56, 121.10, 120.79, 69.71, 68.18, 21.38, 21.30; HRMS (ESI-TOF): calc'd for C$_{33}$H$_{33}$NO$_4$ [M+H]$^+$ 508.2482; found 508.2525.

62. Diethyl 2-(bis(2-vinylphenyl)amino)malonate (59h)

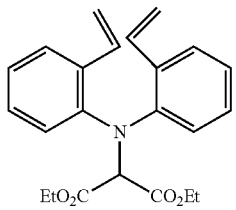

Yield: 47% (Method C); Physical State: beige colored viscous oily liquid; $R_f$=0.38 (20% EtOAc/hexanes); $^1$H NMR (600 MHz, CDCl$_3$): δ 7.34 (dd, J=20.2, 7.7 Hz, 4H), 7.22 (t, J=7.4 Hz, 2H), 7.18-7.12 (m, 2H), 6.69 (dd, J=17.1, 10.9 Hz, 2H), 6.11 (s, 1H), 5.33 (d, J=17.1 Hz, 2H), 4.96 (d, J=10.9 Hz, 2H), 4.11 (q, J=7.1 Hz, 2H), 3.90 (s, 2H), 1.07 (t, J=7.1 Hz, 6H); $^{13}$C NMR (151 MHz, CDCl$_3$): δ 171.10, 137.87, 136.75, 136.09, 129.68, 128.42, 128.30, 127.04, 115.40, 70.05, 62.37, 60.73, 14.45, 13.65; HRMS (ESI-TOF): calc'd for C$_{23}$H$_{25}$NO$_4$ [M+H]$^+$ 380.1856; found 380.1860.

63. Diethyl 2-(bis(2-allylphenyl)amino)malonate (59i)

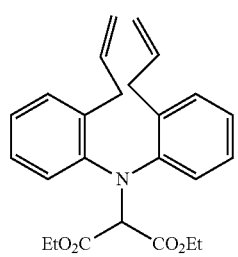

Yield: 26% (Method C); Physical State: beige colored viscous oily liquid; $R_f$=0.41 (20% EtOAc/hexanes); $^1$H NMR (600 MHz, CDCl$_3$): δ 7.41 (d, J=7.8 Hz, 2H), 7.28 (t, J=7.4 Hz, 2H), 7.24 (d, J=6.8 Hz, 2H), 7.20 (t, J=7.6 Hz, 2H), 6.08 (s, 1H), 5.65 (s, 2H), 4.99 (d, J=10.1 Hz, 2H), 4.90 (d, J=17.1 Hz, 2H), 4.28 (q, J=7.1 Hz, 2H), 4.04 (s, 2H), 3.26 (dd, J=15.5, 5.0 Hz, 2H), 3.16 (dd, J=15.7, 5.3 Hz, 2H), 1.23 (t, J=7.1 Hz, 6H); $^{13}$C NMR (151 MHz, CDCl$_3$): δ 170.77, 138.41, 137.57, 137.37, 131.95, 129.35, 128.02, 125.74, 115.99, 70.77, 62.27, 60.79, 37.93, 13.8; HRMS (ESI-TOF): calc'd for C$_{25}$H$_{29}$NO$_4$ [M+H]$^+$ 408.2169; found 408.2169.

64. Dimethyl 2-(bis(2,3-dichlorophenyl)amino)malonate (59j)

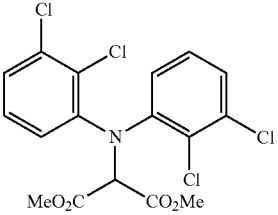

Yield: 54% (Method C); Physical State: beige colored oily liquid; $R_f$=0.24 (20% EtOAc/hexanes); $^1$H NMR (600 MHz, CDCl$_3$): δ 7.53-7.47 (m, 2H), 7.42 (d, J=8.0 Hz, 2H), 7.21 (t, J=8.1 Hz, 2H), 6.56 (s, 1H), 3.79 (s, 3H), 3.60 (s, 3H); $^{13}$C NMR (151 MHz, CDCl$_3$): δ 169.57, 136.45, 134.66, 131.47, 130.60, 130.35, 126.43, 70.20, 53.54, 52.26; HRMS (ESI-TOF): calc'd for C$_{17}$H$_{13}$Cl$_4$NO$_4$ [M+Na]$^+$ 457.9491; found 457.9428.

65. Dimethyl 2-(bis(4-chloro-2-methylphenyl)amino)malonate (59k)

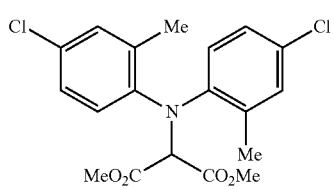

Yield: 72% (Method C); Physical State: beige colored oily liquid; $R_f$=0.23 (20% EtOAc/hexanes); $^1$H NMR (600 MHz, CDCl$_3$): δ 7.37-7.33 (m, 2H), 7.18-7.12 (m, 4H), 6.24 (s, 1H), 3.77 (s, 3H), 3.59 (s, 3H), 2.03 (s, 6H); $^{13}$C NMR (151 MHz, CDCl$_3$): δ 170.78, 138.72, 134.88, 133.75, 132.19, 130.85, 125.35, 69.44, 53.11, 52.16, 21.45; HRMS (ESI-TOF): calc'd for C$_{19}$H$_{19}$Cl$_2$NO$_4$ [M+Na]$^+$ 418.0583; found 418.0588.

66. Diisopropyl 2-(bis(3-fluoro-5-methylphenyl)amino)malonate (59l)

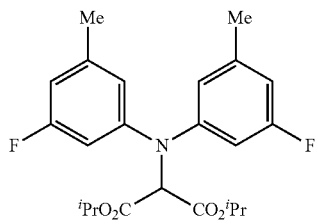

Yield: 29% (Method C); Physical State: yellow colored oily liquid; $R_f$=0.22 (5% EtOAc/hexanes); $^1$H NMR (600

MHz, CDCl$_3$): δ 6.62 (s, 2H), 6.57 (d, J=9.4 Hz, 4H), 5.23 (s, 1H), 5.04 (hept, J=6.2 Hz, 2H), 2.27 (s, 6H), 1.19 (d, J=6.3 Hz, 6H), 1.15 (d, J=6.3 Hz, 6H); $^{13}$C NMR (151 MHz, CDCl$_3$): δ 166.23, 164.07, 162.45, 147.05, 146.98, 140.79, 140.73, 118.42, 118.40, 110.78, 110.64, 106.73, 106.57, 69.99, 67.95, 21.54, 21.52, 21.45, 21.39; HRMS (ESI-TOF): calc'd for C$_{23}$H$_{27}$F$_2$NO$_4$ [M+H]$^+$ 420.1981; found 420.1981.

67. Diisopropyl 2-(bis(4-methoxy-3,5-dimethylphenyl)amino)malonate (59m)

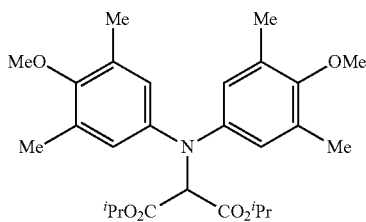

Yield: 67% (Method C); Physical State: brown colored viscous oily liquid; R$_f$=0.36 (10% EtOAc/hexanes); $^1$H NMR (600 MHz, CDCl$_3$): δ 6.66 (s, 4H), 5.21 (s, 1H), 5.02 (hept, J=6.2 Hz, 2H), 3.67 (s, 6H), 2.20 (s, 12H), 1.17 (d, J=6.3 Hz, 6H), 1.13 (d, J=6.3 Hz, 6H); $^{13}$C NMR (151 MHz, CDCl$_3$): δ 166.88, 152.40, 141.89, 131.02, 122.23, 69.35, 68.19, 59.65, 21.40, 21.34, 16.17; HRMS (ESI-TOF): calc'd for C$_{27}$H$_{37}$NO$_6$ [M+H]$^+$ 472.2694; found 472.2726.

68. Diisopropyl 2-(bis(4-fluoro-3,5-dimethylphenyl)amino)malonate (59n)

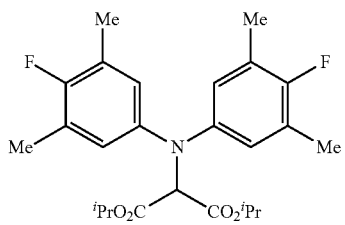

Yield: 45% (Method C); Physical State: light yellow colored solid; R$_f$=0.48 (10% EtOAc/hexanes); $^1$H NMR (600 MHz, CDCl$_3$): δ 6.66 (d, J=5.9 Hz, 4H), 5.21 (s, 1H), 5.04 (dt, J=12.2, 6.0 Hz, 2H), 2.19 (s, 12H), 1.18 (dd, J=18.1, 6.1 Hz, 12H); $^{13}$C NMR (151 MHz, CDCl$_3$): δ 166.75, 156.78, 155.19, 141.63, 141.61, 124.75, 124.63, 122.48, 122.45, 69.55, 68.39, 21.42, 21.39, 14.73, 14.71; HRMS (ESI-TOF): calc'd for C$_{25}$H$_{31}$F$_2$NO$_4$ [M+H]$^+$ 448.2294; found 448.2252.

69. Dimethyl 2-(bis(4-methoxy-2,5-dimethylphenyl)amino)malonate (59o)

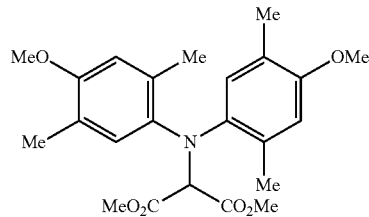

Yield: 55% (Method C); Physical State: pale pink colored puffy solid; R$_f$=0.23 (20% EtOAc/hexanes); $^1$H NMR (600 MHz, CDCl$_3$): δ 7.14 (s, 2H), 6.60 (s, 2H), 6.12 (s, 1H), 3.80 (d, J=16.0 Hz, 9H), 3.62 (s, 3H), 2.18 (s, 6H), 2.06 (s, 6H); $^{13}$C NMR (151 MHz, CDCl$_3$): δ 172.00, 156.71, 135.24, 131.53, 128.65, 122.67, 113.63, 69.42, 54.94, 52.63, 51.88, 21.49, 15.84; HRMS (ESI-TOF): calc'd for C$_{23}$H$_{29}$NO$_6$ [M+H]$^+$ 438.1887; found 438.1886.

70. Diisopropyl 2-(dibenzylamino)malonate (59p)

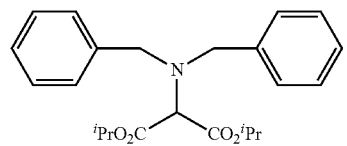

Yield: 53% (Method C); Physical State: yellow-colored oily liquid; R$_f$=0.69 (10% EtOAc/hexanes); $^1$H NMR (600 MHz, CDCl$_3$): δ 7.51 (d, J=7.2 Hz, 4H), 7.36 (t, J=7.6 Hz, 4H), 7.28 (t, J=7.3 Hz, 2H), 5.18 (hept, J=6.2 Hz, 2H), 4.19 (s, 1H), 3.93 (s, 4H), 1.32 (dd, J=6.3, 3.3 Hz, 12H); $^{13}$C NMR (151 MHz, CDCl$_3$): δ 167.57, 138.99, 128.72, 128.16, 127.06, 68.77, 65.48, 55.30, 21.72, 21.64; HRMS (ESI-TOF): calc'd for C$_{23}$H$_{29}$NO$_4$ [M+H]$^+$ 384.2169; found 384.2173.

71. Diisopropyl 2-(dicyclobutylamino)malonate (59q)

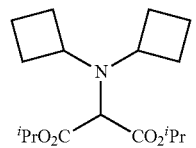

Yield: 39% (Method C); Physical State: colorless oily liquid; R$_f$=0.51 (10% EtOAc/hexanes); $^1$H NMR (600 MHz, CDCl$_3$): δ 5.05 (hept, J=6.3 Hz, 2H), 4.15 (s, 1H), 3.58 (p, J=8.5, 8.1 Hz, 2H), 2.05-1.95 (m, 8H), 1.57 (dq, J=11.8, 6.9, 6.2 Hz, 2H), 1.54-1.46 (m, 2H), 1.25 (d, J=6.3 Hz, 12H); $^{13}$C NMR (151 MHz, CDCl$_3$): δ 168.55, 68.73, 63.84, 54.87, 30.01, 21.66, 21.60, 14.92; HRMS (ESI-TOF): calc'd for C$_{17}$H$_{29}$NO$_4$ [M+H]$^+$ 312.2169; found 312.2176.

72. Diisopropyl 2-(diisopropylamino)malonate (59r)

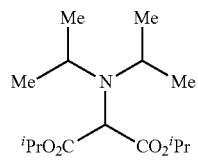

59r

Yield: 32% (Method D); Physical State: light orange colored liquid; R$_f$=0.59 (10% EtOAc/hexanes); $^1$H NMR (600 MHz, CDCl$_3$): δ 5.02 (hept, J=6.3 Hz, 2H), 4.17 (s, 1H), 3.29 (hept, J=6.6 Hz, 2H), 1.23 (dd, J=6.3, 2.1 Hz, 12H), 1.03 (d, J=6.1 Hz, 12H); $^{13}$C NMR (151 MHz, CDCl$_3$): δ 170.43, 68.36, 62.23, 46.62, 22.34, 21.60, 21.53; HRMS (ESI-TOF): calc'd for C$_{15}$H$_{29}$NO$_4$ [M+H]$^+$ 288.2169; found 288.2161.

Note: For this reaction to form 59r, directly iPrMgCl—LiCl solution in THF was added on to the aminating agent 47.

Characterization Data of the Amines Formed by the Addition of Soft C-Nucleophiles onto the Iminomalonates in Scheme 6

1. 2,2-diisopropyl 3-methyl 1-(3-(trifluoromethyl)phenyl)aziridine-2,2,3 tricarboxylate (64a)

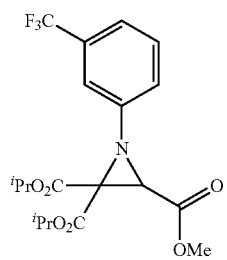

64a

Yield: 49% (Method G); Physical State: pale brown colored viscous oily liquid; R$_f$=0.35 (20% EtOAc/hexanes); $^1$H NMR (600 MHz, CDCl$_3$): δ 7.32 (t, J=7.9 Hz, 1H), 7.25 (d, J=7.8 Hz, 1H), 7.13 (s, 1H), 7.09 (d, J=7.9 Hz, 1H), 5.15 (hept, J=6.2 Hz, 1H), 4.82 (hept, J=6.2 Hz, 1H), 3.76 (s, 1H), 3.75 (s, 3H), 1.26 (dd, J=21.5, 6.3 Hz, 6H), 1.07 (d, J=6.3 Hz, 3H), 0.95 (d, J=6.3 Hz, 3H); $^{13}$C NMR (151 MHz, CDCl$_3$): δ 166.13, 163.03, 162.03, 146.61, 131.38, 131.16, 129.50, 124.43, 122.62, 122.60, 120.58, 120.55, 120.53, 120.50, 116.14, 116.11, 116.09, 116.06, 71.26, 69.99, 52.77, 52.66, 45.52, 21.29, 21.21, 20.83; HRMS (ESI-TOF): calc'd for C$_{19}$H$_{22}$F$_3$NO$_6$ [M+H]$^+$ 418.1472; found 418.1489.

2. 2,2-diisopropyl 3-methyl 1-(4-(2-((tert-butyldimethylsilyl)oxy)ethyl)phenyl) aziridine-2,2,3-tricarboxylate (64b)

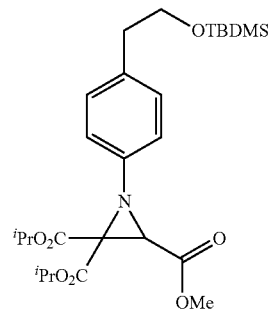

64b

Yield: 63% (Method G); Physical State: brown colored viscous oily liquid; R$_f$=0.41 (20% EtOAc/hexanes); $^1$H NMR (600 MHz, CDCl$_3$): δ 7.02 (d, J=8.2 Hz, 2H), 6.82 (d, J=8.3 Hz, 2H), 5.15 (hept, J=6.2 Hz, 1H), 4.80 (hept, J=6.2 Hz, 1H), 3.74 (s, 3H), 3.72 (s, 1H), 3.69 (t, J=6.8 Hz, 2H), 2.67 (t, J=6.8 Hz, 2H), 1.28 (d, J=6.3 Hz, 3H), 1.25 (d, J=6.3 Hz, 3H), 1.08 (d, J=6.3 Hz, 3H), 0.92 (d, J=6.3 Hz, 3H), 0.81 (s, 9H), −0.09 (d, J=2.1 Hz, 6H); $^{13}$C NMR (151 MHz, CDCl$_3$): δ 166.74, 163.52, 162.27, 144.03, 134.89, 129.44, 119.04, 70.60, 69.64, 64.13, 52.95, 52.52, 45.46, 38.68, 25.72, 21.42, 21.39, 21.29, 20.90, 18.07, −5.62; HRMS (ESI-TOF): calc'd for C$_{26}$H$_{41}$NO$_7$Si [M+H]$^+$ 508.2725; found 508.2768.

3. 2,2-diisopropyl 3-methyl 1-(pyridin-3-yl)aziridine-2,2,3-tricarboxylate (64c)

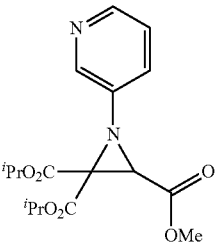

64c

Yield: 40% (Method G); Physical State: brown colored viscous oily liquid; R$_f$=0.27 (50% EtOAc/hexanes); $^1$H NMR (600 MHz, CDCl$_3$): δ 8.25 (s, 2H), 7.20 (d, J=8.1 Hz, 1H), 7.13 (dd, J=7.9, 4.7 Hz, 1H), 5.14 (hept, J=6.2 Hz, 1H), 4.83 (hept, J=6.2 Hz, 1H), 3.75 (s, 3H), 3.72 (s, 1H), 1.25 (dd, J=20.1, 6.3 Hz, 6H), 1.08 (d, J=6.2 Hz, 3H), 0.96 (d, J=6.3 Hz, 3H); $^{13}$C NMR (151 MHz, CDCl$_3$): δ 166.10, 162.96, 161.99, 145.19, 142.22, 141.51, 126.46, 123.23, 1.33, 70.06, 52.77, 52.38, 45.09, 21.43, 21.36, 21.28, 20.98; HRMS (ESI-TOF): calc'd for C$_{17}$H$_{22}$N$_2$O$_6$ [M+H]$^+$ 351.1551; found 351.1593.

4. Diisopropyl 2-((4-methoxyphenyl)(2-oxo-2-phenylethyl)amino)malonate (66)

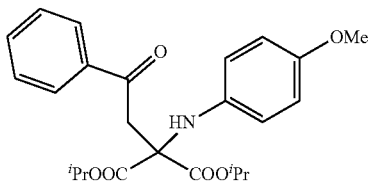

Yield: 60% (Method H); Physical State: brown waxy solid; $R_f$=0.41 (20% EtOAc/hexanes); $^1$H NMR (600 MHz, CDCl$_3$): δ 7.84 (d, J=7.3 Hz, 2H), 7.48 (d, J=14.8 Hz, 1H), 7.36 (t, J=7.8 Hz, 2H), 6.66 (d, J=9.0 Hz, 2H), 6.59 (d, J=9.0 Hz, 2H), 5.15-5.05 (m, 3H), 4.02 (s, 2H), 3.65 (s, 3H), 1.19 (d, J=6.4 Hz, 6H), 1.14 (d, J=6.4 Hz, 6H); $^{13}$C NMR (151 MHz, CDCl$_3$): δ 196.29, 168.81, 153.27, 137.92, 136.50, 133.13, 128.38, 127.81, 117.69, 114.41, 70.08, 66.94, 55.36, 40.86, 21.24; HRMS (ESI-TOF): calc'd for $C_{24}H_{29}NO_6$ [M+H]$^+$ 428.2068; found 428.2069.

General Experimental Procedures for Post-Functionalization of the Amines (as Displayed in FIGS. 6 & 7)

Method I: In a thick-walled flame dried reaction vial, the malonate protected amine (55, 56 or 59; 1.0 mmol, 1.0 equiv) was dissolved in anhydrous THF (10 mL, 0.1M) under argon. To this solution, NaH (60% in mineral oil; 1.0 mmol, 1.0 equiv) was added in one portion and stirred at room temperature for 10 min. Then this reaction mixture was cooled to −78° C. using a dry ice/acetone bath and N-chlorosuccinimide (NCS; 1.0 mmol, 1.0 equiv) dissolved in anhydrous THF (10 mL, 0.1M) was added dropwise over a period of 5 minutes and stirring was continued at −78° C. for 2 h. Then the reaction mixture was quenched using saturated NH$_4$Cl solution (3 mL) and allowed to warm to room temperature. The reaction mixture was then diluted with brine (20 mL) and extracted with ethyl acetate thrice (3×30 mL). The combined organic layers were dried over anhydrous Na$_2$SO$_4$ and concentrated. The crude product was purified by column chromatography.

Method J: This procedure was adapted from the literature with slight modifications (Niwa et al, 2001) In a thick-walled uncapped reaction vial, the malonate protected amine (1.0 mmol, 1.0 equiv) was dissolved in absolute ethanol (12.8 mL, 0.078M). To this solution aqueous KOH solution (1M) (0.5 mmol, 0.5 equiv) was added at room temperature under constant stirring. Then this reaction mixture was heated to 50° C. (bath temperature) and this temperature was maintained for 6 h. Next, the reaction was quenched with saturated Na$_2$SO$_3$ solution (3 mL). Then EtOH was evaporated and the residue was extracted with ethyl acetate thrice (3×30 mL) and the combined organic layers were dried over anhydrous Na$_2$SO$_4$ and concentrated in vacuo. The crude product was purified by column chromatography.

Method K: This procedure is based on the Corey-Bakshi-Shibata reduction and it was not optimized for the sole substrate (66). In a thick-walled flame dried reaction vial, malonate protected amine (66; 1.0 mmol, 1.0 equiv) made using Method H was dissolved in anhydrous THF (5.0 mL, 0.2M) under argon. To this solution, racemic CBS catalyst (1M solution in Toluene, 10 mol %) was added first at room temperature followed by the BH$_3$.THF complex (1M solution in THF) (2.0 mmol, 2.0 equiv) added in one portion and stirred overnight (14 h). Then the reaction was quenched using saturated NH$_4$Cl solution (3 mL). Next, the reaction mixture was diluted with brine (10 mL) and extracted with ethyl acetate thrice (3×20 mL). The combined organic layers were dried over anhydrous Na$_2$SO$_4$ and concentrated. The crude product was purified by column chromatography.

Method L: In a thick walled flamed dried reaction vial, Diisopropyl 2-((2-hydroxy-2-phenylethyl)(4-methoxyphenyl)amino)malonate (67) (147 mg, 0.34 mmol, 1 equiv) was taken in anhydrous toluene (1.7 mL, 0.2M) under argon and to this ZnCl$_2$ (46.6 mg, 0.34 mmol, 1 equiv) was added in one portion at room temperature and this vial was capped with a screw cap. This reaction mixture was then heated at 50° C. overnight under constant stirring. Next day morning when the progress was checked using TLC, the starting material got totally consumed. Then the reaction mixture was diluted with water (4 mL) and extracted with ethyl acetate thrice (3×4 mL). The combined organic layers were dried over anhydrous Na$_2$SO$_4$ and concentrated in vacuo. The crude product was purified by column chromatography.

Method M: This procedure was adapted from the literature and it was unoptimized (Liegault et al., 2008 N,N-diaryl amine (61k; 141 mg, 0.60 mmol), Pd(OAc)$_2$ (13.66 mg, 0.06 mmol, 10 mol %), K$_2$CO$_3$ (8.41 mg, 0.06 mmol, 10 mol %), pivalic acid (540 mg, 3.90 mmol. 6.4 equiv) were weighed open to air and transferred to a reaction vial and heated to 110° C. in an open vial overnight (14h). The solution was then cooled to room temperature and diluted with DCM (10 mL). This mixture was washed with saturated solution of aqueous Na$_2$CO$_3$ twice (2×10 mL). The organic layer was dried over anhydrous Na$_2$SO$_4$ and concentrated in vacuo. The crude product was purified by column chromatography.

Method N: This procedure was adapted from the literature with slight modifications (Marshall et al, 1993). In a 25 mL flame dried round bottom flask, malonate protected amine 57b (1.0 mmol, 1.0 equiv) was dissolved in anhydrous DCM (10 mL, 0.1M). To this, a solution of NaOH in MeOH (2.5M) (5.0 mmol, 5.0 equiv) was added and stirred at −78° C. as ozone was passed through the solution. After 45 min, the initial yellow colored reaction mixture turned blue and a yellow precipitate has formed at the bottom. Then, ozone bubbling was stopped and oxygen flow was continued for 5 min to remove any excess ozone. The reaction mixture was diluted with water (20 mL) and extracted with DCM thrice (3×30 mL). The combined organic layers were dried over anhydrous Na$_2$SO$_4$ and concentrated. The crude product was purified by column chromatography.

Method O: In a thick-walled flame dried reaction vial, malonate protected amine (1.0 mmol, 1.0 equiv) was taken in anhydrous toluene (20 mL, 0.05M) under argon. To this solution Grubbs 2$^{nd}$ generation catalyst (10 or 15 mol %) was added and the reaction vial was sealed with the septum. This reaction mixture was heated to target temperature T for target time t under constant stirring. After confirming the completion of reaction by thin layer chromatography, the reaction was allowed to cool to room temperature. The reaction mixture was then filtered through celite pad. Toluene was evaporated and the crude product was purified by column chromatography. (The exact temperature and reaction times were presented along with the data for each substrate)

Characterization Data of the Post-Functionalized Amines (as Displayed in Scheme 5)

1. N-methylaniline (60a)

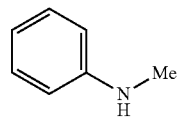

Yield: 53% (Method I); Physical State: dark brown colored oily liquid; $R_f$=0.52 (8:1 EtOAc:hexanes); $^1$H NMR (600 MHz, CDCl$_3$): δ 7.23 (t, J=7.9 Hz, 2H), 6.75 (t, J=7.3 Hz, 1H), 6.65 (d, J=7.8 Hz, 2H), 3.55 (s, 1H), 2.86 (s, 3H); $^{13}$C NMR (151 MHz, CDCl$_3$): δ 149.28, 129.14, 117.20, 112.37, 30.67; HRMS (ESI-TOF): calc'd for C$_7$H$_9$N [M+H]$^+$ 108.0808; found 108.0812.

Spectral data was consistent with the data reported in the literature (Youn & Kim, 2016; Zhou et al, 2016; Pace et al., 2016 and Wang et al., 2015).

2. N-(2,2,2-trifluoroethyl)aniline (60b)

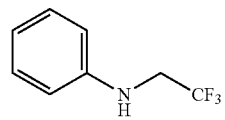

Yield: 86% (Method I); Physical State: wine red colored oily liquid; $R_f$=0.67 (8:1 EtOAc:hexanes); $^1$H NMR (600 MHz, CDCl$_3$): δ 7.14-7.09 (m, 2H), 6.71 (t, J=7.3 Hz, 1H), 6.57 (d, J=7.8 Hz, 2H), 3.78 (s, 1H), 3.63 (q, J=9.0 Hz, 2H); $^{13}$C NMR (151 MHz, CDCl$_3$): δ 146.23, 129.37, 127.83, 125.98, 124.12, 122.27, 119.04, 113.08, 46.28, 46.06, 45.84, 45.62; HRMS (ESI-TOF): calc'd for C$_8$H$_8$F$_3$N [M+H]$^+$ 176.0682; found 176.0680.

Spectral data was consistent with the data reported in the literature (Fu et al., 2015).

3. N-(2-((tert-butyldimethylsilyl)oxy)ethyl)aniline (60c)

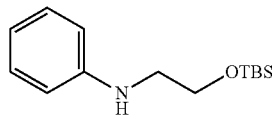

Yield: 90% (Method I); Physical State: dark brownish yellow colored oily liquid; $R_f$=0.73 (8:1 EtOAc:hexanes); $^1$H NMR (600 MHz, CDCl$_3$): δ 7.23 (t, J=7.9 Hz, 2H), 6.77 (t, J=7.3 Hz, 1H), 6.69 (d, J=7.8 Hz, 2H), 4.06 (s, 1H), 3.87 (t, J=5.4 Hz, 2H), 3.27 (t, J=5.4 Hz, 2H), 0.97 (s, 9H), 0.13 (s, 6H); $^{13}$C NMR (151 MHz, CDCl$_3$): δ 148.34, 129.16, 117.49, 113.17, 61.57, 45.95, 25.87, 18.26; HRMS (ESI-TOF): calc'd for C$_{14}$H$_{25}$NOSi [M+H]$^+$ 252.1778; found 252.1772.

4. N-(4-(2-((tert-butyldimethylsilyl)oxy)ethyl)phenyl)-4-fluoro-3,5-dimethylaniline

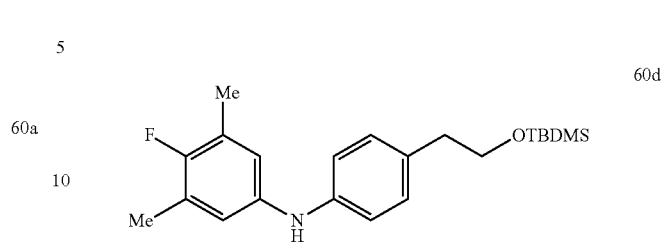

Yield: 82% (Method I); Physical State: dark reddish brown viscous oily liquid; $R_f$=0.50 (10% EtOAc/hexanes); $^1$H NMR (600 MHz, CDCl$_3$): δ 7.11 (d, J=8.2 Hz, 2H), 6.93 (d, J=7.9 Hz, 2H), 6.70 (d, J=6.0 Hz, 2H), 5.41 (s, 1H), 3.81 (t, J=7.2 Hz, 2H), 2.83-2.75 (m, 2H), 2.23 (s, 6H), 0.92 (s, 9H), 0.04 (s, 6H); $^{13}$C NMR (151 MHz, CDCl$_3$): δ 155.81, 154.24, 142.17, 138.53, 131.29, 129.97, 125.05, 124.92, 118.73, 117.40, 64.77, 38.85, 25.94, 18.35, 14.78, 14.75, −5.37; HRMS (ESI-TOF): calc'd for C$_{22}$H$_{32}$FNO$_5$Si [M+H]$^+$ 374.2310; found 374.2271.

5. N-butylaniline (60e)

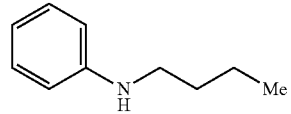

Yield: 84% (Method I); Physical State: dark yellow colored oily liquid; $R_f$=0.69 (8:1 EtOAc:hexanes); $^1$H NMR (600 MHz, CDCl$_3$): δ 7.23 (dd, J=8.6, 7.1 Hz, 2H), 6.75 (t, J=7.3 Hz, 1H), 6.66 (d, J=7.8 Hz, 2H), 3.58 (s, 1H), 3.16 (t, J=7.2 Hz, 2H), 1.66 (p, J=7.3 Hz, 2H), 1.49 (h, J=7.4 Hz, 2H), 1.03 (t, J=7.4 Hz, 3H); $^{13}$C NMR (151 MHz, CDCl$_3$): δ 148.45, 129.14, 117.01, 112.64, 43.62, 31.61, 20.24, 13.85; HRMS (ESI-TOF): calc'd for C$_{10}$H$_{15}$N [M+H]$^+$ 150.1277; found 150.1282. Spectral data was consistent with the data reported in the literature (Yu et al., 2016).

6. N-butyl-2-methylaniline (60f)

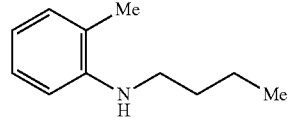

Yield: 76% (Method I); Physical State: dark yellow non-viscous liquid; $R_f$=0.65 (10% EtOAc/hexanes); $^1$H NMR (600 MHz, CDCl$_3$): δ 7.28 (t, J=7.7 Hz, 1H), 7.20 (d, J=7.3 Hz, 1H), 6.80 (t, J=7.3 Hz, 1H), 6.76 (d, J=8.0 Hz, 1H), 3.58 (s, 1H), 3.30 (t, J=7.1 Hz, 2H), 2.27 (s, 3H), 1.80 (p, J=7.3 Hz, 2H), 1.61 (dq, J=14.7, 7.4 Hz, 2H), 1.13 (t, J=7.4 Hz, 3H); $^{13}$C NMR (151 MHz, CDCl$_3$): δ 146.32, 129.88, 127.03, 121.51, 116.50, 109.48, 43.53, 31.66, 20.31, 17.32, 13.87; HRMS (ESI-TOF): calc'd for C$_{11}$H$_{17}$N [M+H]$^+$ 164.1434; found 164.1459.

Spectral data was consistent with the data reported in the literature (Byun et al, 2007).

Note: For this substrate, the reaction did not go to completion at −78° C. even after stirring for 4 hours. Then it was allowed to warm to room temperature and stirred overnight (14 hours) and some starting material was still remaining. Then an additional 1 equiv of NaH and NCS were added at room temperature and stirred at 50° C. for 3 hours and then reaction was totally finished.

7. N-butyl-2-vinylaniline (60g)

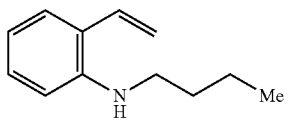

Yield: 79% (Method I); Physical State: dark yellow non-viscous liquid; $R_f$=0.60 (10% EtOAc/hexanes); $^1$H NMR (600 MHz, CDCl$_3$): δ 7.37 (d, J=7.5 Hz, 1H), 7.32-7.26 (m, 1H), 6.91-6.80 (m, 2H), 6.75 (d, J=8.1 Hz, 1H), 5.72 (dd, J=17.3, 1.5 Hz, 1H), 5.42 (dd, J=11.0, 1.5 Hz, 1H), 3.85 (s, 1H), 3.23 (t, J=7.1 Hz, 2H), 1.74 (p, J=7.3 Hz, 2H), 1.56 (h, J=7.4 Hz, 2H), 1.09 (t, J=7.4 Hz, 3H); $^{13}$C NMR (151 MHz, CDCl$_3$): δ 145.41, 132.97, 128.86, 127.30, 123.91, 116.85, 115.85, 110.50, 43.61, 31.58, 20.30, 13.85; HRMS (ESI-TOF): calc'd for C$_{12}$H$_{17}$N [M+H]$^+$ 176.1434; found 176.1471.

Spectral data was consistent with the data reported in the literature (Byun et al, 2007).

Note: For this substrate, the reaction did not go to completion at −78° C. even after stirring for 4 hours. Then it was allowed to warm to room temperature and stirred overnight (14 hours) and the reaction was finished.

8. N-butyl-4-methylaniline (60h)

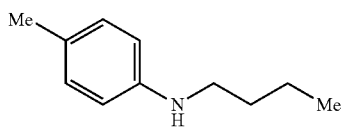

Yield: 59% (Method I); Physical State: dark yellow colored oily liquid; $R_f$=0.68 (8:1 EtOAc:hexanes); $^1$H NMR (600 MHz, CDCl$_3$): δ 7.02 (d, J=8.2 Hz, 2H), 6.58 (d, J=8.3 Hz, 2H), 3.37 (s, 1H), 3.12 (t, J=7.1 Hz, 2H), 2.28 (s, 3H), 1.63 (p, J=7.2 Hz, 2H), 1.46 (h, J=7.3 Hz, 2H), 0.99 (t, J=7.4 Hz, 3H); $^{13}$C NMR (151 MHz, CDCl$_3$): δ 146.19, 129.65, 126.30, 112.93, 44.08, 31.67, 20.32, 20.27, 13.87; HRMS (ESI-TOF): calc'd for C$_{11}$H$_{17}$N [M+H]$^+$ 164.1434; found 164.1441.

Spectral data was consistent with the data reported in the literature (Rataboul et al., 2004).

9. N-butyl-4-chloroaniline (60i)

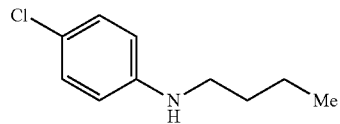

Yield: 49% (Method I); Physical State: dark brownish yellow colored liquid; $R_f$=0.70 (8:1 EtOAc:hexanes); $^1$H NMR (600 MHz, CDCl$_3$): δ 7.12 (d, J=8.7 Hz, 2H), 6.52 (d, J=8.7 Hz, 2H), 3.53 (s, 1H), 3.08 (t, J=7.1 Hz, 2H), 1.60 (p, J=7.2 Hz, 2H), 1.43 (h, J=7.4 Hz, 2H), 0.97 (t, J=7.4 Hz, 3H); $^{13}$C NMR (151 MHz, CDCl$_3$): δ 147.01, 128.96, 121.52, 113.68, 43.77, 31.47, 20.22, 13.84; HRMS (ESI-TOF): calc'd for C$_{10}$H$_{14}$ClN [M+H]$^+$ 184.0888; found 184.0891.

Spectral data was consistent with the data reported in the literature (Shankaraiah et al, 2011).

10. 3-(benzyloxy)-N-butylaniline (60j)

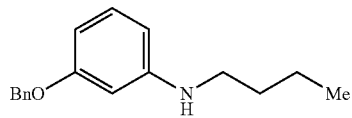

Yield: 41% (Method I); Physical State: dark brown colored oily liquid; $R_f$=0.53 (8:1 EtOAc:hexanes); $^1$H NMR (600 MHz, CDCl$_3$): δ 7.48 (d, J=7.3 Hz, 2H), 7.42 (t, J=7.5 Hz, 2H), 7.36 (t, J=7.2 Hz, 1H), 7.11 (t, J=8.0 Hz, 1H), 6.42-6.35 (m, 1H), 6.32-6.25 (m, 2H), 5.07 (s, 2H), 3.65 (s, 1H), 3.13 (t, J=6.7 Hz, 2H), 1.63 (p, J=12 Hz, 2H), 1.46 (h, J=7.3 Hz, 2H), 1.00 (t, J=7.4 Hz, 3H); $^{13}$C NMR (151 MHz, CDCl$_3$): δ 160.08, 149.84, 137.32, 129.85, 128.46, 127.75, 127.44, 106.22, 102.98, 99.48, 69.76, 43.62, 31.55, 20.23, 13.84; HRMS (ESI-TOF): calc'd for C$_{17}$H$_{21}$NO [M+H]$^+$ 256.1696; found 256.1709.

11. N-butyl-3-fluoro-5-methylaniline (60k)

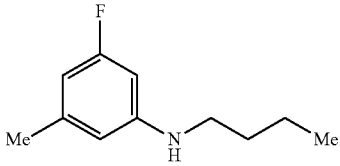

Yield: 92% (Method I); Physical State: dark red colored oily liquid; $R_f$=0.73 (8:1 EtOAc:hexanes); $^1$H NMR (600 MHz, CDCl$_3$): δ 6.24 (dd, J=23.5, 13.9 Hz, 2H), 6.14 (d, J=11.5 Hz, 1H), 3.64 (s, 1H), 3.10 (t, J=7.1 Hz, 2H), 2.28 (s, 3H), 1.61 (p, J=7.2 Hz, 2H), 1.45 (h, J=7.4 Hz, 2H), 1.00 (t, J=7.4 Hz, 3H); $^{13}$C NMR (151 MHz, CDCl$_3$): δ 164.89, 163.29, 150.02, 149.95, 140.59, 140.52, 109.15, 109.14, 104.32, 104.17, 96.42, 96.25, 43.52, 31.47, 21.49, 21.48,

12. N-butyl-3-fluoro-4-methoxyaniline (60l)

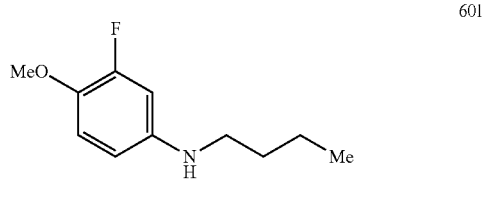 [SMILES: CCCCNc1ccc(OC)c(F)c1]

Yield: 85% (Method I); Physical State: dark yellow-brown oily liquid; $R_f$=0.46 (8:1 EtOAc:hexanes); $^1$H NMR (600 MHz, CDCl$_3$): δ 6.82 (t, J=9.1 Hz, 1H), 6.39 (dd, J=13.5, 2.4 Hz, 1H), 6.29 (d, J=8.5 Hz, 1H), 3.81 (s, 3H), 3.39 (s, 1H), 3.03 (t, J=7.1 Hz, 2H), 1.58 (p, J=7.2 Hz, 2H), 1.42 (h, J=7.3 Hz, 2H), 0.96 (t, J=7.4 Hz, 3H); $^{13}$C NMR (151 MHz, CDCl$_3$): δ 154.39, 152.77, 143.82, 143.76, 139.07, 139.00, 116.11, 116.09, 107.73, 107.71, 101.54, 101.39, 57.55, 44.21, 31.50, 20.18, 13.79; HRMS (ESI-TOF): calc'd for C$_{11}$H$_{16}$FNO [M+H]$^+$ 198.1289; found 198.1299.

13. N-butyl-4-fluoro-3,5-dimethylaniline (60m)

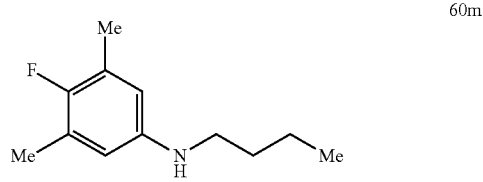 [SMILES: CCCCNc1cc(C)c(F)c(C)c1]

Yield: 60% (Method I); Physical State: yellow colored oily liquid; $R_f$=0.70 (8:1 EtOAc:hexanes); $^1$H NMR (600 MHz, CDCl$_3$): δ 6.26 (d, J=6.0 Hz, 2H), 3.22 (s, 1H), 3.06 (t, J=7.1 Hz, 2H), 2.21 (d, J=1.9 Hz, 6H), 1.60 (p, J=7.2 Hz, 2H), 1.44 (h, J=7.4 Hz, 2H), 0.98 (t, J=7.4 Hz, 3H); $^{13}$C NMR (151 MHz, CDCl$_3$): δ 153.79, 152.25, 144.09, 144.08, 124.72, 124.59, 112.70, 112.67, 44.39, 31.71, 20.27, 14.84, 14.81, 13.87; HRMS (ESI-TOF): calc'd for C$_{12}$H$_{18}$FN [M+H]$^+$ 196.1496; found 196.1508.

14. N-butyl-3-chloro-5-fluoro-4-methoxyaniline (60n)

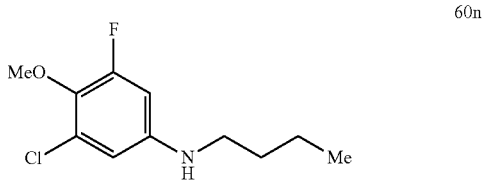 [SMILES: CCCCNc1cc(F)c(OC)c(Cl)c1]

Yield: 85% (Method I); Physical State: brownish-yellow colored oily liquid; $R_f$=0.64 (8:1 EtOAc:hexanes); $^1$H NMR (600 MHz, CDCl$_3$): δ 6.40-6.30 (m, 1H), 6.23 (dd, J=12.7, 2.7 Hz, 1H), 3.82 (s, 3H), 3.61 (s, 1H), 3.01 (t, J=7.1 Hz, 2H), 1.56 (p, J=7.2 Hz, 2H), 1.40 (h, J=7.4 Hz, 2H), 0.95 (t, J=1.4 Hz, 3H); $^{13}$C NMR (151 MHz, CDCl$_3$): δ 157.81, 156.18, 145.26, 145.18, 135.05, 134.96, 128.97, 128.93, 108.55, 108.54, 99.56, 99.40, 61.61, 61.60, 43.69, 31.26, 20.12, 13.73; HRMS (ESI-TOF): calc'd for C$_{11}$H$_{15}$ClFNO [M+H]$^+$ 232.0899; found 232.0908.

15. N-butylnaphthalen-2-amine (60o)

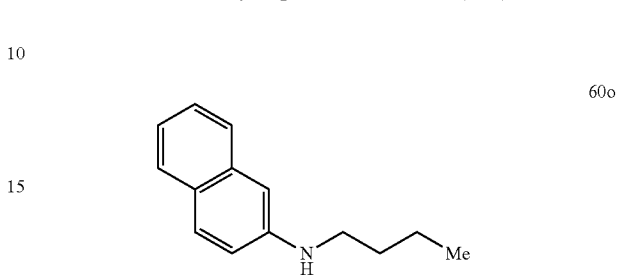

Yield: 59% (Method I); Physical State: brown colored waxy solid; $R_f$=0.65 (8:1 EtOAc:hexanes); $^1$H NMR (600 MHz, CDCl$_3$): δ 7.56 (d, J=8.1 Hz, 1H), 7.51 (t, J=7.7 Hz, 2H), 7.25 (t, J=7.5 Hz, 1H), 7.08 (t, J=6.9 Hz, 1H), 6.74 (dd, J=8.8, 2.3 Hz, 1H), 6.69 (d, J=2.1 Hz, 1H), 3.60 (s, 1H), 3.08 (t, J=7.1 Hz, 2H), 1.54 (p, J=7.3 Hz, 2H), 1.35 (dq, J=14.7, 7.4 Hz, 2H), 0.88 (t, J=7.4 Hz, 3H); $^{13}$C NMR (151 MHz, CDCl$_3$): δ 146.09, 135.27, 128.77, 127.58, 127.36, 126.21, 125.82, 121.73, 117.94, 104.14, 43.66, 31.46, 20.32, 13.89; HRMS (ESI-TOF): calc'd for C$_{14}$H$_{17}$N [M+H]$^+$ 200.1434; found 200.1446.

Spectral data was consistent with the data reported in the literature (Huang & Yang, 2011).

16. N-cyclopentylaniline (60p)

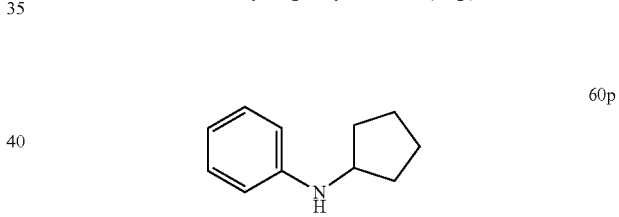

Yield: 90% (Method I); Physical State: dark brown colored oily liquid; $R_f$=0.75 (8:1 EtOAc:hexanes); $^1$H NMR (600 MHz, CDCl$_3$): δ 7.23 (t, J=7.9 Hz, 2H), 6.75 (t, J=7.3 Hz, 1H), 6.67 (d, J=7.8 Hz, 2H), 3.85 (p, J=6.2 Hz, 1H), 3.65 (s, 1H), 2.08 (dq, J=12.7, 6.7, 6.2 Hz, 2H), 1.83-1.75 (m, 2H), 1.69 (tt, J=11.6, 5.5 Hz, 2H), 1.53 (dq, J=12.0, 6.3, 5.6 Hz, 2H); $^{13}$C NMR (151 MHz, CDCl$_3$): δ 147.94, 129.09, 116.82, 113.10, 54.58, 33.50, 24.00; HRMS (ESI-TOF): calc'd for C$_{11}$H$_{15}$N [M+H]$^+$ 162.1277; found 162.1283.

Spectral data was consistent with the data reported in the literature (Vantourout et al, 2016).

17. N-cyclopentyl-4-methylaniline (60q)

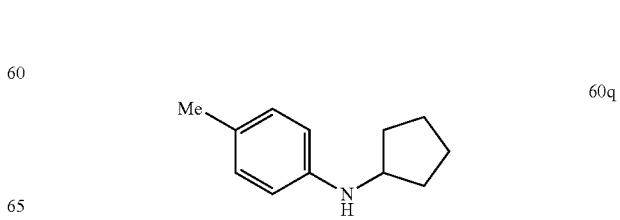

Yield: 53% (Method I); Physical State: dark brown colored oily liquid; $R_f$=0.58 (10% EtOAc/hexanes); $^1$H NMR (600 MHz, CDCl$_3$): δ 7.02 (d, J=7.9 Hz, 2H), 6.57 (d, J=7.9 Hz, 2H), 3.80 (p, J=6.1 Hz, 1H), 3.52 (s, 1H), 2.28 (s, 3H), 2.04 (dt, J=12.4, 6.1 Hz, 2H), 1.81-1.70 (m, 2H), 1.69-1.60 (m, 2H), 1.50 (dt, J=11.9, 5.7 Hz, 2H); $^{13}$C NMR (151 MHz, CDCl$_3$): δ 145.70, 129.62, 126.09, 113.39, 54.95, 33.53, 24.04, 20.32; HRMS (ESI-TOF): calc'd for $C_{12}H_{17}N$ [M+H]$^+$ 176.1434; found 176.1425.

Spectral data was consistent with the data reported in the literature (Zhou et al., 2015).

18. N-cyclopentyl-4-methoxy-3,5-dimethylaniline (60r)

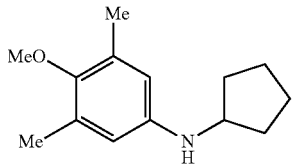

Yield: 74% (Method I); Physical State: pale orange colored solid (m.p.=44-49° C.); $R_f$=0.41 (10% EtOAc/hexanes); $^1$H NMR (600 MHz, CDCl$_3$): δ 6.29 (s, 2H), 3.74 (p, J=6.2 Hz, 1H), 3.68 (s, 3H), 3.34 (s, 1H), 2.25 (s, 6H), 2.02 (dq, J=12.7, 5.6 Hz, 2H), 1.75 (dq, J=10.4, 6.3 Hz, 2H), 1.64 (dq, J=9.0, 5.8, 4.6 Hz, 2H), 1.47 (dq, J=14.0, 7.3 Hz, 2H); $^{13}$C NMR (151 MHz, CDCl$_3$): δ 148.52, 144.04, 131.16, 113.16, 59.92, 55.02, 33.60, 23.98, 16.21; HRMS (ESI-TOF): calc'd for $C_{14}H_{21}NO$ [M+H]$^+$ 220.1696; found 220.1702.

19. N-cyclohexylaniline (60s)

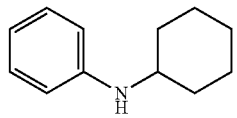

Yield: 61% (Method I); Physical State: pale yellow oily liquid; $R_f$=0.63 (8:1 EtOAc:hexanes); $^1$H NMR (600 MHz, CDCl$_3$): δ 7.20-7.12 (m, 2H), 6.67 (t, J=7.3 Hz, 1H), 6.61 (d, J=1.9 Hz, 2H), 3.72 (s, 1H), 3.26 (tt, J=10.1, 3.7 Hz, 1H), 2.07 (dd, J=13.1, 4.0 Hz, 2H), 1.77 (dt, J=13.4, 3.6 Hz, 2H), 1.66 (dt, J=12.8, 3.7 Hz, 1H), 1.43-1.33 (m, 2H), 1.24 (ddd, J=16.1, 9.8, 3.4 Hz, 1H), 1.21-1.11 (m, 2H); $^{13}$C NMR (151 MHz, CDCl$_3$): δ 147.18, 129.24, 116.98, 113.28, 51.83, 33.41, 25.91, 25.00; HRMS (ESI-TOF): calc'd for $C_{12}H_{17}N$ [M+H]$^+$ 176.1434; found 176.1440.

Spectral data was consistent with the data reported in the literature (Yan et al, 2016).

20. Tert-butyl 4-(phenylamino)piperidine-1-carboxylate (60t)

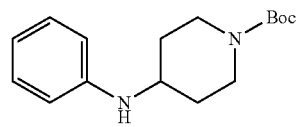

Yield: 88% (Method I); Physical State: pale yellow colored flaky solid (m.p.=130-138° C.); $R_f$=0.20 (8:1 EtOAc:hexanes); $^1$H NMR (600 MHz, CDCl$_3$): δ 7.17 (t, J=7.9 Hz, 2H), 6.70 (t, J=7.3 Hz, 1H), 6.60 (d, J=7.8 Hz, 2H), 4.05 (s, 2H), 3.43 (tt, J=10.1, 3.8 Hz, 2H), 2.93 (t, J=11.0 Hz, 2H), 2.03 (d, J=10.9 Hz, 2H), 1.47 (s, 9H), 1.39-1.28 (m, 2H); $^{13}$C NMR (151 MHz, CDCl$_3$): δ 154.71, 146.72, 129.29, 117.39, 113.23, 79.50, 50.02, 42.54, 32.32, 28.38; HRMS (ESI-TOF): calc'd for $C_{16}H_{24}N_2O_2$ [M+H]$^+$ 277.1911; found 277.1917.

Spectral data was consistent with the data reported in the literature (Mattson et al, 1990).

21. Tert-butyl 4-((2,3-dihydrobenzofuran-5-yl)amino)piperidine-1-carboxylate (60u)

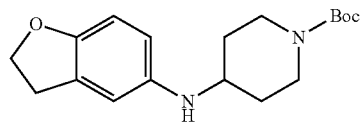

Yield: 80% (Method I); Physical State: pale brown colored waxy solid; $R_f$=0.28 (30% EtOAc/hexanes); $^1$H NMR (600 MHz, CDCl$_3$): δ 6.61 (d, J=8.4 Hz, 1H), 6.54 (s, 1H), 6.39 (dd, J=8.7, 2.5 Hz, 1H), 4.47 (t, J=8.6 Hz, 2H), 4.02 (s, 2H), 3.29 (dt, J=10.1, 6.4 Hz, 1H), 3.12 (t, J=8.5 Hz, 3H), 2.88 (s, 2H), 2.00 (d, J=11.7 Hz, 2H), 1.45 (s, 9H), 1.32-1.21 (m, 2H); $^{13}$C NMR (151 MHz, CDCl$_3$): δ 154.66, 152.69, 140.78, 127.77, 113.68, 111.58, 109.32, 79.39, 70.76, 51.59, 32.46, 30.23, 28.33; HRMS (ESI-TOF): calc'd for $C_{18}H_{26}N_2O_3$ [M+H]$^+$ 319.2016; found 319.2004.

22. N-benzylaniline (60v)

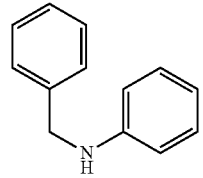

Yield: 34% (Method I); Physical State: yellow colored waxy solid; $R_f$=0.62 (10% EtOAc/hexanes); $^1$H NMR (600 MHz, CDCl$_3$): δ 7.38 (dt, J=15.1, 7.5 Hz, 4H), 7.30 (t, J=7.1 Hz, 1H), 7.20 (t, J=7.9 Hz, 2H), 6.75 (t, J=7.3 Hz, 1H), 6.67 (d, J=7.9 Hz, 2H), 4.36 (s, 2H), 4.06 (s, 1H); $^{13}$C NMR (151 MHz, CDCl$_3$): δ 148.09, 139.39, 129.22, 128.60, 127.48, 127.19, 117.55, 112.83, 48.30; HRMS (ESI-TOF): calc'd for $C_{13}H_{13}N$ [M+H]$^+$ 184.1121; found 184.1117.

Spectral data was consistent with the data reported in the literature (Yu et al., 2016).

23. N-phenethylaniline (60w)

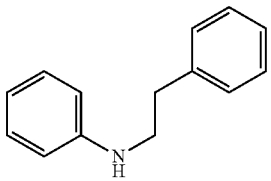

Yield: 88% (Method I); Physical State: yellow-brown colored oily liquid; $R_f$=0.49 (10% EtOAc/hexanes); $^1$H NMR (600 MHz, CDCl$_3$): δ 7.33 (t, J=7.5 Hz, 2H), 7.24 (dd, J=11.2, 7.3 Hz, 3H), 7.21-7.17 (m, 2H), 6.72 (t, J=7.3 Hz, 1H), 6.62 (d, J=7.8 Hz, 2H), 3.67 (s, 1H), 3.41 (t, J=6.0 Hz, 2H), 2.92 (t, J=7.0 Hz, 2H); $^{13}$C NMR (151 MHz, CDCl$_3$): δ 147.95, 139.27, 129.23, 128.74, 128.56, 126.37, 117.44, 117.39, 112.98, 112.91, 44.98, 35.48; HRMS (ESI-TOF): calc'd for $C_{14}H_{15}N$ [M+H]$^+$ 198.1277; found 198.1276.

Spectral data was consistent with the data reported in the literature (Kawahara et al., 2011).

24. 3,5-difluoro-4-methoxy-N-phenethylaniline (60x)

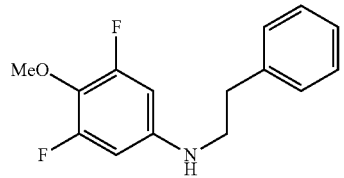

Yield: 53% (Method I); Physical State: yellow colored oily liquid; $R_f$=0.35 (10% EtOAc/hexanes); $^1$H NMR (600 MHz, CDCl$_3$): δ 7.23 (t, J=7.5 Hz, 2H), 7.17-7.13 (m, 1H), 7.11 (d, J=7.2 Hz, 2H), 6.01 (d, J=10.5 Hz, 2H), 3.76 (s, 3H), 3.59 (s, 1H), 3.21 (t, J=7.0 Hz, 2H), 2.79 (t, J=7.0 Hz, 2H); $^{13}$C NMR (151 MHz, CDCl$_3$): δ 157.74, 157.69, 156.12, 156.06, 144.14, 138.73, 128.67, 128.65, 127.39, 126.57, 126.56, 96.42, 96.25, 62.23, 45.00, 35.13; HRMS (ESI-TOF): calc'd for $C_{15}H_{15}F_2NO$ [M+H]$^+$ 264.1194; found 264.1199.

25. Diphenylamine (60y)

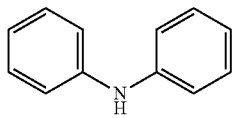

Yield: 90% (Method J); Physical State: off white waxy solid; $R_f$=0.55 (10% EtOAc/hexanes); $^1$H NMR (600 MHz, CDCl$_3$): δ 7.29 (t, J=7.9 Hz, 4H), 7.10 (d, J=7.7 Hz, 4H), 6.96 (t, J=7.3 Hz, 2H), 5.71 (s, 1H); $^{13}$C NMR (151 MHz, CDCl$_3$): δ 143.09, 129.31, 120.97, 117.79; HRMS (ESI-TOF): calc'd for $C_{12}H_{11}N$ [M+H]$^+$ 170.0964; found 179.0959.

Spectral data was consistent with the data reported in the literature (Rataboul et al, 2004).

26. Di-p-tolylamine (60z)

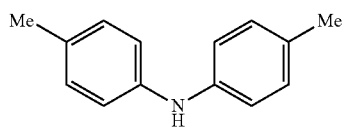

Yield: 76% (Method J); Physical State: off white waxy solid; $R_f$=0.73 (10% EtOAc/hexanes); $^1$H NMR (600 MHz, CDCl$_3$): δ 7.11 (d, J=8.2 Hz, 4H), 6.99 (d, J=8.3 Hz, 4H), 5.54 (s, 1H), 2.35 (s, 6H); $^{13}$C NMR (151 MHz, CDCl$_3$): δ 141.09, 130.09, 129.76, 117.87, 20.59; HRMS (ESI-TOF): calc'd for $C_{14}H_{15}N$ [M+H]$^+$ 198.1277; found 198.1234.

Spectral data was consistent with the data reported in the literature (Li et al., 2001).

27. Bis(4-chlorophenyl)amine (61a)

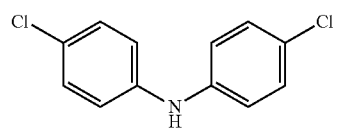

Yield: 85% (Method I); Physical State: off white waxy solid; $R_f$=0.47 (10% EtOAc/hexanes); $^1$H NMR (600 MHz, CDCl$_3$): δ 7.23 (d, J=8.8 Hz, 4H), 6.96 (d, J=8.8 Hz, 4H), 5.64 (s, 1H); $^{13}$C NMR (151 MHz, CDCl$_3$): δ 141.33, 129.33, 125.99, 119.05; HRMS (ESI-TOF): calc'd for $C_{12}H_9Cl_2N$ [M+H]$^+$ 238.0185; found 238.0191.

Spectral data was consistent with the data reported in the literature (Cai et al, 2014).

28. Di([1,1'-biphenyl]-3-yl)amine (61b)

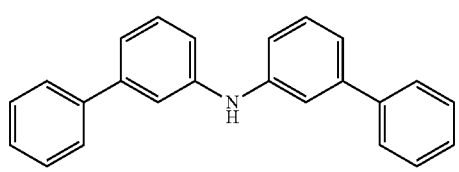

Yield: 78% (Method I); Physical State: pale yellow colored oily liquid; $R_f$=0.37 (10% EtOAc/hexanes); $^1$H NMR (600 MHz, CDCl$_3$): δ 7.70 (d, J=7.2 Hz, 4H), 7.54 (t, J=7.7 Hz, 4H), 7.49-7.41 (m, 6H), 7.30 (d, J=1.1 Hz, 2H), 7.21 (dd, J=8.0, 1.6 Hz, 2H), 5.92 (s, 1H); $^{13}$C NMR (151 MHz, CDCl$_3$): δ 143.38, 142.50, 141.01, 129.70, 128.67, 127.32, 127.05, 120.04, 116.72, 116.68; HRMS (ESI-TOF): calc'd for $C_{24}H_{19}N$ [M+H]$^+$ 322.1590; found 322.1640.

29. Bis(4-fluoro-3,5-dimethylphenyl)amine (61c)

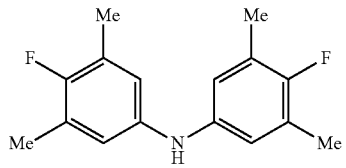

Yield: 88% (Method I); Physical State: orange colored solid; $R_f$=0.54 (10% EtOAc/hexanes); $^1$H NMR (600 MHz, CDCl$_3$): δ 6.64 (d, J=6.0 Hz, 4H), 5.23 (s, 1H), 2.23 (s, 12H); $^{13}$C NMR (151 MHz, CDCl$_3$): δ 155.73, 154.16, 139.13, 125.11, 124.99, 118.41, 118.38, 14.77, 14.75; HRMS (ESI-TOF): calc'd for $C_{16}H_{17}F_2N$ [M+H]$^+$ 262.1402; found 262.1403.

30. Bis(4-methoxy-3,5-dimethylphenyl)amine (61d)

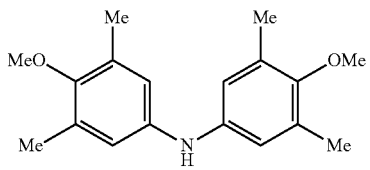

Yield: 76% (Method J); Physical State: off white waxy solid; $R_f$=0.46 (10% EtOAc/hexanes); $^1$H NMR (600 MHz, CDCl$_3$): δ 6.69 (s, 4H), 5.37 (s, 1H), 3.72 (s, 6H), 2.27 (s, 12H); $^{13}$C NMR (151 MHz, CDCl$_3$): δ 151.10, 139.42, 131.45, 118.12, 59.84, 16.17; HRMS (ESI-TOF): calc'd for $C_{18}H_{23}NO_2$ [M+H]$^+$ 286.1802; found 286.1768.

31. 4-methyl-N-phenylaniline (61e)

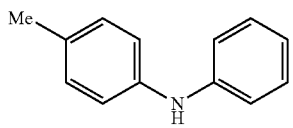

Yield: 83% (Method I); Physical State: grey colored waxy solid; $R_f$=0.60 (10% EtOAc/hexanes); $^1$H NMR (600 MHz, CDCl$_3$): δ 7.12 (t, J=7.7 Hz, 2H), 6.97 (d, J=7.9 Hz, 2H), 6.88 (dd, J=7.5, 4.2 Hz, 4H), 6.77 (t, J=7.3 Hz, 1H), 5.43 (s, 1H), 2.19 (s, 3H); $^{13}$C NMR (151 MHz, CDCl$_3$): δ 143.88, 140.22, 130.81, 129.78, 129.23, 120.21, 118.84, 116.80, 20.63; HRMS (ESI-TOF): calc'd for $C_{13}H_{13}N$ [M+H]$^+$ 184.1121; found 184.1098.

Spectral data was consistent with the data reported in the literature (Fors & Buchwald, 2010).

32. N-phenyl-[1,1'-biphenyl]-4-amine (61f)

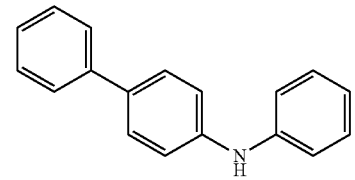

Yield: 61% (Method I); Physical State: off white colored solid (m.p.=102-109° C.); $R_f$=0.71 (10% EtOAc/hexanes); $^1$H NMR (600 MHz, CDCl$_3$): δ 7.64-7.59 (m, 2H) 7.55, (d, J=8.6 Hz, 2H), 7.46 (t, J=7.8 Hz, 2H), 7.37-7.30 (m, 3H), 7.16 (dd, J=10.4, 8.1 Hz, 4H), 7.00 (t, J=7.3 Hz, 1H), 5.79 (s, 1H); $^{13}$C NMR (151 MHz, CDCl$_3$): δ 142.80, 142.51, 140.80, 133.67, 129.36, 128.70, 127.93, 126.55, 126.49, 121.19, 118.05, 117.75; HRMS (ESI-TOF): calc'd for $C_{18}H_{15}N$ [M+H]$^+$ 246.1277; found 246.1321.

Spectral data was consistent with the data reported in the literature (Driver & Hartwig, 1996).

33. 4-phenoxy-N-phenylaniline (61g)

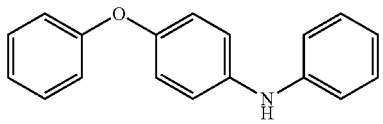

Yield: 63% (Method I); Physical State: off white solid (m.p.=100-105° C.); $R_f$=0.37 (10% EtOAc/hexanes); $^1$H NMR (600 MHz, CDCl$_3$): δ 7.19 (d, J=38.2 Hz, 4H), 7.05-6.73 (m, 10H), 5.51 (s, 1H); $^{13}$C NMR (151 MHz, CDCl$_3$): δ 158.12, 151.19, 143.84, 138.68, 129.61, 129.33, 122.60, 120.46, 120.34, 117.90, 116.85; HRMS (ESI-TOF): calc'd for $C_{18}H_{15}NO$ [M+H]$^+$ 262.1226; found 262.1224.

Spectral data was consistent with the data reported in the literature (Kim et al., 2012).

34. 3-methyl-N-(p-tolyl)aniline (61h)

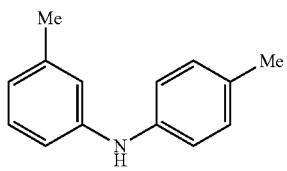

Yield: 82% (Method I); Physical State: pale brown colored oily liquid; $R_f$=0.50 (10% EtOAc/hexanes); $^1$H NMR (600 MHz, CDCl$_3$): δ 7.29-7.24 (m, 1H), 7.22 (d, J=8.2 Hz, 2H), 7.12 (d, J=8.3 Hz, 2H), 6.99-6.93 (m, 2H), 6.85 (d, J=7.4 Hz, 1H), 5.63 (s, 1H), 2.44 (d, J=9.2 Hz, 6H); $^{13}$C NMR (151 MHz, CDCl$_3$): δ 144.04, 140.54, 139.26, 130.88, 129.97, 129.27, 121.33, 119.07, 117.72, 114.16, 21.67, 20.83; HRMS (ESI-TOF): calc'd for $C_{14}H_{15}N$ [M+H]$^+$ 198.1277; found 198.1310.

Spectral data was consistent with the data reported in the literature (Hajra et al, 2012).

35. 4-chloro-N-(4-methoxyphenyl)aniline (61i)

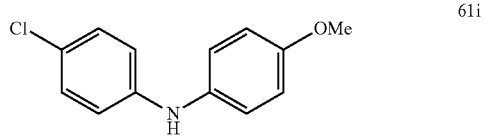 [SMILES: COc1ccc(Nc2ccc(Cl)cc2)cc1]

Yield: 76% (Method I); Physical State: dark brown colored waxy solid; $R_f$=0.51 (10% EtOAc/hexanes); $^1$H NMR (600 MHz, CDCl$_3$): δ 7.16 (d, J=8.9 Hz, 2H), 7.05 (d, J=6.7 Hz, 2H), 6.88 (d, J=8.8 Hz, 2H), 6.82 (d, J=8.3 Hz, 2H), 5.44 (s, 1H), 3.81 (s, 3H); $^{13}$C NMR (151 MHz, CDCl$_3$): δ 155.57, 143.85, 135.12, 129.10, 123.91, 122.50, 116.60, 114.70, 55.51; HRMS (ESI-TOF): calc'd for C$_{13}$H$_{12}$ClNO [M+H]$^+$ 234.0680; found 234.0673.

Spectral data was consistent with the data reported in the literature (Altman et al., 2008).

36. 4-fluoro-N-(4-methoxyphenyl)-3,5-dimethylaniline (61j)

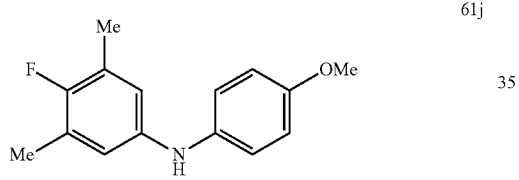

Yield: 74% (Method I); Physical State: gray colored solid; $R_f$=0.33 (10% EtOAc/hexanes); $^1$H NMR (600 MHz, CDCl$_3$): δ 7.01 (d, J=8.7 Hz, 2H), 6.88 (d, J=8.8 Hz, 2H), 6.60 (d, J=5.9 Hz, 2H), 5.26 (s, 1H), 3.82 (s, 3H), 2.23 (s, 1H); $^{13}$C NMR (151 MHz, CDCl$_3$): δ 155.24, 154.71, 153.68, 140.00, 136.88, 124.97, 124.84, 120.91, 116.95, 116.92, 114.65, 55.51, 14.75, 14.73; HRMS (ESI-TOF): calc'd for C$_{15}$H$_{16}$FNO [M+H]$^+$ 246.1289; found 246.1288.

37. N-(4-chlorophenyl)-3,5-dimethylaniline (61k)

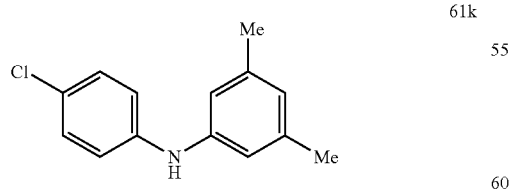

Yield: 63% (Method I); Physical State: off white, pale brown colored solid (m.p.=56-62° C.); $R_f$=0.50 (10% EtOAc/hexanes); $^1$H NMR (600 MHz, CDCl$_3$): δ 7.08 (d, J=8.8 Hz, 2H), 6.83 (d, J=8.8 Hz, 2H), 6.55 (s, 2H), 6.51 (s, 1H), 5.42 (s, 1H), 2.16 (s, 6H); $^{13}$C NMR (151 MHz, CDCl$_3$): δ 142.50, 142.02, 139.08, 129.14, 125.13, 123.33, 118.77, 115.88, 21.34; HRMS (ESI-TOF): calc'd for C$_{14}$H$_{14}$ClN [M+H]$^+$ 232.0888; found 232.0916.

Spectral data was consistent with the data reported in the literature (Tzschucke et al., 2007).

38. N-(3,5-dimethylphenyl)-[1,1'-biphenyl]-3-amine (61l)

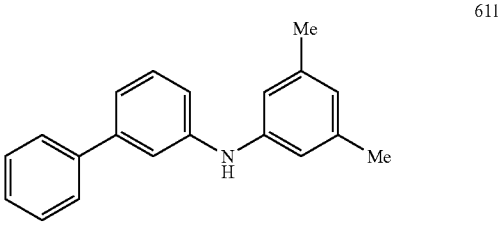 [SMILES: Cc1cc(C)cc(Nc2cccc(-c3ccccc3)c2)c1]

Yield: 77% (Method I); Physical State: Brown colored viscous oily liquid; $R_f$=0.49 (10% EtOAc/hexanes); $^1$H NMR (600 MHz, CDCl$_3$): δ 7.53 (d, J=8.4 Hz, 2H), 7.38 (t, J=7.0 Hz, 2H), 7.28 (dt, J=10.4, 7.6 Hz, 2H), 7.21 (t, J=1.9 Hz, 1H), 7.10 (d, J=7.7 Hz, 1H), 7.03-6.98 (m, 1H), 6.70 (s, 2H), 6.57 (s, 1H), 5.61 (s, 1H), 2.23 (s, 6H); $^{13}$C NMR (151 MHz, CDCl$_3$): δ 143.75, 142.90, 142.41, 141.16, 139.03, 129.60, 128.65, 127.26, 127.07, 123.03, 119.67, 116.57, 116.55, 115.83, 21.39; HRMS (ESI-TOF): calc'd for C$_{20}$H$_{19}$N [M+H]$^+$ 274.1590; found 274.1615.

39. 3,5-dimethyl-N-(4-phenoxyphenyl)aniline (61m)

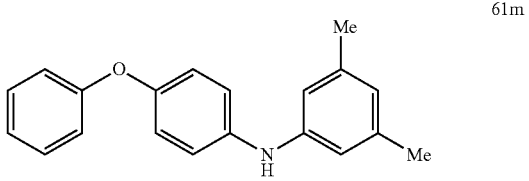 [SMILES: Cc1cc(C)cc(Nc2ccc(Oc3ccccc3)cc2)c1]

Yield: 82% (Method I); Physical State: reddish brown colored viscous oily liquid $R_f$=0.44 (10% EtOAc/hexanes); $^1$H NMR (600 MHz, CDCl$_3$): δ 7.42 (ddd, J=8.5, 5.8, 1.9 Hz, 2H), 7.15 (td, J=14.9, 7.6 Hz, 5H), 7.07 (d, J=8.9 Hz, 2H), 6.75 (s, 2H), 6.68 (s, 1H), 5.60 (s, 1H), 2.38 (s, 6H); $^{13}$C NMR (151 MHz, CDCl$_3$): δ 158.13, 150.86, 143.73, 138.93, 129.56, 122.51, 122.34, 120.37, 120.17, 117.85, 114.66, 21.35; HRMS (ESI-TOF): calc'd for C$_{20}$H$_{19}$NO [M+H]$^+$ 290.1539; found 290.1580.

40. N-(3,5-dimethylphenyl)-4-fluoro-3,5-dimethylaniline (61n)

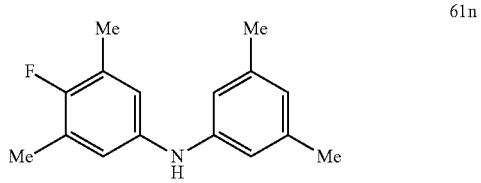 [SMILES: Cc1cc(C)cc(Nc2cc(C)c(F)c(C)c2)c1]

Yield: 80% (Method I); Physical State: dark reddish brown viscous oily liquid; $R_f$=0.51 (10% EtOAc/hexanes); $^1$H NMR (600 MHz, CDCl$_3$): δ 6.77 (d, J=6.1 Hz, 2H), 6.64 (s, 2H), 6.60 (s, 1H), 5.39 (s, 1H), 2.32 (s, 6H), 2.28 (s, 6H); $^{13}$C NMR (151 MHz, CDCl$_3$): δ 156.05, 154.48, 144.27, 138.98, 138.09, 138.07, 125.03, 124.91, 122.13, 119.77, 119.74, 114.52, 21.37, 14.75, 14.72; HRMS (ESI-TOF): calc'd for C$_{16}$H$_{18}$FN [M+H]$^+$ 244.1496; found 244.1520.

41. 2-bromo-N-(p-tolyl)aniline (61o)

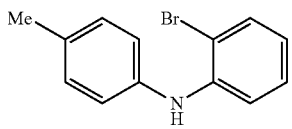

Yield: 67% (Method I); Physical State: pale purple colored oily liquid; $R_f$=0.71 (10% EtOAc/hexanes); $^1$H NMR (600 MHz, CDCl$_3$): δ 7.42 (d, J=8.4 Hz, 1H), 7.08-7.04 (m, 4H), 6.99 (d, J=8.3 Hz, 2H), 6.61 (ddd, J=8.4, 5.8, 3.0 Hz, 1H), 5.94 (s, 1H), 2.26 (s, 3H); $^{13}$C NMR (151 MHz, CDCl$_3$): δ 142.15, 138.76, 132.85, 132.75, 129.97, 128.07, 121.37, 120.20, 120.19, 114.95, 111.44, 20.80; HRMS (ESI-TOF): calc'd for C$_{13}$H$_{12}$BrN [M+H]$^+$ 262.0226; found 262.0207.

Characterization Data of the Post-Functionalized Amines in Scheme 6

5. Diisopropyl 2-((2-hydroxy-2-phenylethyl)(4-methoxyphenyl)amino)malonate (67)

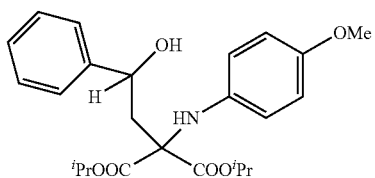

Yield: 53% (Method K); Physical State: Brown colored viscous oily liquid; $R_f$=0.26 (20% EtOAc/hexanes); $^1$H NMR (600 MHz, CDCl$_3$): δ 7.25-7.21 (m, 4H), 7.16 (td, J=5.8, 5.2, 3.3 Hz, 1H), 6.72 (d, J=9.0 Hz, 2H), 6.67 (d, J=9.0 Hz, 2H), 5.07 (s, 1H), 5.01 (hept, J=6.2 Hz, 1H), 4.86 (hept, J=6.2 Hz, 1H), 4.76 (d, J=8.4 Hz, 1H), 3.91 (s, 1H), 3.64 (s, 3H), 2.66-2.51 (m, 2H), 1.19 (d, J=6.3 Hz, 3H), 1.10 (d, J=6.3 Hz, 3H), 1.03 (d, J=6.3 Hz, 3H), 0.93 (d, J=6.3 Hz, 3H); $^{13}$C NMR (151 MHz, CDCl$_3$): δ 169.09, 168.49, 154.11, 144.16, 137.54, 128.24, 127.26, 125.49, 118.74, 114.48, 70.80, 70.19, 69.90, 68.99, 55.46, 41.72, 21.53, 21.32, 21.27, 21.24; HRMS (ESI-TOF): calc'd for C$_{24}$H$_{31}$NO$_6$ [M+H]$^+$ 430.2224; found 430.2262.

6. Isopropyl 4-(4-methoxyphenyl)-2-oxo-6-phenylmorpholine-3-carboxylate (68)

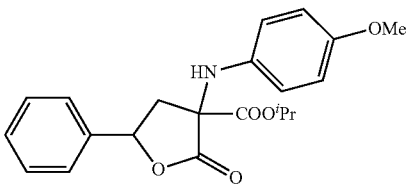

Yield: 55% (Method L); Physical State: Yellow colored waxy solid; $R_f$=0.37 (20% EtOAc/hexanes); $^1$H NMR (600 MHz, CDCl$_3$): δ 7.43-7.34 (m, 5H), 6.76 (d, J=8.9 Hz, 2H), 6.64 (d, J=8.9 Hz, 2H), 5.70 (dd, J=10.3, 6.1 Hz, 1H), 5.04 (hept, J=6.2 Hz, 1H), 4.76 (s, 1H), 3.73 (s, 3H), 3.49 (dd, J=13.0, 6.1 Hz, 1H), 2.56 (dd, J=13.0, 10.4 Hz, 1H), 1.27 (d, J=6.3 Hz, 3H), 1.05 (d, J=6.2 Hz, 3H); $^{13}$C NMR (151 MHz, CDCl$_3$): δ 172.25, 167.85, 153.85, 137.96, 137.81, 128.92, 128.83, 125.81, 117.38, 114.70, 80.05, 71.13, 68.05, 55.56, 42.77, 21.50, 21.24. HRMS (ESI-TOF): calc'd for C$_{21}$H$_{23}$NO$_5$ [M+H]$^+$ 370.1649; found 370.1632.

7. 6-chloro-2,4-dimethyl-9H-carbazole (69)

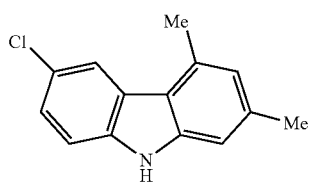

Yield: 14% (Method M); Physical State: Brown colored waxy solid; $R_f$=0.26 (10% EtOAc/hexanes); $^1$H NMR (600 MHz, DMSO-d$_6$): δ 11.32 (s, 1H), 8.01 (d, J=2.1 Hz, 1H), 7.47 (d, J=8.5 Hz, 1H), 7.35 (dd, J=8.6, 2.1 Hz, 1H), 7.14 (s, 1H), 6.80 (s, 1H), 2.73 (s, 3H), 2.44 (s, 3H); $^{13}$C NMR (151 MHz, DMSO-d$_6$): δ 140.89, 138.09, 135.77, 132.31, 124.10, 124.08, 122.58, 121.95, 120.76, 117.89, 111.95, 108.73, 21.51, 20.15; HRMS (APCI-TOF): calc'd for C$_{14}$H$_{12}$ClN [M+H$^+$] 230.0731; found 230.0737.

8. Diethyl 2-((2,6-dichlorophenyl)(2-(2-methoxy-2-oxoethyl)phenyl)amino)malonate (70)

Yield: 50% (Method N); Physical State: white solid (m.p.=106-113° C.); $R_f$=0.24 (20% EtOAc/hexanes); $^1$H NMR (600 MHz, CDCl$_3$): δ 7.41 (d, J=7.8 Hz, 1H), 7.22-7.18 (m, 1H), 7.09 (d, J=7.5 Hz, 1H), 7.05 (t, J=7.4 Hz, 1H), 6.94 (ddd, J=24.3, 16.9, 7.0 Hz, 3H), 5.90 (s, 1H), 4.10 (dtd, J=37.6, 12.4, 10.4, 4.7 Hz, 4H), 3.95 (d, J=15.8 Hz, 1H), 3.63 (d, J=14.2 Hz, 4H), 1.13 (t, J=7.1 Hz, 3H), 1.07 (t, J=7.1 Hz, 3H); $^{13}$C NMR (151 MHz, CDCl$_3$): δ 171.12, 169.41, 154.98, 137.51, 135.53, 135.05, 133.74, 130.85, 130.71, 130.02, 129.02, 128.56, 128.38, 127.78, 126.64, 62.41, 61.23, 61.01, 51.83, 38.49, 14.28, 13.82; HRMS (ESI-TOF): calc'd for C$_{22}$H$_{23}$Cl$_2$NO$_6$ [M+H]$^+$ 468.0975; found 468.0976.

9. Diethyl 2-(5H-dibenzo[b,f]azepin-5-yl)malonate (71)

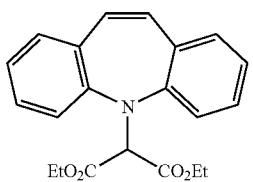

Yield: 61% (Method O); Physical State: colorless oily liquid; $R_f$=0.23 (20% EtOAc/hexanes); T=80° C. for 24 hours and 100° C. for 12 hours and 120° C. for another 12 hours; J=48 hours; $^1$H NMR (600 MHz, CDCl$_3$): δ 7.65 (s, 2H), 7.40 (dd, J=17.5, 7.7 Hz, 4H), 7.30 (t, J=7.4 Hz, 2H), 7.07 (s, 2H), 6.00 (s, 1H), 4.14 (s, 4H), 1.35-1.07 (m, 6H); $^{13}$C NMR (151 MHz, CDCl$_3$): δ 168.97, 154.81, 136.70, 133.56, 131.22, 129.08, 128.23, 126.92, 123.09, 67.28, 61.53, 61.25, 14.46, 13.84; HRMS (ESI-TOF): calc'd for C$_{21}$H$_{21}$NO$_4$ [M+Na]$^+$ 374.1363; found 374.1339.

Note: For the reaction to obtain this product (71), the conditions were unoptimized. After 24 hours of stirring at 80° C., additional 5 mol % of the catalyst was added and the temperature increased to 100° C. and stirred for 12 hours and again increased to 120° C. and stirred for another 12 hours. Still the starting material was not totally consumed.

10. Diethyl 2-(5,8-dihydro-13H-dibenzo[b,h]azonin-13-yl)malonate (72)

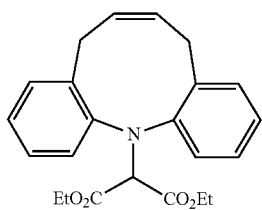

Yield: 63% (Method O); Physical State: colorless oily liquid; $R_f$=0.56 (20% EtOAc/hexanes); T=80° C.; t=15 hours; $^1$H NMR (600 MHz, CDCl$_3$): δ 7.56 (d, J=7.5 Hz, 1H), 7.28-7.19 (m, 3H), 7.18-7.12 (m, 2H), 7.05 (d, J=5.4 Hz, 2H), 6.96 (d, J=7.8 Hz, 1H), 6.08-5.93 (m, 2H), 4.16 (ddt, J=18.7, 11.6, 7.1 Hz, 2H), 4.04 (s, 1H), 3.90 (p, J=6.8 Hz, 1H), 3.73 (dd, J=27.6, 15.3 Hz, 2H), 3.00 (dd, J=15.2, 9.1 Hz, 2H), 1.18 (s, 3H), 1.09 (t, J=7.1 Hz, 3H); $^{13}$C NMR (151 MHz, CDCl$_3$): δ 172.85, 153.44, 139.81, 139.65, 138.50, 135.96, 132.62, 132.18, 128.36, 128.25, 127.90, 126.15, 125.71, 124.94, 70.00, 63.01, 60.52, 32.58, 31.72, 14.48, 13.47; HRMS (ESI-TOF): calc'd for C$_{23}$H25NO$_4$ [M+H]$^+$ 380.1856, [M+Na]$^+$ 402.1676; found 380.1790, 402.1676.

Note: For the reaction to get this product (72), 10 mol % of the catalyst was used.

Computational Details

Ground-state and transition-state geometries were optimized using Gaussian 09 (Frisch et al, 2009) with the M06-2X (Zhao & Truhlar, 2008a and Zhao & Truhlar, 2008b) functional and the ultrafine integration grid. Stationary points were confirmed to be either minima or saddle-point structures by calculation and visualization of vibrational frequencies. Intrinsic reaction coordinate (IRC) calculations were used to verify key transition states. For geometries, 6-31+G(d,p) was used for all atoms expect Br where LANL2DZ was used. All optimizations were also carried out with the SMD continuum model for tetrahydrofuran (THF) or dichloromethane (DCM) (Marenich et al, 2009). M06-2X/def2-TZVP electronic energies were calculated in THF or DCM solvent using the M06-2X/6-31+G (d,p)[LANL2DZ] geometries. The def2-TZVP basis set was obtained from EMSL (https://bse.pnl.gov/bse/portal, accessed Aug. 1, 2016). Free energies and enthalpies reported refer to M06-2X/def2-TZVP//M06-2X/6-31+G(d, p)[LANL2DZ] where zero-point energy, thermal, and entropy corrections are used from the M06-2X/6-31+G(d, p)[LANL2DZ] geometries. 3D structures were generated using CYLview. A dinuclear phenylmagnesium bromide model where the phenyl groups bridge between two Mg centers was adopted in all reported calculations.

Proton Affinities and Reduction Potentials

Below reports absolute proton affinities (in kcal/mol) for a variety of ester and diester aminating reagents. THF values are nearly identical to DCM values. As expected, the highly electrophilic diester imine with an N-OMs group has the smallest proton affinity of 106 kcal/mol (reaction a). Change of the N-OMs group to N-Ph increases the proton affinity by 22 kcal/mol (c.f. reaction d). Similarly, the N-PMP type diester imines have proton affinities greater than 129 kcal/mol. Comparison of the N-OMs diester (reaction a) to the N-OMs monoester shows the proton affinities increases to 119 kcal/mol. These proton affinities show the importance of the N-OMs group and diester group on controlling the electrophilicity of the imine.

Scheme 8. Proton affinities (kcal/mol) for ester and diester aminating agents in THF (red) and DCM (blue)

a

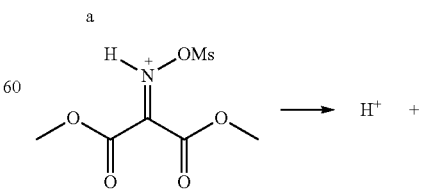

values in THF  ΔG = 0.0
values in DCM  ΔG = 0.0

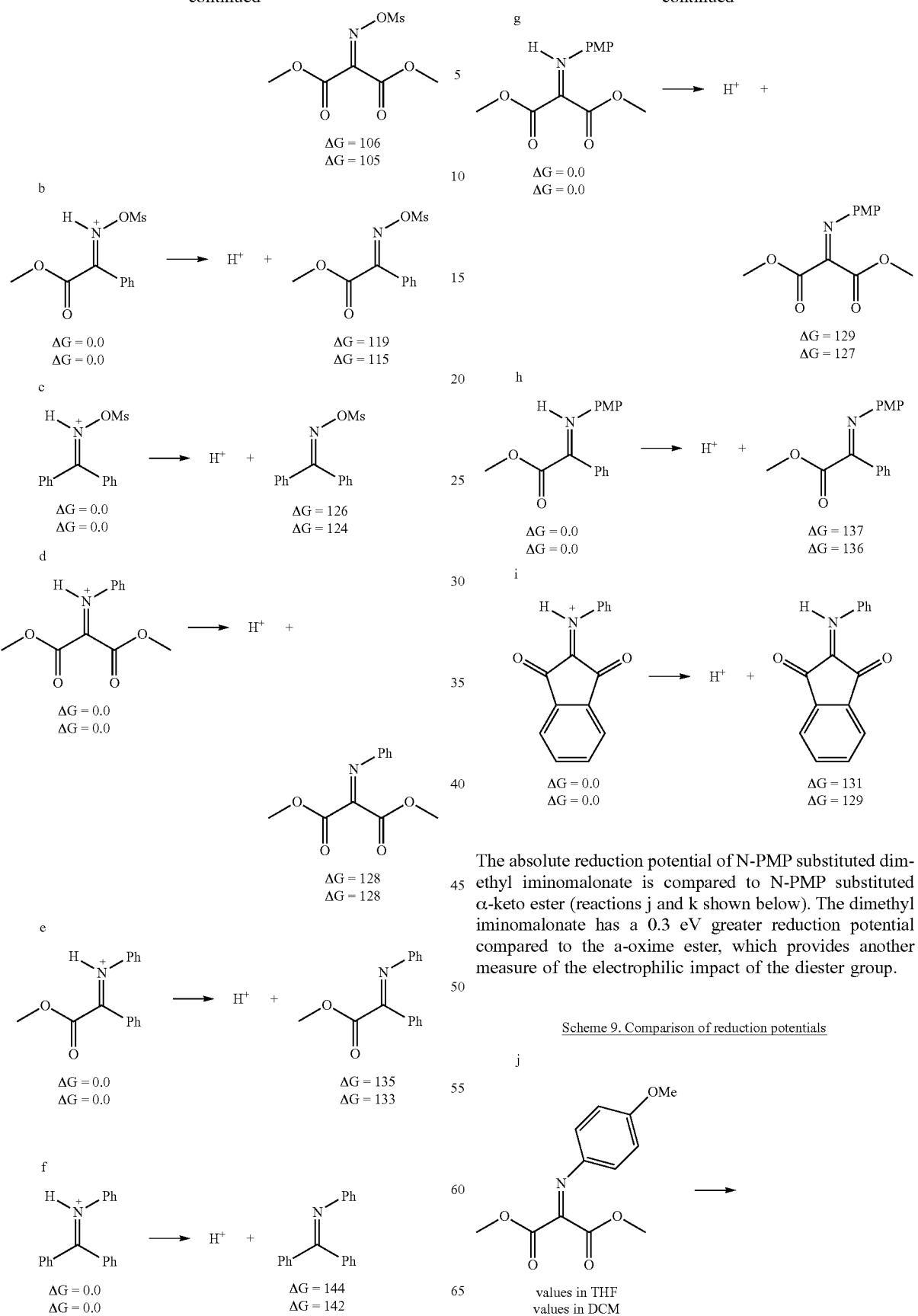
The absolute reduction potential of N-PMP substituted dimethyl iminomalonate is compared to N-PMP substituted α-keto ester (reactions j and k shown below). The dimethyl iminomalonate has a 0.3 eV greater reduction potential compared to the a-oxime ester, which provides another measure of the electrophilic impact of the diester group.

k

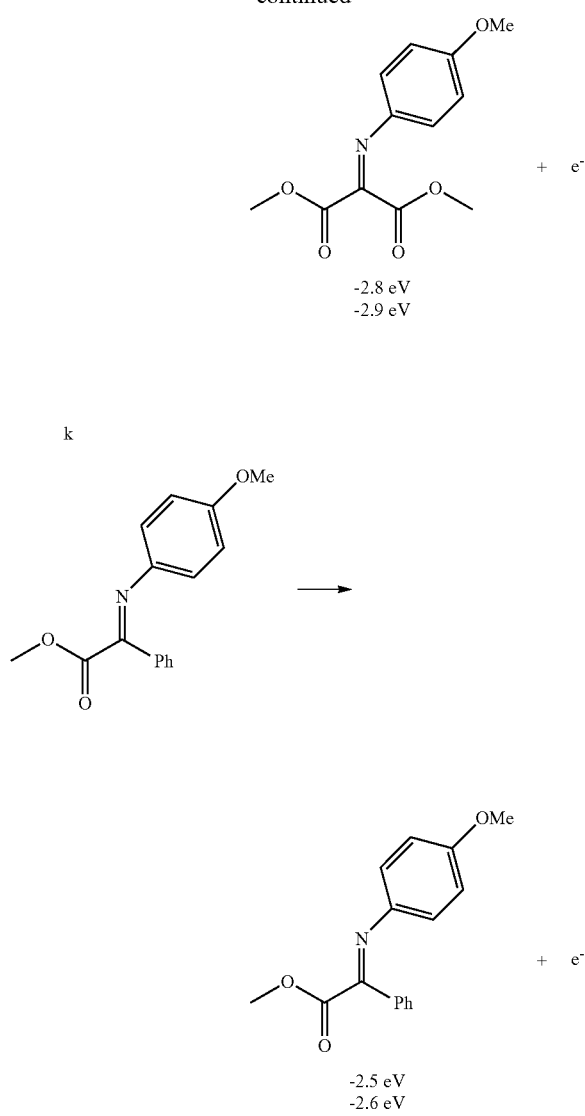

Alkyl Versus Aryl Grignard Reagents

The calculations suggest a larger energy difference between transitions states for alkyl-type versus aryl-type Grignard additions to α-iminoesters. Below shows that the free energy barriers for the ethyl Grignard is less than 10 kcal/mol while for the phenyl Grignard the free energy barrier is greater than 20 kcal/mol.

Scheme 10. Comparison of free energies of alkyl and aryl Grignard reagents

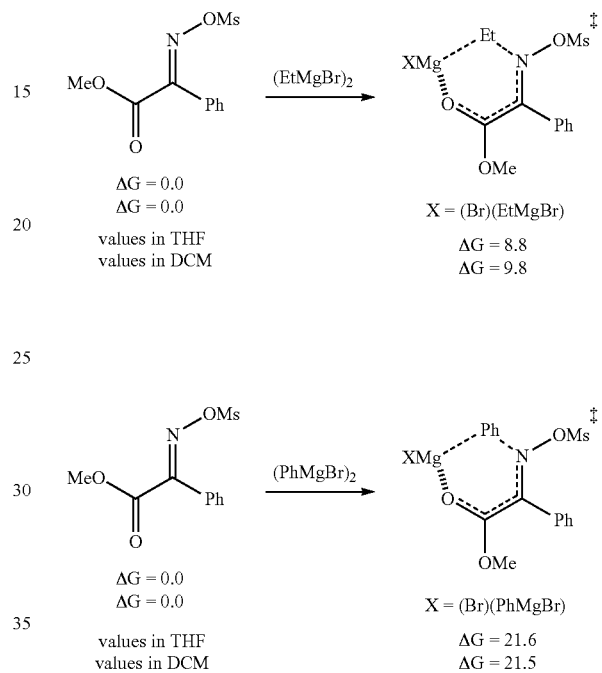

Further Reaction Pathway Details

The initial calculations focused on THF solvent since the Grignard reagents are prepared in this solvent. THF free energies are reported in red color below (kcal/mol). The energies were also calculated in DCM solvent, including re-optimization of structures. DCM free energies are reported in blue color below. THF and DCM energies are nearly identical.

Scheme 11. Comparison of free energies in THF (red) and DCM (blue)

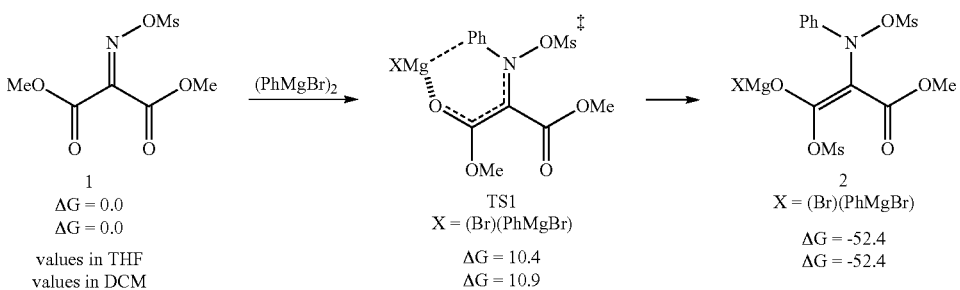

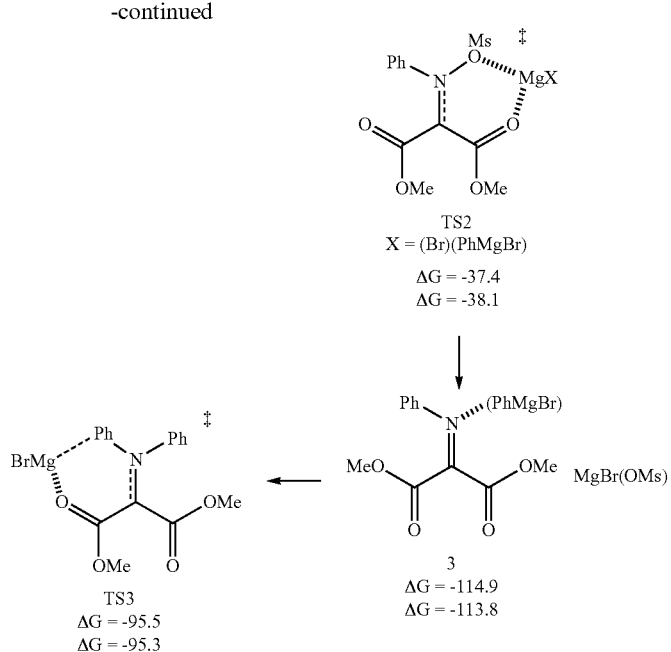

Experimentally, a mixture of N-attack and C-attack products are observed. The calculations replicate the small the energy difference between these transition states. In THF solvent the N-attack transition state is slightly favored, but in DCM the C-attack transition state is slightly favored. The possibility of reaction at ester carbonyl was also ruled out. The C-attack transition state has a free energy barrier that is >20 kcal/mol.

Scheme 12. Comparison of free energies of N-attack and C-attack

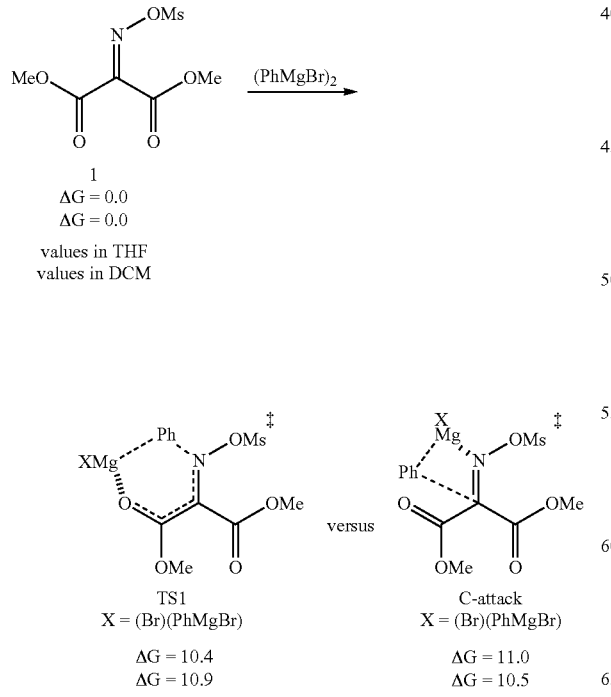

Scheme 13. Additional Compounds

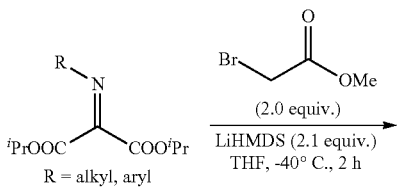

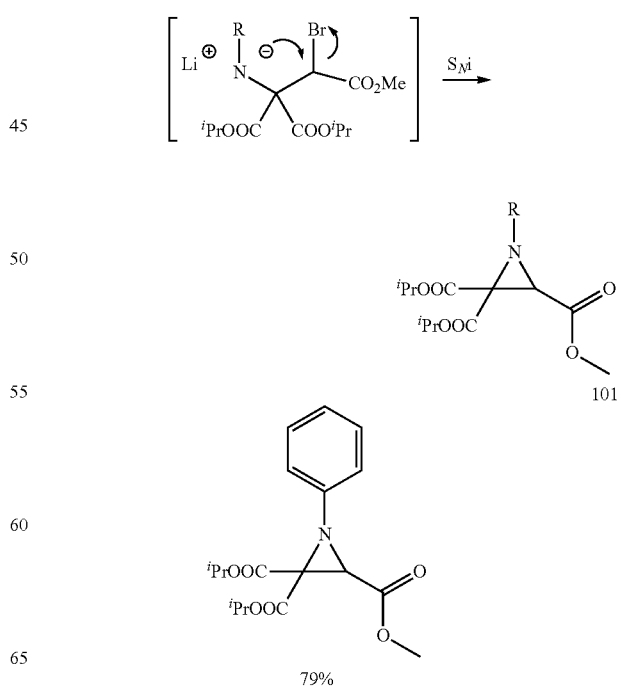

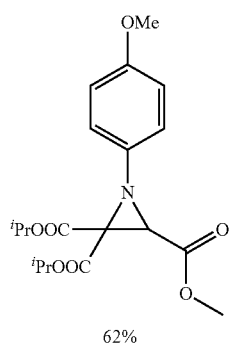
102
62%
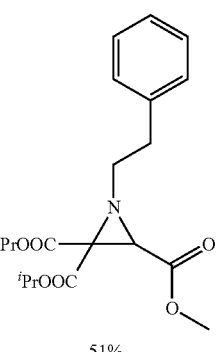
51%
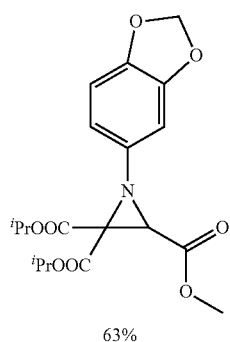
63%
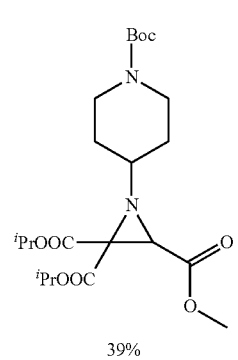
39%
103
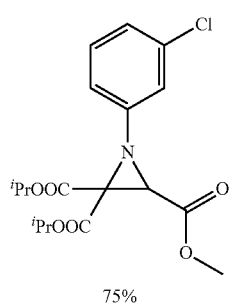
75%
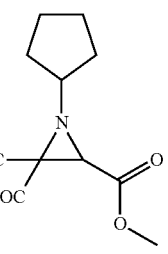
44%
104
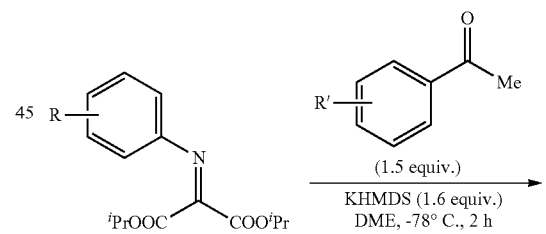
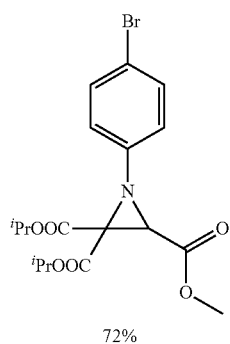
72%
105
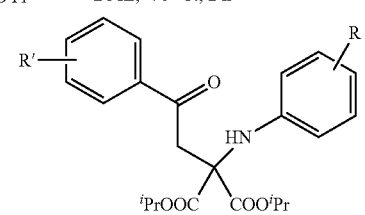
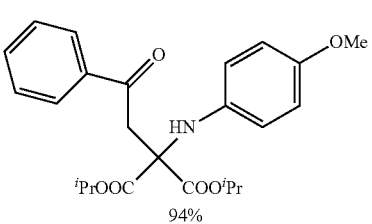
94%
106
107
108
109

-continued
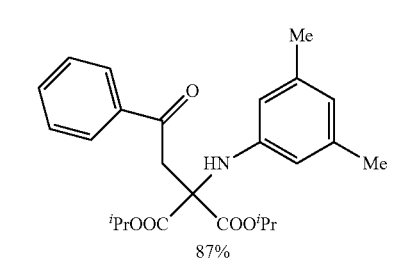
110
87%
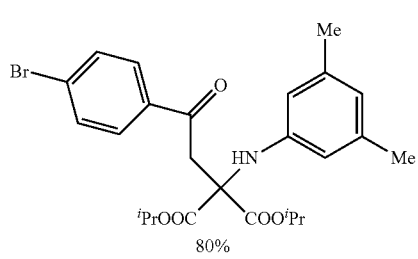
111
80%
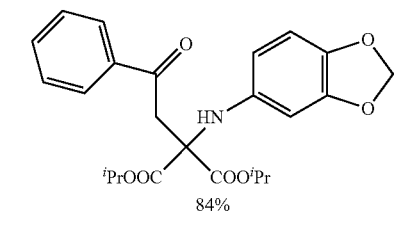
112
84%
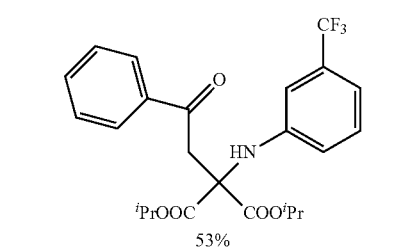
113
53%
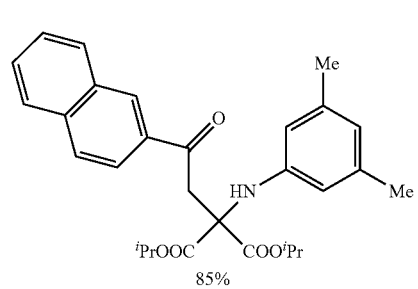
114
85%
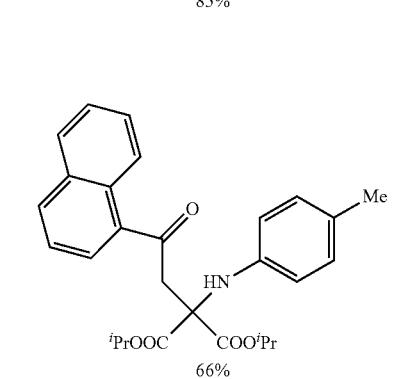
115
66%
-continued
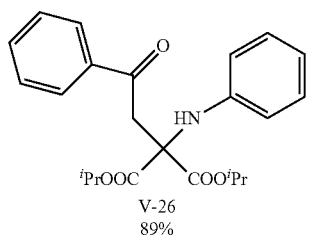
116
V-26
89%
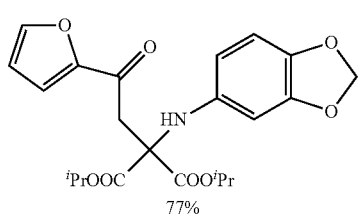
117
77%
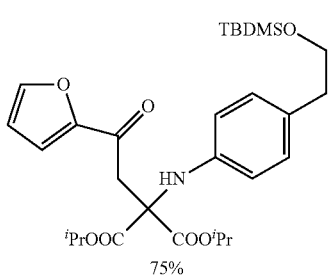
118
75%
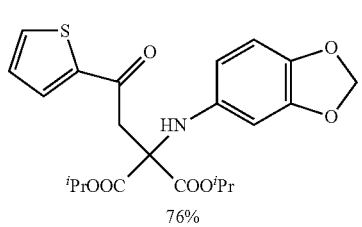
119
76%
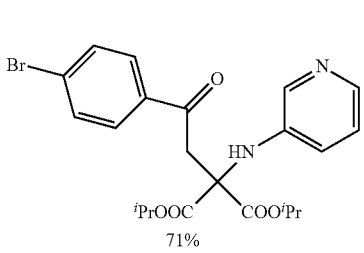
120
71%
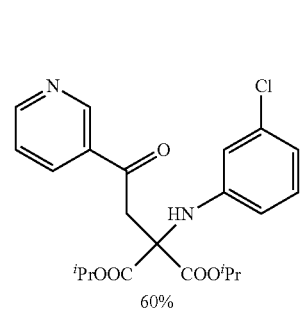
121
60%

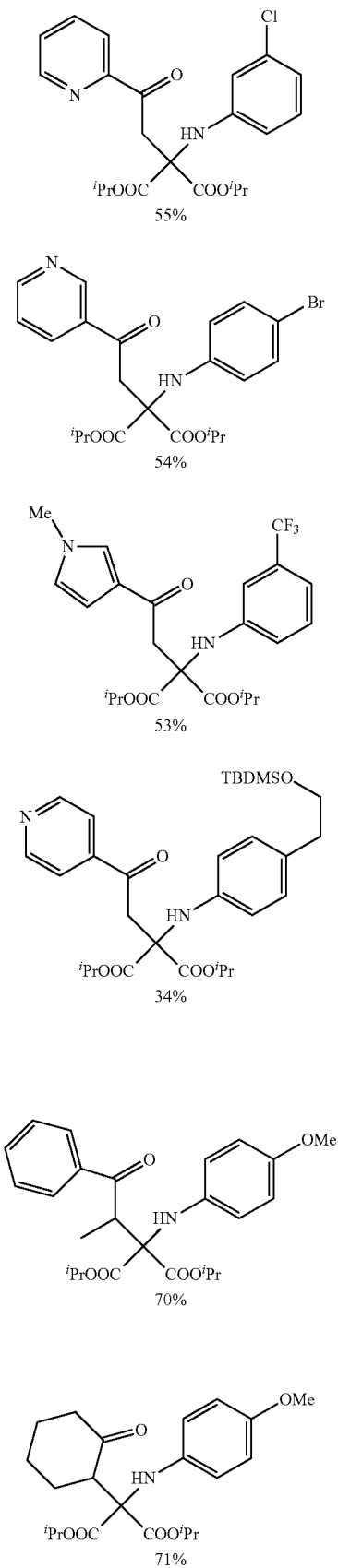
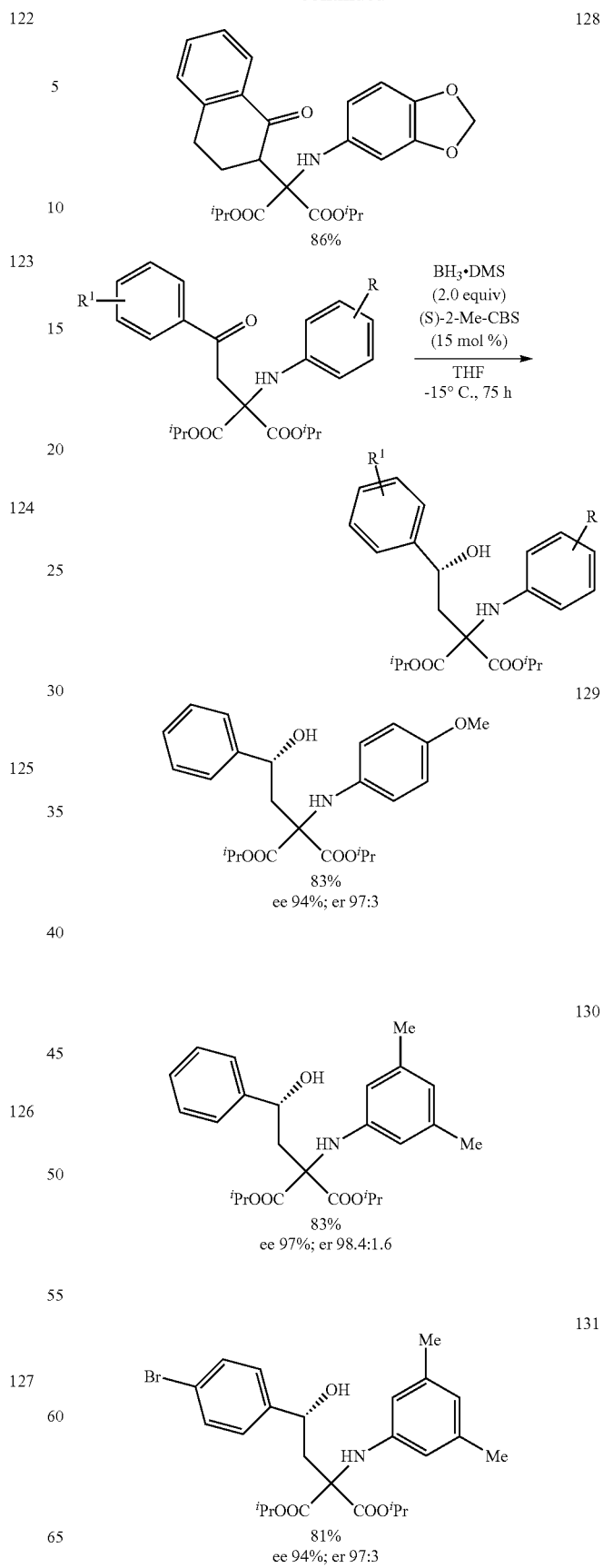

132
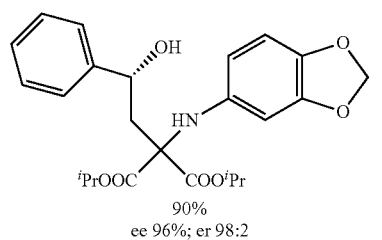
90%
ee 96%; er 98:2
133
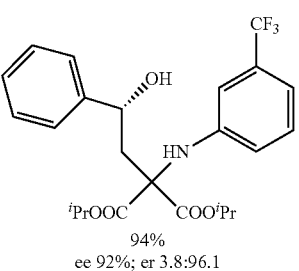
94%
ee 92%; er 3.8:96.1
134
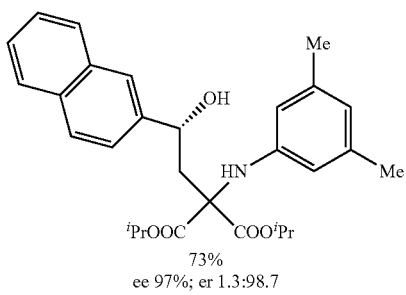
73%
ee 97%; er 1.3:98.7
135
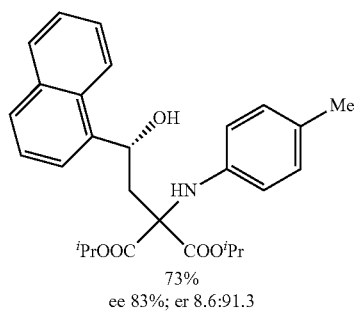
73%
ee 83%; er 8.6:91.3
136
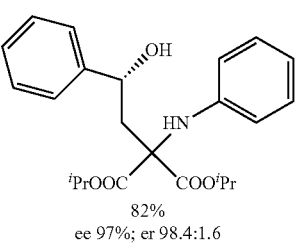
82%
ee 97%; er 98.4:1.6
137
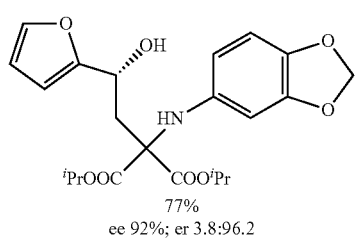
77%
ee 92%; er 3.8:96.2
138
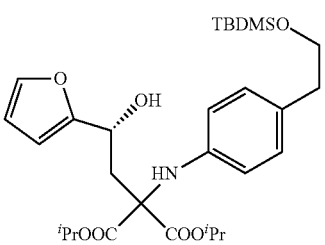
73%
ee 94%; er 3:97
139
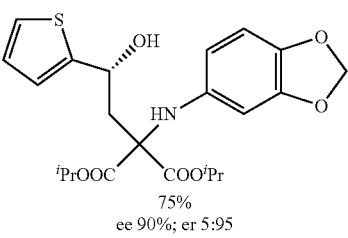
75%
ee 90%; er 5:95
140
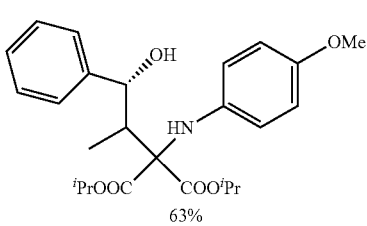
63%
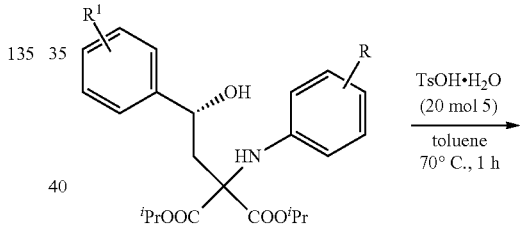
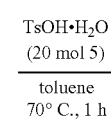
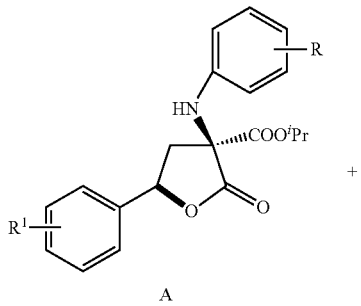
A
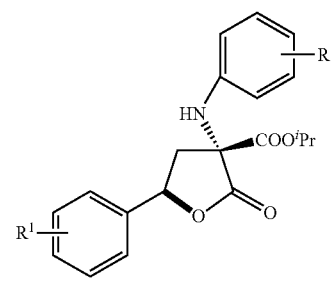
B -continued
141
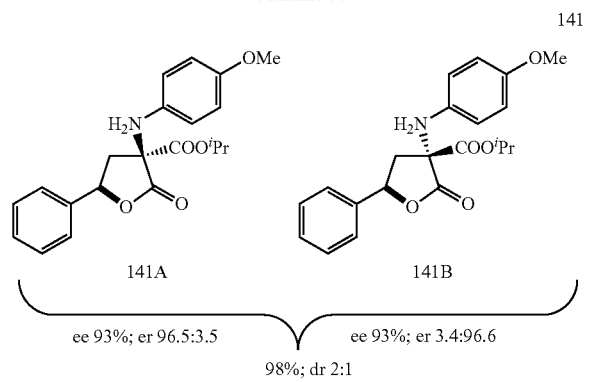
ee 93%; er 96.5:3.5   ee 93%; er 3.4:96.6
98%; dr 2:1
142
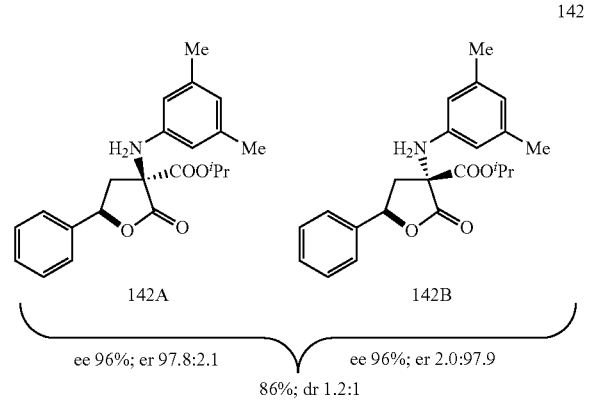
ee 96%; er 97.8:2.1   ee 96%; er 2.0:97.9
86%; dr 1.2:1
143
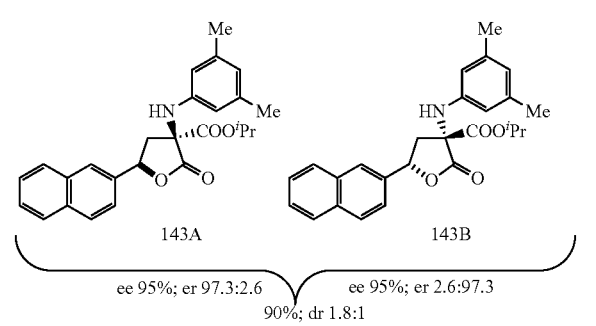
ee 95%; er 97.3:2.6   ee 95%; er 2.6:97.3
90%; dr 1.8:1
144
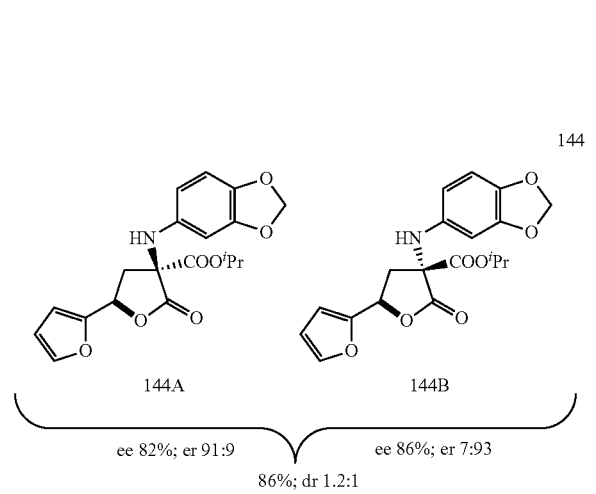
ee 82%; er 91:9   ee 86%; er 7:93
86%; dr 1.2:1
-continued
145
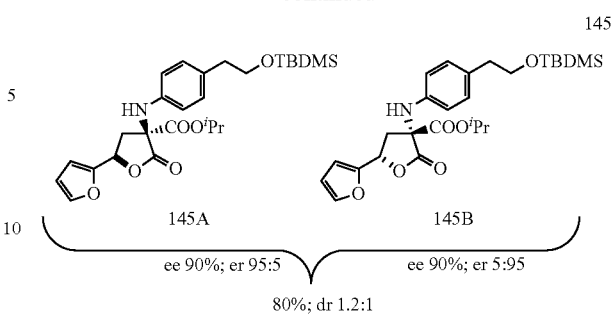
ee 90%; er 95:5   ee 90%; er 5:95
80%; dr 1.2:1
146
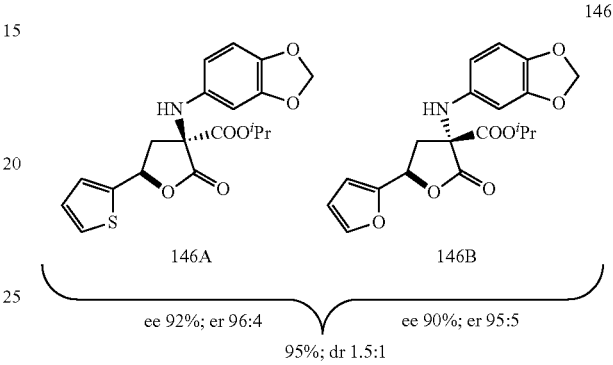
ee 92%; er 96:4   ee 90%; er 95:5
95%; dr 1.5:1
147
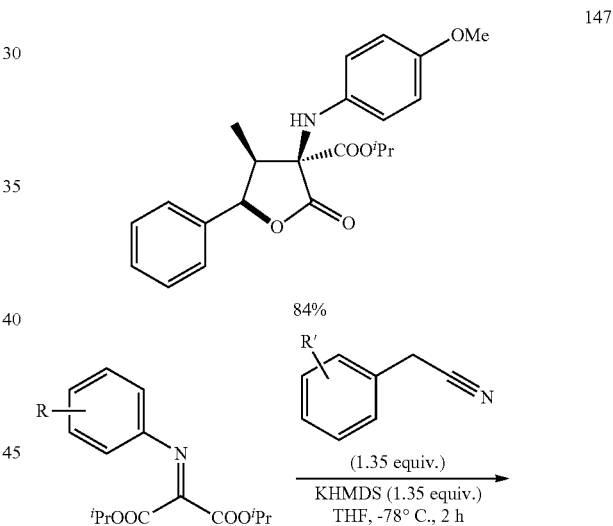
84%
148
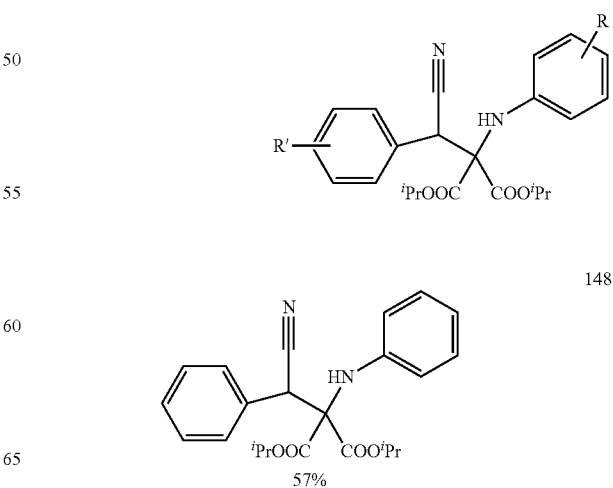
57%

149
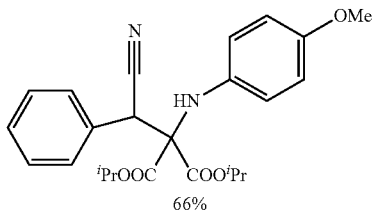
66%
150
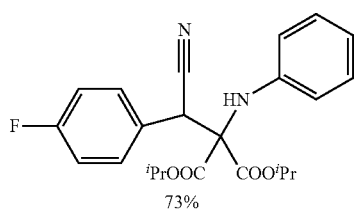
73%
151
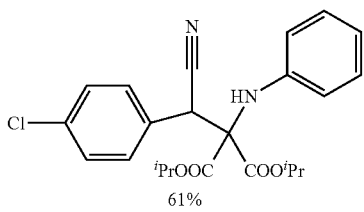
61%
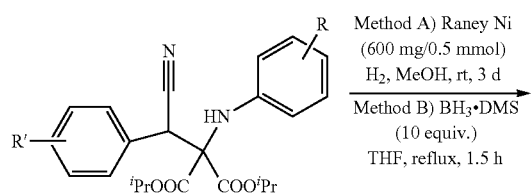
Method A) Raney Ni
(600 mg/0.5 mmol)
H$_2$, MeOH, rt, 3 d
Method B) BH$_3$·DMS
(10 equiv.)
THF, reflux, 1.5 h
152
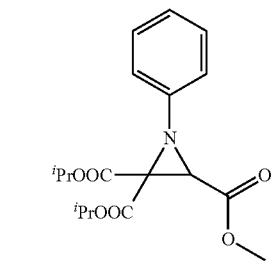
60% (A)
153
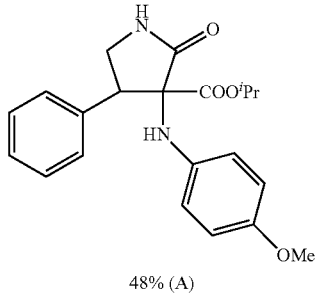
48% (A)
154
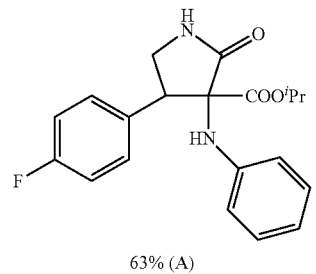
63% (A)
155
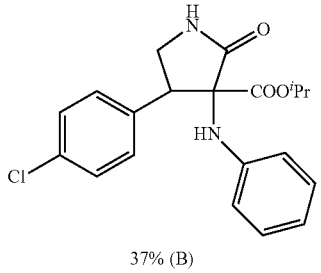
37% (B)
101
79%
Yield: 79%; Physical State: Pale yellow colored viscous oily liquid; R$_f$=0.45 (20% EtOAc/hexanes); $^1$H NMR (600 MHz, CDCl$_3$): δ 7.16 (t, J=1.1 Hz, 2H), 6.96 (t, J=7.3 Hz, 1H), 6.89 (d, J=7.8 Hz, 2H), 5.14 (hept, J=6.3 Hz, 1H), 4.78 (hept, J=6.3 Hz, 1H), 3.72 (d, J=6.8 Hz, 4H), 1.25 (dd, J=19.3, 6.2 Hz, 6H), 1.05 (d, J=6.2 Hz, 3H), 0.88 (d, J=6.2 Hz, 3H); $^{13}$C NMR (151 MHz, CDCl$_3$): δ 166.5, 163.3, 162.2, 145.8, 128.6, 123.7, 119.1, 70.6, 69.5, 52.7, 52.4, 45.2, 21.2, 21.1, 20.7; HRMS (ESI-TOF): calc'd for C$_{18}$H$_{23}$NO$_6$ [M+H]$^+$ 350.1598; Found 350.1598.

169

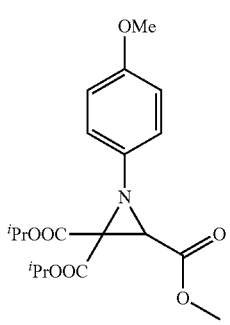

102

62%

Yield: 62%; Physical State: Brown colored viscous oily liquid; $R_f$=0.19 (20% EtOAc/hexanes); $^1$H NMR (600 MHz, CDCl$_3$): δ 6.83 (d, J=8.8 Hz, 2H), 6.71 (d, J=8.8 Hz, 2H), 5.13 (hept, J=6.2 Hz, 1H), 4.80 (hept, J=6.2 Hz, 1H), 3.71 (d, J=6.3 Hz, 4H), 3.66 (s, 3H), 1.25 (dd, J=20.4, 6.3 Hz, 6H), 1.07 (d, J=6.2 Hz, 3H), 0.94 (d, J=6.3 Hz, 3H); $^{13}$C NMR (151 MHz, CDCl$_3$): δ 166.7, 163.5, 162.2, 156.1, 138.9, 120.1, 113.9, 70.61, 70.60, 69.5, 55.1, 53.1, 52.4, 45.4, 21.34, 21.33, 21.2, 20.8; HRMS (ESI-TOF): calc'd for C$_{17}$H$_{25}$NO$_7$ [M+H]$^+$ 380.1704; Found 380.1706.

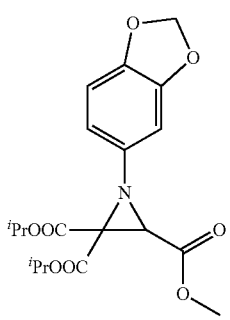

103

63%

Yield: 63%; Physical State: Brown colored viscous oily liquid; $R_f$=0.23 (20% EtOAc/hexanes); $^1$H NMR (600 MHz, CDCl$_3$): δ 6.59 (d, J=8.2 Hz, 1H), 6.45 (s, 1H), 6.35 (d, J=7.9 Hz, 1H), 5.83 (s, 2H), 5.13 (hept, J=6.3 Hz, 1H), 4.85 (hept, J=6.4 Hz, 1H), 3.70 (d, J=20.6 Hz, 4H), 1.25 (dd, J=20.9, 6.2 Hz, 6H), 1.10 (d, J=6.1 Hz, 3H), 1.01 (d, J=6.2 Hz, 3H); $^{13}$C NMR (151 MHz, CDCl$_3$): δ 166.4, 163.2, 162.0, 147.6, 143.9, 140.4, 111.3, 107.7, 101.1, 101.0, 77.2, 70.6, 69.5, 53.0, 52.4, 45.6, 21.25, 21.22, 21.1, 20.8; HRMS (ESI-TOF): calc'd for C$_{19}$H$_{23}$NO$_8$ [M+H]$^+$ 394.1496; Found 394.1489.

170

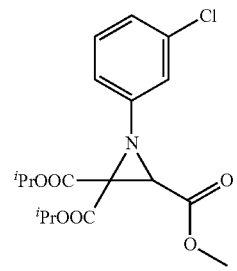

104

75%

Yield: 75%; Physical State: Pale yellow colored viscous oily liquid; $R_f$=0.36 (20% EtOAc/hexanes); $^1$H NMR (600 MHz, CDCl$_3$): δ 7.12 (t, J=8.0 Hz, 1H), 6.96 (d, J=8.0 Hz, 1H), 6.91 (s, 1H), 6.80 (d, J=8.9 Hz, 1H), 5.15 (hept, J=6.1 Hz, 1H), 4.86 (hept, J=6.1 Hz, 1H), 3.73 (d, J=16.4 Hz, 4H), 1.26 (dd, J=20.3, 6.3 Hz, 6H), 1.11 (d, J=6.2 Hz, 3H), 0.99 (d, J=6.3 Hz, 3H); $^{13}$C NMR (151 MHz, CDCl$_3$): δ 166.2, 163.1, 162.0, 147.2, 134.3, 129.9, 124.0, 119.5, 117.5, 71.1, 69.9, 52.7, 52.6, 45.4, 21.4, 21.3, 21.2, 20.9; HRMS (ESI-TOF): calc'd for C$_{18}$H$_{22}$ClNO$_6$ [M+H]$^+$ 384.1208; Found 384.1211.

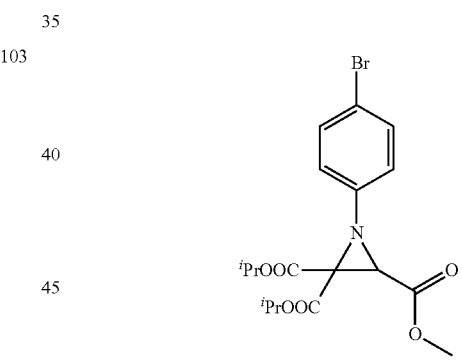

105

72%

Yield: 72%; Physical State: Yellow colored viscous oily liquid; $R_f$=0.32 (20% EtOAc/hexanes); $^1$H NMR (600 MHz, CDCl$_3$): δ 7.29 (d, J=8.6 Hz, 2H), 6.79 (d, J=8.6 Hz, 2H), 5.13 (hept, J=6.2 Hz, 1H), 4.83 (hept, J=6.3 Hz, 1H), 3.73 (s, 3H), 3.69 (s, 1H), 1.25 (dd, J=21.3, 6.3 Hz, 6H), 1.08 (d, J=6.2 Hz, 3H), 0.96 (d, J=6.3 Hz, 3H); $^{13}$C NMR (151 MHz, CDCl$_3$): δ 166.4, 163.3, 162.2, 145.2, 131.9, 121.1, 116.7, 71.2, 70.0, 52.9, 52.8, 45.6, 21.6, 21.5, 21.4, 21.1; HRMS (ESI-TOF): calc'd for C$_{18}$H$_{22}$BrNO$_6$ [M+H]$^+$ 428.0703; Found 428.0705.

106

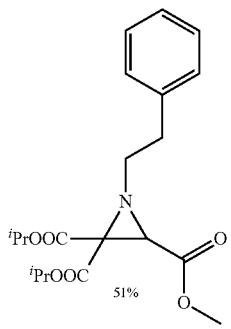

51%

Yield: 51%; Physical State: Pale yellow colored viscous oily liquid; $R_f$=0.29 (20% EtOAc/hexanes); $^1$H NMR (600 MHz, CDCl$_3$): δ 7.22 (t, J=6.9 Hz, 2H), 7.15 (d, J=6.1 Hz, 3H), 5.14-5.02 (m, 2H), 3.66 (s, 3H), 3.01 (d, J=19.4 Hz, 4H), 2.84-2.72 (m, 1H), 1.24 (t, J=6.2 Hz, 9H), 1.19 (d, J=6.0 Hz, 3H); $^{13}$C NMR (151 MHz, CDCl$_3$): δ 167.2, 163.7, 163.2, 138.6, 128.5, 128.1, 126.1, 70.6, 69.1, 52.8, 52.1, 51.5, 47.5, 35.4, 21.4, 21.28, 21.22; HRMS (ESI-TOF): calc'd for C$_{20}$H$_{27}$NO$_6$ [M+H]$^+$ 378.1911; Found 378.1909.

107

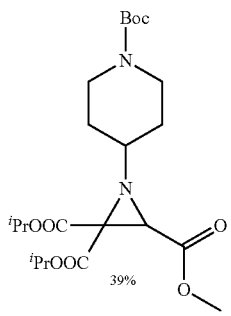

39%

Yield: 39%; Physical State: Pale yellow colored viscous oily liquid; $R_f$=0.4 (30% EtOAc/hexanes); $^1$H NMR (600 MHz, CDCl$_3$): δ 5.04 (dp, J=15.5, 6.3 Hz, 2H), 3.86 (s, 1H), 3.65 (s, 3H), 3.15 (s, 1H), 2.95 (dt, J=35.9, 9.6 Hz, 2H), 2.55 (s, 1H), 1.69-1.53 (m, 3H), 1.47 (d, J=10.7 Hz, 1H), 1.38 (s, 9H), 1.26-1.18 (m, 9H), 1.15 (d, J=6.2 Hz, 3H); $^{13}$C NMR (151 MHz, CDCl$_3$): δ 167.3, 163.8, 163.6, 154.6, 79.2, 70.7, 69.2, 55.9, 52.3, 51.8, 46.4, 28.2, 21.37, 21.34, 21.32, 21.30, 21.2; HRMS (ESI-TOF): calc'd for C$_{22}$H$_{36}$N$_2$O$_8$ [M+H]$^+$ 457.2544; Found 457.2548.

108

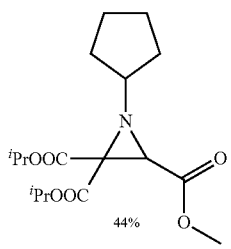

44%

Yield: 44%; Physical State: Colorless viscous oily liquid; $R_f$=0.15 (10% EtOAc/hexanes); $^1$H NMR (600 MHz, CDCl$_3$): δ 5.03 (dp, J=14.8, 6.3 Hz, 2H), 3.64 (s, 3H), 3.12 (s, 1H), 2.86 (td, J=6.6, 3.3 Hz, 1H), 1.85-1.74 (m, 2H), 1.66 (ddt, J=27.7, 9.8, 5.4 Hz, 3H), 1.53-1.41 (m, 3H), 1.23-1.17 (m, 9H), 1.14 (d, J=6.3 Hz, 3H); $^{13}$C NMR (151 MHz, CDCl$_3$): δ 167.6, 164.0, 163.5, 70.3, 68.9, 62.2, 52.5, 52.1, 47.5, 32.4, 32.0, 24.3, 24.2, 21.34, 21.30, 21.24; HRMS (ESI-TOF): calc'd for C$_{17}$H$_{27}$NO$_6$ [M+H]$^+$ 342.1911; Found 342.1936.

109

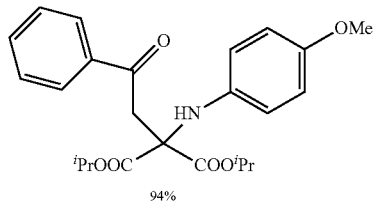

94%

Yield: 94%; Physical State: Brown colored waxy solid; $R_f$=0.41 (20% EtOAc/hexanes); $^1$H NMR (600 MHz, CDCl$_3$): δ 7.85 (d, J=8.4 Hz, 2H), 7.50 (t, J=7.4 Hz, 1H), 7.38 (t, J=7.8 Hz, 2H), 6.66 (d, J=8.9 Hz, 2H), 6.60 (d, J=9.0 Hz, 2H), 5.11 (h, J=6.3 Hz, 3H), 4.02 (s, 2H), 3.67 (s, 3H), 1.20 (d, J=6.3 Hz, 6H), 1.15 (d, J=6.3 Hz, 6H); $^{13}$C NMR (151 MHz, CDCl$_3$): δ 196.3, 168.8, 153.3, 138.0, 136.5, 133.1, 128.4, 127.8, 117.7, 114.4, 70.1, 67.0, 55.4, 40.9, 21.3; HRMS (ESI-TOF): calc'd for C$_{24}$H$_{19}$NO$_6$ [M+H]$^+$ 428.2068; found 428.2069.

110

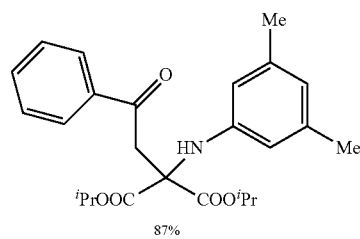

87%

Yield: 87%; Physical State: Pale yellow colored viscous oily liquid; $R_f$=0.57 (20% EtOAc/hexanes); $^1$H NMR (600 MHz, CDCl$_3$): δ 7.89 (d, J=7.4 Hz, 2H), 7.51 (t, J=7.4 Hz, 1H), 7.40 (t, J=7.8 Hz, 2H), 6.36 (s, 1H), 6.26 (s, 2H), 5.35 (s, 1H), 5.13 (hept, J=6.2 Hz, 2H), 4.13 (s, 2H), 2.18 (s, 6H), 1.22 (d, J=6.3 Hz, 6H), 1.15 (d, J=6.3 Hz, 6H); $^{13}$C NMR (151 MHz, CDCl$_3$): δ 196.2, 168.6, 144.1, 138.4, 136.5, 133.1, 128.3, 127.8, 120.4, 112.5, 70.1, 66.1, 40.8, 21.27, 21.25, 21.1; HRMS (ESI-TOF): calc'd for C$_{25}$H$_{31}$NO$_5$ [M+H]$^+$ 426.2275; Found 426.2275.

111

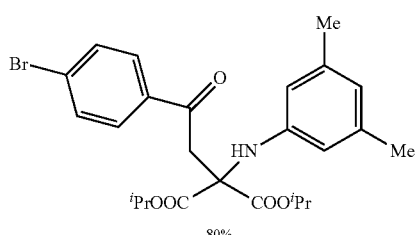

80%

Yield: 80%; Physical State: Pale yellow colored waxy solid; $R_f$=0.57 (20% EtOAc/hexanes); $^1$H NMR (600 MHz, CDCl$_3$): δ 7.73 (d, J=8.5 Hz, 2H), 7.53 (d, J=8.5 Hz, 2H), 6.36 (s, 1H), 6.22 (s, 2H), 5.29 (s, 1H), 5.11 (hept, J=6.1 Hz, 2H), 4.05 (s, 2H), 2.17 (s, 6H), 1.21 (d, J=6.3 Hz, 6H), 1.14 (d, J=6.3 Hz, 6H); $^{13}$C NMR (151 MHz, CDCl$_3$): δ 195.5, 168.6, 144.1, 138.6, 135.3, 131.7, 129.5, 128.4, 120.6, 112.6, 70.4, 66.2, 40.8, 21.38, 21.36, 21.2; HRMS (ESI-TOF): calc'd for C$_{25}$H$_{30}$BrNO$_5$ [M+H]$^+$ 504.1380; Found 504.1378.

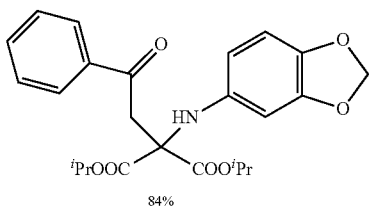

112

Yield: 84%; Physical State: Yellow colored waxy solid; $R_f$=0.49 (20% EtOAc/hexanes); $^1$H NMR (600 MHz, CDCl$_3$): δ 7.86 (d, J=7.3 Hz, 2H), 7.51 (t, J=7.4 Hz, 1H), 7.39 (t, J=7.8 Hz, 2H), 6.53 (d, J=8.3 Hz, 1H), 6.25 (d, J=2.3 Hz, 1H), 6.06 (dd, J=8.3, 2.3 Hz, 1H), 5.78 (s, 2H), 5.17 (s, 1H), 5.11 (hept, J=6.2 Hz, 2H), 4.02 (s, 2H), 1.20 (d, J=6.3 Hz, 6H), 1.16 (d, J=6.3 Hz, 6H); $^{13}$C NMR (151 MHz, CDCl$_3$): δ 196.2, 168.7, 148.0, 140.8, 139.3, 136.4, 133.2, 128.4, 127.8, 108.1, 107.9, 100.5, 99.1, 70.2, 66.8, 40.7, 21.3, 21.2; HRMS (ESI-TOF): calc'd for C$_{24}$H$_{27}$NO$_7$ [M+H]$^+$ 442.1860; Found 442.1868.

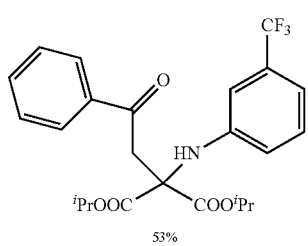

113

Yield: 53%; Physical State: White colored solid (m.p. 132-134° C.); $R_f$=0.53 (20% EtOAc/hexanes); $^1$H NMR (600 MHz, CDCl$_3$): δ 7.89 (d, J=8.4 Hz, 2H), 7.52 (t, J=7.4 Hz, 1H), 7.41 (t, J=7.8 Hz, 2H), 7.19 (t, J=7.9 Hz, 1H), 6.93 (d, J=7.6 Hz, 1H), 6.83 (s, 1H), 6.77 (d, J=8.2 Hz, 1H), 5.70 (s, 1H), 5.13 (hept, J=6.3 Hz, 2H), 4.12 (s, 2H), 1.21 (d, J=6.3 Hz, 6H), 1.13 (d, J=6.3 Hz, 6H); $^{13}$C NMR (151 MHz, CDCl$_3$): δ 195.9, 168.2, 144.6, 136.3, 133.4, 131.7, 131.5, 131.3, 131.1, 129.5, 128.5, 127.9, 126.7, 124.9, 123.1, 121.3, 117.3, 114.94, 114.92, 114.89, 114.87, 110.52, 110.50, 110.47, 110.44, 70.7, 65.9, 40.5, 21.28, 21.22; $^{19}$F NMR (471 MHz, CDCl$_3$): δ -62.0 (S); HRMS (ESI-TOF): calc'd for C$_{24}$H$_{26}$F$_3$NO$_5$ [M+H]$^+$ 466.1836; found 466.1827.

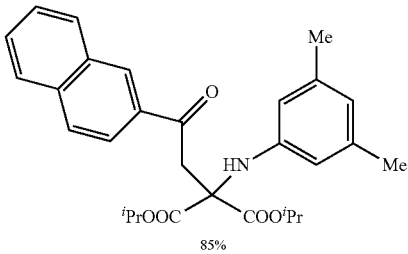

114

Yield: 85%; Physical State: Yellowish brown colored viscous gummy oily liquid; $R_f$=0.5 (20% EtOAc/hexanes); $^1$H NMR (600 MHz, CDCl$_3$): δ 8.37 (s, 1H), 7.95 (dd, J=8.6, 1.5 Hz, 1H), 7.85 (d, J=8.1 Hz, 1H), 7.81 (d, J=8.7 Hz, 2H), 7.55 (ddd, J=8.2, 6.8, 1.4 Hz, 1H), 7.50 (t, J=7.5 Hz, 1H), 6.38 (s, 1H), 6.32 (s, 2H), 5.41 (s, 1H), 5.19 (hept, J=6.3 Hz, 2H), 4.28 (s, 2H), 2.19 (s, 6H), 1.26 (d, J=6.3 Hz, 6H), 1.20 (d, J=6.3 Hz, 6H); $^{13}$C NMR (151 MHz, CDCl$_3$): δ 196.3, 168.7, 144.1, 138.5, 135.4, 133.8, 132.1, 129.8, 129.3, 128.3, 128.1, 127.5, 126.5, 123.3, 120.5, 112.6, 70.2, 66.3, 40.8, 21.27, 21.21; HRMS (ESI-TOF): calc'd for C$_{28}$H$_{31}$NO$_5$ [M+H]$^+$ 476.2431; Found 476.2433.

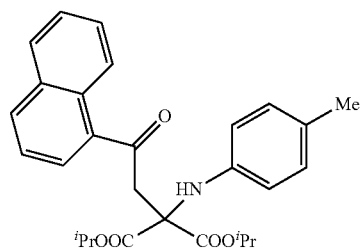

115

Yield: 66%; Physical State: Yellow colored viscous oily liquid; $R_f$=0.53 (20% EtOAc/hexanes); $^1$H NMR (600 MHz, CDCl$_3$): δ 8.45 (d, J=7.8 Hz, 1H), 7.91 (d, J=8.2 Hz, 1H), 7.81 (d, J=9.0 Hz, 1H), 7.68 (d, J=7.1 Hz, 1H), 7.49 (p, J=6.1, 5.5 Hz, 2H), 7.38 (t, J=7.7 Hz, 1H), 6.93 (d, J=8.1 Hz, 2H), 6.61 (d, J=8.4 Hz, 2H), 5.40 (s, 1H), 5.18 (hept, J=6.2 Hz, 2H), 4.21 (s, 2H), 2.20 (s, 3H), 1.28 (d, J=6.3 Hz, 6H), 1.19 (d, J=6.3 Hz, 6H); $^{13}$C NMR (151 MHz, CDCl$_3$): δ 200.4, 168.8, 141.9, 135.3, 133.6, 132.6, 129.8, 129.5, 128.2, 128.1, 127.7, 127.5, 126.3, 125.5, 124.1, 115.5, 70.2, 66.7, 44.2, 21.37, 21.30, 20.29; HRMS (ESI-TOF): calc'd for C$_{28}$H$_{31}$NO$_5$ [M+H]$^+$ 462.2275; found 462.2277.

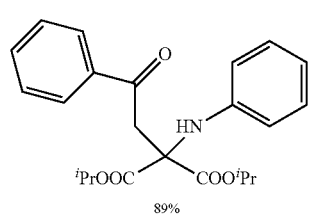

116

Yield: 89%; Physical State: Browinish yellow colored viscous oily liquid; $R_f$=0.53 (20% EtOAc/hexanes); $^1$H NMR (600 MHz, CDCl$_3$): δ 7.87 (d, J=8.2 Hz, 2H), 7.50 (t, J=6.8 Hz, 1H), 7.38 (t, J=7.2 Hz, 2H), 7.10 (t, J=7.9 Hz, 2H), 6.70 (t, J=7.3 Hz, 1H), 6.63 (d, J=8.1 Hz, 2H), 5.46 (s, 1H), 5.12 (hept, J=6.2 Hz, 2H), 4.14 (s, 2H), 1.21 (d, J=6.3 Hz, 6H), 1.12 (d, J=6.3 Hz, 6H); $^{13}$C NMR (151 MHz, CDCl$_3$): δ 196.2, 168.6, 144.3, 136.5, 133.2, 129.0, 128.4, 127.9, 118.5, 114.5, 70.3, 66.1, 40.8, 21.29, 21.24; HRMS (ESI-TOF): calc'd for C$_{23}$H$_{27}$NO$_5$ [M+H]$^+$ 398.1962; Found 398.1958.

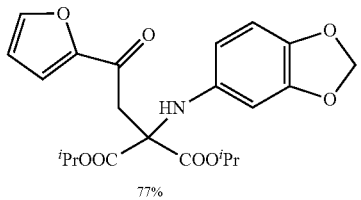

117

77%

Yield: 77%; Physical State: Dark brown colored viscous oily liquid; R$_f$=0.27 (20% EtOAc/hexanes); $^1$H NMR (600 MHz, CDCl$_3$): δ 7.49 (s, 1H), 7.06 (d, J=3.5 Hz, 1H), 6.53 (d, J=8.3 Hz, 1H), 6.43 (dd, J=3.5, 1.7 Hz, 1H), 6.24 (d, J=2.3 Hz, 1H), 6.05 (dd, J=8.3, 2.3 Hz, 1H), 5.79 (s, 2H), 5.08 (hept, J=6.3 Hz, 3H), 3.85 (s, 2H), 1.20 (d, J=6.3 Hz, 6H), 1.13 (d, J=6.3 Hz, 6H); $^{13}$C NMR (151 MHz, CDCl$_3$): δ 185.0, 168.4, 152.2, 147.9, 146.5, 140.8, 139.3, 117.5, 112.2, 108.1, 107.8, 100.5, 99.0, 70.3, 66.7, 40.5, 21.29, 21.27; HRMS (ESI-TOF): calc'd for C$_{22}$H$_{25}$NO$_8$ [M+H]$^+$ 432.1653; found 432.1657.

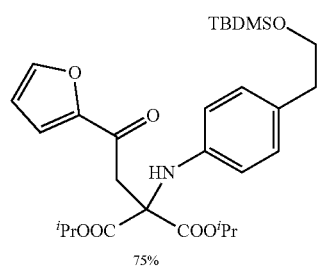

118

75%

Yield: 75%; Physical State: Brown colored viscous oily liquid; R$_f$=0.44 (20% EtOAc/hexanes); $^1$H NMR (600 MHz, CDCl$_3$): δ 7.45 (s, 1H), 7.02 (d, J=3.5 Hz, 1H), 6.91 (d, J=8.3 Hz, 2H), 6.52 (d, J=8.4 Hz, 2H), 6.38 (dd, J=3.6, 1.7 Hz, 1H), 5.25 (s, 1H), 5.08 (h, J=6.3 Hz, 2H), 3.91 (s, 2H), 3.66 (t, J=7.1 Hz, 2H), 2.63 (t, J=7.0 Hz, 2H), 1.20 (d, J=6.3 Hz, 6H), 1.09 (d, J=6.3 Hz, 6H), 0.82 (s, 9H), −0.08 (s, 6H); $^{13}$C NMR (151 MHz, CDCl$_3$): δ 184.9, 168.4, 152.1, 146.4, 142.4, 129.5, 129.2, 117.3, 114.7, 112.0, 70.2, 66.1, 64.5, 40.4, 38.5, 25.7, 21.2, 21.1, 18.1, −5.5; HRMS (ESI-TOF): calc'd for C$_{29}$H$_{43}$NO$_7$Si [M+H]$^+$ 546.2882; found 546.2883.

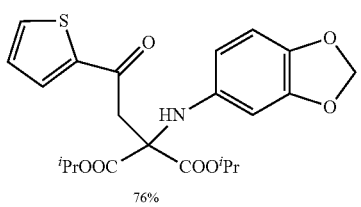

119

76%

Yield: 76%; Physical State: Dark brownish yellow colored viscous gummy substance; R$_f$=0.38 (20% EtOAc/hexanes); $^1$H NMR (600 MHz, CDCl$_3$): δ 7.60 (ddd, J=14.6, 4.3, 0.8 Hz, 2H), 7.04 (dd, J=4.8, 3.9 Hz, 1H), 6.55 (d, J=8.3 Hz, 1H), 6.25 (d, J=2.3 Hz, 1H), 6.07 (dd, J=8.3, 2.3 Hz, 1H), 5.80 (s, 2H), 5.15-5.07 (m, 3H), 3.94 (s, 2H), 1.22 (d, J=6.3 Hz, 6H), 1.17 (s, 6H); $^{13}$C NMR (151 MHz, CDCl$_3$): δ 189.1, 168.5, 148.0, 143.8, 140.9, 139.3, 134.1, 132.2, 128.0, 108.2, 107.8, 100.6, 99.1, 70.3, 66.9, 41.2, 21.3; HRMS (ESI-TOF): calc'd for C$_{22}$H$_{25}$NO$_7$S [M+H]$^+$ 448.1424; found 448.1425.

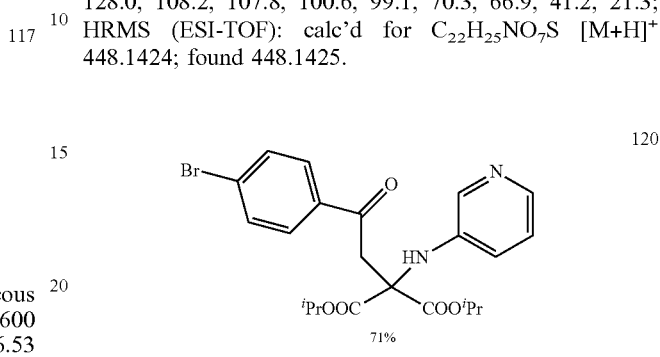

120

71%

Yield: 71%; Physical State: Reddish brown colored viscous gummy substance; R$_f$=0.16 (30% EtOAc/hexanes); $^1$H NMR (600 MHz, CDCl$_3$): δ 7.98 (s, 1H), 7.92-7.87 (m, 1H), 7.65 (d, J=8.2 Hz, 2H), 7.44 (d, J=8.2 Hz, 2H), 6.96-6.91 (m, 1H), 6.84 (d, J=7.0 Hz, 1H), 5.47 (s, 1H), 5.04 (hept, J=6.2 Hz, 2H), 3.99 (s, 2H), 1.12 (d, J=6.1 Hz, 6H), 1.04 (d, J=6.1 Hz, 6H); $^{13}$C NMR (151 MHz, CDCl$_3$): δ 194.7, 167.7, 140.2, 139.9, 137.1, 134.8, 131.7, 129.2, 128.5, 123.2, 120.2, 70.6, 65.6, 40.2, 21.0; HRMS (ESI-TOF): calc'd for C$_{22}$H$_{25}$BrN$_2$O$_5$ [M+H]$^+$ 477.1020; found 477.1021.

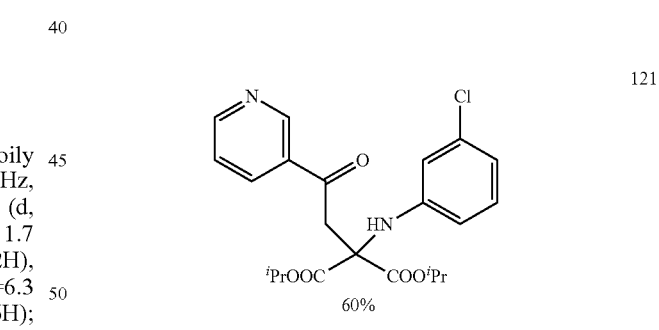

121

60%

Yield: 60%; Physical State: Viscous yellow colored gummy oily liquid; R$_f$=0.20 (30% EtOAc/hexanes); $^1$H NMR (600 MHz, CDCl$_3$): δ 9.05 (s, 1H), 8.67 (s, 1H), 8.07 (d, J=1.1 Hz, 1H), 7.32-7.27 (m, 1H), 6.95 (t, J=8.0 Hz, 1H), 6.60 (d, J=7.6 Hz, 1H), 6.54 (s, 1H), 6.44 (d, J=7.8 Hz, 1H), 5.52 (s, 1H), 5.07 (hept, J=6.3 Hz, 2H), 4.06 (s, 2H), 1.16 (d, J=6.2 Hz, 6H), 1.08 (d, J=6.2 Hz, 6H); $^{13}$C NMR (151 MHz, CDCl$_3$): δ 195.0, 167.8, 153.6, 149.2, 145.1, 135.0, 134.6, 131.5, 130.0, 123.3, 118.4, 114.0, 112.2, 70.6, 65.6, 40.6, 21.15, 21.11; HRMS (ESI-TOF): calc'd for C$_{22}$H$_{25}$ClN$_2$O$_5$ [M+H]$^+$ 433.1525; found 433.1525.

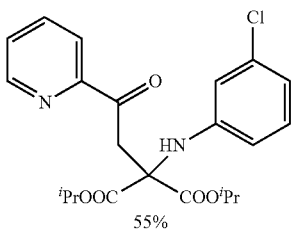

122

55%

Yield: 55%; Physical State: Yellow colored solid (m.p. 110-113° C.); $R_f$=0.62 (30% EtOAc/hexanes); $^1$H NMR (600 MHz, CDCl$_3$): δ 8.68-8.55 (m, 1H), 7.94 (d, J=1.1 Hz, 1H), 7.77 (t, J=7.1 Hz, 1H), 7.48-7.36 (m, 1H), 7.00 (t, J=7.8 Hz, 1H), 6.65 (d, J=7.8 Hz, 1H), 6.54 (d, J=7.5 Hz, 1H), 5.57 (s, 1H), 5.13 (hept, J=6.2 Hz, 2H), 4.43 (s, 2H), 1.23 (d, J=6.1 Hz, 6H), 1.14 (d, J=6.1 Hz, 6H); $^{13}$C NMR (151 MHz, CDCl$_3$): δ 197.6, 168.1, 152.5, 148.7, 145.5, 136.6, 134.4, 129.8, 127.2, 121.4, 118.2, 114.3, 112.5, 70.3, 65.9, 40.0, 21.2, 21.1; HRMS (ESI-TOF): calc'd for $C_{22}H_{25}ClN_2O_5$ [M+H]$^+$ 433.1525; found 433.1527.

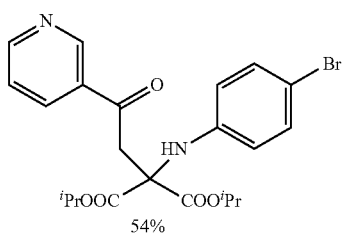

123

54%

Yield: 54%; Physical State: Yellow colored viscous gummy substance; $R_f$=0.21 (30% EtOAc/hexanes); $^1$H NMR (600 MHz, CDCl$_3$): δ 9.05 (s, 1H), 8.70 (d, J=4.1 Hz, 1H), 8.07 (d, J=8.0 Hz, 1H), 7.31 (dd, J=7.8, 4.9 Hz, 1H), 7.15 (d, J=8.6 Hz, 2H), 6.47 (d, J=8.6 Hz, 2H), 5.46 (s, 1H), 5.08 (hept, J=6.2 Hz, 2H), 4.06 (s, 2H), 1.17 (d, J=6.3 Hz, 6H), 1.10 (d, J=6.3 Hz, 6H); $^{13}$C NMR (151 MHz, CDCl$_3$): δ 195.1, 168.0, 153.6, 149.3, 143.0, 135.0, 131.8, 131.6, 123.4, 115.9, 110.5, 70.7, 65.8, 40.5, 21.2; HRMS (ESI-TOF): calc'd for $C_{22}H_{25}BrN_2O_5$ [M+H]$^+$ 477.1020; found 477.1017.

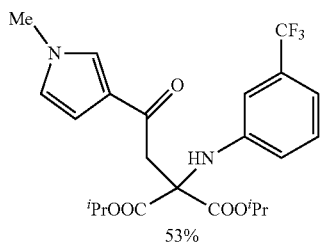

124

53%

Yield: 53%; Physical State: White colored solid (m.p. 160-162° C.); $R_f$=0.31 (30% EtOAc/hexanes); $^1$H NMR (600 MHz, CDCl$_3$): δ 7.18 (t, J=7.9 Hz, 1H), 7.07 (t, J=1.1 Hz, 1H), 6.92 (d, J=7.6 Hz, 1H), 6.80 (s, 1H), 6.78-6.73 (m, 1H), 6.53-6.44 (m, 2H), 5.66 (s, 1H), 5.12 (hept, J=6.3 Hz, 2H), 3.82 (s, 2H), 3.58 (s, 3H), 1.23 (d, J=6.3 Hz, 6H), 1.13 (d, J=6.3 Hz, 6H); $^{13}$C NMR (151 MHz, CDCl$_3$): δ 190.6, 168.4, 144.9, 131.6, 131.4, 131.1, 130.9, 129.4, 126.9, 126.8, 125.4, 125.0, 123.4, 123.2, 121.4, 117.5, 114.59, 114.56, 114.54, 114.51, 110.43, 110.40, 110.38, 110.35, 109.2, 70.5, 66.0, 41.0, 36.4, 21.3, 21.2; $^{19}$F NMR (471 MHz, CDCl$_3$): δ -61.9 (S); HRMS (ESI-TOF): calc'd for $C_{23}H_{27}F_3N_2O_5$ [M+H]$^+$ 469.1945; found 469.1944.

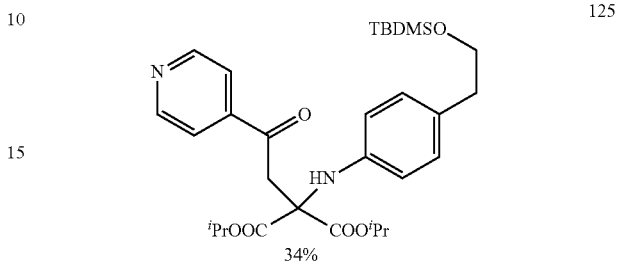

125

34%

Yield: 34%; Physical State: Brown colored viscous oily liquid; $R_f$=0.37 (30% EtOAc/hexanes); $^1$H NMR (600 MHz, CDCl$_3$): δ 8.70 (d, J=5.9 Hz, 2H), 7.58 (d, J=5.9 Hz, 2H), 6.92 (d, J=8.3 Hz, 2H), 6.52 (d, J=8.3 Hz, 2H), 5.27 (s, 1H), 5.10 (hept, J=6.1, 5.2 Hz, 2H), 4.05 (s, 2H), 3.66 (t, J=7.0 Hz, 2H), 2.63 (t, J=7.0 Hz, 2H), 1.20 (d, J=6.3 Hz, 6H), 1.12 (d, J=6.3 Hz, 6H), 0.82 (s, 9H), -0.09 (s, 6H); $^{13}$C NMR (151 MHz, CDCl$_3$): δ 196.1, 168.4, 150.7, 142.3, 142.1, 129.8, 129.7, 120.7, 114.9, 70.5, 66.2, 64.6, 40.8, 38.5, 25.8, 21.35, 21.30, 21.2, 18.2, 5.5; HRMS (ESI-TOF): calc'd for $C_{30}H_{44}N_2O_6Si$ [M+H]$^+$ 557.3041; found 557.3041.

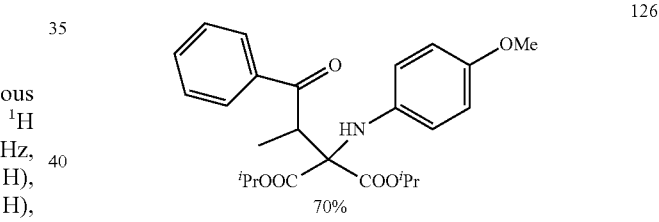

126

70%

Yield: 70%; Physical State: Yellow colored viscous oily liquid; $R_f$=0.36 (15% EtOAc/hexanes); $^1$H NMR (600 MHz, CDCl$_3$): δ 7.85 (d, J=8.4 Hz, 2H), 7.49 (t, J=7.4 Hz, 1H), 7.38 (t, J=7.8 Hz, 2H), 6.67 (s, 4H), 5.22 (hept, J=6.4 Hz, 1H), 5.17 (s, 1H), 4.97 (hept, J=6.3 Hz, 1H), 4.65 (q, J=7.2 Hz, 1H), 3.68 (s, 3H), 1.40 (d, J=12 Hz, 3H), 1.30 (d, J=6.3 Hz, 3H), 1.22 (d, J=6.3 Hz, 3H), 1.13 (d, J=63 Hz, 3H), 1.00 (d, J=6.3 Hz, 3H); $^{13}$C NMR (151 MHz, CDCl$_3$): δ 201.5, 169.1, 168.5, 153.4, 138.1, 136.3, 132.8, 128.4, 128.1, 118.5, 114.2, 70.9, 70.1, 69.8, 55.4, 43.7, 21.4, 21.3, 21.18, 21.17, 14.6; HRMS (ESI-TOF): calc'd for $C_{25}H_{31}NO_6$ [M+H]$^+$ 442.2224; found 442.2219.

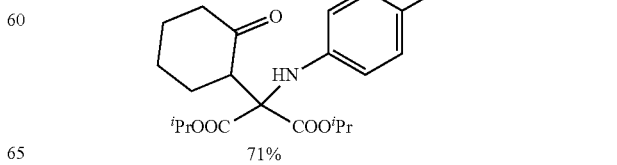

127

71%

Yield: 71%; Physical State: Brown colored viscous oily liquid; $R_f$=0.37 (20% EtOAc/hexanes); $^1$H NMR (600 MHz, CDCl$_3$): δ 6.68-6.55 (m, 4H), 4.98 (hept, J=6.2 Hz, 1H), 4.90 (hept, J=6.2 Hz, 1H), 4.85 (s, 1H), 3.64 (s, 3H), 3.44 (dd, J=12.6, 4.9 Hz, 1H), 2.47 (dd, J=7.8, 2.7 Hz, 1H), 2.29 (d, J=13.5 Hz, 1H), 2.19 (td, J=13.4, 6.1 Hz, 1H), 2.03-1.95 (m, 1H), 1.90-1.75 (m, 2H), 1.70-1.50 (m, 2H), 1.12 (t, J=6.6 Hz, 6H), 1.09 (d, J=6.2 Hz, 3H), 0.92 (d, J=6.3 Hz, 3H); $^{13}$C NMR (151 MHz, CDCl$_3$): δ 209.6, 168.8, 167.8, 153.3, 139.0, 118.8, 113.8, 69.6, 69.3, 56.2, 55.2, 42.1, 30.1, 27.2, 25.0, 21.1, 20.9; HRMS (ESI-TOF): calc'd for $C_{22}H_{31}NO_6$ [M+H]$^+$ 406.2224; found 406.2227.

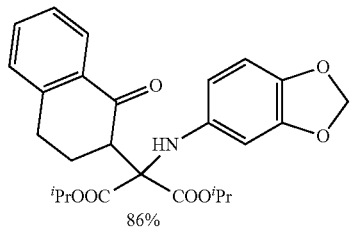

128

86%

Yield: 86%; Physical State: Viscous brown colored gummy substance; $R_f$=0.37 (20% EtOAc/hexanes); $^1$H NMR (600 MHz, CDCl$_3$): δ 7.98-7.96 (m, 1H), 7.43 ltd, J=7.5, 1.3 Hz, 1H), 7.28-7.24 (m, 1H), 7.20 (d, J=7.6 Hz, 1H), 6.56 (d, J=8.4 Hz, 1H), 6.39 (d, J=2.3 Hz, 1H), 6.21 (dd, J=8.4, 2.3 Hz, 1H), 5.81 (s, 2H), 5.14 (dq, J=12.5, 6.6 Hz, 2H), 4.98 (hept, J=6.2 Hz, 1H), 3.71 (dd, J=13.5, 4.0 Hz, 1H), 3.11 (td, J=15.0, 13.1, 4.0 Hz, 1H), 2.99 (dt, J=16.6, 3.3 Hz, 1H), 2.70 (dq, J=11.2, 3.9 Hz, 1H), 2.16 (qd, J=13.0, 4.1 Hz, 1H), 1.24 (d, J=6.3 Hz, 3H), 1.15 (dd, J=16.3, 6.3 Hz, 6H), 0.99 (d, J=6.3 Hz, 3H); $^{13}$C NMR (151 MHz, CDCl$_3$): δ 196.6, 169.1, 167.7, 147.6, 143.5, 140.9, 140.7, 133.4, 132.4, 128.3, 127.3, 126.5, 109.4, 107.8, 100.5, 100.0, 70.7, 70.3, 69.6, 54.3, 29.4, 26.5, 21.37, 21.32, 21.2, 21.1; HRMS (ESI-TOF): calc'd for $C_{26}H_{29}NO_7$ [M+H]$^+$ 468.2017; found 468.2016.

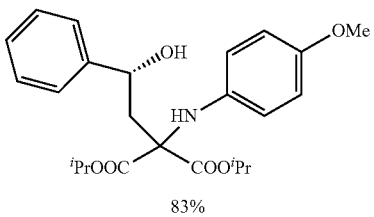

129

83%
ee 94%; er 97:3

Yield: 83%; Physical State: Beige colored viscous oily liquid; $R_f$=0.33 (20% EtOAc/hexanes); $^1$H NMR (600 MHz, CDCl$_3$): δ 7.35-7.31 (m, 4H), 7.28-7.24 (m, 1H), 6.82 (d, J=8.9 Hz, 2H), 6.76 (d, J=9.0 Hz, 2H), 5.16 (s, 1H), 5.11 (hept, J=6.3 Hz, 1H), 4.95 (hept, J=6.3 Hz, 1H), 4.85 (d, J=10.0 Hz, 1H), 3.98 (s, 1H), 3.74 (s, 3H), 2.74-2.62 (m, 2H), 1.29 (d, J=6.3 Hz, 3H), 1.19 (d, J=6.3 Hz, 3H), 1.13 (d, J=6.3 Hz, 3H), 1.02 (d, J=6.3 Hz, 3H); $^{13}$C NMR (126 MHz, CDCl$_3$): δ 169.1, 168.4, 154.1, 144.1, 137.5, 128.3, 127.3, 125.5, 118.8, 114.5, 70.9, 70.2, 69.9, 69.0, 55.5, 41.7, 21.5, 21.36, 21.32, 21.2; HRMS (ESI-TOF): calc'd for $C_{24}H_{31}NO_6$ [M+H]$^+$ 430.2224; found 430.2228; HPLC Analysis: Chiralpak IC, 20% IP/hexanes, continuous flow at 0.5 ml/min, 250 nm; $t_{major}$=13.6 min, $t_{minor}$=15.2 min, ee 94%, er 97:3; $[\alpha]_D^{20}$=+42.3 (C=1, CHCl$_3$).

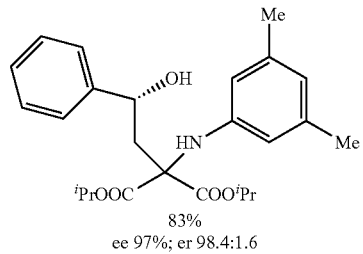

130

83%
ee 97%; er 98.4:1.6

Yield: 83%; Physical State: Beige colored viscous gummy substance; $R_f$=0.47 (20% EtOAc/hexanes); $^1$H NMR (600 MHz, CDCl$_3$): δ 7.36-7.30 (m, 4H), 7.29-7.23 (m, 1H), 6.49 (s, 1H), 6.42 (s, 2H), 5.35 (s, 1H), 5.09 (hept, J=6.3 Hz, 1H), 5.02 (hept, J=6.3 Hz, 1H), 4.84 (t, J=6.3 Hz, 1H), 3.42 (s, 1H), 2.75 (d, J=6.4 Hz, 2H), 2.23 (s, 6H), 1.26 (dd, J=17.6, 6.3 Hz, 6H), 1.11 (d, J=6.3 Hz, 3H), 1.05 (d, J=6.3 Hz, 3H); $^{13}$C NMR (126 MHz, CDCl$_3$): δ 169.0, 168.8, 144.24, 144.22, 138.6, 128.2, 127.2, 125.5, 121.6, 113.8, 70.6, 70.1, 70.0, 68.0, 41.7, 21.5, 21.3, 21.2, 21.1; HRMS (ESI-TOF): calc'd for $C_{25}H_{33}NO_5$ [M+H]$^+$ 428.2431; found 428.2431; HPLC Analysis: Chiralpak IC, 20% IP/hexanes, continuous flow at 0.5 ml/min, 250 nm; $t_{major}$=8.8 min, $t_{minor}$=9.4 min, ee 97%, er 98.4:1.6; $[\alpha]_D^{20}$=+32.7 (C=1, CHCl$_3$).

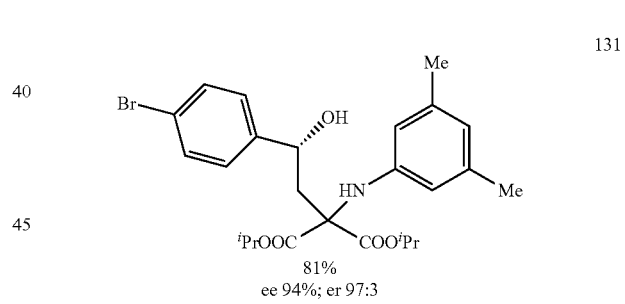

131

81%
ee 94%; er 97:3

Yield: 81%; Physical State: Pale yellow colored foamy solid; $R_f$=0.55 (20% EtOAc/hexanes); $^1$H NMR (600 MHz, CDCl$_3$): δ 7.43 (d, J=8.4 Hz, 2H), 7.16 (d, J=8.3 Hz, 2H), 6.49 (s, 1H), 6.38 (s, 2H), 5.32 (s, 1H), 5.08 (hept, J=6.2 Hz, 1H), 5.00 (hept, J=6.2 Hz, 1H), 4.78 (dd, J=8.3, 3.9 Hz, 1H), 3.60 (s, 1H), 2.74-2.63 (m, 2H), 2.22 (s, 6H), 1.27 (d, J=6.3 Hz, 3H), 1.23 (d, J=6.3 Hz, 3H), 1.11 (d, J=6.3 Hz, 3H), 1.04 (d, J=6.3 Hz, 3H); $^{13}$C NMR (151 MHz, CDCl$_3$): δ 168.9, 168.7, 144.0, 143.2, 138.7, 131.3, 127.2, 121.8, 120.9, 113.8, 70.2, 70.1, 70.0, 68.0, 41.6, 21.5, 21.3, 21.2, 21.1; HRMS (ESI-TOF): calc'd for $C_{25}H_{33}BrNO_5$ [M+H]$^+$ 506.1537; found 506.1536; HPLC Analysis: Chiralpak IC, 20% IP/hexanes, continuous flow at 0.5 ml/min, 250 nm; $t_{major}$=8.1 min, $t_{minor}$=8.7 min, ee 94%, er 97:3; $[\alpha]_D^{20}$=+26.8 (C=1, CHCl$_3$).

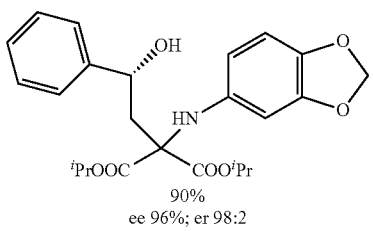

132

90%
ee 96%; er 98:2

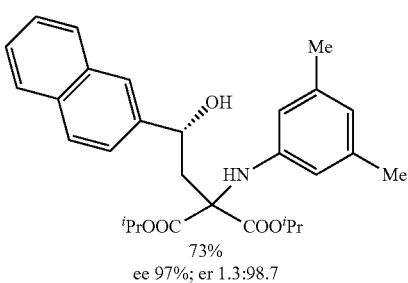

134

73%
ee 97%; er 1.3:98.7

Yield: 90%; Physical State: Pale yellow colored wax; $R_f$=0.35 (20% EtOAc/hexanes); $^1$H NMR (600 MHz, CDCl$_3$): δ 7.26-7.20 (m, 4H), 7.19-7.14 (m, 1H), 6.54 (d, J=8.3 Hz, 1H), 6.36 (d, J=2.2 Hz, 1H), 6.17 (dd, J=8.3, 2.3 Hz, 1H), 5.77 (s, 2H), 5.12 (s, 1H), 5.00 (hept, J=6.2 Hz, 1H), 4.91 (hept, J=6.3 Hz, 1H), 4.74 (dd, J=9.5, 2.8 Hz, 1H), 3.58 (s, 1H), 2.66-2.52 (m, 2H), 1.19 (d, J=6.3 Hz, 3H), 1.14 (d, J=6.3 Hz, 3H), 1.05 (d, J=6.3 Hz, 3H), 0.99 (d, J=6.3 Hz, 3H); $^{13}$C NMR (151 MHz, CDCl$_3$): δ 169.0, 168.5, 148.0, 144.1, 141.6, 139.0, 128.3, 127.3, 125.5, 109.0, 108.2, 100.7, 99.9, 70.7, 70.2, 70.0, 68.7, 41.5, 21.5, 21.34, 21.30; HRMS (ESI-TOF): calc'd for C$_{24}$H$_{29}$NO$_7$ [M+H]$^+$ 444.2017; found 444.2022; HPLC Analysis: Chiralpak IB, 20% IP/hexanes, continuous flow at 0.5 ml/min, 250 nm; $t_{major}$=14.0 min, $t_{minor}$=15.3 min, ee 96%, er 98:2; $[α]_D^{20}$=+36.2 (C=1, CHCl$_3$).

Yield: 73%; Physical State: Pale yellow colored foamy solid; $R_f$=0.51 (20% EtOAc/hexanes); $^1$H NMR (600 MHz, CDCl$_3$): δ 7.87-7.75 (m, 4H), 7.51-7.44 (m, 2H), 7.41 (dd, J=8.5, 1.8 Hz, 1H), 6.52 (s, 1H), 6.45 (s, 2H), 5.41 (s, 1H), 5.11 (hept, J=6.4 Hz, 1H), 5.07-4.99 (m, 2H), 3.55 (s, 1H), 2.91-2.79 (m, 2H), 2.25 (s, 6H), 1.29 (dd, J=14.3, 6.3 Hz, 6H), 1.13 (d, J=6.2 Hz, 3H), 1.07 (d, J=6.2 Hz, 3H); $^{13}$C NMR (151 MHz, CDCl$_3$): δ 169.0, 168.9, 144.2, 141.6, 138.7, 133.2, 132.8, 128.0, 127.9, 127.5, 125.9, 125.6, 124.1, 123.9, 121.7, 113.8, 70.7, 70.2, 70.1, 68.1, 41.7, 21.5, 21.4, 21.3, 21.27, 21.21; HRMS (ESI-TOF): calc'd for C$_{29}$H$_{35}$NO$_5$ [M+H]$^+$ 478.2588; found 478.2589; HPLC Analysis: Chiralpak IB, 2% IP/hexanes, continuous flow at 0.4 ml/min, 230 nm; $t_{major}$=26.7 min, $t_{minor}$=25.4 min, ee 98%, er 1:99; $[α]_D^{20}$=+18.8 (C=1, CHCl$_3$).

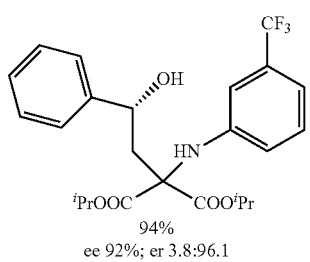

133

94%
ee 92%; er 3.8:96.1

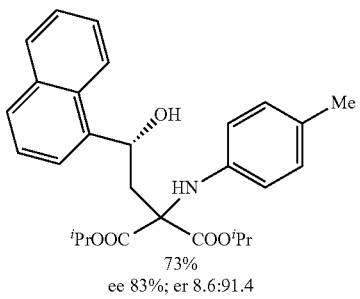

135

73%
ee 83%; er 8.6:91.4

Yield: 94%; Physical State: Colorless viscous gummy substance; $R_f$=0.43 (20% EtOAc/hexanes); $^1$H NMR (600 MHz, CDCl$_3$): δ 7.33 (t, J=13 Hz, 2H), 7.31-7.25 (m, 4H), 7.07 (d, J=7.5 Hz, 1H), 6.99 (s, 1H), 6.88 (d, J=7.8 Hz, 1H), 5.77 (s, 1H), 5.13 (hept, J=6.3 Hz, 1H), 5.06 (hept, J=6.4 Hz, 1H), 4.84 (s, 1H), 2.85-2.72 (m, 3H), 1.33 (d, J=6.2 Hz, 3H), 1.26 (d, J=6.2 Hz, 3H), 1.17 (d, J=6.2 Hz, 3H), 1.07 (d, J=6.2 Hz, 3H); $^{13}$C NMR (151 MHz, CDCl$_3$): δ 168.9, 168.5, 144.8, 144.0, 131.8, 131.6, 131.4, 131.2, 129.6, 128.3, 127.5, 126.7, 125.4, 124.9, 123.1, 121.3, 117.5, 115.37, 115.34, 111.54, 111.52, 70.6, 70.3, 70.2, 67.2, 41.3, 21.3, 21.27, 21.20, 21.1; $^{19}$F NMR (471 MHz, CDCl$_3$): δ −61.9 (S); HRMS (ESI-TOF): calc'd for C$_{24}$H$_{28}$F$_3$NO$_5$ [M+H]$^+$ 468.1992; found 468.1993; HPLC Analysis: Chiralpak IB, 2% IP/hexanes, continuous flow at 0.4 ml/min, 230 nm; $t_{major}$=21.1 min, $t_{minor}$=18.8 min, ee 92%, er 4:96; $[α]_D^{20}$=+6.2 (C=1, CHCl$_3$).

Yield: 73%; Physical State: Beige colored solid (m.p. 95-98° C.); $R_f$=0.48 (20% EtOAc/hexanes); $^1$H NMR (600 MHz, CDCl$_3$): δ 7.84 (d, J=8.2 Hz, 1H), 7.75 (t, J=8.5 Hz, 2H), 7.66 (d, J=8.5 Hz, 1H), 7.48 (t, J=7.7 Hz, 1H), 7.43 (t, J=7.5 Hz, 1H), 7.29-7.22 (m, 1H), 7.03 (d, J=8.1 Hz, 2H), 6.75 (d, J=8.3 Hz, 2H), 5.68 (d, J=10.7 Hz, 1H), 5.47 (s, 1H), 5.14-5.04 (m, 2H), 3.31 (s, 1H), 3.00 (d, J=15.4 Hz, 1H), 2.79 (dd, J=15.4, 10.8 Hz, 1H), 2.31 (s, 3H), 1.29 (dd, J=15.6, 6.3 Hz, 6H), 1.12 (dd, J=21.7, 6.3 Hz, 6H); $^{13}$C NMR (151 MHz, CDCl$_3$): δ 169.3, 141.8, 140.0, 133.5, 129.8, 129.7, 128.8, 128.6, 127.6, 125.5, 125.4, 125.2, 122.9, 122.8, 116.0, 70.2, 70.1, 67.9, 67.2, 40.6, 21.4, 21.36, 21.31, 20.4; HRMS (ESI-TOF): calc'd for C$_{28}$H$_{33}$NO$_5$ [M+H]$^+$ 464.2431; found 464.2434; HPLC Analysis: Chiralpak ID, 91% IP/hexanes, continuous flow at 0.4 ml/min, 250 nm; $t_{major}$=12.8 min, $t_{minor}$=11.7 min, ee 83%, er 8.6:91.4; $[α]_D^{20}$=+28.5 (C=1, CHCl$_3$).

136

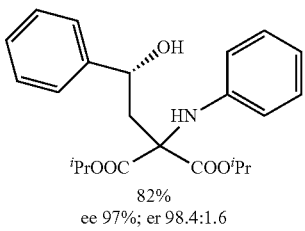

82%
ee 97%; er 98.4:1.6

Yield: 82%; Physical State: Colorless viscous oily liquid; $R_f$=0.42 (20% EtOAc/hexanes); $^1$H NMR (600 MHz, CDCl$_3$): δ 7.34-7.23 (m, 5H), 7.18 (dd, J=8.4, 7.5 Hz, 2H), 6.82 (t, J=7.3 Hz, 1H), 6.77 (d, J=7.7 Hz, 2H), 6.77 (d, J=7.7 Hz, 1H), 5.05 (ddt, J=20.7, 12.6, 6.3 Hz, 2H), 4.84 (dt, J=6.5, 3.2 Hz, 1H), 3.16 (s, 1H), 2.79-2.71 (m, 2H), 1.25 (dd, J=6.3, 1.9 Hz, 6H), 1.06 (dd, J=11.3, 6.3 Hz, 6H); $^{13}$C NMR (126 MHz, CDCl$_3$): δ 169.0, 168.9, 144.3, 144.1, 129.1, 128.3, 127.3, 125.5, 119.6, 115.6, 70.5, 70.2, 67.9, 41.7, 21.5, 21.3, 21.25, 21.22; HRMS (ESI-TOF): calc'd for C$_{23}$H$_{29}$NO$_5$ [M+H]$^+$ 400.2118; found 400.2120; HPLC Analysis: Chiralpak IC, 14% IP/hexanes, continuous flow at 0.4 ml/min, 250 nm; $t_{major}$=14.8 min, $t_{minor}$=16.3 min, ee 97%, er 98.4:1.6; $[α]_D^{20}$=+26.2 (C=1, CHCl$_3$).

137

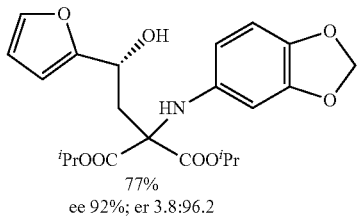

77%
ee 92%; er 3.8:96.2

Yield: 77%; Physical State: Pale yellow colored wax; $R_f$=0.26 (20% EtOAc/hexanes); $^1$H NMR (600 MHz, CDCl$_3$): δ 7.33 (dd, J=1.8, 0.9 Hz, 1H), 6.59 (d, J=8.3 Hz, 1H), 6.38 (d, J=2.3 Hz, 1H), 6.29 (dd, J=3.1, 1.8 Hz, 1H), 6.24-6.16 (m, 2H), 5.83 (s, 2H), 5.14 (s, 1H), 5.00 (ddt, J=15.7, 12.5, 6.3 Hz, 2H), 4.88 (dd, J=10.0, 2.6 Hz, 1H), 3.35 (s, 1H), 2.88-2.74 (m, 2H), 1.21 (d, J=6.4 Hz, 6H), 1.08 (dd, J=16.5, 6.3 Hz, 6H); $^{13}$C NMR (151 MHz, CDCl$_3$): δ 168.8, 168.7, 155.9, 148.0, 141.8, 141.4, 139.0, 110.0, 108.6, 108.2, 105.6, 100.7, 99.6, 70.2, 70.1, 68.1, 64.3, 37.9, 21.36, 21.30, 21.27, 21.25; HRMS (ESI-TOF): calc'd for C$_{22}$H$_{27}$NO$_8$ [M+H]$^+$ 434.1809; found 434.1811; HPLC Analysis: Chiralpak IB, 20% IP/hexanes, continuous flow at 0.8 ml/min, 250 nm; $t_{major}$=14.1 min, $t_{minor}$=10.3 min, ee 92%, er 4:96; $[α]_D^{20}$=+12.0 (C=1, CHCl$_3$).

138

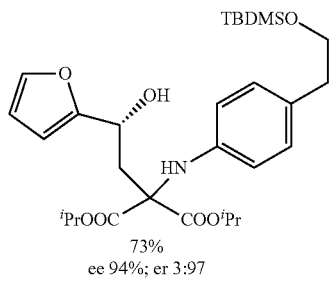

73%
ee 94%; er 3:97

Yield: 73%; Physical State: Colorless viscous oily liquid; $R_f$=0.37 (20% EtOAc/hexanes); $^1$H NMR (600 MHz, CDCl$_3$): δ 7.33 (s, 1H), 6.98 (d, J=8.1 Hz, 2H), 6.66 (d, J=8.1 Hz, 2H), 6.32-6.28 (m, 1H), 6.22 (d, J=2.9 Hz, 1H), 5.28 (s, 1H), 5.01 (pd, J=6.1, 2.1 Hz, 2H), 4.90-4.85 (m, 1H), 3.70 (t, J=7.1 Hz, 2H), 3.03 (s, 1H), 2.94-2.83 (m, 2H), 2.69 (t, J=7.1 Hz, 2H), 1.22 (dd, J=10.3, 6.3 Hz, 6H), 1.05 (dd, J=28.9, 6.2 Hz, 6H), 0.86 (s, 9H), 0.03 (s, 6H); $^{13}$C NMR (126 MHz, CDCl$_3$): δ 169.0, 168.9, 155.9, 142.4, 141.8, 130.2, 129.7, 115.7, 110.0, 105.7, 70.3, 70.1, 67.5, 64.7, 64.3, 38.6, 37.9, 25.8, 21.4, 21.3, 21.26, 21.25, 18.2, 5.4; HRMS (ESI-TOF): calc'd for C$_{29}$H$_{45}$NO$_7$Si [M+H]$^+$ 548.3038; found 548.3040; HPLC Analysis: Chiralpak IC, 20% IP/hexanes, continuous flow at 0.5 ml/min, 250 nm; $t_{major}$=13.7 min, $t_{minor}$=8.4 min, ee 94%, er 3:97; $[α]_D^{20}$=+1.5 (C=1, CHCl$_3$).

139

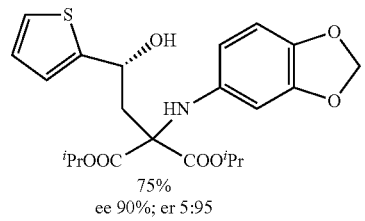

75%
ee 90%; er 5:95

Yield: 75%; Physical State: Dark brown colored foamy gummy substance; $R_f$=0.32 (20% EtOAc/hexanes); $^1$H NMR (600 MHz, CDCl$_3$): δ 7.22 (dd, J=5.0, 1.2 Hz, 1H), 6.95 (dd, J=5.0, 3.5 Hz, 1H), 6.91 (d, J=3.4 Hz, 1H), 6.62 (d, J=8.3 Hz, 1H), 6.43 (d, J=2.3 Hz, 1H), 6.24 (dd, J=8.3, 2.3 Hz, 1H), 5.86 (s, 2H), 5.16 (s, 1H), 5.12-5.04 (m, 2H), 4.99 (hept, J=6.2 Hz, 1H), 3.71 (s, 1H), 2.86-2.75 (m, 2H), 1.25 (d, J=6.3 Hz, 3H), 1.22 (d, J=6.3 Hz, 3H), 1.12 (d, J=6.3 Hz, 3H), 1.08 (d, J=6.3 Hz, 3H); $^{13}$C NMR (126 MHz, CDCl$_3$): δ 168.8, 168.4, 148.1, 148.0, 141.7, 138.8, 126.5, 124.3, 122.9, 109.1, 108.3, 100.8, 99.9, 70.3, 70.2, 68.6, 67.0, 41.7, 21.5, 21.37, 21.33; HRMS (ESI-TOF): calc'd for C$_{22}$H$_{27}$NO$_7$S [M+H]$^+$ 450.1581; found 450.1581; HPLC Analysis: Chiralpak IC, 20% IP/hexanes, continuous flow at 0.8 ml/min, 250 nm; $t_{major}$=12.3 min, $t_{minor}$=10.6 min, ee 90%, er 5:95; $[α]_D^{20}$=+20.3 (C=1, CHCl$_3$).

140

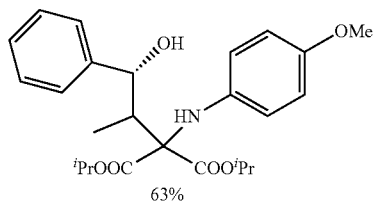

63%

Yield: 63%; Physical State: Dark yellowish brown colored viscous oily liquid; $R_f$=0.39 (20% EtOAc/hexanes); $^1$H NMR (600 MHz, CDCl$_3$): δ 7.33 (dt, J=15.3, 7.6 Hz, 4H), 7.22 (t, J=7.2 Hz, 1H), 6.81-6.74 (m, 4H), 5.51 (s, 1H), 5.10 (hept, J=6.2 Hz, 2H), 4.96 (hept, J=6.0 Hz, 1H), 3.74 (s, 3H), 3.37 (s, 1H), 2.86 (q, J=7.0 Hz, 1H), 1.26 (d, J=6.3 Hz, 3H), 1.21 (d, J=6.3 Hz, 3H), 1.17 (d, J=63 Hz, 3H), 0.94 (dd, J=14.0, 6.7 Hz, 6H); $^{13}$C NMR (151 MHz, CDCl$_3$): δ 169.9, 168.5, 153.9, 143.6, 138.4, 127.9, 126.6, 125.5, 118.7, 114.5, 72.3, 71.9, 70.5, 69.8, 55.6, 43.8, 21.5, 21.45, 21.40, 21.1, 7.5; HRMS (ESI-TOF): calc'd for C$_{25}$H$_{33}$NO$_6$ [M+H]$^+$ 444.2381; found 444.2386; HPLC Analysis: Racemic mixture

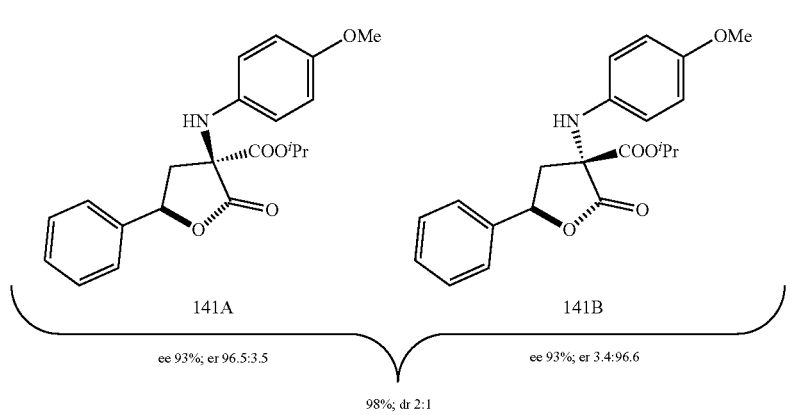

141

Yield: 98%; Diasteromeric ratio: 2:1 (By crude $^1$H NMR);

141A: Physical State: Beige colored waxy solid; $R_f$=0.41 (20% EtOAc/hexanes); $^1$H NMR (600 MHz, CDCl$_3$): δ 7.39 (dt, J=14.0, 7.1 Hz, 5H), 6.76 (d, J=8.9 Hz, 2H), 6.64 (d, J=8.9 Hz, 2H), 5.70 (dd, J=10.3, 6.1 Hz, 1H), 5.04 (hept, J=6.3 Hz, 1H), 4.76 (s, 1H), 3.73 (s, 3H), 3.49 (dd, J=13.0, 6.1 Hz, 1H), 2.56 (dd, J=13.0, 10.4 Hz, 1H), 1.27 (d, J=6.3 Hz, 3H), 1.05 (d, J=62 Hz, 3H); $^{13}$C NMR (151 MHz, CDCl$_3$): δ 172.2, 167.8, 153.8, 137.9, 137.8, 128.9, 128.8, 125.8, 117.3, 114.7, 80.0, 71.1, 68.0, 55.5, 42.7, 21.4, 21.2; HRMS (ESI-TOF): calc'd for C$_{21}$H$_{23}$NO$_5$ [M+H]$^+$ 370.1649; found 370.1646; HPLC Analysis: Chiralpak ID, 90% IP/hexanes, continuous flow at 0.7 ml/min, 250 nm; $t_{major}$=12.6 min, $t_{minor}$=13.8 min, ee 93%, er 96.5:3.5; [α]$_D^{20}$=−6.5 (C=1, CHCl$_3$).

141B: Physical State: Beige colored waxy solid; $R_f$=0.36 (20% EtOAc/hexanes); $^1$H NMR (600 MHz, CDCl$_3$): δ 7.38 (dq, J=13.0, 6.8, 6.2 Hz, 5H), 6.81 (d, J=8.9 Hz, 2H), 6.74 (d, J=8.9 Hz, 2H), 5.56 (t, 1=1.1 Hz, 1H), 5.03 (hept, J=6.2 Hz, 1H), 4.49 (s, 1H), 3.76 (s, 3H), 3.02 (qd, 1=13.8, 7.7 Hz, 2H), 1.13 (dd, J=10.5, 6.3 Hz, 6H); $^{13}$C NMR (151 MHz, CDCl$_3$): δ 172.7, 168.5, 154.6, 138.7, 136.9, 128.6, 128.5, 125.5, 119.6, 114.7, 79.0, 70.9, 67.4, 55.5, 39.6, 21.3, 21.2; HRMS (ESI-TOF): calc'd for C$_{21}$H$_{23}$NO$_5$ [M+H]$^+$ 370.1649; found 370.1648; HPLC Analysis: Chiralpak ID, 90% IP/hexanes, continuous flow at 0.7 ml/min, 250 nm; $t_{major}$=11.0 min, $t_{minor}$=13.9 min, ee 93%, er 3.4:96.6; [α]$_D^{20}$=−3.7 (C=1, CHCl$_3$).

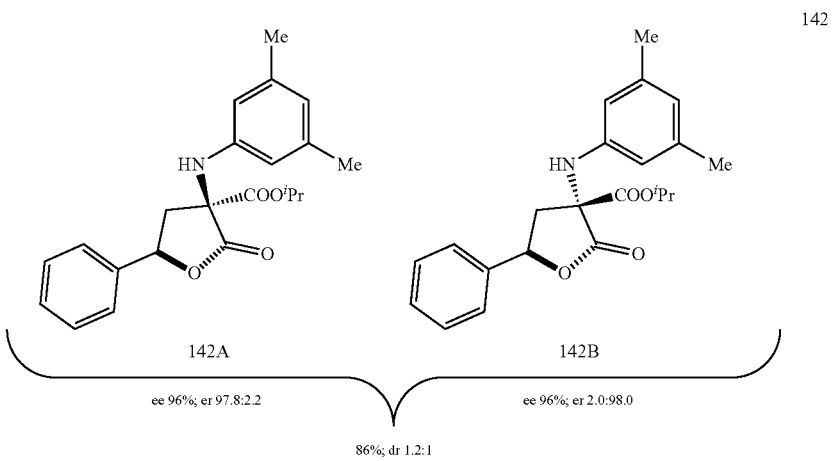

142

Yield: 86%; Diasteromeric ratio: 1.2:1 (By crude $^1$H NMR);

142A: Physical State: Beige colored solid (m.p. 106-108° C.); $R_f$=0.57 (20% EtOAc/hexanes); $^1$H NMR (600 MHz, CDCl$_3$): δ 7.46-7.41 (m, 4H), 7.38 (ddd, J=8.5, 5.1, 2.4 Hz, 1H), 6.48 (s, 1H), 6.28 (s, 2H), 5.78 (dd, J=10.3, 6.3 Hz, 1H), 5.11 (hept, J=62 Hz, 1H), 4.96 (s, 1H), 3.49 (dd, J=13.2, 6.3 Hz, 1H), 2.64 (dd, J=13.2, 10.3 Hz, 1H), 2.23 (s, 6H), 1.31 (d, J=6.3 Hz, 3H), 1.11 (d, J=6.3 Hz, 3H); $^{13}$C NMR (151 MHz, CDCl$_3$): δ 172.0, 167.7, 143.8, 138.7, 138.0, 128.8, 128.7, 125.6, 121.4, 112.8, 79.8, 71.1, 67.1, 42.2, 21.4, 21.2, 21.0; HRMS (ESI-TOF): calc'd for C$_{22}$H$_{25}$NO$_4$ [M+H]$^+$ 368.1856; found 368.1859; HPLC Analysis: Chiralpak ID, 90% IP/hexanes, continuous flow at 0.5 ml/min, 250 nm; $t_{major}$=12.9 min, $t_{minor}$=15.5 min, ee 96%, er 97.8:2.2; [α]$_D^{20}$=−6.7 (C=1, CHCl$_3$).

142B: Physical State: Pale yellow colored waxy solid; $R_f$=0.52 (20% EtOAc/hexanes); $^1$H NMR (600 MHz, CDCl$_3$): δ 7.47-7.41 (m, 4H), 7.39 (ddd, 1=8.5, 5.3, 2.1 Hz, 1H), 6.56 (s, 1H), 6.32 (s, 2H), 5.72 (t, 1=1.6 Hz, 1H), 5.05

(hept, J=6.3 Hz, 1H), 4.74 (s, 1H), 3.17 (dd, J=13.8, 8.1 Hz, 1H), 3.08 (dd, J=13.8, 7.1 Hz, 1H), 2.28 (s, 6H), 1.13 (dd, J=16.4, 6.3 Hz, 6H); $^{13}$C NMR (151 MHz, CDCl$_3$): δ 172.5, 168.3, 143.6, 138.9, 138.8, 128.6, 128.4, 125.4, 122.0, 113.6, 78.9, 70.9, 66.3, 39.5, 21.4, 21.1, 21.0; HRMS (ESI-TOF): calc'd for C$_{22}$H$_{25}$NO$_4$ [M+H]$^+$ 368.1856; found 368.1859; HPLC Analysis: Chiralpak ID, 90% IP/hexanes, continuous flow at 0.5 ml/min, 250 nm; t$_{major}$=14.5 min, t$_{minor}$=12.8 min, ee 96%, er 2:98; [α]$_D^{20}$=−3.3 (C=1, CHCl$_3$).

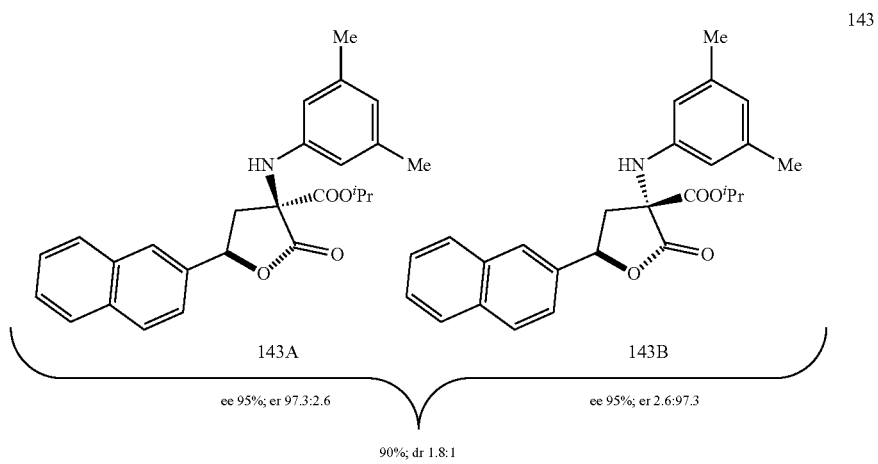

Yield: 90%; Diasteromeric ratio: 1.8:1 (By crude $^1$H NMR);

143A: Physical State: White foamy solid; R$_f$=0.42 (15% EtOAc/hexanes); $^1$H NMR (600 MHz, CDCl$_3$): δ 7.93-7.89 (m, 2H), 7.87 (d, J=6.3 Hz, 2H), 7.55-7.51 (m, 2H), 7.50 (d, J=1.1 Hz, 1H), 7.50 (d, J=7.7 Hz, 1H), 6.30 (s, 2H), 5.94 (dd, J=10.1, 6.4 Hz, 1H), 5.13 (hept, J=6.1 Hz, 1H), 4.99 (s, 1H), 3.55 (dd, J=13.2, 6.3 Hz, 1H), 2.73 (dd, J=13.1, 10.5 Hz, 1H), 2.22 (s, 6H), 1.34 (d, J=6.2 Hz, 3H), 1.13 (d, J=6.2 Hz, 3H); $^{13}$C NMR (151 MHz, CDCl$_3$): δ 172.1, 167.8, 143.9, 138.8, 135.3, 133.3, 133.0, 128.9, 128.0, 127.7, 126.63, 126.60, 125.0, 122.9, 121.5, 112.9, 80.0, 71.2, 67.2, 42.2, 21.5, 21.3, 21.1; HRMS (ESI-TOF): calc'd for C$_{26}$H$_{27}$NO$_4$ [M+H]$^+$ 418.2013; found 418.2007; HPLC Analysis: Chiralpak IB, 10% IP/hexanes, continuous flow at 0.4 ml/min, 230 nm; t$_{major}$=19.3 min, t$_{minor}$=22.9 min, ee 95%, er 97.3:2.6; [α]$_D^{20}$=−14.2 (C=1, CHCl$_3$).

143B: Physical State: Brown colored viscous gummy liquid; R$_f$=0.37 (15% EtOAc/hexanes); $^1$H NMR (600 MHz, CDCl$_3$): δ 7.92 (d, J=8.5 Hz, 1H), 7.87 (t, J=10.0 Hz, 3H), 7.57-7.46 (m, 3H), 6.56 (s, 1H), 6.33 (s, 2H), 5.86 (t, J=1.5 Hz, 1H), 5.02 (hept, J=6.4 Hz, 1H), 4.77 (s, 1H), 3.22 (dd, J=13.7, 8.2 Hz, 1H), 3.15 (dd, J=13.8, 7.1 Hz, 1H), 2.28 (s, 6H), 1.07 (d, J=6.2 Hz, 6H); $^{13}$C NMR (151 MHz, CDCl$_3$):δ 172.6, 168.3, 143.6, 138.9, 136.1, 133.1, 132.9, 128.7, 127.9, 127.6, 126.5, 126.4, 124.6, 122.8, 122.0, 113.7, 79.1, 70.9, 66.3, 39.4, 21.4, 21.1, 21.0; HRMS (ESI-TOF): calc'd for C$_{26}$H$_{27}$NO$_4$ [M+H]$^+$ 418.2013; found 418.2017; HPLC Analysis: Chiralpak IC, 20% IP/hexanes, continuous flow at 0.5 ml/min, 250 nm; t$_{major}$=21.3 min, t$_{minor}$=17.7 min, ee 95%, er 2.6:97.3; [α]D$^{20}$=−8.2 (C=1, CHCl$_3$).

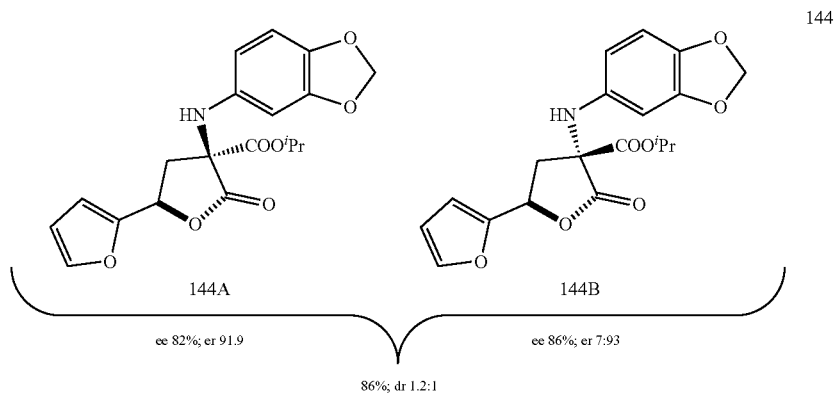

144

{ 144A ee 82%; er 91.9 } { 144B ee 86%; er 7:93 }

86%; dr 1.2:1

Yield: 86%; Diasteromeric ratio: 1.2:1 (By crude $^1$H NMR):

144A: Physical State: Brown colored viscous oily liquid; $R_f$=0.35 (20% EtOAc/hexanes); $^1$H NMR (600 MHz, CDCl$_3$): δ 7.48 (d, J=1.9 Hz, 1H), 6.65 (d, J=8.3 Hz, 1H), 6.53 (d, J=3.3 Hz, 1H), 6.41 (dd, J=3.4, 1.8 Hz, 1H), 6.31 (d, J=2.5 Hz, 1H), 6.08 (dd, J=8.2, 2.4 Hz, 1H), 5.87 (s, 2H), 5.70 (dd, J=10.5, 6.3 Hz, 1H), 5.06 (hept, J=6.4 Hz, 1H), 4.81 (s, 1H), 3.27 (dd, J=13.1, 6.3 Hz, 1H), 2.96 (dd, J=13.1, 10.5 Hz, 1H), 1.27 (d, J=6.3 Hz, 3H), 1.10 (d, J=6.2 Hz, 3H); $^{13}$C NMR (151 MHz, CDCl$_3$): δ 171.3, 167.7, 149.0, 148.4, 144.1, 141.4, 139.1, 111.1, 110.7, 108.4, 107.2, 100.8, 98.5, 73.0, 71.3, 67.4, 37.8, 21.5, 21.3; HRMS (ESI-TOF): calc'd for C$_{19}$H$_{19}$NO$_7$ [M+H]$^+$ 374.1234; found 450.1234; HPLC Analysis: Chiralpak IC, 20% IP/hexanes, continuous flow at 0.5 ml/min, 250 nm; t$_{major}$=24.7 min, t$_{minor}$=26.8 min, ee 82%, er 91:9; [α]$_D^{20}$=−7.3 (C=1, CHCl$_3$).

144B: Physical State: Dark brown colored viscous oily liquid; $R_f$=0.29 (20% EtOAc/hexanes); $^1$H NMR (600 MHz, CDCl$_3$): δ 7.47 (d, J=1.9 Hz, 1H), 6.67 (d, J=8.3 Hz, 1H), 6.52 (d, J=3.3 Hz, 1H), 6.43-6.35 (m, 2H), 6.18 (dd, J=8.3, 2.3 Hz, 1H), 5.90 (s, 2H), 5.57 (t, J=7.7 Hz, 1H), 5.07 (hept, J=6.3 Hz, 1H), 4.48 (s, 1H), 3.35 (dd, J=13.9, 7.7 Hz, 1H), 2.88 (dd, J=13.9, 7.8 Hz, 1H), 1.25 (d, J=6.3 Hz, 3H), 1.16 (d, J=6.2 Hz, 3H); $^{13}$C NMR (151 MHz, CDCl$_3$): δ 172.0, 168.2, 149.7, 148.3, 143.7, 142.5, 138.3, 110.7, 110.2, 110.1, 108.4, 101.0, 100.8, 72.6, 71.1, 67.2, 35.4, 21.5, 21.3; HRMS (ESI-TOF): calc'd for C$_{19}$H$_{19}$NO$_7$ [M+H]$^+$ 374.1234; found 450.1244; HPLC Analysis: Chiralpak IC, 35% IP/hexanes, continuous flow at 0.5 ml/min, 250 nm; t$_{major}$=24.5 min, t$_{minor}$=21.7 min, ee 86%, er 7:93; [α]$_D^{20}$=−5.2 (C=1, CHCl$_3$).

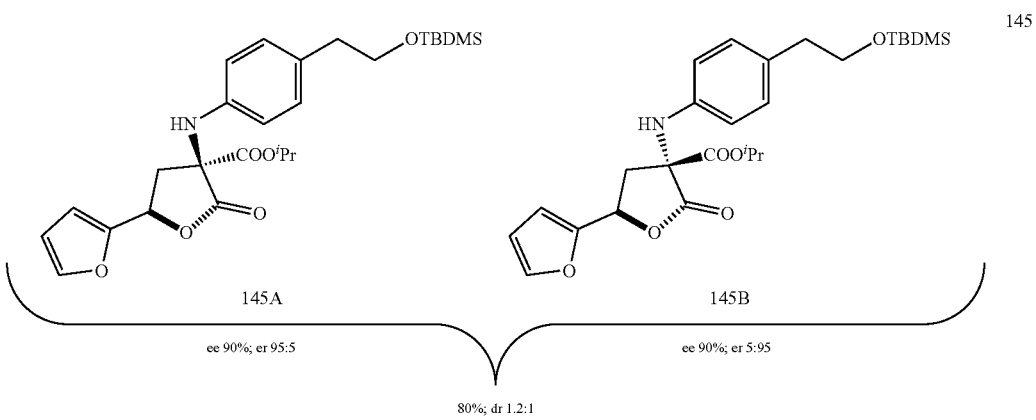

145

{ 145A ee 90%; er 95:5 } { 145B ee 90%; er 5:95 }

80%; dr 1.2:1

Yield: 80%; Diasteromeric ratio: 1.2:1 (By crude $^1$H NMR);

145A: Physical State: Pale yellow colored viscous oily liquid; $R_f$=0.58 (20% EtOAc/hexanes); $^1$H NMR (600 MHz, CDCl$_3$): δ 7.48 (s, 1H), 7.04 (d, J=8.1 Hz, 2H), 6.58 (d, J=8.2 Hz, 2H), 6.54 (d, J=2.9 Hz, 1H), 6.41 (s, 1H), 5.73 (dd, J=10.4, 6.4 Hz, 1H), 5.05 (hept, J=7.3, 6.6 Hz, 1H), 4.96 (s, 1H), 3.74 (t, J=7.1 Hz, 2H), 3.28 (dd, J=13.2, 6.3 Hz, 1H), 3.03-2.95 (m, 1H), 2.72 (t, J=7.0 Hz, 2H), 1.27 (d, J=6.2 Hz, 3H), 1.07 (d, J=6.2 Hz, 3H), 0.88 (s, 9H), −0.00 (s, 6H); $^{13}$C NMR (151 MHz, CDCl$_3$): δ 171.3, 167.8, 149.1, 144.1, 142.1, 130.2, 129.9, 114.8, 111.0, 110.7, 72.9, 71.3, 66.9, 64.7, 38.6, 37.6, 25.9, 21.4, 21.2, 18.3, −5.3, −5.4; HRMS (ESI-TOF): calc'd for C$_{26}$H$_{37}$NO$_6$Si [M+H]$^+$ 488.2463; found 488.2464; HPLC Analysis: Chiralpak IB, 2% IP/hexanes, continuous flow at 0.4 ml/min, 230 nm; t$_{major}$=19.4 min, t$_{minor}$=20.9 min, ee 90%, er 95:5; [α]$_D^{20}$=−5 (C=1, CHCl$_3$).

145B: Physical State: Pale yellow colored viscous oily liquid; $R_f$=0.52 (20% EtOAc/hexanes); $^1$H NMR (600 MHz, CDCl$_3$): δ 7.47 (s, 1H), 7.05 (d, J=8.1 Hz, 2H), 6.61 (d, J=8.2 Hz, 2H), 6.53 (d, J=2.7 Hz, 1H), 6.41 (s, 1H), 5.63 (t, J=7.6 Hz, 1H), 5.05 (hept, J=6.3 Hz, 1H), 4.65 (s, 1H), 3.74 (t, J=7.0 Hz, 2H), 3.39 (dd, J=13.8, 7.4 Hz, 1H), 2.93 (dd, J=13.8, 8.0 Hz, 1H), 2.73 (t, J=6.9 Hz, 2H), 1.23 (d, J=6.2

Hz, 3H), 1.11 (d, J=6.2 Hz, 3H), 0.87 (s, 9H), −0.01 (s, 6H); $^{13}$C NMR (151 MHz, CDCl$_3$): δ 172.0, 168.2, 149.8, 143.6, 141.8, 131.3, 129.9, 116.3, 110.6, 110.0, 72.6, 71.0, 66.4, 64.6, 38.6, 35.3, 25.9, 21.4, 21.2, 18.3, −5.41; HRMS (ESI-TOF): calc'd for C$_{26}$H$_{37}$NO$_6$Si[M+H]$^+$ 488.2463; found 488.2465; HPLC Analysis: Chiralpak ID, 15% IP/hexanes, continuous flow at 0.5 ml/min, 250 nm; $t_{major}$=18.5 min, $t_{minor}$=17.2 min, ee 90%, er 5:95; $[α]_D^{20}$=−4.3 (C=1, CHCl$_3$).

1H), 3.05 (dd, J=13.9, 7.6 Hz, 1H), 1.21 (d, J=6.3 Hz, 3H), 1.15 (d, J=6.2 Hz, 3H); $^{13}$C NMR (151 MHz, CDCl$_3$): δ 171.8, 168.2, 148.3, 142.4, 140.8, 138.2, 126.9, 126.6, 126.4, 110.0, 108.3, 100.9, 100.7, 75.3, 71.1, 67.4, 39.3, 21.3, 21.1; HRMS (ESI-TOF): calc'd for C$_{19}$H$_{19}$NO$_6$S [M+H]$^+$ 390.1006; found 390.1008; HPLC Analysis: Chiralpak IB, 40% IP/hexanes, continuous flow at 0.5 ml/min, 250 nm; $t_{major}$=16.2 min, $t_{minor}$=19.1 min, ee 90%, er 95:5; $[α]_D^{20}$=−4.7 (C=1, CHCl$_3$).

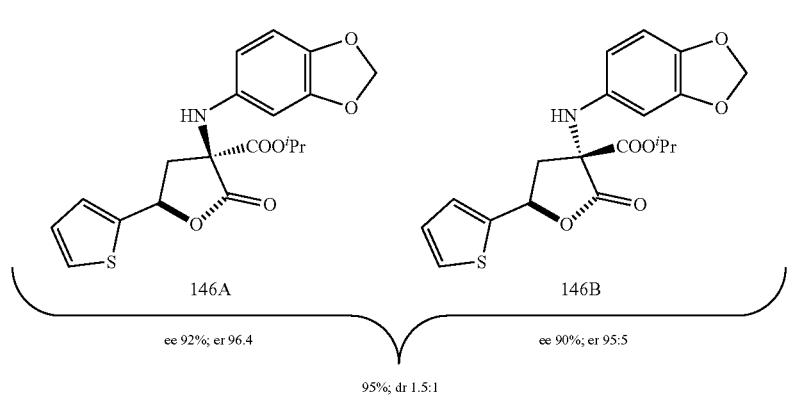

146

Yield: 95%; Diasteromeric ratio: 1.5:1 (By crude $^1$H NMR);

146A: Physical State: Yellow colored viscous oily liquid; R$_f$=0.33 (20% EtOAc/hexanes); $^1$H NMR (600 MHz, CDCl$_3$): δ 7.38 (d, J=4.5 Hz, 1H), 7.17 (d, J=3.2 Hz, 1H), 7.04-7.00 (m, 1H), 6.64 (d, J=8.3 Hz, 1H), 6.30 (d, J=2.2 Hz, 1H), 6.07 (dd, J=8.3, 2.2 Hz, 1H), 5.93 (dd, J=10.3, 6.1 Hz, 1H), 5.86 (s, 2H), 5.05 (hept, J=6.2 Hz, 1H), 4.81 (s, 1H), 3.45 (dd, J=13.1, 6.1 Hz, 1H), 2.74 (dd, J=13.1, 10.5 Hz, 1H), 1.26 (d, J=6.3 Hz, 3H), 1.09 (d, J=6.2 Hz, 3H); $^{13}$C NMR (151 MHz, CDCl$_3$): δ 171.2, 167.5, 148.3, 141.4, 139.9, 139.0, 127.2, 127.1, 127.0, 108.3, 107.3, 100.8, 98.7, 75.8, 71.2, 67.8, 42.1, 21.4, 21.2; HRMS (ESI-TOF): calc'd for C$_{19}$H$_{19}$NO$_6$S [M+H]$^+$ 390.1006; found 390.1011; HPLC Analysis: Chiralpak IC, 25% IP/hexanes, continuous flow at 0.5 ml/min, 250 nm; $t_{major}$=21.1 min, $t_{minor}$=24.9 min, ee 92%, er 96:4; $[α]_D^{20}$=−8.7 (C=1, CHCl$_3$).

146B: Physical State: Beige colored waxy solid; R$_f$=0.25 (20% EtOAc/hexanes); $^1$H NMR (600 MHz, CDCl$_3$): δ 7.37 (d, J=4.9 Hz, 1H), 7.14 (d, J=3.2 Hz, 1H), 7.03-7.00 (m, 1H), 6.67 (d, J=8.3 Hz, 1H), 6.38 (d, J=2.0 Hz, 1H), 6.17 (dd, J=8.2, 2.0 Hz, 1H), 5.89 (s, 2H), 5.80 (t, J=IF Hz, 1H), 5.06 (hept, J=6.2 Hz, 1H), 4.51 (s, 1H), 3.16 (dd, J=13.9, 7.6 Hz,

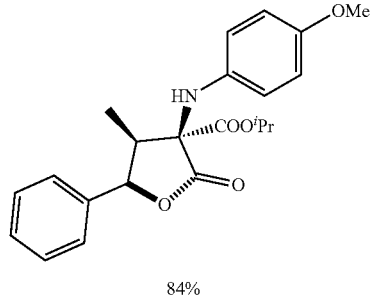

147

Yield: 84%; Physical State: Beige colored viscous gummy substance; R$_f$=0.51 (20% EtOAc/hexanes); $^1$H NMR (600 MHz, CDCl$_3$): δ 7.40 (t, J=7.6 Hz, 2H), 7.33 (t, J=7.3 Hz, 2H), 6.75 (d, J=8.9 Hz, 2H), 6.58 (d, J=8.9 Hz, 2H), 6.01 (d, J=5.1 Hz, 1H), 4.94 (hept, J=6.3 Hz, 1H), 4.71 (s, 1H), 3.82-3.75 (m, 1H), 3.73 (s, 3H), 1.19 (d, J=6.3 Hz, 3H), 0.82 (d, J=6.2 Hz, 3H), 0.82 (d, J=6.2 Hz, 3H); $^{13}$C NMR (151 MHz, CDCl$_3$): δ 172.1, 167.1, 153.3, 138.6, 135.5, 128.5, 128.0, 125.2, 115.1, 114.7, 82.5, 71.5, 70.7, 55.5, 43.8, 21.4, 21.0, 9.9; HRMS (ESI-TOF): calc'd for C$_{22}$H$_{25}$NO$_5$ [M+H]$^+$ 384.1805; found 384.1808; HPLC Analysis: Racemic mixture.

148

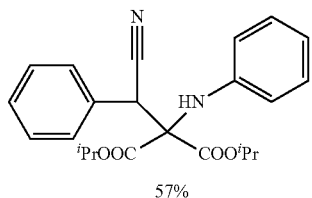

57%

Yield: 57%; Physical State: Yellowish viscous oily liquid; $R_f$=0.24 (20% EtOAc/hexanes); $^1$H (600 MHz, CDCl$_3$): 7.26 (td, J=6.1, 5.0, 3.1 Hz, 1H), 7.21 (t, J=7.4 Hz, 2H), 7.19-7.16 (m, 2H), 7.12-7.08 (m, 2H), 6.74 (t, J=7.4 Hz, 1H), 6.57 (d, J=7.8 Hz, 2H), 5.10 (hept, J=6.2 Hz, 1H), 5.01 (p, J=6.3 Hz, 1H), 4.93 (s, 1H), 4.87 (s, 1H), 1.39 (d, J=6.3 Hz, 3H), 1.18 (d, J=6.3 Hz, 3H), 1.15 (d, J=6.2 Hz, 3H), 0.95 (d, J=6.3 Hz, 3H); $^{13}$C (151 MHz, CDCl$_3$): 166.8, 166.1, 143.4, 130.8, 129.6, 129.4, 129.0, 128.5, 119.5, 118.9, 114.9, 72.4, 71.4, 70.5, 40.0, 21.7, 21.4, 21.3, 21.2; HRMS (ESI-TOF): calc'd for C$_{23}$H$_{26}$N$_2$O$_4$ [M+H]$^+$ 395.1926; found 395.1990.

149

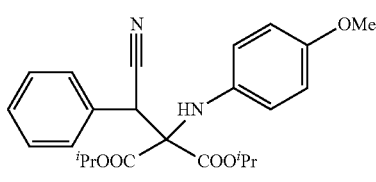

66%

Yield: 66%; Physical State: Bright yellowish viscous oily liquid; $R_f$=0.35 (20% EtOAc/hexanes); $^1$H (600 MHz, CDCl$_3$): 7.33-7.22 (m, 5H), 6.72 (d, J=8.8 Hz, 2H), 6.59 (d, J=8.8 Hz, 2H), 5.10 (hept, J=6.2 Hz, 1H), 5.01 (hept, J=6.7 Hz, 1H), 4.84 (s, 1H), 4.74 (s, 1H), 3.72 (s, 3H), 1.40 (d, J=6.3 Hz, 3H), 1.21 (d, J=6.3 Hz, 3H), 1.16 (d, J=6.2 Hz, 3H), 1.0 (d, J=6.2 Hz, 3H); $^{13}$C (151 MHz, CDCl$_3$): 166.9, 166.2, 153.6, 137.2, 130.8, 129.7, 129.0, 128.5, 119.1, 117.0, 114.8, 72.1, 71.3, 71.2, 55.6, 40.5, 21.6, 21.5, 21.3, 21.2; HRMS (ESI-TOF): calc'd for C$_{24}$H$_{28}$N$_2$O$_5$ [M+H]$^+$ 425.2100; found 425.2065.

150

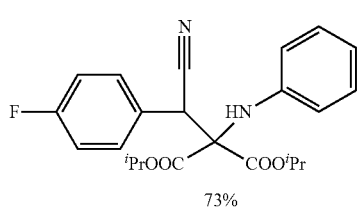

73%

Yield: 73%; Physical State: Yellowish viscous oily liquid; $R_f$=0.24 (20% EtOAc/hexanes); $^1$H (600 MHz, CDCl$_3$): 7.22 (dd, J=8.6, 5.2 Hz, 2H), 7.15 (t, J=7.9 Hz, 2H), 6.96 (t, J=8.6 Hz, 2H), 6.80 (t, J=7.3 Hz, 1H), 6.59 (d, J=1.9 Hz, 2H), 5.15 (hept, J=6.3 Hz, 1H), 5.05 (hept, J=6.3 Hz, 1H), 4.99 (s, 1H), 4.92 (s, 1H), 1.44 (d, J=6.3 Hz, 3H), 1.23 (d, J=6.3 Hz, 3H), 1.21 (d, J=6.3 Hz, 3H), 0.99 (d, J=6.3 Hz, 3H); $^{13}$C (151 MHz, CDCl$_3$): 166.7, 166.0, 163.9, 162.2, 143.3, 131.5, 131.4, 129.4, 126.6, 126.5, 119.7, 118.7, 115.6, 115.5, 114.9, 114.8, 72.6, 72.5, 71.5, 71.4, 70.5, 39.4, 21.7, 21.6, 21.5, 21.4, 21.3, 21.2, 21.1; $^{19}$F NMR (471 MHz, CDCl$_3$): δ −111.3 (tt, J=8.4, 5.1 Hz); HRMS (ESI-TOF): calc'd for C$_{23}$H$_{25}$FN$_2$O$_4$ [M+H]$^+$ 413.1832; found 413.1866.

151

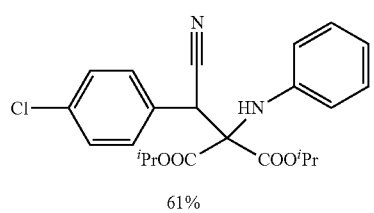

61%

Yield: 61%; Physical State: Yellowish oily liquid; $R_f$=0.24 (20% EtOAc in Hexane); $^1$H (600 MHz, CDCl$_3$): 7.27 (d, J=8.5 Hz, 2H), 7.18 (dd, J=17.6, 8.2 Hz, 4H), 6.83 (t, J=7.3 Hz, 1H), 6.62 (d, J=7.9 Hz, 2H), 5.17 (hept, J=6.3 Hz, 1H), 5.08 (hept, J=6.2 Hz, 1H), 5.01 (s, 1H), 4.93 (s, 1H), 1.46 (d, J=63 Hz, 3H), 1.25 (d, J=6.3 Hz, 3H), 1.23 (d, J=6.2 Hz, 3H), 1.01 (d, J=6.3 Hz, 3H); $^{13}$C (151 MHz, CDCl$_3$): 166.6, 165.9, 143.2, 135.2, 131.0, 129.5, 129.3, 128.7, 119.7, 118.5, 114.9, 72.6, 71.5, 70.4, 39.5, 21.7, 21.4, 21.3, 21.2; HRMS (ESI-TOF): calc'd for C$_{23}$H$_{25}$ClN$_2$O$_4$ [M+H]$^+$ 429.1576; found 429.1582.

152

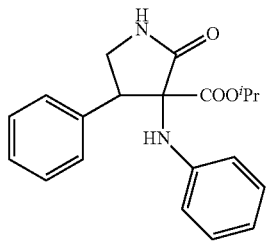

60%

Yield: 60%; Physical State: White colored solid (m.p. 198-203° C.); $R_f$=0.33 (40% EtOAc/hexanes); $^1$H (600 MHz, CDCl$_3$): 7.22-7.14 (m, 5H), 7.03 (t, J=7.9 Hz, 2H), 6.66 (t, J=7.3 Hz, 1H), 6.50 (d, J=7.8 Hz, 2H), 6.47 (s, 1H), 4.94 (hept, J=6.2 Hz, 1H), 4.68 (s, 1H), 4.52 (d, J=5.9 Hz, 1H), 4.10 (dd, J=9.7, 6.6 Hz, 1H), 3.50 (d, J=9.7 Hz, 1H), 1.16 (d, J=6.3 Hz, 3H), 0.82 (d, J=6.3 Hz, 3H); $^{13}$C (151 MHz, CDCl$_3$): 172.0, 169.4, 145.3, 139.2, 128.6, 128.3, 128.0, 127.4, 118.5, 114.3, 70.3, 69.8, 49.1, 47.7, 21.5, 21.0; HRMS (ESI-TOF): calc'd for C$_{20}$H$_{22}$N$_2$O$_3$ [M+H]$^+$ 339.1703; found 339.1703.

153

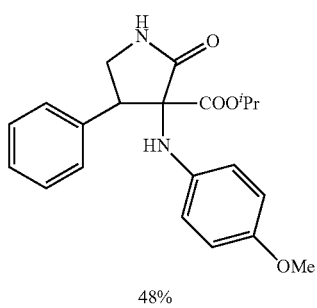

48%

Yield: 48%; Physical State: White colored solid (m.p. 185-187° C.); $R_f$=0.35 (40% EtOAc/hexanes); $^1$H (600 MHz, CDCl$_3$): 7.23-7.15 (m, 5H), 6.76 (s, 1H), 6.63 (d, J=8.7 Hz, 2H), 6.48 (d, J=8.7 Hz, 2H), 4.95 (hept, J=6.1 Hz, 1H), 4.47 (d, J=5.5 Hz, 1H), 4.43 (s, 1H), 4.04 (dd, J=9.6, 6.8 Hz, 1H), 3.68 (s, 3H), 3.50 (d, J=9.7 Hz, 1H), 1.17 (d, J=6.2 Hz, 3H), 0.88 (d, J=6.2 Hz, 3H); $^{13}$C (151 MHz, CDCl$_3$): 172.4, 169.6, 152.9, 139.2, 139.0, 128.3, 128.1, 127.4, 116.0, 114.3, 70.2, 70.1, 55.7, 49.3, 47.5, 21.6, 21.2; HRMS (ESI-TOF): calc'd for $C_{21}H_{24}N_2O_4$ [M+H]$^+$ 369.1809; found 369.1809.

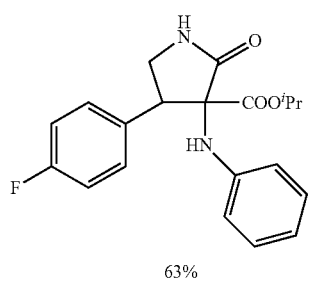

154

63%

Yield: 63%; Physical State: White colored solid (m.p. 191-193° C.); $R_f$=0.35 (40% EtOAc in Hexane); $^1$H (600 MHz, CDCl$_3$): 7.16 (dd, J=8.6, 5.3 Hz, 2H), 7.04 (t, J=7.9 Hz, 2H), 6.86 (s, 1H), 6.84 (t, J=8.7 Hz, 2H), 6.67 (t, J=7.3 Hz, 1H), 6.47 (d, J=7.8 Hz, 2H), 4.94 (hept, J=6.2 Hz, 1H), 4.70 (s, 1H), 4.53 (d, J=6.4 Hz, 1H), 4.11 (dd, J=9.8, 6.7 Hz, 1H), 3.45 (d, J=9.8 Hz, 1H), 1.16 (d, J=6.3 Hz, 3H), 0.82 (d, J=6.3 Hz, 3H); $^{13}$C (151 MHz, CDCl$_3$): 172.1, 169.3, 162.7, 161.1, 145.1, 135.1, 129.5, 129.4, 128.7, 118.7, 115.2, 115.0, 114.2, 70.4, 69.8, 48.3, 47.9, 21.5, 21.0; $^{19}$F NMR (471 MHz, CDCl$_3$): δ −114.0 (tt, J=8.6, 5.3 Hz); HRMS (ESI-TOF): calc'd for $C_{20}H_{21}FN_2O_3$ [M+H]$^+$ 357.1609; found 357.1695.

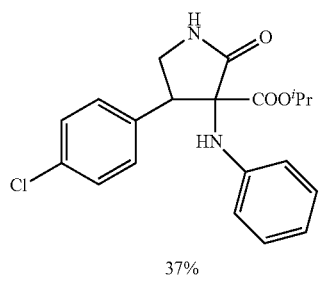

155

37%

Yield: 37%; Physical State: White colored solid (m.p. 184-186° C.); $R_f$=0.35 (40% EtOAc in Hexane); $^1$H (600 MHz, CDCl$_3$): 7.13 (m, 4H), 7.04 (t, J=7.8 Hz, 2H), 6.68 (t, J=7.3 Hz, 1H), 6.55 (s, 1H), 6.47 (d, J=7.8 Hz, 2H), 4.93 (hept, J=6.1 Hz, 1H), 4.71 (s, 1H), 4.53 (d, J=6.3 Hz, 1H), 4.11 (dd, J=9.7, 6.7 Hz, 1H), 3.43 (d, J=9.7 Hz, 1H), 1.16 (d, J=6.2 Hz, 3H), 0.80 (d, J=6.2 Hz, 3H); $^{13}$C (151 MHz, CDCl$_3$): δ 171.9, 169.2, 145.0, 137.9, 133.1, 129.3, 128.8, 128.4, 118.7, 114.2, 70.4, 69.7, 48.4, 47.8, 21.5, 20.9. HRMS (ESI-TOF): calc'd for $C_{20}H_{21}ClN_2O_3$ [M+H]$^+$ 373.1313; found 373.1309.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VIII. REFERENCES

The following references, to the extent that they provide exemplary procedural or other details supplementary to those set forth herein, are specifically incorporated herein by reference:

Aksenov et al, *RSC Adv.* 5:84849, 2015.
Altman et al., *J. Org. Chem.* 73:5167-5169, 2008.
Buchwald et al., *Adv. Synth. Catal.* 348:23, 2006.
Byun et al., *J. Org. Chem.* 72:9815-9817, 2007.
Cai et al., *Tetrahedron,* 70:4754-4759, 2014.
Cheung & Hu, *Nat. Commun.* 7:12494, 2016.
Corcoran et al. *Science* 353:279, 2016.
Driver & Hartwig, *J. Am. Chem. Soc.* 118:7217-7218, 1996.
Fors & Buchwald, *J. Am. Chem. Soc.* 132:15914-15917, 2010.
Frisch et al., *Gaussian* 09, Revision B.01, Gaussian, Inc., Wallingford Conn., 2009.
Fu et al., *Angew. Chem. bit. Ed.* 54:9042-9046, 2015.
Gao et al., *Angew: Chem., bit. Ed.* 53:2701, 2014.
Gao et al., *Nat Chem. advance online publication,* 2016.
Garrett, *Adv. Synth. Catal.* 346:889, 2004.
Gui et al. *Science* 348:886, 2015.
Hajra et al., *Org. Lett.* 14:5488-5491, 2012.
Hili & Yudin, *Nat. Chem. Biol.* 2,284, 2006.
Huang & Yang, *Org. Lett.* 13:3750-3753, 2011.
Kattamuri et al., *Org. Biomol. Chem.* 11:3400-3408, 2013.
Kawahara et al., *Adv. Synth. Catal.* 353:1161-1168, 2011.
Kim et al., *Tetrahedron,* 68:287-293, 2012.
Kitamura et al., *Org. Lett.* 6:4619, 2004.
Krasovskiy & Knochel, *Angew. Chem. Int. Ed.* 43:3333-3336, 2004.
Kürti, *Science* 348:863, 2015.
Li et al., *J. Org. Chem.* 66:8677-8681, 2001.
Liegault et al., *J. Org. Chem.* 73:5022-5028, 2008.
Love & Jones, *J. Org. Chem.* 64:3755-3756, 1999.
Marenich et al., *J. Phys. Chem. B* 113:6378-6396, 2009.
Marshall et al., *J. Org. Chem.* 58:3675-3680, 1993.
Mattson et al., *J. Org. Chem.* 55:2552-2554, 1990.
May & Lash, *J. Org. Chem.* 57:4820-4828, 1992.
Monnier & Taillefer, *Top. Organomet. Chem.* 46:173, 2013.
Narasaka & Kitamura, *Eur. J. Org. Chem.,* 4505, 2005.
Niwa et al., *Tetrahedron Lett* 42:5473-5476, 2001.
Nohira, et al., *Bull. Chem. Soc. Jpn.* 36:870-872, 1963.
Pace et al., *Org. Lett.* 18:2750-2753, 2016.
Paudyal et al., *Science* 353:1144, 2016.
Peng, et al., *Org. Lett.* 13:5244-5247, 2011.
Qiao & Lam, *Boronic Acids (2nd Ed.),* D. G. Hall, Ed., vol. 1, pp. 315-361, 2011a.
Qiao & Lam, *Synthesis,* 829, 2011b.
Qiu & Norwood, *J. Liq. Chromatogr. Relat. Technol.* 30:877, 2007.

Rappoport, *The Chemistry of Anilines*, Parts 1-2., John Wiley & Sons, Chichester, 2007.
Rataboul et al., *Chem. Eur. J.* 10:2983-2990,2004.
Ricci, *Amino Group Chemistry: From Synthesis to the Life Sciences.*, Wiley-VCH, pp. 394, 2008.
Rios & Cordova, *Comprehensive Chirality*, E. M. Carreira, H. Yamamoto, Eds. (Elsevier B. V.), vol. 6, pp. 399-413, 2012.
Romero et al., *Science* 349:1326, 2015.
Sapountzis & Knochel, *J. Am. Chem. Soc.* 124:9390, 2002.
Shankaraiah et al., *J. Org. Chem.* 76:7017-7026, 2011.
Shaw & Nolan, *J. Org. Chem.* 22:1668-1670, 1957.
Shin et al, *Acc. Chem. Res.* 48:1040, 2015.
Sivan & Deepthi, *Tetrahedron Lett* 55:1890, 2014.
Surry & Buchwald, *Chem. Sci.* 2:27, 2011.
Sweeney, *Eur. J. Org. Chem.*, 4911, 2009.
Thome & Bolm, *Org. Lett.* 14:1892, 2012.
Tzschucke et al., *Org. Lett.* 9, 761-764, 2007.
Vantourout et al., *J. Org. Chem.* 81:3942-3950, 2016.
Wang et al., *Adv. Synth. Catal.* 357:714-718,2015.
Welch et al, *Org. Process Res. Dev.* 9:198, 2005.
Wisniewski et al., *J. Org. Chem.* 79:365-378, 2014.
Wolfe et al, *Acc. Chem. Res.* 31:805, 1998.
Yan et al, *Catal. Sci. Technol.* 4:4169, 2014.
Yan et al., *RSC Adv.* 6:109702-109705, 2016.
Youn & Kim, *Org. Lett.* 18:6140-6143, 2016.
Yu et al., *Tetrahedron Lett.* 57:4588-4591, 2016.
Zhao & Truhlar, *Acc. Chem. Res.* 41:157-167, 2008a.
Zhao & Truhlar, *Theor. Chem. Acc.* 120:215-241, 2008b.
Zhou et al., *J. Am. Chem. Soc.* 137:11942-11945, 2015.
Zhou et al., *J. Am. Chem. Soc.* 139:115, 2017.
Zhou et al., *Org. Lett.* 18:2427-2430, 2016.
Zhu et al., *J. Am. Chem. Soc.* 134:18253, 2012.

What is claimed is:

1. A compound of the formula:

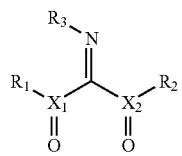

(I)

wherein:
$X_1$ and $X_2$ are each independently C, S, or S(O);
$R_1$ and $R_2$ are each isopropoxy; and
$R_3$ is a leaving group, wherein the leaving group is selected from the group consisting of halo, alkylsulfonyl$_{(C \leq 12)}$, substituted alkylsulfonyl$_{(C \leq 12)}$, arylsulfonyl$_{(C \leq 12)}$, substituted arylsulfonyl$_{(C \leq 12)}$, alkylsulfonyloxy$_{(C \leq 12)}$, substituted alkylsulfonyloxy$_{(C \leq 12)}$, arylsulfonyloxy$_{(C \leq 12)}$, and substituted arylsulfonyloxy$_{(C \leq 12)}$;
or a salt thereof.

2. The compound of claim 1, wherein the compound is further defined as:

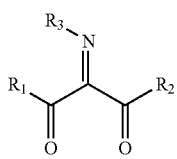

(II)

wherein:
$R_1$ and $R_2$ are isopropoxy; and
$R_3$ is a leaving group, wherein the leaving group is selected from the group consisting of halo, alkylsulfonyl$_{(C \leq 12)}$, substituted alkylsulfonyl$_{(C \leq 12)}$, arylsulfonyl$_{(C \leq 12)}$, substituted arylsulfonyl$_{(C \leq 12)}$, alkylsulfonyloxy$_{(C \leq 12)}$, substituted alkylsulfonyloxy$_{(C \leq 12)}$, arylsulfonyloxy$_{(C \leq 12)}$, and substituted arylsulfonyloxy$_{(C \leq 12)}$;
or a salt thereof.

3. The compound of claim 1, wherein $R_3$ is a leaving group is selected from the group consisting of alkylsulfonyl$_{(C \leq 12)}$, substituted alkylsulfonyl$_{(C \leq 12)}$, arylsulfonyl$_{(C \leq 12)}$, substituted arylsulfonyl$_{(C \leq 12)}$, alkylsulfonyloxy$_{(C \leq 12)}$, substituted alkylsulfonyloxy$_{(C \leq 12)}$, arylsulfonyloxy$_{(C \leq 12)}$, and substituted arylsulfonyloxy$_{(C \leq 12)}$.

4. The compound of claim 1, wherein $X_1$ and $X_2$ are C.

5. The compound of claim 1, wherein the compound is further defined as:

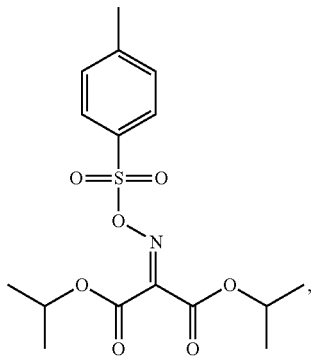

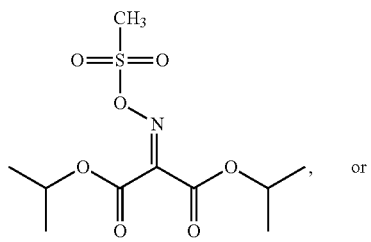, or

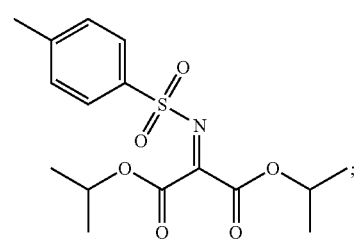;

or a salt thereof.

6. The compound of claim 5, wherein the compound is:

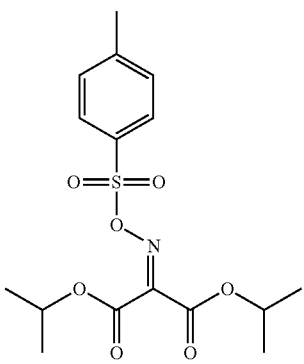 [SMILES: Cc1ccc(S(=O)(=O)ON=C(C(=O)OC(C)C)C(=O)OC(C)C)cc1]

or a salt thereof.

7. The compound of claim 1, wherein the compound is further defined as:

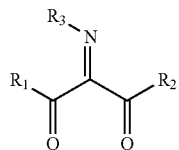

(II)

wherein:

$R_1$ and $R_2$ are each isopropoxy; and $R_3$ is a leaving group, wherein alkylsulfonyl$_{(C\leq12)}$, substituted alkylsulfonyl$_{(C\leq12)}$, arylsulfonyl$_{(C\leq12)}$, substituted arylsulfonyl$_{(C\leq12)}$, alkylsulfonyloxy$_{(C\leq12)}$, substituted alkylsulfonyloxy$_{(C\leq12)}$, arylsulfonyloxy$_{(C\leq12)}$, or substituted arylsulfonyloxy$_{(C\leq12)}$;

or a salt thereof.

8. The compound of claim 7, wherein $R_3$ is arylsulfonyl$_{(C\leq12)}$ or substituted arylsulfonyl$_{(C\leq12)}$.

9. The compound of claim 7, wherein $R_3$ is alkylsulfonyloxy$_{(C\leq12)}$ or substituted alkylsulfonyloxy$_{(C\leq12)}$.

10. The compound of claim 7, wherein $R_3$ is arylsulfonyloxy$_{(C\leq12)}$ or substituted arylsulfonyloxy$_{(C\leq12)}$.

11. The compound of claim 10, wherein $R_3$ is arylsulfonyloxy$_{(C\leq12)}$.

* * * * *